US008865756B2

(12) United States Patent
Li et al.

(10) Patent No.: US 8,865,756 B2
(45) Date of Patent: Oct. 21, 2014

(54) INHIBITORS OF HCV NS5A

(75) Inventors: Leping Li, San Francisco, CA (US); Min Zhong, San Francisco, CA (US)

(73) Assignee: Presidio Pharmaceuticals, Inc., San Francisco, CA (US)

( * ) Notice: Subject to any disclaimer, the term of this patent is extended or adjusted under 35 U.S.C. 154(b) by 67 days.

(21) Appl. No.: 13/132,604

(22) PCT Filed: Dec. 2, 2009

(86) PCT No.: PCT/US2009/066451
§ 371 (c)(1),
(2), (4) Date: Jan. 20, 2012

(87) PCT Pub. No.: WO2010/065668
PCT Pub. Date: Jun. 10, 2010

(65) Prior Publication Data
US 2012/0115855 A1    May 10, 2012

Related U.S. Application Data

(60) Provisional application No. 61/119,723, filed on Dec. 3, 2008, provisional application No. 61/173,590, filed on Apr. 28, 2009, provisional application No. 61/182,952, filed on Jun. 1, 2009.

(51) Int. Cl.
A61K 31/4178    (2006.01)
A61K 31/4184    (2006.01)
C07D 235/04    (2006.01)
C07D 235/02    (2006.01)
C07D 233/54    (2006.01)
C07D 403/14    (2006.01)

(52) U.S. Cl.
CPC .................................. C07D 403/14 (2013.01)
USPC ..... 514/394; 514/397; 548/302.1; 548/306.1; 548/313.1

(58) Field of Classification Search
USPC .......... 514/394, 397; 548/302.1, 306.1, 313.1
See application file for complete search history.

(56) References Cited

U.S. PATENT DOCUMENTS

| 5,807,876 | A  | 9/1998  | Armistead et al. |
| 6,054,472 | A  | 4/2000  | Armistead et al. |
| 6,344,465 | B1 | 2/2002  | Armistead et al. |
| 6,498,178 | B2 | 12/2002 | Stamos et al. |

FOREIGN PATENT DOCUMENTS

| CN | 101027051 A  | 8/2007 |
| EP | 0511943 A2   | 11/1992 |
| EP | 1256628 A2   | 11/2002 |
| WO | 9740028 A1   | 10/1997 |
| WO | 9817679 A1   | 4/1998 |
| WO | 9822496 A2   | 5/1998 |
| WO | 9840381 A1   | 9/1998 |
| WO | 9901582 A1   | 1/1999 |
| WO | 9907734 A2   | 2/1999 |
| WO | 0006529 A1   | 2/2000 |
| WO | 0009543 A2   | 2/2000 |
| WO | 0010573 A1   | 3/2000 |
| WO | 0013708 A1   | 3/2000 |
| WO | 0018231 A1   | 4/2000 |
| WO | 0056331 A1   | 9/2000 |
| WO | 0132153 A2   | 5/2001 |
| WO | 0185172 A1   | 11/2001 |
| WO | 0204425 A2   | 1/2002 |
| WO | 0218369 A2   | 3/2002 |
| WO | 02100846 A1  | 12/2002 |
| WO | 02100851 A2  | 12/2002 |
| WO | 03000254 A1  | 1/2003 |
| WO | 03007945 A1  | 1/2003 |
| WO | 03010141 A2  | 2/2003 |
| WO | 03037893 A1  | 5/2003 |
| WO | 03037894 A1  | 5/2003 |
| WO | 03037895 A1  | 5/2003 |
| WO | 2004046095 A1 | 6/2004 |
| WO | 2004099241 A1 | 11/2004 |
| WO | 2005073195 A2 | 8/2005 |
| WO | 2005073216 A2 | 8/2005 |
| WO | 2006019831 A1 | 2/2006 |
| WO | 2008021927 A2 | 2/2008 |
| WO | 2008021936 A2 | 2/2008 |
| WO | 2008058393 A1 | 5/2008 |
| WO | 2010017401 A1 | 2/2010 |
| WO | 2010039793 A1 | 4/2010 |
| WO | 2010132601 A1 | 11/2010 |

OTHER PUBLICATIONS

Alcon et al., Copper complexes with multidentate ligands derived from L-proline. X-ray crystal structure of {[Cu(N,N'-bis[(S)-prolyl]ethylenediamine)] ClO4}2. (MeCN)2. Inorganica Chimica Acta Aug. 1, 2000;306(1):117-122.
Alcon et al., Rh and Ir complexes containing multidentate, C2-symmetry ligands. Structural and catalytic properties in asymmetric hydrogenation. J Organometallic Chem. 2000:601(2):284-292.
Extended European Search Report dated Jun. 27, 2012 issued in PCT/US2009/066451.
Hopkins et al., Synthesis and Structure of Chiral Macrocycles Containing 2,2'-Bipyridine Subunits. Bioorg Med Chem. Jul. 1996;4(7):1121-1128.
Iwase and Mural, N-Trifluoroacetyl-L-prolylamine Derivatives for the Ultramicrodetermination of Amines by Mass Fragmentography. Chem Pharm Bull. (Tokyo) 1977:25(6):1215-1219.
Kitagawa et al., New Nickel (II) Complexes of Some Optically Active Tetraamines with Pyrrolidinyl Groups. Inorganic Chemistry 1975;14(10):2347-2352.
Naya et al., RE: The Predictors of Pelvic Lymph Node Metastasis at Radical Retropubic Prostatectomy. J Urol. Oct. 2004;172(4 Pt 1):1545-1546.
Parrish et al., Supramolecular Materials from Multifunctional Pyroglutamic Acid Derivatives. Macromolecules 2003;36(12):4250-4252.

(Continued)

Primary Examiner — Samantha Shterengarts
(74) Attorney, Agent, or Firm — Sam K. Tahmassebi; TechLaw LLP

(57) ABSTRACT

Provided herein are compounds, pharmaceutical compositions and combination therapies for inhibition of hepatitis C.

24 Claims, No Drawings

(56) References Cited

OTHER PUBLICATIONS

Samanta et al., C2—Symmetric Bisprolinamide as a Highly Efficient Catalyst for Direct Aldol Reaction. Org Lett. Nov. 10, 2005;7(23):5321-5323.
Weeks et al., Nickel(ii) complexes with amide ligands: oxidative dehydrogenation of the amines in a tetradentate diamide-diamine ligand. J Chem Soc. 2002:931-940.
Zhang et al., Synthesis of 2-Substituted Benzimidazoles by Iodine-Mediated Condensation of Orthoesters with 1,2-Phenylenediamines. J Heterocyclic Chem. Nov.-Dec. 2007;44:1509-1512.
Iwase and Murai., N-Trifluoroacetyl-L-prolylamine Derivatives for the Ultramicrodetermination of Amines by Mass Fragmentography. Chem Pharm Bull. (Tokyo) 1977;25(6):1215-1219.
Beaulieu, Non-nucleoside inhibitors of the HCV NS5B polymerase: progress in the discovery and development of novel agents for the treatment of HCV infections. Curr Opin Investig Drugs. Aug. 2007;8(8):614-634.
Berge et al., Pharmaceutical salts. J Pharm Sci. Jan. 1977;66(1):1-19.
First Office Action issued by SIPO in application No. 200980155930.1 dated Jan. 25, 2013 (incl Engl transl).
Ghany et al., AASLD Practice Guidelines. 2009:1-22.
Huang et al., Recent development of therapeutics for chronic HCV infection. Antiviral Res. Sep. 2006;71(2-3):351-362.
Kim et al., Protein Kinase C-related Kinase 2 Regulates Hepatitis C Virus RNA Polymerase Function by Phosphorylation. J Biol Chem. Nov. 26, 2004;279(48):50031-50041.
Klebl et al., Host cell targets in HCV therapy: novel strategy or proven practice? Antivir Chem Chemother. 2005;16 (2):69-90.
Lindenbach and Rice, Unravelling hepatitis C virus replication from genome to function. Nature. Aug. 18, 2005;436 (7053):933-938.
Manns, et al., The way forward in HCV treatment—finding the right path. Nat Rev Drug Discov. Dec. 2007;6 (12):991-1000.
Murata et al., Hydrogen-bonded networks of 2,20-substituted 4,40-biimidazoles: New ligands for the assembled metal complexes. Polyhedron 2005;24:2625-2631.
Murineddu et al., Tricyclic pyrazoles. 3. Synthesis, biological evaluation, and molecular modeling of analogues of the cannabinoid antagonist 8-chloro-1-(2',4'-dichlorophenyl)-N-piperidin-l-yl-1,4,5,6-tetrahydrobenzo[6,7]cyclohepta [1,2-c]pyrazole-3-carboxamide. J Med Chem. Nov. 17, 2005;48(23):7351-7362.
Neyts, Selective inhibitors of hepatitis C virus replication. Antiviral Res. Sep. 2006;71(2-3):363-371.
Okamoto et al., Hepatitis C virus RNA replication is regulated by FKBP8 and Hsp90. EMBO J. Oct. 18, 2006;25 (20):5015-5025.
Pawlotsky et al., The Hepatitis C Virus Life Cycle as a Target for New Antiviral Therapies. Gastroenterology. May 2007;132(5):1979-1998.
Rossignol and Keeffe, Thiazolides: a new class of drugs for the treatment of chronic hepatitis B and C. Future Microbiol. Oct. 2008;3(5):539-545.
Soriano et al., New Therapies for Hepatitis C Virus Infection. Clin Infect Dis. Feb. 1, 2009;48(3):313-320.

INHIBITORS OF HCV NS5A

STATEMENT OF RELATED APPLICATIONS

This application claims the benefit of U.S. provisional applications 61/119,723 filed Dec. 3, 2008; 61/173,590 filed Apr. 28, 2009; and 61/182,952 filed Jun. 1, 2009.

FIELD OF THE INVENTION

The invention relates to compounds useful for inhibiting hepatitis C virus ("HCV") replication, particularly functions of the non-structural 5A ("NS5A") protein of HCV.

BACKGROUND OF THE INVENTION

HCV is a single-stranded RNA virus that is a member of the Flaviviridae family. The virus shows extensive genetic heterogeneity as there are currently seven identified genotypes and more than 50 identified subtypes. In HCV infected cells, viral RNA is translated into a polyprotein that is cleaved into ten individual proteins. At the amino terminus are structural proteins: the core (C) protein and the envelope glycoproteins, E1 and E2. p7, an integral membrane protein, follows E1 and E2. Additionally, there are six non-structural proteins, NS2, NS3, NS4A, NS4B, NS5A and NS5B, which play a functional role in the HCV lifecycle. (see, for example, Lindenbach, B. D. and C. M. Rice, Nature. 436:933-938, 2005).

Infection by HCV is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves interferon-alpha, alone, or in combination with ribavirin. The treatment is cumbersome and sometimes has debilitating and severe side effects and many patients do not durably respond to treatment. New and effective methods of treating HCV infection are urgently needed.

SUMMARY OF THE INVENTION

Essential features of the NS5A protein of HCV make it an ideal target for inhibitors. The present disclosure describes a class of compounds targeting the NS5A protein and methods of their use to treat HCV infection in humans.

In a first aspect, compounds of formula I are provided:

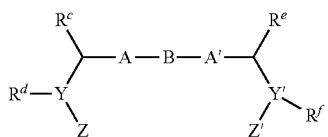

wherein:
A and A' are independently selected from the group consisting of a single bond, $-(CR_2)_n-C(O)-(CR_2)_p-$, $-(CR_2)_n-O-(CR_2)_p-$, $-(CR_2)_n-N(R^N)-(CR_2)_p-$, $-(CR_2)_n-S(O)_k-N(R^N)-(CR_2)_p-$, $-(CR_2)_n-C(O)-N(R^N)-(CR_2)_p-$, $-(CR_2)_n-N(R^N)-C(O)-N(R^N)-(CR_2)_p-$, $-(CR_2)_n-C(O)-O-(CR_2)_p-$, $-(CR_2)_n-N(R^N)-S(O)_k-N(R^N)-(CR_2)_p-$ and $-(CR_2)_n-N(R^N)-C(O)-O-(CR_2)_p-$ and a heteroaryl group selected from the group consisting of

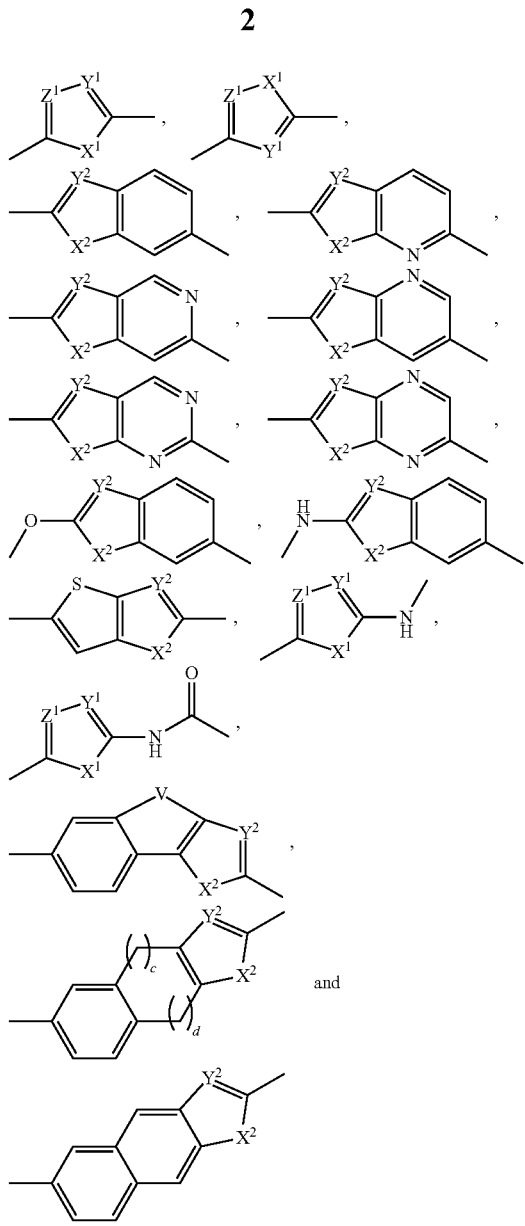

wherein:
$X^1$ is $CH_2$, NH, O or S,
$Y^1, Y^2$ and $Z^1$ are each independently CH or N,
$X^2$ is NH, O or S,
V is $-CH_2-CH_2-$, $-CH=CH-$, $-N=CH(CH_2)_a-N(R^N)-(CH_2)_b-$ or $-(CH_2)_a-O-(CH_2)_b-$, wherein a and b are independently 0, 1, 2, or 3 with the proviso that a and b are not both 0, optionally includes 1 or 2 nitrogens as heteroatoms on the phenyl residue,
the carbons of the heteroaryl group are each independently optionally substituted with a substituent selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, the nitrogens, if present, of the heteroaryl group are each independently optionally substituted with a substituent selected from the group consisting of —OH, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, a and b are independently 1, 2, or 3.

c and d are independently 1 or 2, n and p are independently 0, 1, 2 or 3, k is 0, 1, or 2, each independently selected from the group consisting of hydrogen, —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, each $R^N$ is independently selected from the group consisting of hydrogen, —OH, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide, and wherein for each A and A', B may be attached to either side of A and A' so that in the example of A or A' being

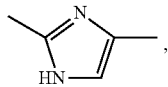

the A-B-A' can be any of:

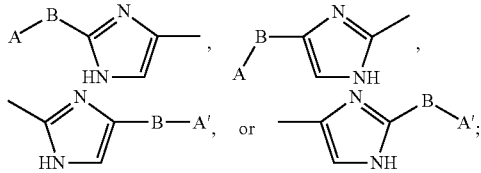

B is selected from the group consisting of a single bond, triple bond,

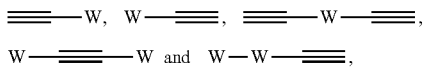

wherein each W is independently selected from the group consisting of a cycloalkenyl group, aryl group and heteroaryl group, with the proviso that a triple bond does not attach to W at a heteroatom;

$R^c$, $R^d$, $R^e$ and $R^f$ are each independently selected from the group consisting of: hydrogen, C₁ to C₈ alkyl, C₁ to C₈ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by C₁ to C₈ alkyl, C₁ to C₈ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 6-membered heterocycle or heteroaryl ring, and $R^e$ and $R^f$ are optionally joined to form a 4- to 8-membered heterocycle which is optionally fused to another 3- to 6-membered heterocycle or heteroaryl ring;

Y and Y' are each independently carbon or nitrogen; and

Z and Z' are independently selected from the group consisting of hydrogen, C₁ to C₈ alkyl, C₁ to C₈ heteroalkyl, cycloalkyl, heterocycle, aryl, heteroaryl, aralkyl, 1-3 amino acids, —[U—(CR⁴₂)ₜ—NR⁵—(CR⁴₂)ₜ]ᵤ—U—(CR⁴₂)ₜ—NR⁷—(CR⁴₂)ₜ—R⁸, —U—(CR⁴₂)ₜ—R⁸ and [U—(CR⁴₂)ₜ—NR⁵—(CR⁴₂)ₜ]ᵤ—U—(CR⁴₂)ₜ—O—(CR⁴₂)ₜ—R⁸, wherein, U is selected from the group consisting of —C(O)—, —C(S)— and —S(O)₂—, each $R^4$, $R^5$ and $R^7$ is independently selected from the group consisting of hydrogen, C₁ to C₈ alkyl, C₁ to C₈ heteroalkyl, cycloalkyl, heterocycle, aryl, heteroaryl and aralkyl, $R^8$ is selected from the group consisting of hydrogen, C₁ to C₈ alkyl, C₁ to C₈ heteroalkyl, cycloalkyl, heterocycle, aryl, heteroaryl, aralkyl, —C(O)—R⁸¹, —C(S)—R⁸¹, —C(O)—O—R⁸¹, —C(O)—N—R⁸¹₂, —S(O)₂—R⁸¹ and —S(O)₂—N—R⁸¹₂, wherein each $R^{81}$ is independently chosen from the group consisting of hydrogen, C₁ to C₈ alkyl, C₁ to C₈ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the first aspect, each W is independently optionally substituted with one or more substituents each independently selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and if W is not aromatic, it is optionally substituted with oxo.

In second embodiment each W is independently optionally substituted with one of the group consisting of —CN, —OCF₃, —OCHF₂, —CF₃ and —F.

In a third embodiment B is selected from the group consisting of a triple bond,

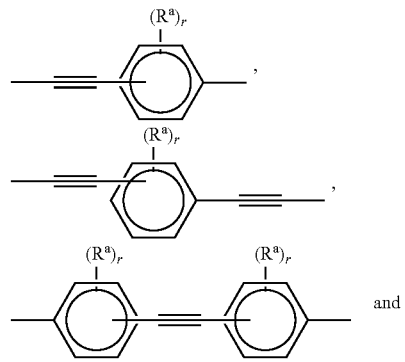

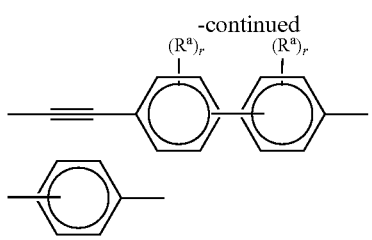

wherein:

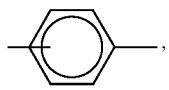

is a divalent aryl or heteroaryl group which may be polycyclic with varying connective patterns;
each r is independently from 0 to 4; and
each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino.

In a fourth embodiment,

when present, is selected from the group consisting of:

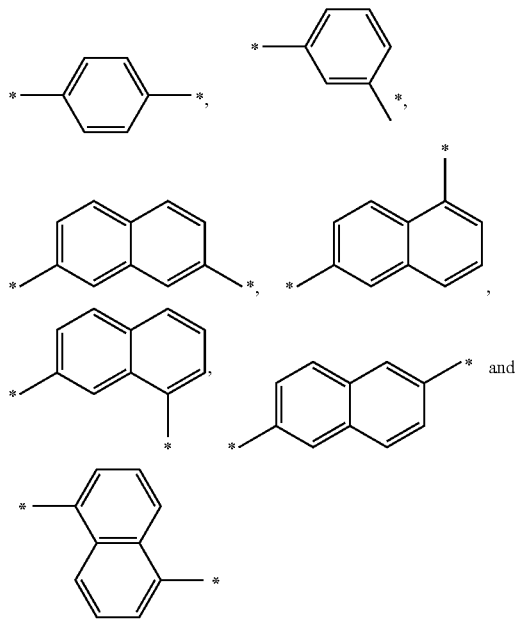

wherein * indicates attachment points to the remainder of the compound and each phenyl residue independently optionally includes 1 or 2 nitrogens as heteroatoms.

In a fifth embodiment,

when present, is selected from the group consisting of:

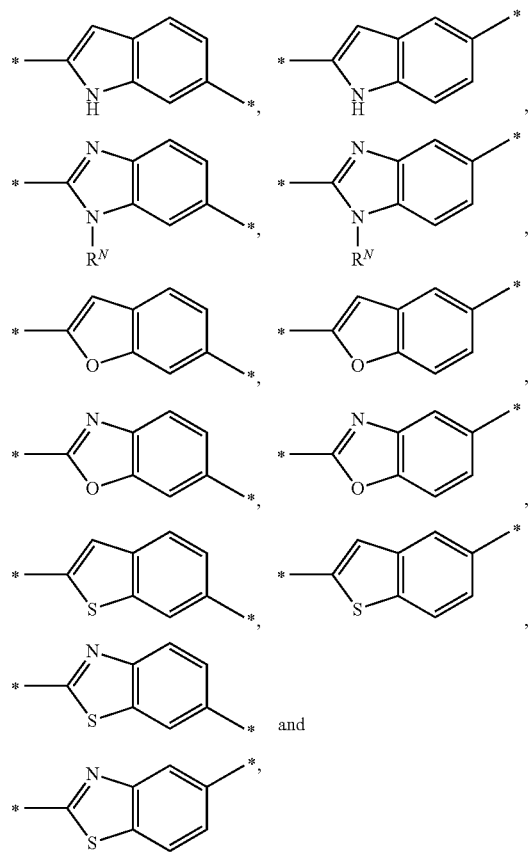

wherein * indicates attachment points to the remainder of the compound, the phenyl residue optionally includes 1 or 2 nitrogens as heteroatoms, and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment,

when present, is selected from the group consisting of:

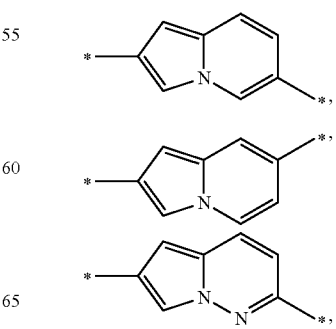

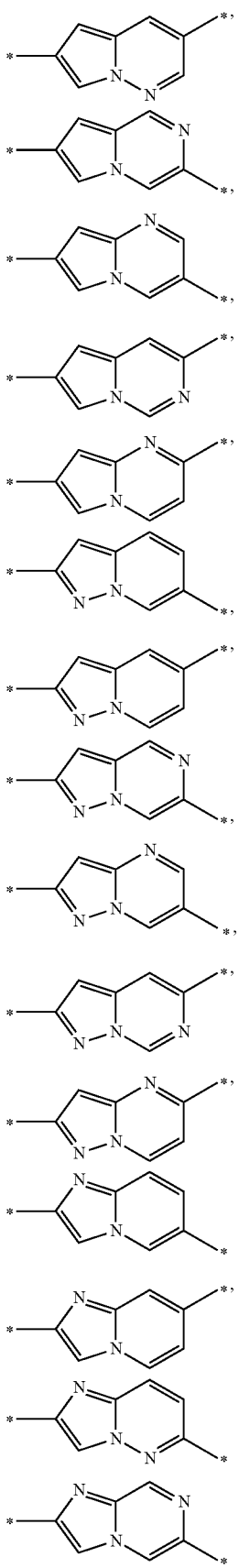

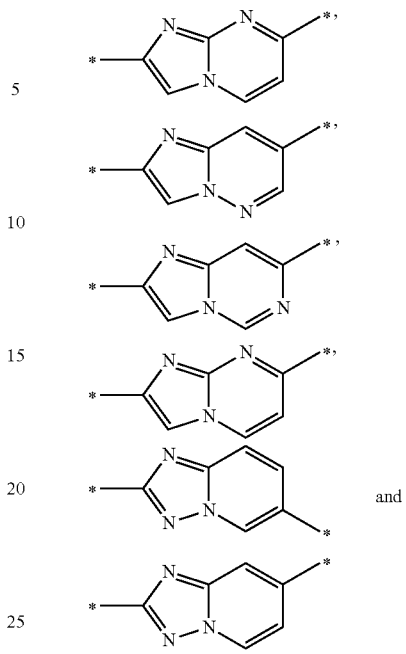

wherein * indicates attachment points to the remainder of the compound, and the phenyl residue optionally includes 1 or 2 additional nitrogens as heteroatoms with the proviso that there are no more than 2 total nitrogens on the phenyl residue.

In a seventh embodiment, each $R^a$, when present, is independently selected from the group consisting of —CN, —OCF$_3$, —OCHF$_2$, —CF$_3$, or —F.

In an eighth embodiment, A and A' are independently selected from the group consisting of a single bond, —(CR$_2$)$_n$—O—(CR$_2$)$_p$—, —(CR$_2$)$_n$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$— and —(CR$_2$)$_n$—N(R$^N$)—C(O)—O—(CR$_2$)$_p$— and a heteroaryl group selected from the group consisting

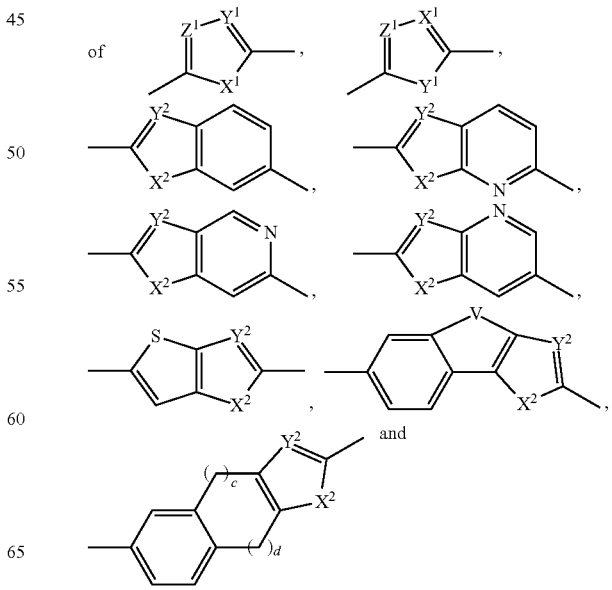

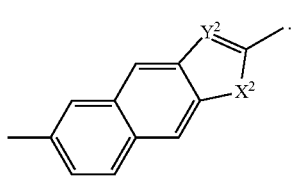

In a ninth embodiment A and A' are independently selected from the group consisting of a single bond,

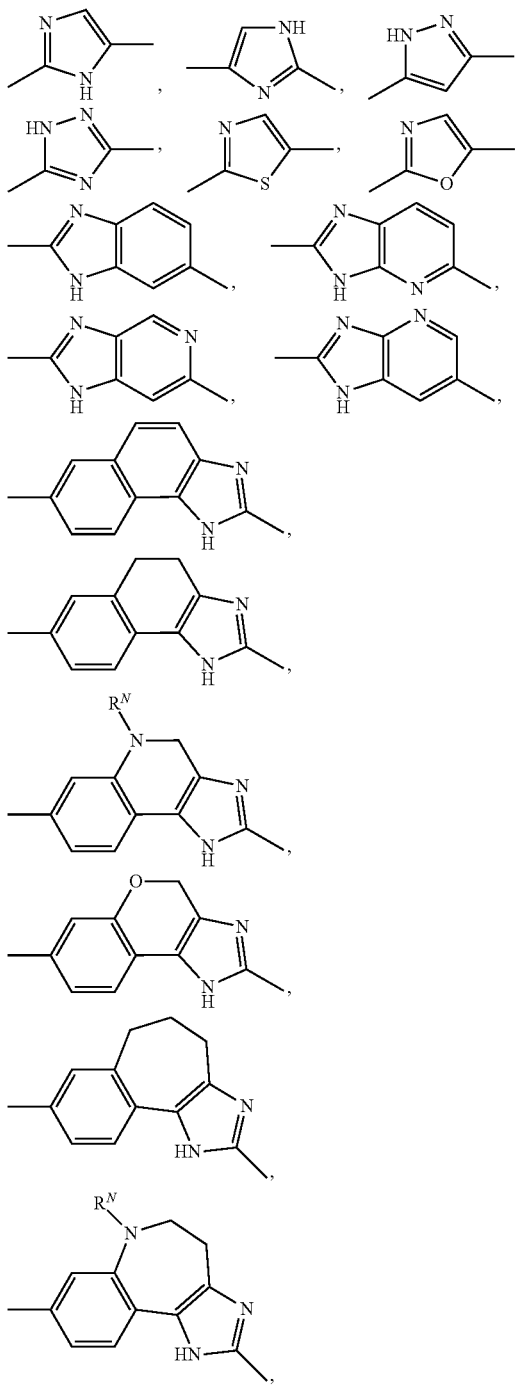

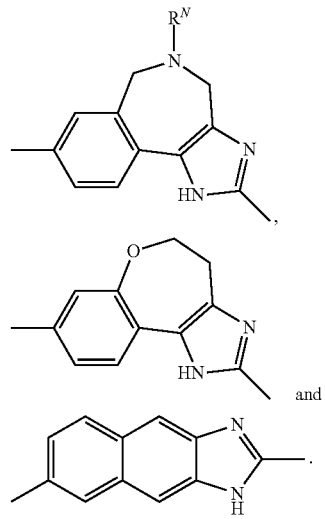

In a tenth embodiment, $R^c$, $R^d$, $R^e$ and $R^f$ are each independently selected from the group consisting of: hydrogen, $C_1$ to $C_8$ alkyl and $C_1$ to $C_8$ heteroalkyl, wherein, each hetero atom, if present, is independently N, O or S, $R^c$ and $R^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In an eleventh embodiment one or both of $R^c$ and $R^d$ or $R^e$ and $R^f$ are optionally joined to form a 4- to 8-membered heterocycle which is optionally fused to another 3- to 6-membered heterocycle.

In a twelfth embodiment $R^c$ and $R^d$ are joined and form a heterocyclic fused ring system selected from the group consisting of:

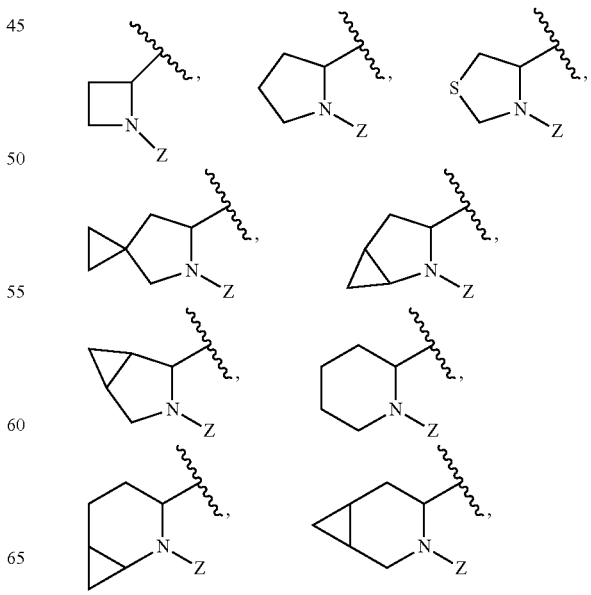

-continued

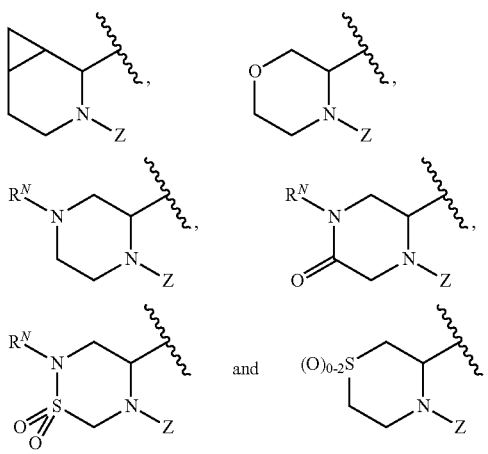

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a thirteenth embodiment $R^e$ and $R^f$ are joined and form a heterocyclic fused ring system selected from the group consisting of:

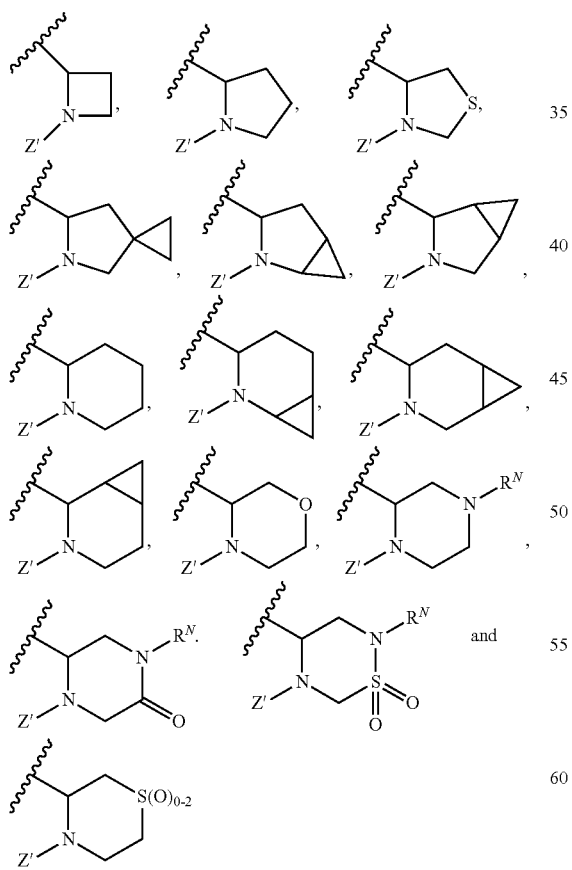

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds of formula III are provided:

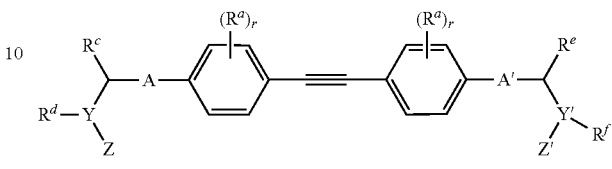

wherein A and A' are independently selected from the group consisting of single bond,

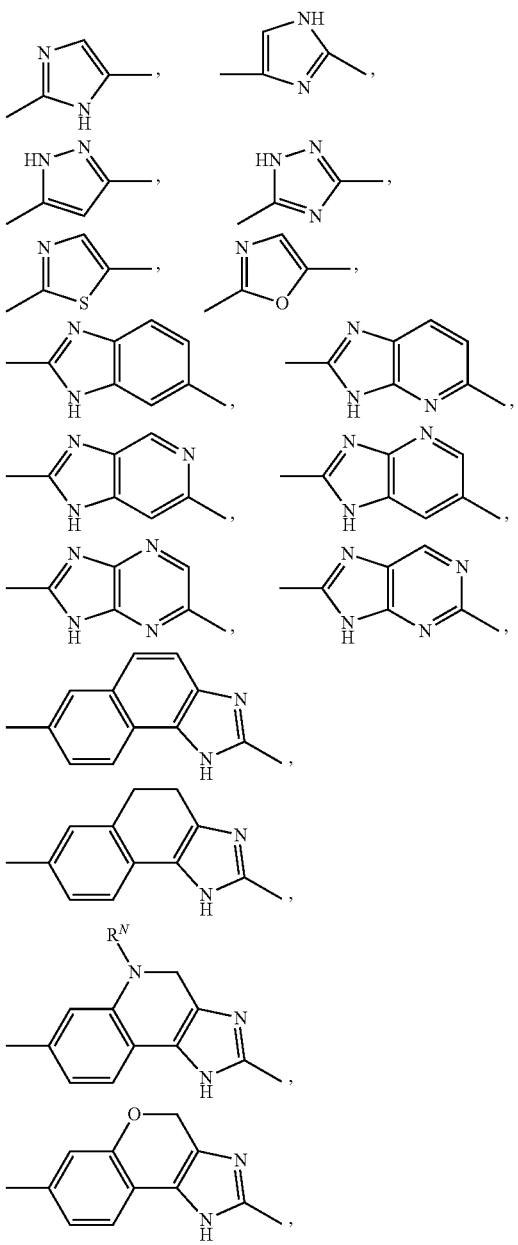

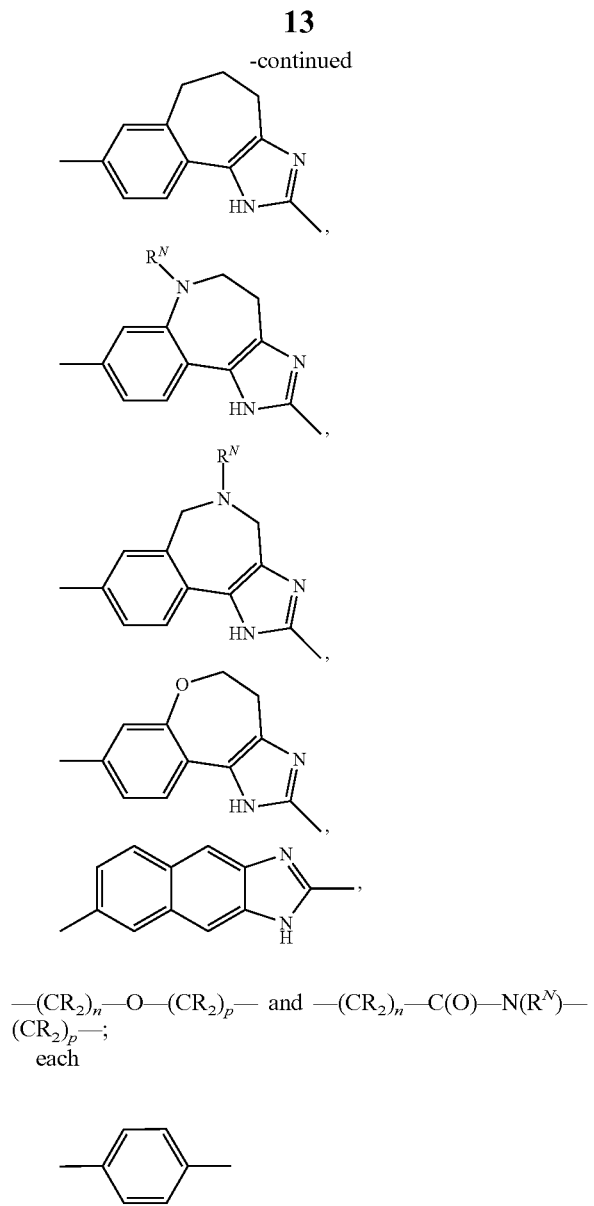

—(CR$_2$)$_n$—O—(CR$_2$)$_p$— and —(CR$_2$)$_n$—C(O)—N(R$^N$)—(CR$_2$)$_p$—;
each

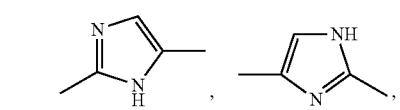

optionally independently includes 1 or 2 nitrogens as heteroatoms;
  each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
  each r is independently 0, 1, 2, 3 or 4.

In a first embodiment of the second aspect, A and A' are each independently

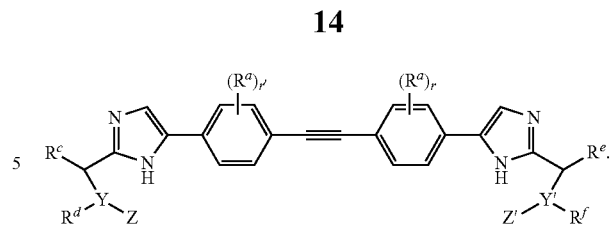

or —(CR$_2$)$_n$—C(O)N(R$^N$)—(CR$_2$)$_p$—.

In a second embodiment of the second aspect, the compound is of formula IIIa:

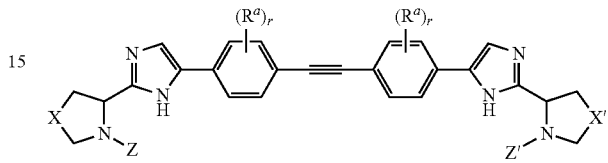

In a third embodiment of the second aspect, the compound is of formula IIIb:

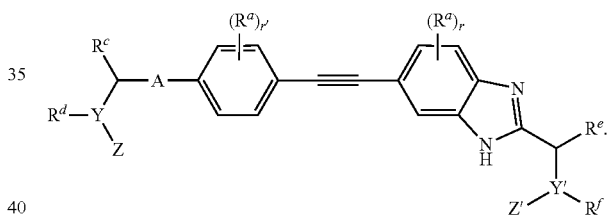

wherein, X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a third aspect of the invention compounds of formula IV are disclosed:

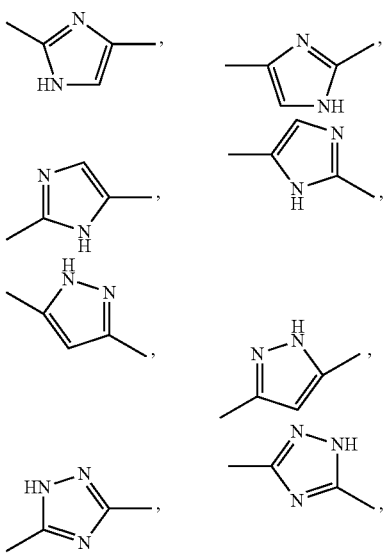

wherein:
  A is selected from the group consisting of a single bond,

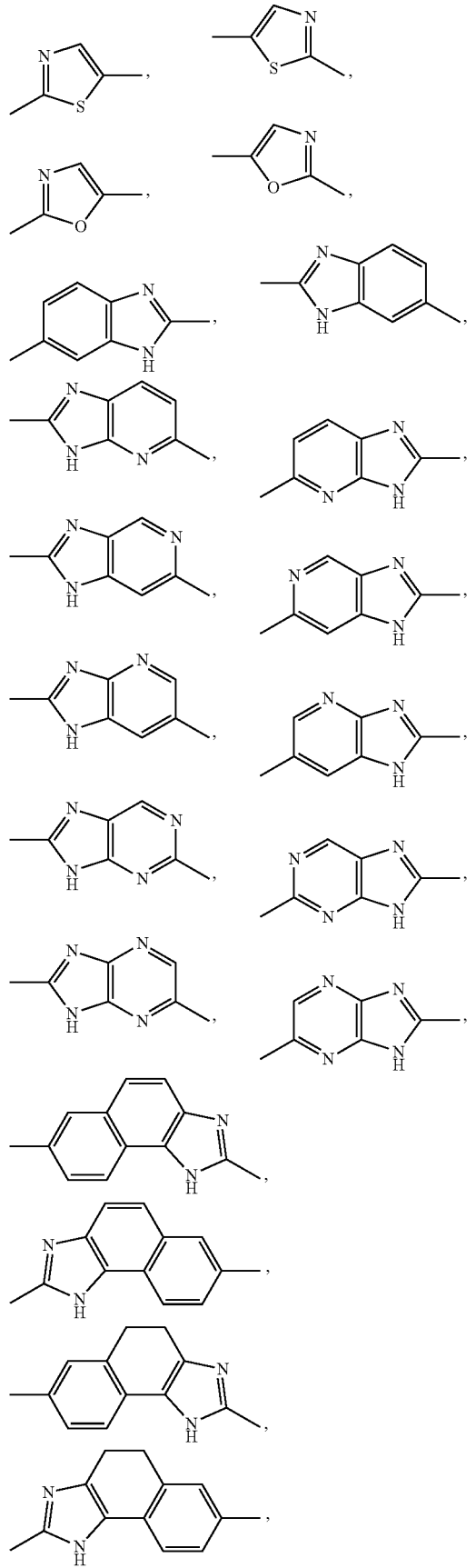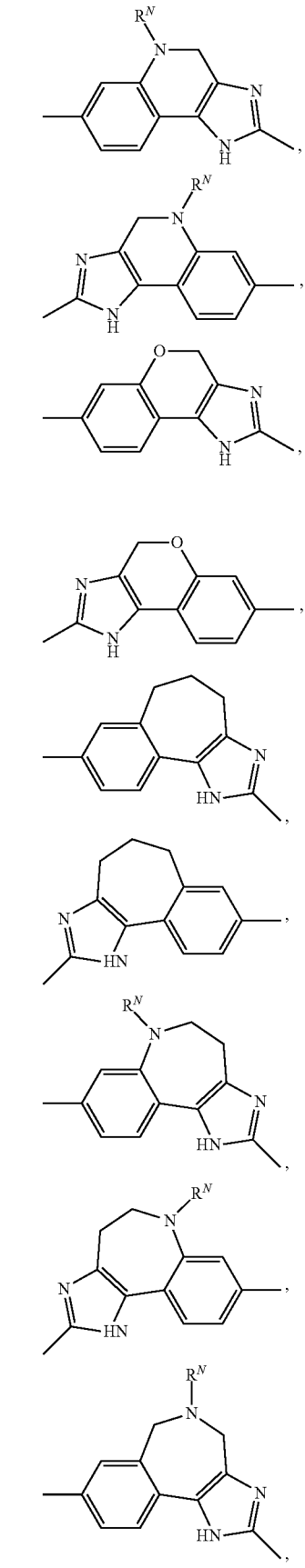

-continued

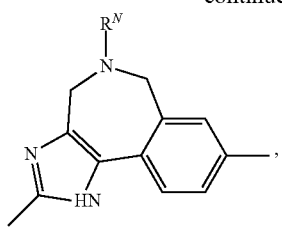

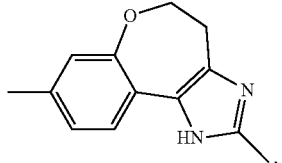

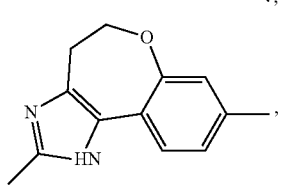

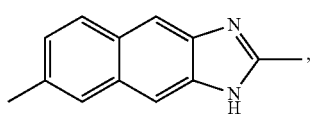

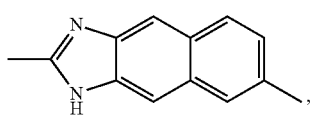

—(CR$_2$)$_n$—O—(CR$_2$)$_p$—,  —(CR$_2$)$_n$—C(O)N(R$^N$)—(CR$_2$)$_p$— and —(CR$_2$)$_n$—N(R$^N$)C(O)—(CR$_2$)$_p$—;

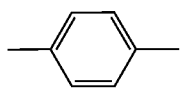

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, or 3; and r' is 0, 1, 2, 3, or 4.

In a first embodiment of the third aspect of the invention A is a single bond,

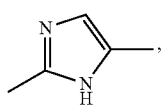

—(CR$_2$)$_n$—C(O)N(R$^N$)—(CR$_2$)$_p$—, or —(CR$_2$)$_n$—N(R$^N$)C(O)—(CR$_2$)$_p$—.

In a second embodiment of the third aspect the compounds are of formula IVa:

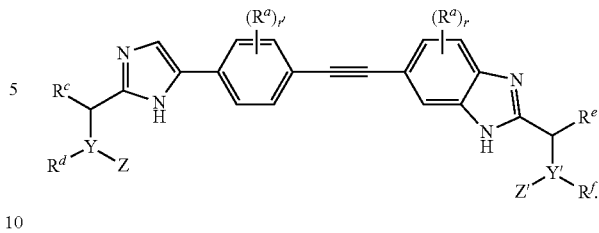

In a third embodiment of the third aspect the compounds are of formula IVb:

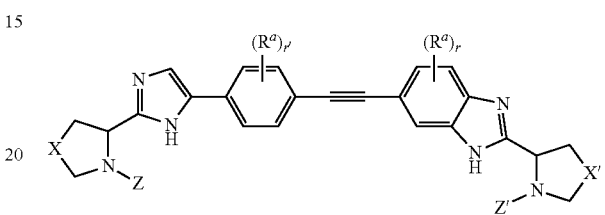

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth aspect of the invention, compounds are of formula V:

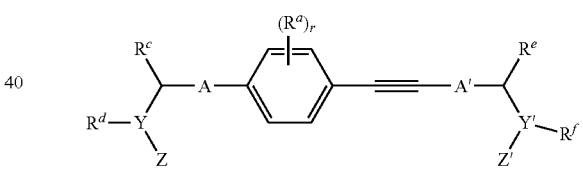

wherein:

A and A' are independently selected from the group consisting of single bond,

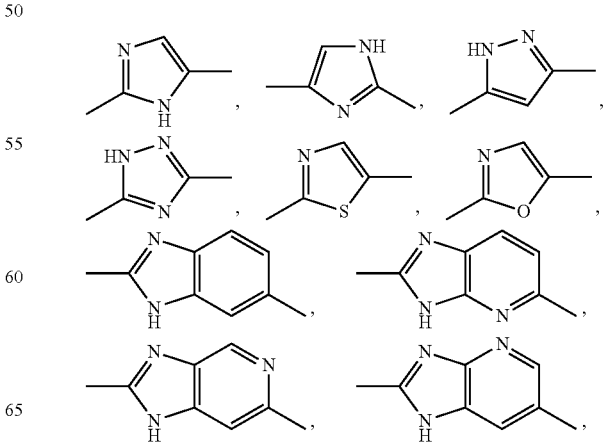

-continued

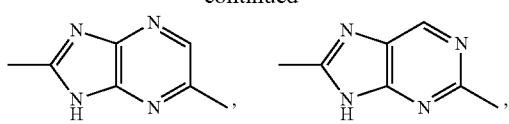,

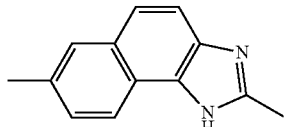,

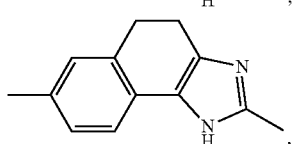,

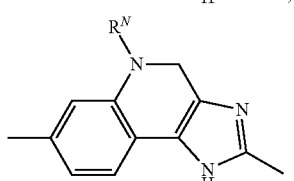,

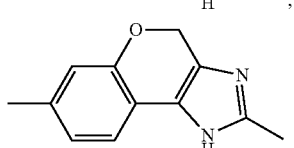,

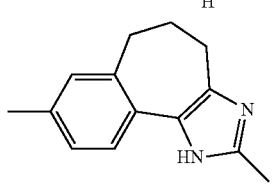,

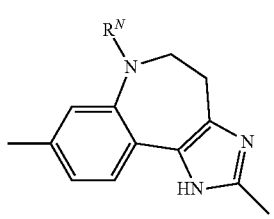,

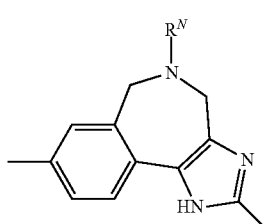,

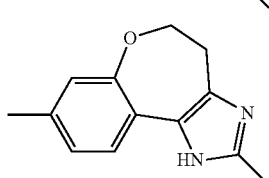,

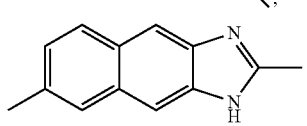,

—(CR$_2$)$_n$—O—(CR$_2$)$_p$— and —(CR$_2$)$_n$—C(O)N(R$^N$)—(CR$_2$)$_p$—;

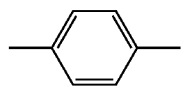

optionally includes 1 or 2 nitrogens as heteroatoms;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
r is 0, 1, 2, 3, or 4.

In a first embodiment of the fourth aspect, A and A' are each independently

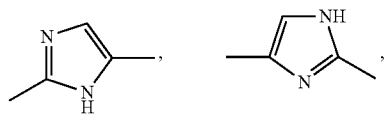

or —(CR$_2$)$_n$—C(O)N(R$^N$)—(CR$_2$)$_p$—.

In a second embodiment of the fourth aspect, compounds have formula Va:

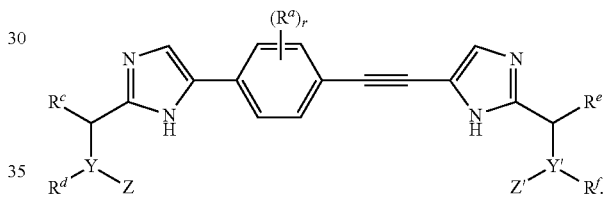

In a third embodiment of the fourth aspect, compounds have formula Vb:

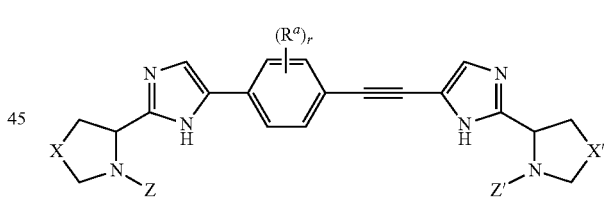

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth embodiment of the fourth aspect, compounds have formula V wherein:
A is selected from the group consisting of

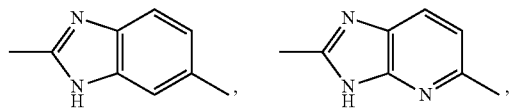,

-continued

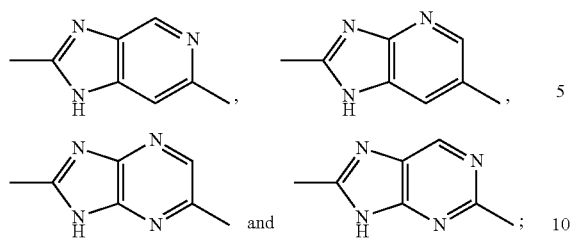

and

A' is selected from the group consisting of

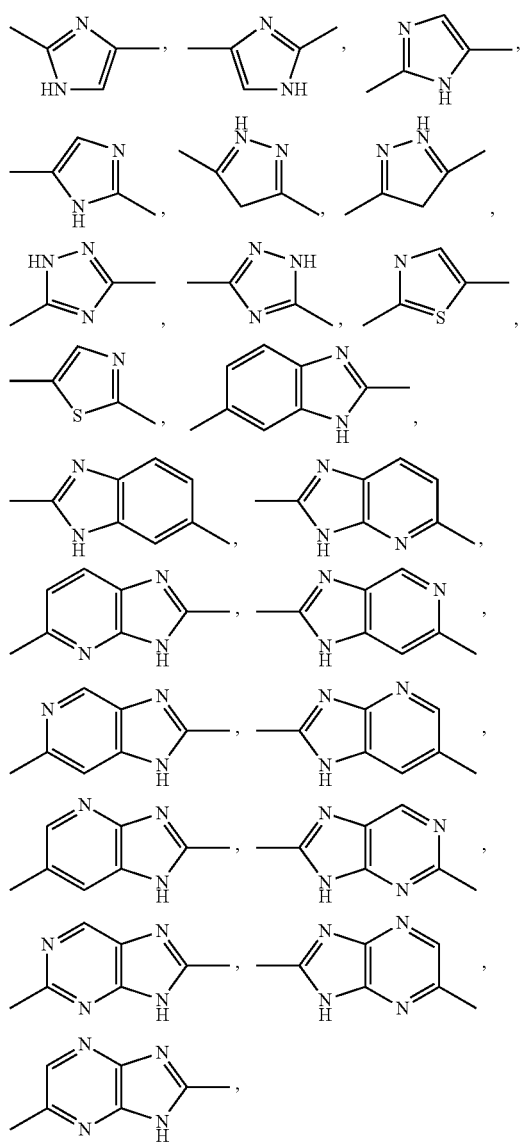

—(CR$_2$)$_n$—O—(CR$_2$)$_p$—, —(CR$_2$)$_n$—C(O)N(R$^N$)—(CR$_2$)$_n$— and —(CR$_2$)$_n$—N(R$^N$)C(O)—(CR$_2$)$_p$—.

In a fifth embodiment of the fourth aspect, compounds have formula V wherein:

A is selected from the group consisting of

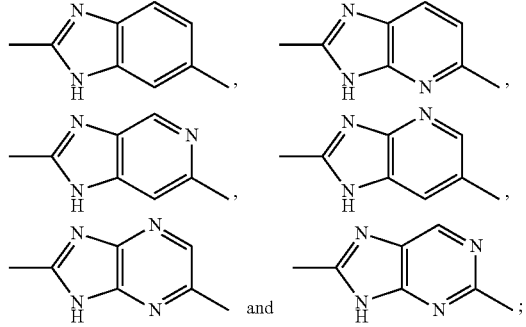

and

A' is

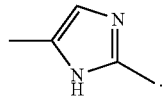

In a sixth embodiment of the fourth aspect, the compounds have formula Vc:

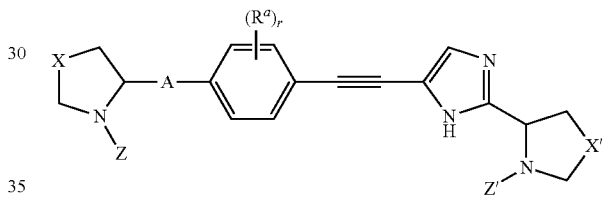

wherein:

A is selected from the group consisting of

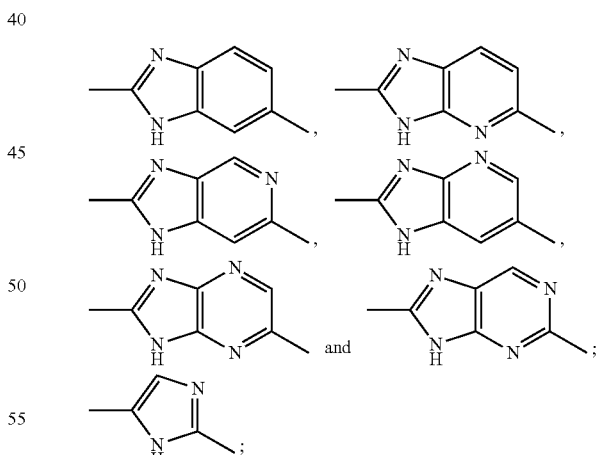

A' is

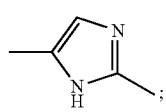

and

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a seventh embodiment of the fourth aspect, compounds have formula V wherein:

A is selected from the group consisting of

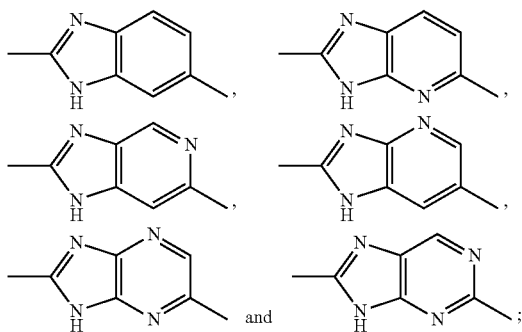

and

A' is selected from the group consisting of

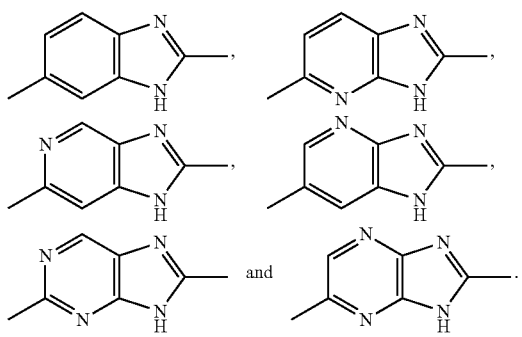

In a eighth embodiment of the fourth aspect, the compounds have formula Vd:

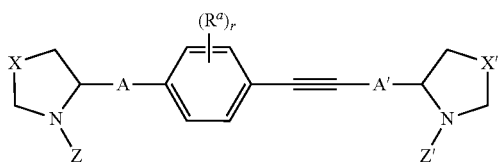

wherein:

A is selected from the group consisting of

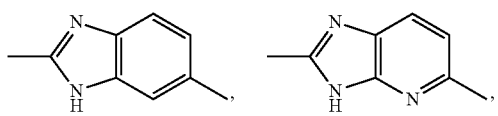

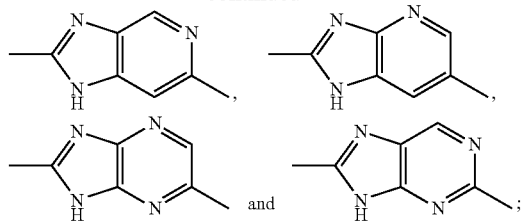

A' is selected from the group consisting of

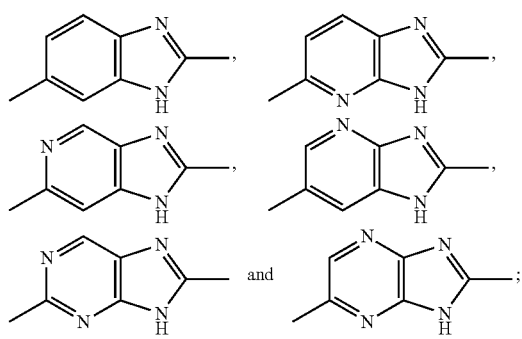

and

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifth aspect of the invention, compounds have formula VI:

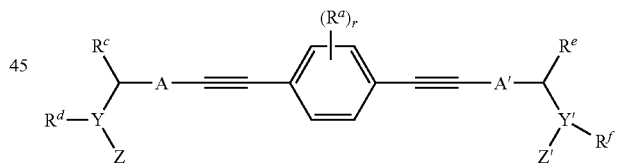

wherein

A and A' are independently selected from the group consisting of single bond,

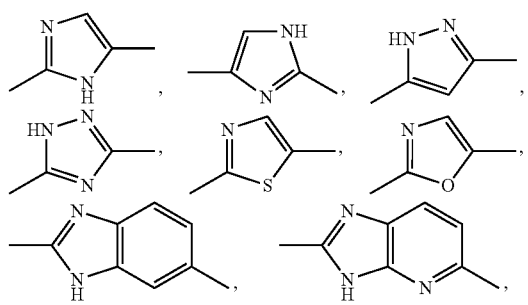

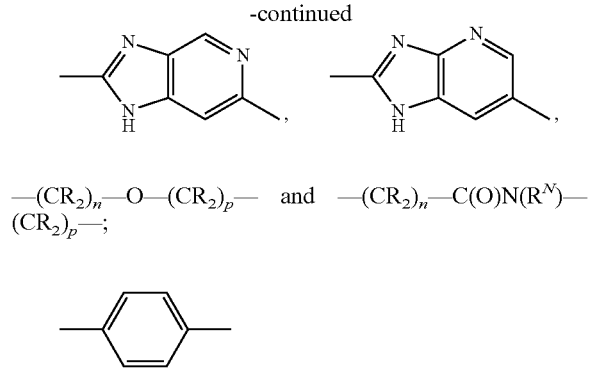

—(CR$_2$)$_n$—O—(CR$_2$)$_p$— and —(CR$_2$)$_n$—C(O)N(R$^N$)—(CR$_2$)$_p$—;

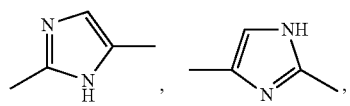

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is 0, 1, 2, 3 or 4.

In a first embodiment of the fifth aspect, A and A' are each independently

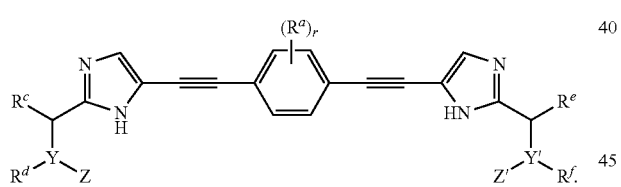

or —(CR$_2$)$_n$—C(O)N(R$^N$)—(CR$_2$)$_p$—.

In a second embodiment of the fifth aspect, compounds have formula VIa:

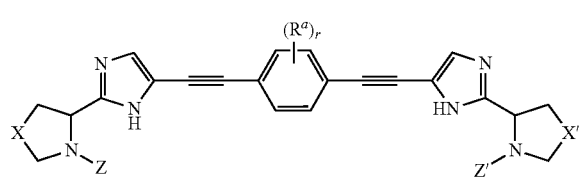

In a third embodiment of the fifth aspect, compounds have formula VIb:

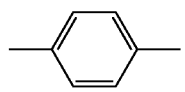

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a sixth aspect of the invention, compounds have formula VII:

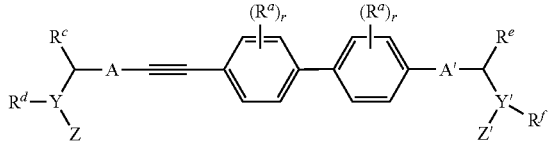

wherein,

A and A' are independently selected from the group consisting of single bond,

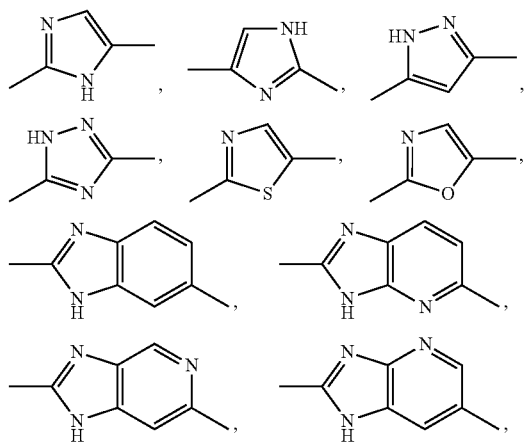

—(CR$_2$)$_n$—O—(CR$_2$)$_p$— and —(CR$_2$)$_n$—C(O)N(R$^N$)—(CR$_2$)$_p$—;

each

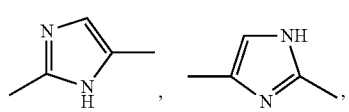

optionally independently includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each r is independently 0, 1, 2, 3 or 4.

In a first embodiment of the sixth aspect, A and A' are each independently

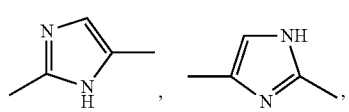

or —(CR$_2$)$_n$—C(O)N(R$^N$)—(CR$_2$)$_p$—.

In a second embodiment of the sixth aspect, compounds have formula VIIa:

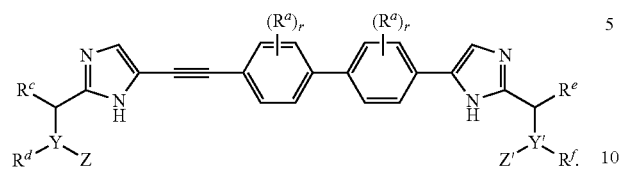

In a third embodiment of the sixth aspect, compounds have formula VIIb:

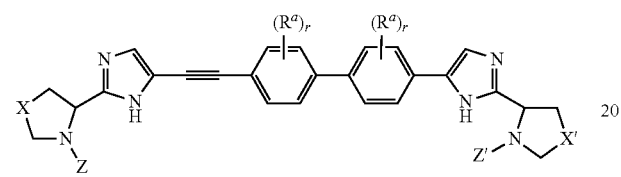

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a seventh aspect of the invention, compounds have formula VIII:

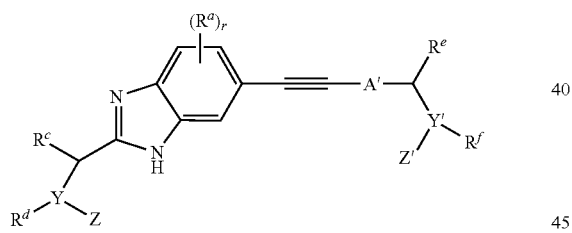

wherein

A' is selected from the group consisting of single bond,

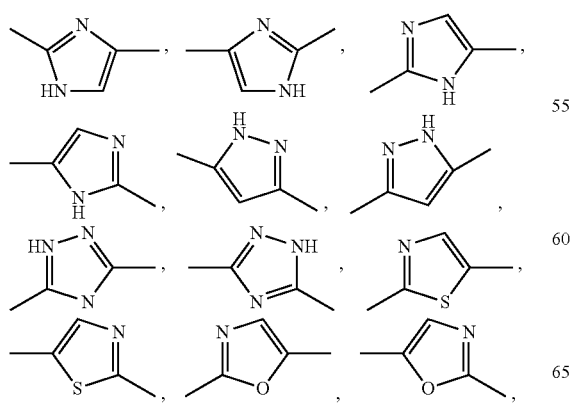

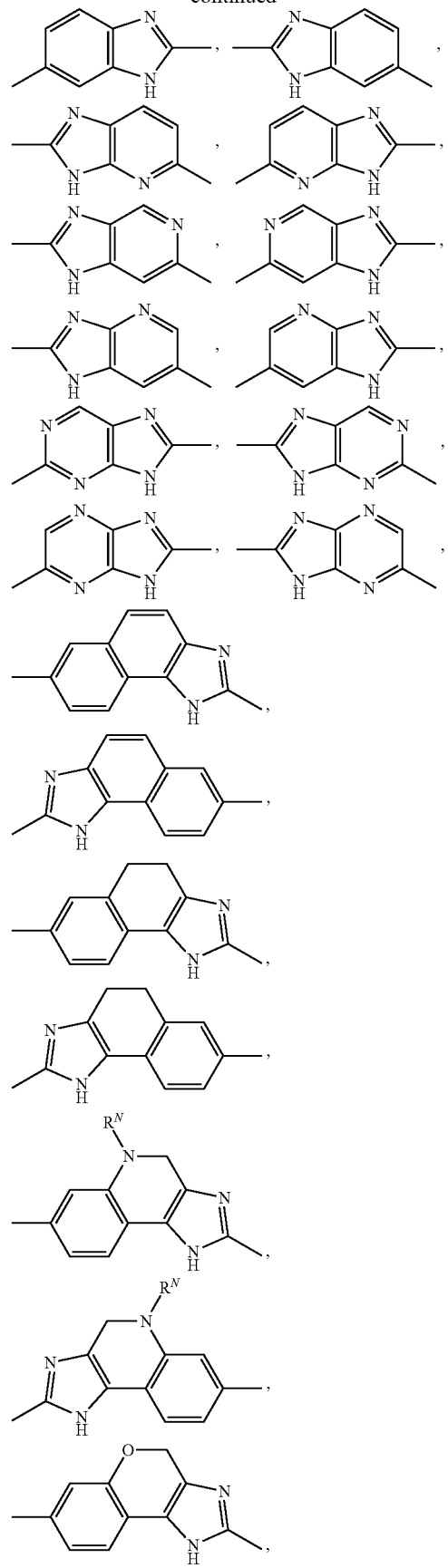

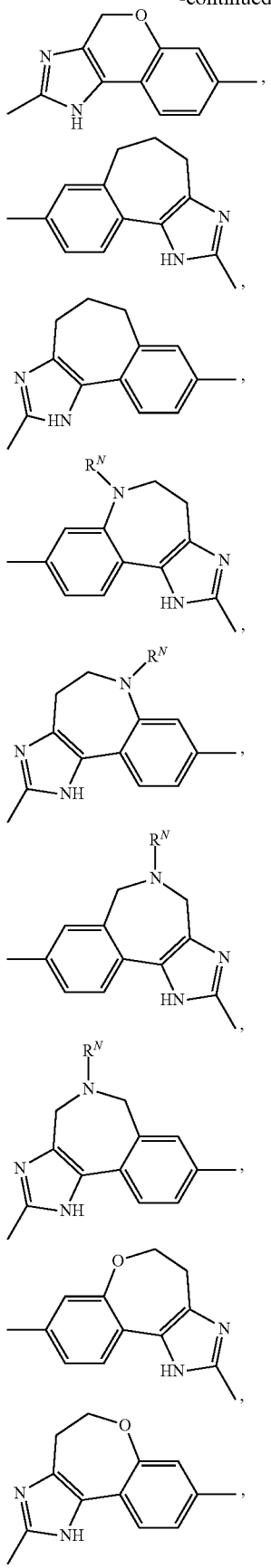

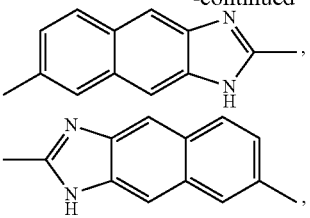

—(CR$_2$)$_n$—O—(CR$_2$)$_p$—, —(CR$_2$)$_n$—C(O)N(R$^N$)—(CR$_2$)$_p$— and —(CR$_2$)$_n$—N(R$^N$)C(O)—(CR$_2$)$_p$—;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is 0, 1, 2, or 3.

In a first embodiment of the seventh aspect, the compounds have formula VIII wherein A' is a single bond,

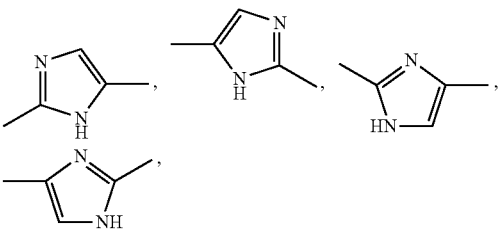

—(CR$_2$)$_n$—C(O)N(R$^N$)—(CR$_2$)$_p$—, or —(CR$_2$)$_n$—N(R$^N$)C(O)—(CR$_2$)$_p$—.

In a second embodiment of the seventh aspect, compounds have formula VIIIa:

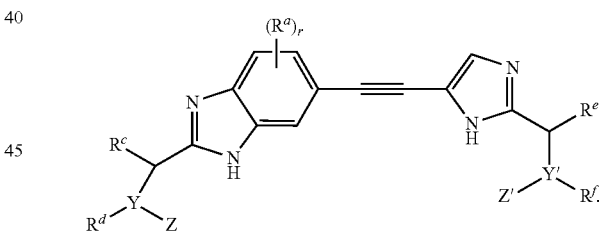

In a third embodiment of the seventh aspect, compounds have formula VIIIb:

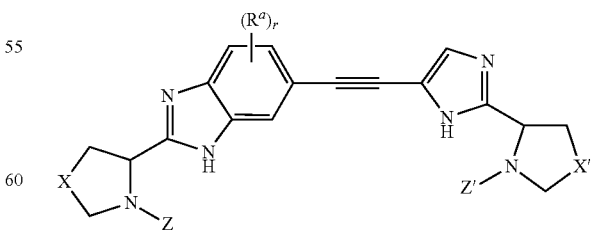

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R¹ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

In an eighth aspect of the invention, compounds have formula IX:

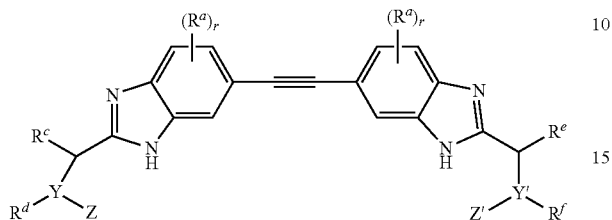

wherein
 each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
 each r is independently 0, 1, 2, or 3.

In a first embodiment of the eighth aspect, compounds have formula IXa:

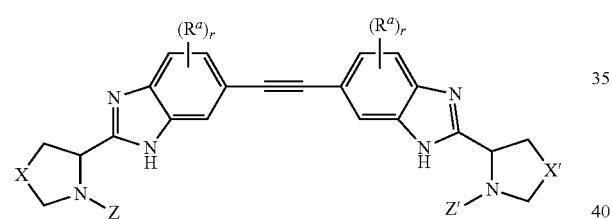

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R¹)—, wherein R¹ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

In an ninth aspect of the invention, compounds have formula X:

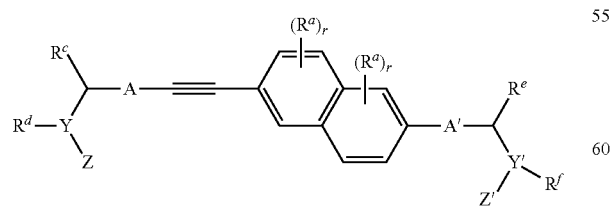

wherein
 A and A' are independently selected from the group consisting of single bond,

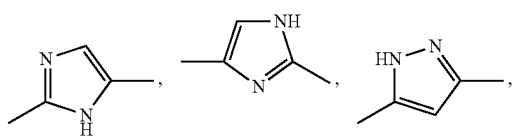

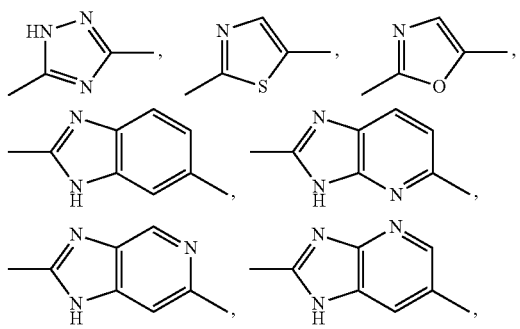

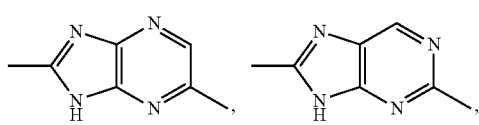

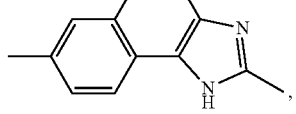

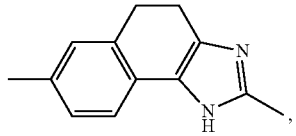

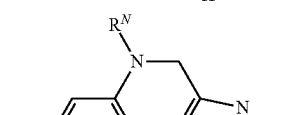

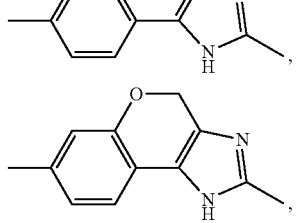

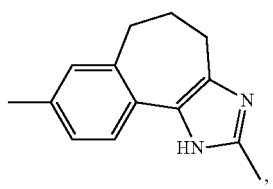

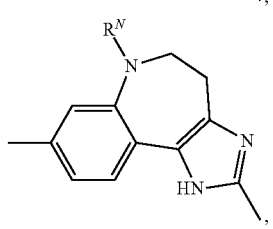

-continued

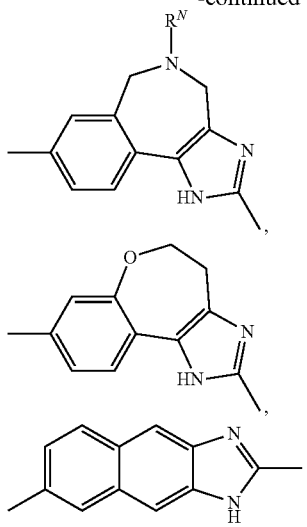

—(CR$_2$)$_n$—O—(CR$_2$)$_p$— and —(CR$_2$)$_n$—C(O)N(R$^N$)—(CR$_2$)$_p$—;

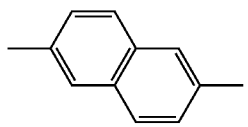

optionally includes 1, 2, 3 or 4 nitrogens as heteroatoms;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
each r is independently 0, 1, 2, or 3.

In a first embodiment of the ninth aspect, A and A' are each independently

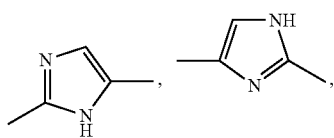

or —(CR$_2$)$_n$—C(O)N(R$^N$)—(CR$_2$)$_p$—.

In a second embodiment of the ninth aspect, compounds have formula Xa:

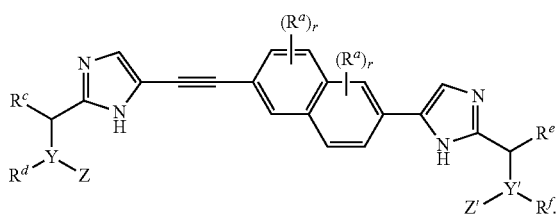

In a third embodiment of the ninth aspect, compounds have formula Xb:

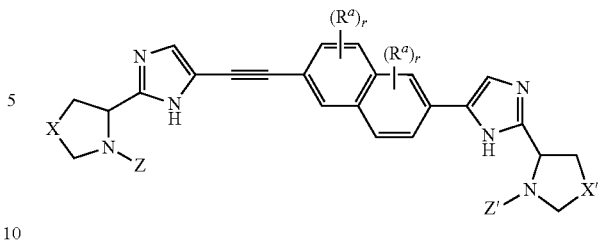

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth embodiment of the ninth aspect, compounds have formula X wherein:
A is selected from the group consisting of

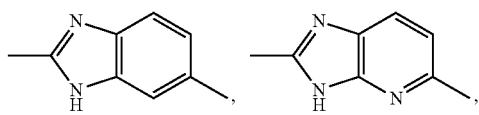

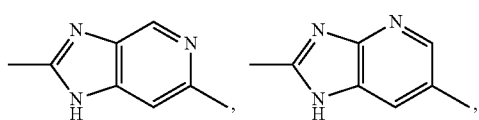

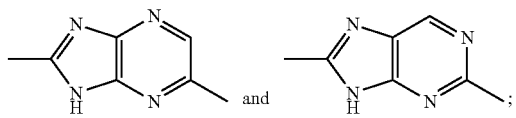

and
A' is

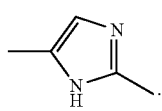

In a fifth embodiment of the ninth aspect, compounds have formula Xc:

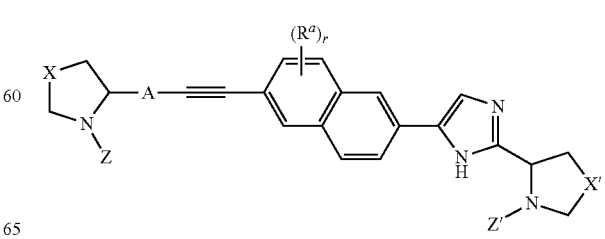

wherein:
A is selected from the group consisting of

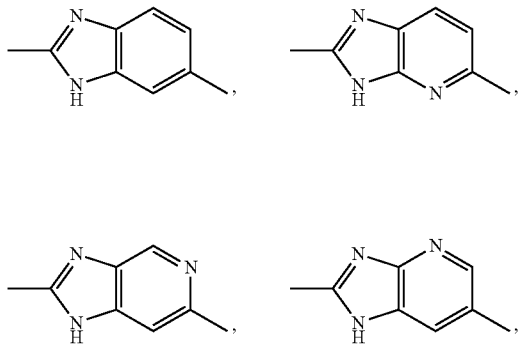

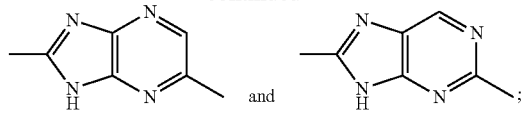

and

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^f$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a sixth embodiment of the ninth aspect, compounds have formula Xd:

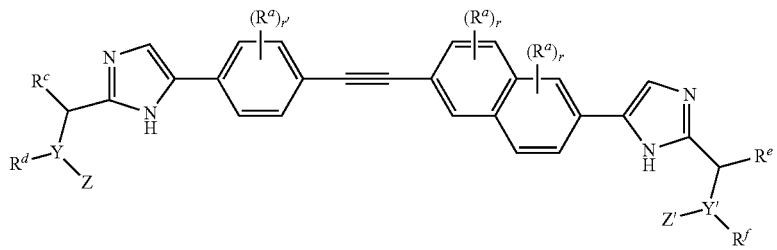

wherein:
r is 0, 1, 2, or 3; and
r' is 0, 1, 2, 3, or 4.

In a seventh embodiment of the ninth aspect, compounds have formula Xe:

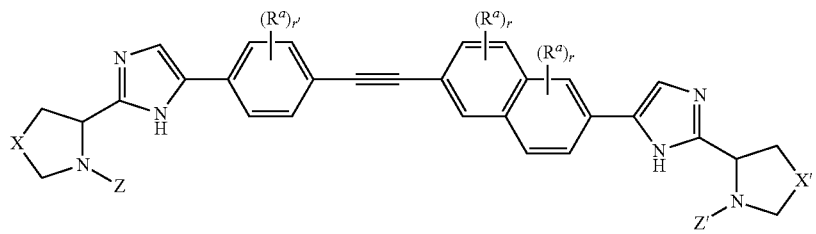

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^f$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a tenth aspect of the invention, compounds have formula XI:

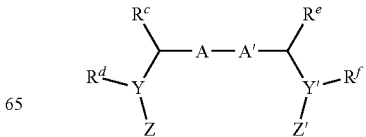

wherein A and A' are independently selected from the group consisting of

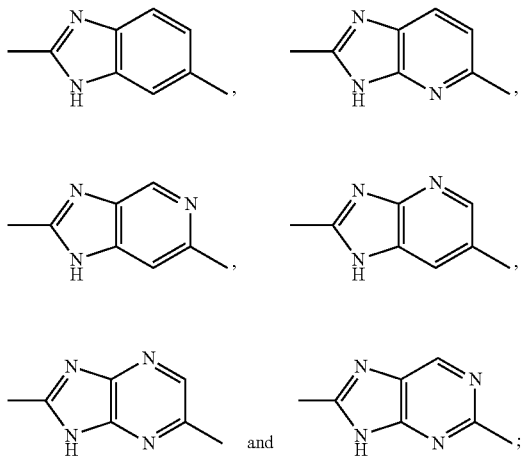 and ;

In a first embodiment of the tenth aspect, compounds have formula XIa:

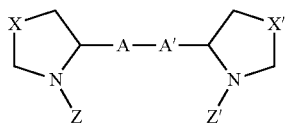

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In an eleventh aspect of the invention, compounds have formula XII:

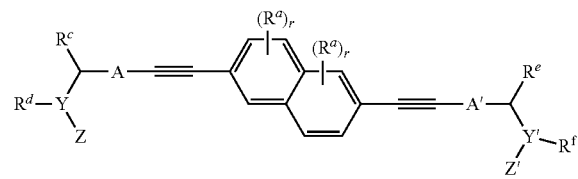

wherein:

A and A' are independently selected from the group consisting of single bond,

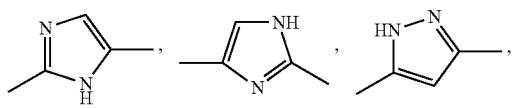

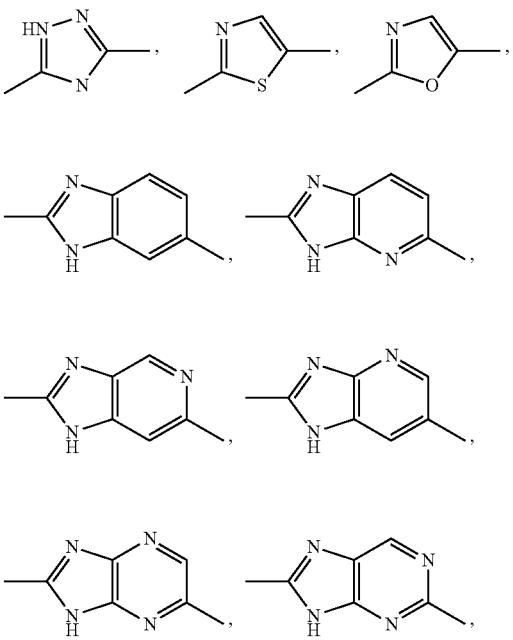

—(CR$_2$)$_n$—O—(CR$_2$)$_p$— and —(CR$_2$)$_n$—C(O)N(R$^N$)—(CR$_2$)$_p$—;

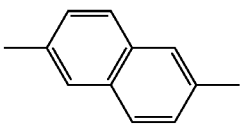

optionally includes 1, 2, 3 or 4 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each r is independently 0, 1, 2, or 3.

In a first embodiment of the eleventh aspect, A and A' are each independently

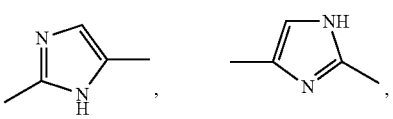

or —(CR$_2$)$_n$—C(O)N(R$^N$)—(CR$_2$)$_p$—.

In a second embodiment of the eleventh aspect, compounds have formula XIIa:

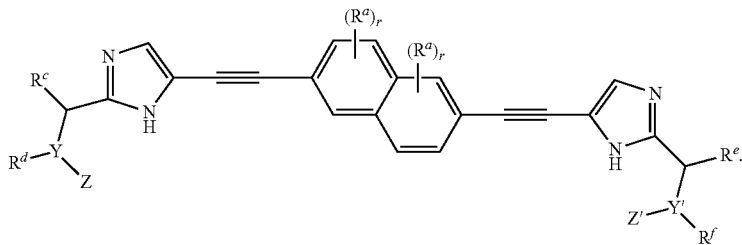

In a third embodiment of the eleventh aspect, compounds have formula XIIb:

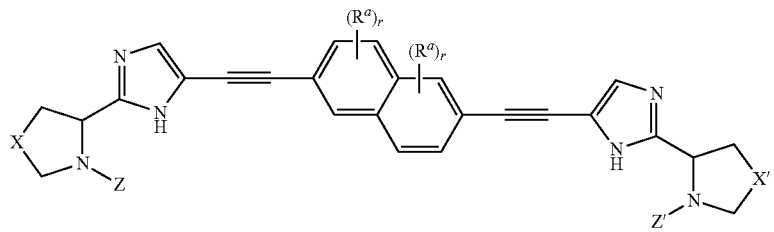

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a twelfth aspect of the invention, compounds have formula XIII:

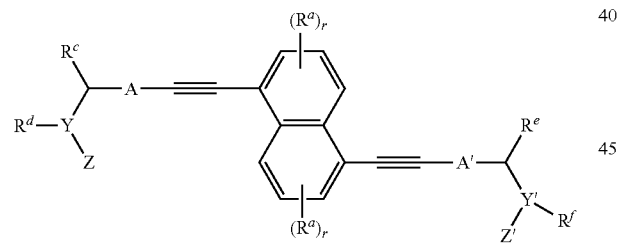

wherein
A and A' are independently selected from the group consisting of single bond,

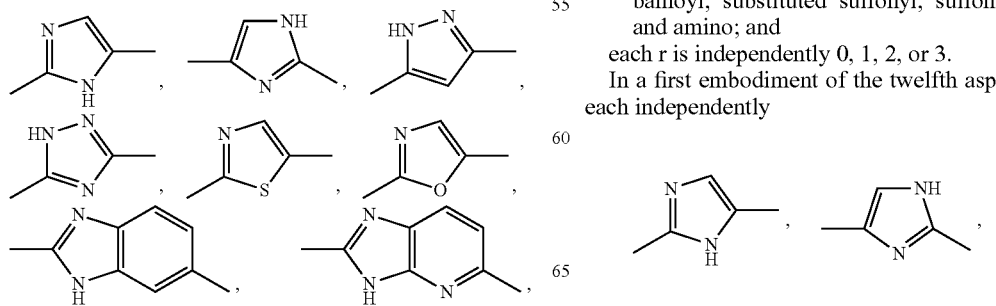

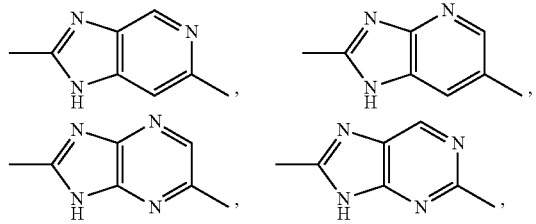

—(CR$_2$)$_n$—O—(CR$_2$)$_p$— and —(CR$_2$)$_n$—C(O)N(R$^N$)—(CR$_2$)$_p$—;

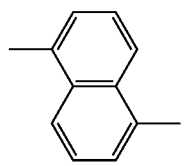

optionally includes 1, 2, 3 or 4 nitrogens as heteroatoms;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
each r is independently 0, 1, 2, or 3.

In a first embodiment of the twelfth aspect, A and A' are each independently or —(CR$_2$)$_n$—C(O)N(R$^N$)—(CR$_2$)$_p$—.

In a second embodiment of the twelfth aspect, compounds have formula XIIIa:

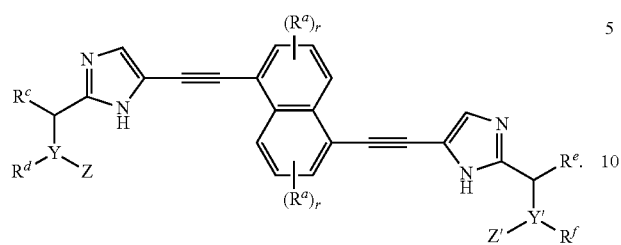

In a third embodiment of the twelfth aspect, compounds have formula XIIIb:

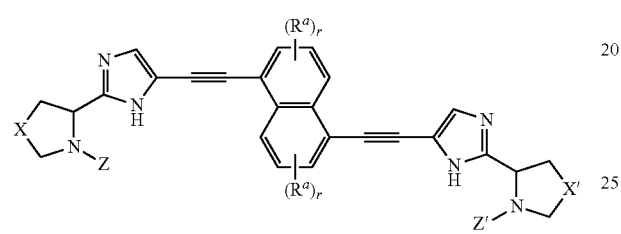

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In an thirteenth aspect of the invention, compounds have formula XIV:

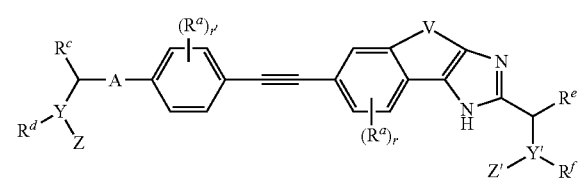

wherein:

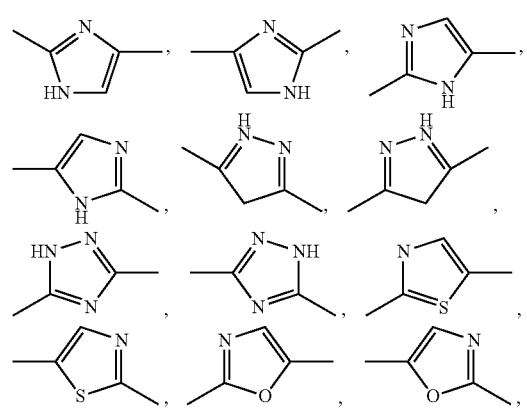

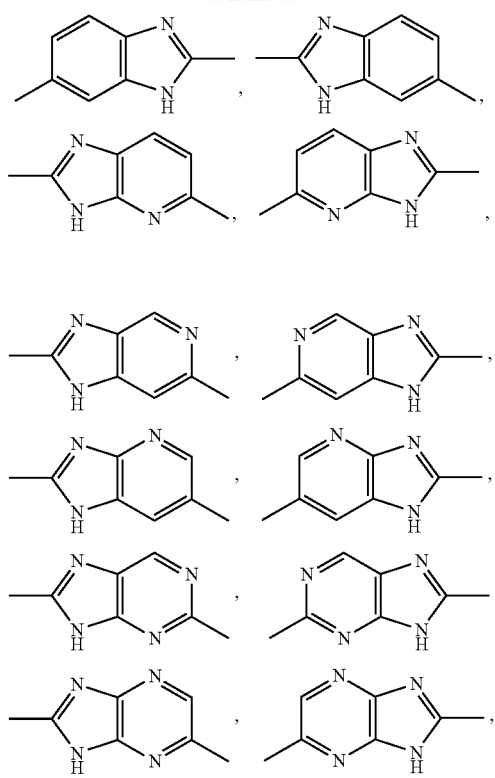

A is selected from the group consisting of a single bond, —(CR$_2$)$_n$—O—(CR$_2$)$_p$—, —(CR$_2$)—C(O)N(R$^N$)—(CR$_2$)$_p$— and —(CR$_2$)$_n$—N(R$^N$)C(O)—(CR$_2$)$_p$—;

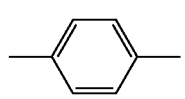

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, or 3; and r' is 0, 1, 2, 3, or 4.

In a first embodiment of the thirteenth aspect, A is a single bond,

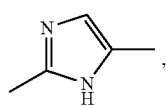

—(CR$_2$)—C(O)N(R$^N$)—(CR$_2$)$_p$—, or —(CR$_2$)$_n$—N(R$^N$)C(O)—(CR$_2$)$_p$—.

In a second embodiment of the thirteenth aspect, compounds have formula XIVa:

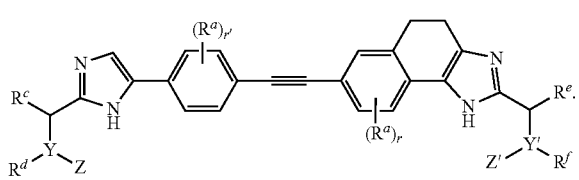

In a third embodiment of the thirteenth aspect, compounds have formula XIVb:

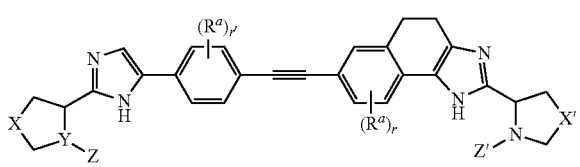

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth embodiment of the thirteenth aspect, compounds have XIVc:

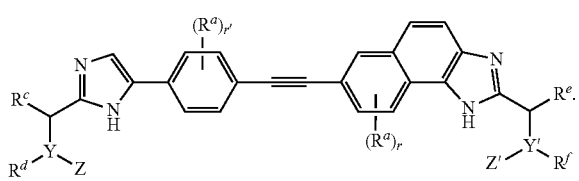

In a fifth embodiment of the thirteenth aspect, compounds have formula XIVd:

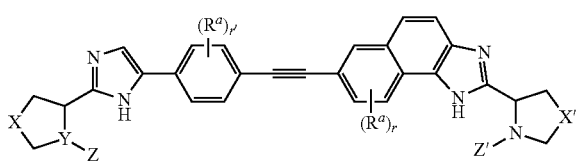

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a sixth embodiment of the thirteenth aspect, compounds have formula XIVe:

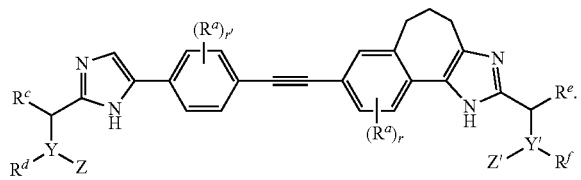

In a seventh embodiment of the thirteenth aspect, compounds have formula XIVf:

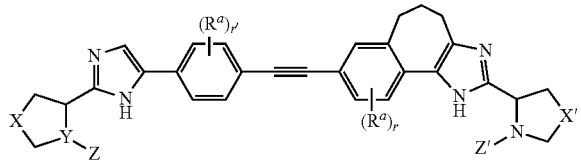

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourteenth aspect of the invention, compounds have formula XV:

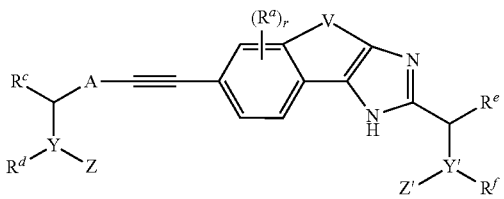

wherein:
A is selected from the group consisting of

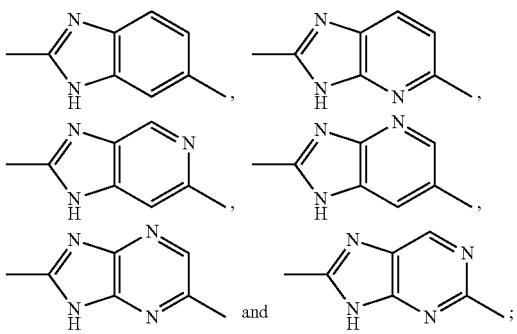

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
r is 0, 1, 2, or 3.

In a first embodiment of the fourteenth aspect, compounds have formula XVa:

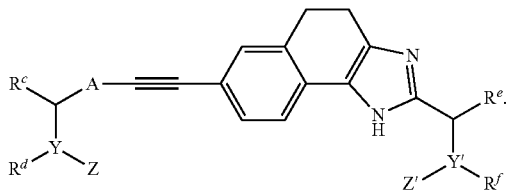

In a second embodiment of the fourteenth aspect, compounds have formula XVb:

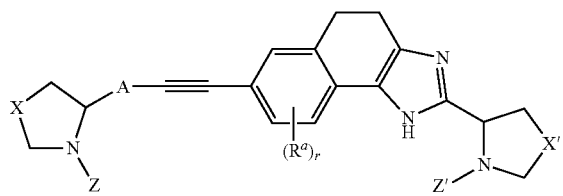

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a third embodiment of the fourteenth aspect, compounds have formula XVc:

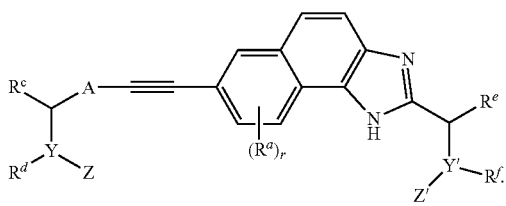

In a fourth embodiment of the fourteenth aspect, compounds have formula XVd:

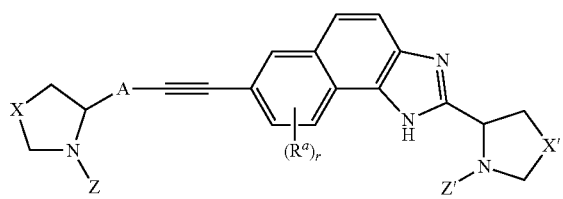

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifth embodiment of the fourteenth aspect, compounds have formula XVe:

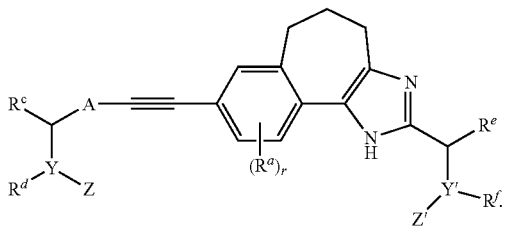

In a sixth embodiment of the fourteenth aspect, compounds have formula XVf:

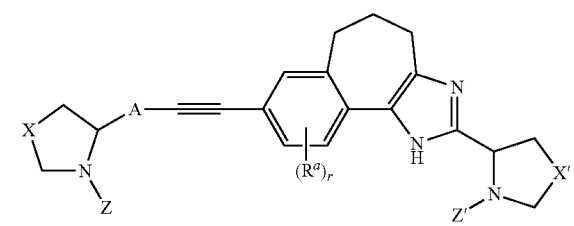

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifteenth aspect of the invention, in any compound of any of the second through fourteenth aspects, R$^c$, R$^d$, R$^e$ and R$^f$ are each independently selected from the group consisting of: hydrogen, C$_1$ to C$_8$ alkyl and C$_1$ to C$_8$ heteroalkyl, wherein,
  each hetero atom, if present, is independently N, O or S,
  R$^c$ and R$^d$ are optionally joined to form a 4- to 8-membered heterocycle which is optionally fused to another 3- to 6-membered heterocycle, and
  R$^e$ and R$^f$ are optionally joined to form a 4- to 8-membered heterocycle which is optionally fused to another 3- to 6-membered heterocycle.

In a first embodiment of the fifteenth aspect one of R$^c$ and R$^d$ or R$^e$ and R$^f$ are joined to form a 4- to 8-membered heterocycle which is optionally fused to another 3- to 6-membered heterocycle.

In a second embodiment of the fifteenth aspect both of R$^c$ and R$^d$ and R$^e$ and R$^f$ are joined to form a 4- to 8-membered heterocycle which is optionally fused to another 3- to 6-membered heterocycle.

In a sixteenth aspect of the invention, each R$^a$, if present in any of the second through fifteenth aspects, is independently —CN, —OCF$_3$, —OCHF$_2$, —CF$_3$, or —F.

In a seventeenth aspect of the invention, if present in any compound of any of the previous aspects, one of Y and Y' is N.

In a first embodiment of the seventeenth aspect, both Y and Y', if present, are N.

In an eighteenth aspect of the invention, Z and Z' in any of the previous aspects are each 1-3 amino acids.

In a first embodiment of the eighteenth aspect, the amino acids are in the D configuration.

In a second embodiment of the eighteenth aspect, Z and Z' are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$.

In a third embodiment of the eighteenth aspect, one or both of Z and Z' are —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a fourth embodiment of the eighteenth aspect, one or both of Z and Z' are —U—(CR$^4_2$)$_t$—NR$^5$—(CR$^4_2$)$_t$—U—(CR$^4_2$)$_t$—NR$^7$—(CR$^4_2$)$_t$—R$^8$.

In a fifth embodiment of the eighteenth aspect, one or both of Z and Z' are —U—(CR$^4_2$)$_t$—NR$^7$—(CR$^4_2$)$_t$—R$^8$.

In a sixth embodiment of the eighteenth aspect, one or both of Z and Z' are —[C(O)—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a seventh embodiment of the eighteenth aspect, one or both of Z and Z' are —C(O)—(CR$^4_2$)$_t$—NR$^5$—(CR$^4_2$)$_t$—U—(CR$^4_2$)$_t$—NR$^7$—(CR$^4_2$)$_t$—R$^8$.

In an eighth embodiment of the eighteenth aspect, one or both of Z and Z' are —[C(O)—(CR$^4_2$)$_t$—NR$^5$—(CR$^4_2$)$_t$]$_u$—C(O)—(CR$^4_2$)$_t$—NR$^7$—(CR$^4_2$)$_t$—R$^8$.

In a ninth embodiment of the eighteenth aspect, one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

In a tenth embodiment of the eighteenth aspect, one or both of Z and Z' are —C(O)—(CR$^4_2$)$_t$—NR$^7$—(CR$^4_2$)$_t$—R$^8$.

In an eleventh embodiment of the eighteenth aspect, one or both of Z and Z' are —C(O)—(CR$^4_2$)$_n$—NR$^7$—(CR$^4_2$)$_n$—C(O)—R$^{81}$.

In a twelfth embodiment of the eighteenth aspect, one or both of Z and Z' are —C(O)—(CR$^4_2$)$_n$—NR$^7$—C(O)—R$^{81}$.

In a thirteenth embodiment of the eighteenth aspect, one or both of Z and Z' are —C(O)—(CR$^4_2$)$_n$—NR$^7$—(CR$^4_2$)$_n$—C(O)—O—R$^{81}$.

In a fourteenth embodiment of the eighteenth aspect, one or both of Z and Z' are —C(O)—(CR$^4_2$)$_n$—NR$^7$—C(O)—O—R$^{81}$.

In a fifteenth embodiment of the eighteenth aspect, one or both of Z and Z' are —U—(CR$^4_2$)$_t$—R$^8$.

In a sixteenth embodiment of the eighteenth aspect, one or both of Z and Z' are —C(O)—(CR$^4_2$)$_t$—R$^8$.

In a seventeenth embodiment of the eighteenth aspect, one or both of Z and Z' are —[U—(CR$^4_2$)$_t$—NR$^5$—(CR$^4_2$)$_t$]$_u$—U—(CR$^4_2$)$_t$—O—(CR$^4_2$)$_t$—R$^8$.

In an eighteenth embodiment of the eighteenth aspect, one or both of Z and Z' are —U—(CR$^4_2$)$_t$—NR$^5$—(CR$^4_2$)$_t$—U—(CR$^4_2$)$_t$—O—(CR$^4_2$)$_t$—R$^8$.

In a nineteenth embodiment of the eighteenth aspect, one or both of Z and Z' are —C(O)—(CR$^4_2$)$_t$—NR$^5$—(CR$^4_2$)$_t$—C(O)—(CR$^4_2$)$_t$—O—(CR$^4_2$)$_t$—R$^8$.

In a twentieth embodiment of the eighteenth aspect, one or both of Z and Z' are —U—(CR$^4_2$)$_t$—O—(CR$^4_2$)$_t$—R$^8$.

In a twenty-first embodiment of the eighteenth aspect, one or both of Z and Z' are —C(O)—(CR$^4_2$)$_t$—O—(CR$^4_2$)$_t$—R$^8$.

In a twenty-second embodiment of the eighteenth aspect, one or both of Z and Z' are —C(O)—(CR$^4_2$)$_n$—NR$^7$—R$^8$ wherein R$^7$ and R$^8$ together form a 4-7 membered ring.

In a nineteenth aspect of the invention, compounds have formula XVI:

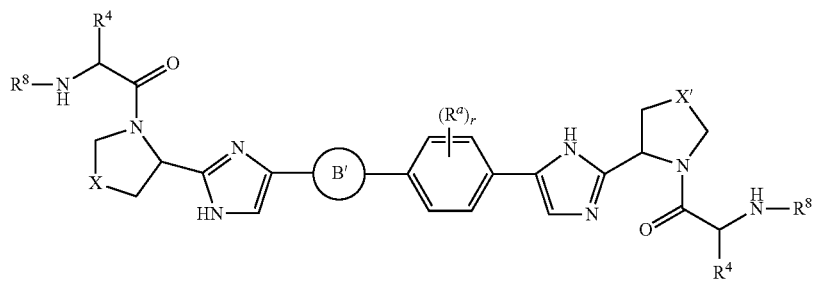

wherein:
B' is selected from the group consisting of:

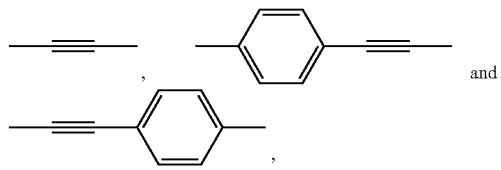

wherein B' is optionally substituted with between 1 and 4 R$^a$;

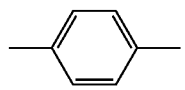

optionally includes 1, 2, 3, or 4 nitrogens as heteroatoms;
  each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  r is 0, 1, 2, 3 or 4;
  X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;
  each R$^8$ is independently chosen from the group consisting of hydrogen, C$_1$ to C$_8$ alkyl, C$_1$ to C$_8$ heteroalkyl, cycloalkyl, heterocycle, aryl, heteroaryl aralkyl, —C(O)—R$^{81}$, —C(S)—R$^{81}$, —C(O)—O—R$^{81}$, —C(O)—N—R$^{81}_2$, —S(O)$_2$—R" and —S(O)$_2$—N—

$R^{81}{}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl; and each $R^4$ is independently selected from the group consisting of hydrogen, $C_1$ to $C_8$ alkyl, $C_1$ to $C_8$ heteroalkyl, cycloalkyl, heterocycle, aryl, heteroaryl and aralkyl.

In a first embodiment of the nineteenth aspect, each $R^a$, if present, is selected from the group consisting of —CN, —OCF$_3$, —OCHF$_2$, —CF$_3$ and —F.

In a twentieth aspect of the invention, compounds have formula XVII:

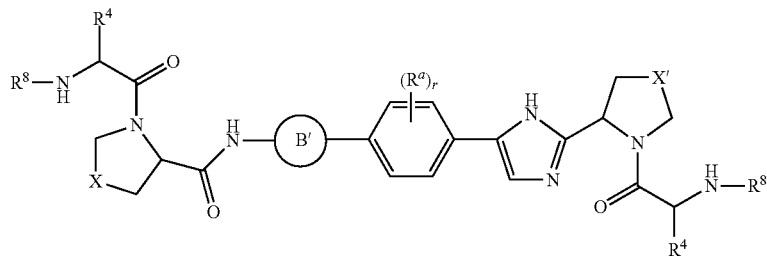

wherein:

B' is

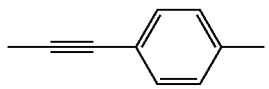

is optionally substituted with between 1 and 4 $R^a$;

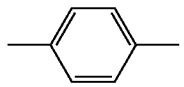

optionally includes 1, 2, 3, or 4 nitrogens as heteroatoms;

each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl;

each $R^8$ is independently chosen from the group consisting of hydrogen, $C_1$ to $C_8$ alkyl, $C_1$ to $C_8$ heteroalkyl, cycloalkyl, heterocycle, aryl, heteroaryl aralkyl, —C(O)—R$^{81}$, —C(S)—R$^{81}$, —C(O)—O—R$^{81}$, —C(O)—N—R$^{81}{}_2$, —S(O)$_2$—R$^{81}$ and —S(O)$_2$—N—R$^{81}{}_2$, wherein each R$^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl; and each $R^4$ is independently selected from the group consisting of hydrogen, $C_1$ to $C_8$ alkyl, $C_1$ to $C_8$ heteroalkyl, cycloalkyl, heterocycle, aryl, heteroaryl and aralkyl.

In a first embodiment of the twentieth aspect, each $R^a$, if present, is selected from the group consisting of —CN, —OCF$_3$, —OCHF$_2$, —CF$_3$ and —F.

In a twenty-first aspect of the invention, compounds have formula XVIII:

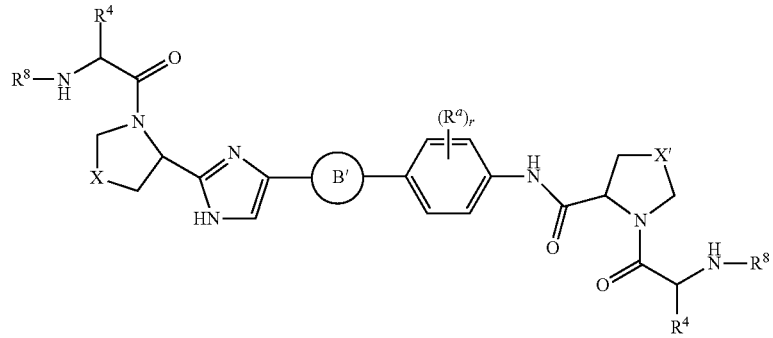

wherein:

B' is selected from the group consisting of:

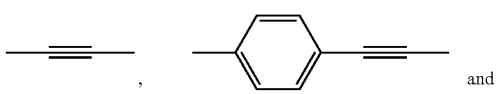

and

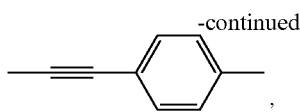

wherein B' is optionally substituted with between 1 and 4 $R^a$;

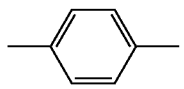

optionally includes 1, 2, 3, or 4 nitrogens as heteroatoms;
each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
r is 0, 1, 2, 3 or 4;
X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl;
each $R^8$ is independently chosen from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}$$_2$, —S(O)$_2$—R$^{81}$ and —S(O)$_2$—N—R$^{81}$$_2$, wherein each R$^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl; and each $R^4$ is independently selected from the group consisting of hydrogen, $C_1$ to $C_8$ alkyl, $C_1$ to $C_8$ heteroalkyl, cycloalkyl, heterocycle, aryl, heteroaryl and aralkyl.

In a first embodiment of the twenty-first aspect, each $R^a$, if present, is selected from the group consisting of —CN, —OCF$_3$, —OCHF$_2$, —CF$_3$ and —F.

A twenty-second aspect of the invention provides a pharmaceutical composition comprising the compounds of the invention.

A twenty-third aspect of the invention provides use of the compounds of the invention in the manufacture of a medicament.

In a first embodiment of the twenty-third aspect the medicament is for the treatment of hepatitis C.

A twenty-fourth aspect of the invention provides a method of treating hepatitis C comprising administering to a subject in need thereof, a therapeutically effective amount of a compound of the invention.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry 5$^{th}$ Ed." Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

The term "alkanoyl" as used herein contemplates a carbonyl group with a lower alkyl group as a substituent.

The term "alkenyl" as used herein contemplates substituted or unsubstituted, straight and branched chain alkene radicals, including both the E- and Z-forms, containing from two to eight carbon atoms. The alkenyl group may be optionally substituted with one or more substituents selected from the group consisting of halogen, —CN, —NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, S(O)R, SO$_2$R, —SO$_3$R, —S(O)$_2$N(R$^N$)$_2$, phosphate, phosphonate, cycloalkyl, cycloalkenyl, aryl and heteroaryl.

The term "alkoxy" as used herein contemplates an oxygen with a lower alkyl group as a substituent and includes methoxy, ethoxy, butoxy, trifluoromethoxy and the like. It also includes divalent substituents linked to two separated oxygen atoms such as, without limitation, —O—(CH$_2$)$_{1-4}$—O—, —O—CF$_2$—O—, —O—(CH$_2$)$_{1-4}$—O—(CH$_2$CH$_2$—O)$_{1-4}$— and —(O—CH$_2$CH$_2$—O)$_{1-4}$—.

The term "alkoxycarbonyl" as used herein contemplates a carbonyl group with an alkoxy group as a substituent.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "alkylene," "alkenylene" and "alkynylene" as used herein refers to the groups "alkyl," "alkenyl" and "alkynyl" respectively, when they are divalent, ie, attached to two atoms.

The term "alkylsulfonyl" as used herein contemplates a sulfonyl group which has a lower alkyl group as a substituent.

The term "alkynyl" as used herein contemplates substituted or unsubstituted, straight and branched carbon chain containing from two to eight carbon atoms and having at least one carbon-carbon triple bond. The term alkynyl includes, for example ethynyl, 1-propynyl, 2-propynyl, 1-butynyl, 3-methyl-1-butynyl and the like. The alkynyl group may be optionally substituted with one or more substituents selected from halo, —CN, NO$_2$, CO$_2$R, C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "amino" as used herein contemplates a group of the structure —NR$^N$$_2$.

The term "amino acid" as used herein contemplates a group of the structure

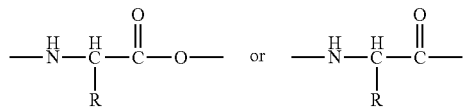

in either the D or the L configuration and includes but is not limited to the twenty "standard" amino acids: isoleucine, leucine, lysine, methionine, phenylalanine, threonine, tryptophan, valine, alanine, asparagine, aspartate, cysteine, glutamate, glutamine, glycine, proline, serine, tyrosine, arginine and histidine. The present invention also includes, without limitation, D-configuration amino acids, beta-amino acids, amino acids having side chains as well as all non-natural amino acids known to one skilled in the art.

The term "aralkyl" as used herein contemplates a lower alkyl group which has as a substituent an aromatic group, which aromatic group may be substituted or unsubstituted. The aralkyl group may be optionally substituted with one or more substituents selected from halogen, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "arylsulfonyl" as used herein contemplates a sulfonyl group which has as a substituent an aryl group. The term is meant to include, without limitation, monovalent as well as multiply valent aryls (eg, divalent aryls).

The term "carbamoyl" as used herein contemplates a group of the structure

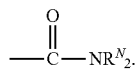

The term "carbonyl" as used herein contemplates a group of the structure

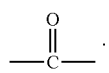

The term "carboxyl" as used herein contemplates a group of the structure

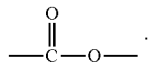

The term "cycloalkyl" as used herein contemplates substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "cycloalkenyl" as used herein contemplates substituted or unsubstituted cyclic alkenyl radicals containing from four to twelve carbon atoms in which there is at least one double bond between two of the ring carbons and includes cyclopentenyl, cyclohexenyl and the like. The term "cycloalkenyl" also includes polycyclic systems having two rings in which two or more atoms are common to two adjoining rings (the rings are "fused"). The cycloalkenyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "halo" or "halogen" as used herein includes fluorine, chlorine, bromine and iodine.

The term "heteroalkyl" as used herein contemplates an alkyl with one or more heteroatoms.

The term "heteroatom", particularly within a ring system, refers to N, O and S.

The term "heterocyclic group," "heterocycle" or "heterocyclic ring" as used herein contemplates substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidino and the like and cyclic ethers, such as tetrahydropyran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "oxo" as used herein contemplates an oxygen atom attached with a double bond.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

"Pharmaceutically acceptable salt" refers to a salt of a compound of the invention which is made with counterions understood in the art to be generally acceptable for pharmaceutical uses and which possesses the desired pharmacological activity of the parent compound. Such salts include: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galactunoric acids and the like (see, e.g., Berge et al., 1977, *J. Pharm. Sci.* 66:1-19).

The terms "phosphate" and "phosphonate" as used herein refer to the moieties having the following structures, respectively:

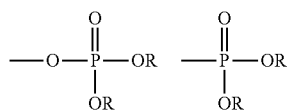

The terms "salts" and "hydrates" refers to the hydrated forms of the compound that would favorably affect the physical or pharmacokinetic properties of the compound, such as solubility, palatability, absorption, distribution, metabolism and excretion. Other factors, more practical in nature, which those skilled in the art may take into account in the selection include the cost of the raw materials, ease of crystallization, yield, stability, solubility, hygroscopicity, flowability and manufacturability of the resulting bulk drug.

The term sulfonamide as used herein contemplates a group having the structure

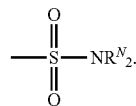

The term "sulfonate" as used herein contemplates a group having the structure

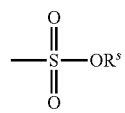

wherein R$^s$ is selected from the group consisting of hydrogen, C$_1$-C$_{10}$ alkyl, C$_2$-C$_{10}$ alkenyl, C$_2$-C$_{10}$ alkynyl, C$_1$-C$_{10}$ alkanoyl, or C$_1$-C$_{10}$ alkoxycarbonyl.

The term "sulfonyl" as used herein contemplates a group having the structure

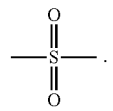

"Substituted sulfonyl" as used herein contemplates a group having the structure

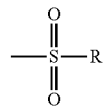

including, but not limited to alkylsulfonyl and arylsulfonyl.

The term "thiocarbonyl," as used herein, means a carbonyl wherein an oxygen atom has been replaced with a sulfur.

Each R is independently selected from hydrogen, —OH, —CN, —NO$_2$, halogen, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino and oxo.

Each R$^N$ is independently selected from the group consisting of hydrogen, —OH, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide. Two R$^N$ may be taken together with C, O, N or S to which they are attached to form a five to seven membered ring which may optionally contain a further heteroatom.

The compounds of the present invention may be used to inhibit or reduce the activity of HCV, particularly HCV's NS5A protein. In these contexts, inhibition and reduction of activity of the NS5A protein refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100%, or any number in between, may be preferred for particular applications.

In a first aspect, compounds of formula I are provided:

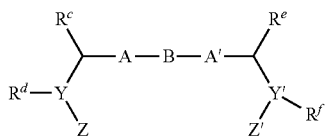

wherein:
A and A' are independently selected from the group consisting of a single bond, —(CR$_2$)$_n$—C(O)—(CR$_2$)$_p$—, —(CR$_2$)$_n$—O—(CR$_2$)$_p$—, —(CR$_2$)$_n$—N(R$^N$)—(CR$_2$)$_p$—, —(CR$_2$)$_n$—S(O)$_k$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$—, —(CR$_2$)$_n$—C(O)—O—(CR$_2$)$_p$—, —(CR$_2$)$_n$—N(R$^N$)—S(O)$_k$—N(R$^N$)—(CR$_2$)$_p$— and —(CR$_2$)$_n$—N(R$^N$)—C(O)—O—(CR$_2$)$_p$—and a heteroaryl group selected from the group consisting of

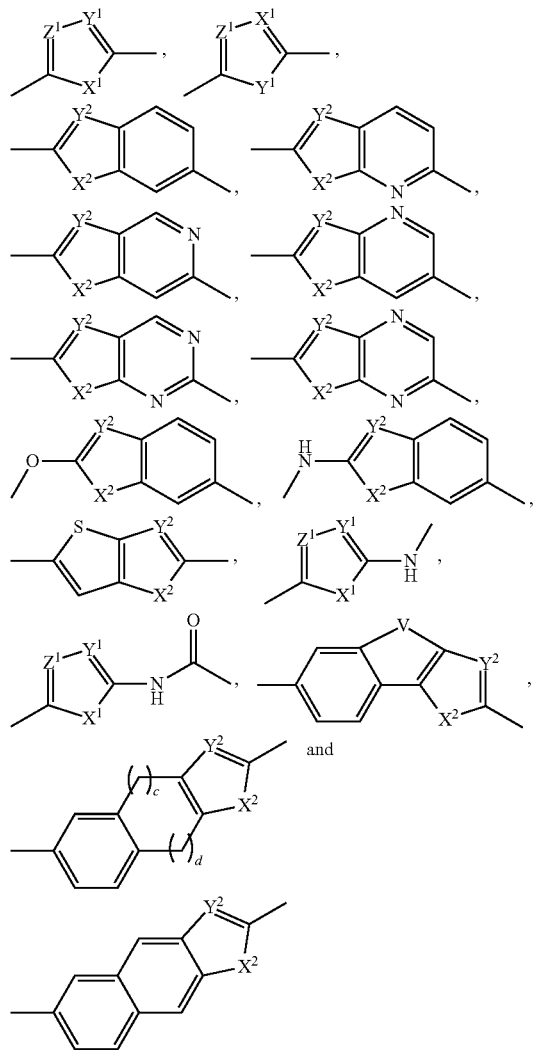

wherein:
X$^1$ is CH$_2$, NH, O or S,
Y$^1$, Y$^2$ and Z$^1$ are each independently CH or N,
X$^2$ is NH, O or S,
V is —CH$_2$—CH$_2$—, —CH=CH—, —N=CH—, (CH$_2$)—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0,

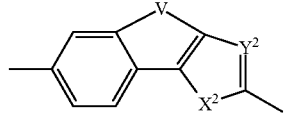

optionally includes 1 or 2 nitrogens as heteroatoms on the phenyl residue,
the carbons of the heteroaryl group are each independently optionally substituted with a substituent selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
the nitrogens, if present, of the heteroaryl group are each independently optionally substituted with a substituent selected from the group consisting of —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide,
a and b are independently 1, 2, or 3.
c and d are independently 1 or 2,
n and p are independently 0, 1, 2 or 3,
k is 0, 1, or 2,
each R is independently selected from the group consisting of hydrogen, —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino,
each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide and
wherein for each A and A', B may be attached to either side of A and A' so that in the example of A or A' being

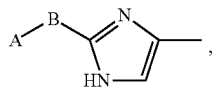

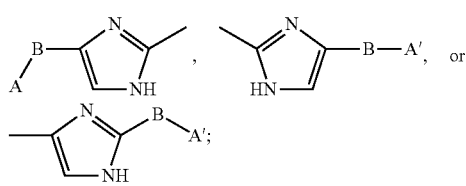

the A-B-A' can be any of:

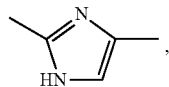

B is selected from the group consisting of a single bond, triple bond,

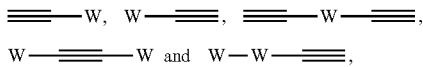

wherein each W is independently selected from the group consisting of a cycloalkenyl group, aryl group and heteroaryl group, with the proviso that a triple bond does not attach to W at a heteroatom;

$R^c$, $R^d$, $R^e$ and $R^f$ are each independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S,
each of $R^c$, $R^d$, $R^e$ and $R^f$ may optionally be substituted by $C_1$ to $C_8$ alkyl, $C_1$ to $C_8$ heteroalkyl, aralkyl and a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 6-membered heterocycle or heteroaryl ring, and
$R^e$ and $R^f$ are optionally joined to form a 4- to 8-membered heterocycle which is optionally fused to another 3- to 6-membered heterocycle or heteroaryl ring;

Y and Y' are each independently carbon or nitrogen; and
Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, $—[U—(CR^4_2)_t—NR^5—(CR^4_2)_t]_u—U—(CR^4_2)_t—NR^7—(CR^4_2)_t—R^8$, $—U—(CR^4_2)_t—R^8$ and $—[U—(CR^4_2)_t—NR^5—(CR^4_2)_t]_u—U—(CR^4_2)_t—O—(CR^4_2)_t—R^8$, wherein, U is selected from the group consisting of —C(O)—, —C(S)— and —S(O)$_2$—,
each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl,
$R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —S(O)$_2$—$R^{81}$ and —S(O)$_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl,
optionally, $R^7$ and $R^8$ together form a 4-7 membered ring,
each t is independently 0, 1, 2, 3, or 4, and
u is 0, 1, or 2.

The compounds of the present invention include pharmaceutically acceptable salts of I as well as an optically pure enantiomer, racemate or diastereomeric mixtures thereof.

In a first embodiment of the first aspect, each W is independently optionally substituted with one or more substituents each independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino and if W is not aromatic, it is optionally substituted with oxo.

In second embodiment each W is independently optionally substituted with one of the group consisting of —CN, —OCF$_3$, —OCHF$_2$, —CF$_3$ and —F.

In a third embodiment B is selected from the group consisting of a triple bond,

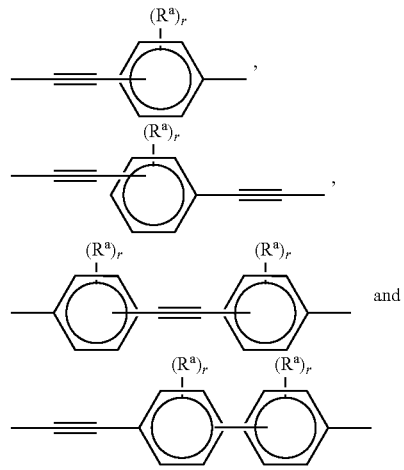

wherein:

is a divalent aryl or heteroaryl group which may be polycyclic with varying connective patterns;

each r is independently 0, 1, 2, 3 or 4; and
each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino.

In a fourth embodiment,

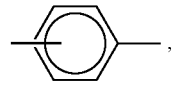

when present, is selected from the group consisting of:

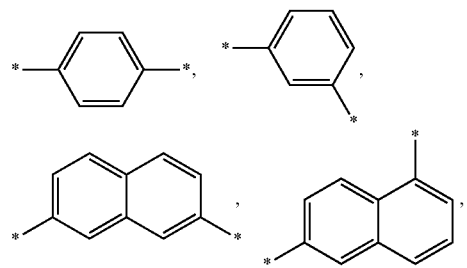

-continued

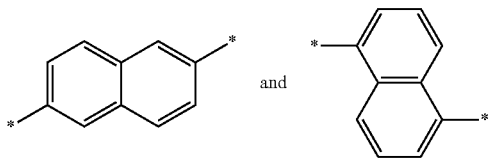
and

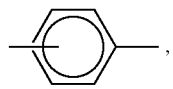, when present, is selected from the group consisting of:

wherein * indicates attachment points to the remainder of the compound and each phenyl residue independently optionally includes 1 or 2 nitrogens as heteroatoms.

In a fifth embodiment,

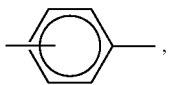, when present, is selected from the group consisting of:

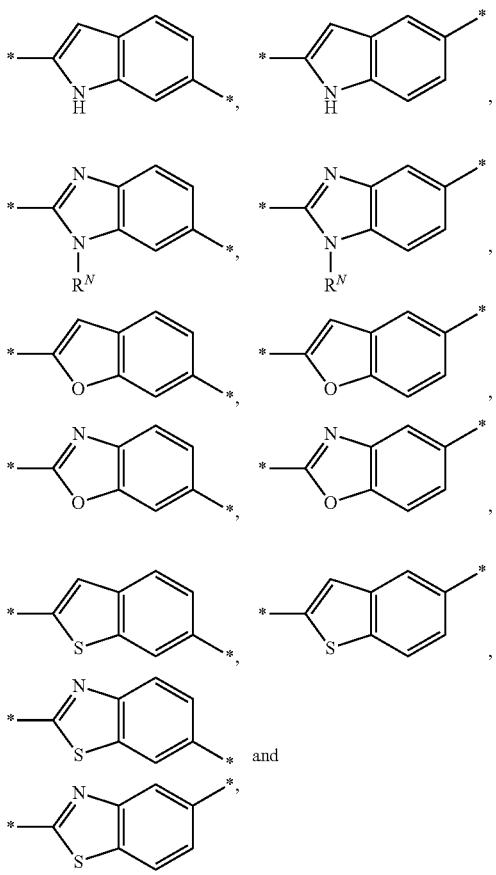

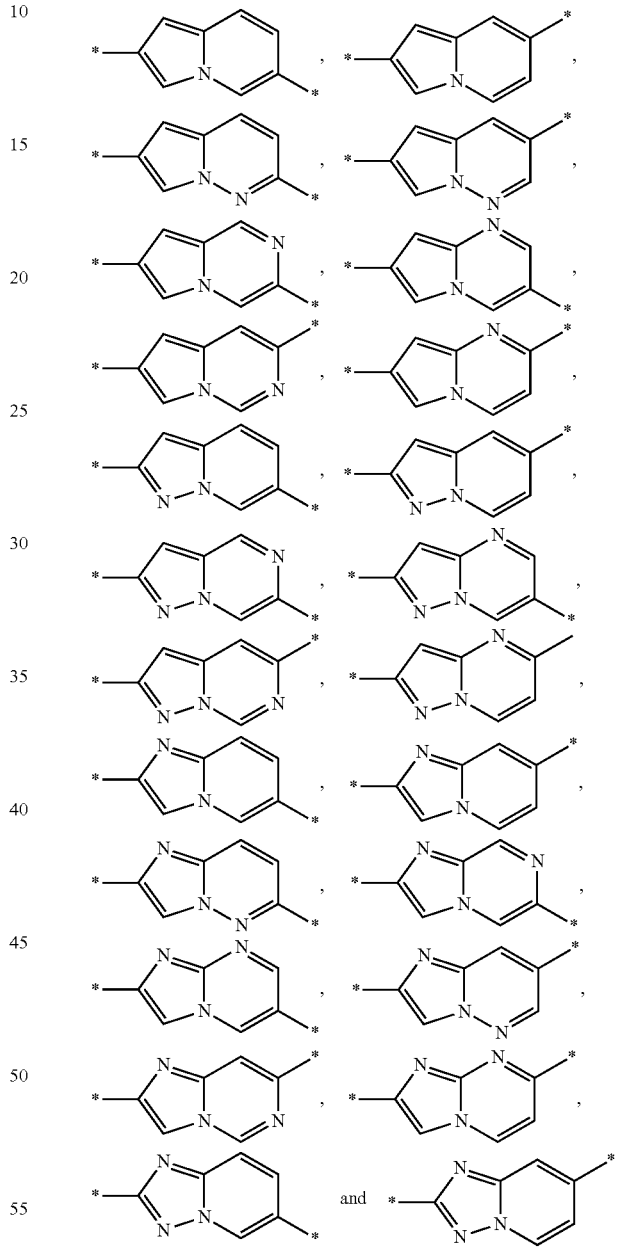

wherein * indicates attachment points to the remainder of the compound, the phenyl residue optionally includes 1 or 2 nitrogens as heteroatoms, and $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment, wherein * indicates attachment points to the remainder of the compound and the phenyl residue optionally includes 1 or 2 additional nitrogens as heteroatoms with the proviso that there are no more than 2 total nitrogens on the phenyl residue.

In a seventh embodiment, each $R^a$, when present, is independently selected from the group consisting of —CN, —OCF$_3$, —OCHF$_2$, —CF$_3$ and —F.

In an eighth embodiment, compounds are of formula II:

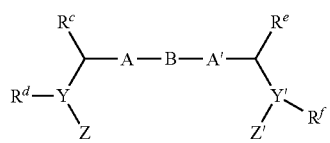

wherein:
A and A' are independently selected from the group consisting of a single bond, —(CR$_2$)$_n$—O—(CR$_2$)$_p$—, —(CR$_2$)$_n$—N(R$^N$)—(CR$_2$)$_p$—, —(CR$_2$)$_n$—C(O)—N(R$^N$)—(CR$_2$)$_p$—, —(CR$_2$)$_n$—N(R$^N$)—C(O)—N(R$^N$)—(CR$_2$)$_p$— and —(CR$_2$)$_n$—N(R$^N$)—C(O)—O—(CR$_2$)$_p$— and a heteroaryl group selected from the group consisting of

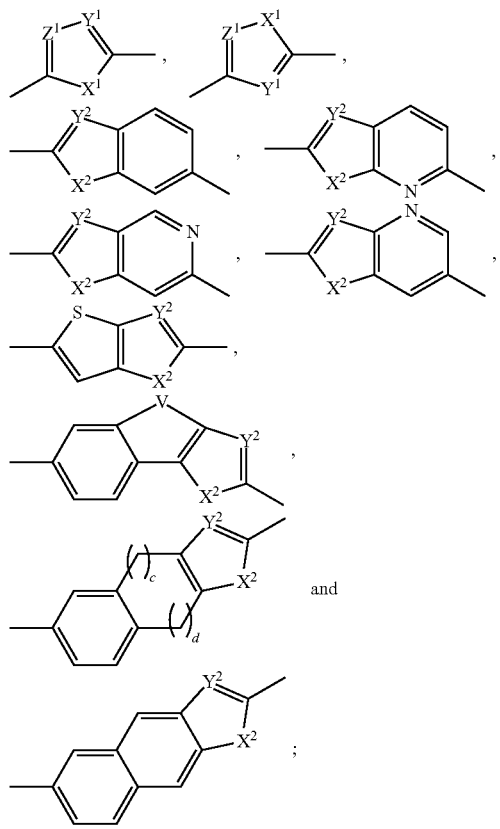

and
B, Y, Y', Z, Z', R$^c$, R$^d$, R$^e$ and R$^f$ are as defined for formula I.

The compounds of the present invention include pharmaceutically acceptable salts of II as well as an optically pure enantiomer, racemate or diastereomeric mixtures thereof.

In a ninth embodiment, compounds have formula II and A and A' are independently selected from the group consisting of a single bond,

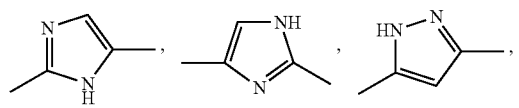

-continued

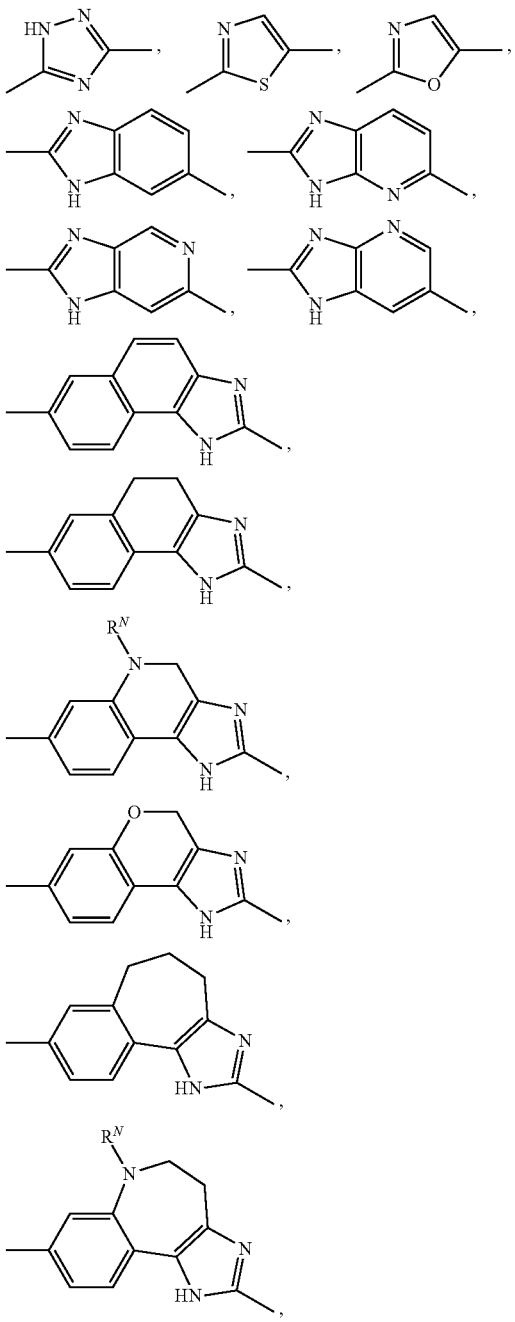

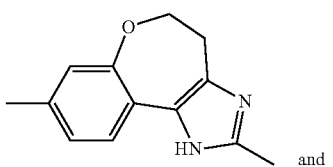

and

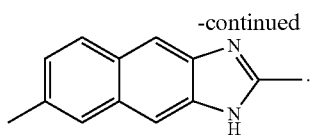

In a tenth embodiment, compounds have formula II and $R^c$, $R^d$, $R^e$ and $R^f$ are each independently selected from the group consisting of: hydrogen, $C_1$ to $C_8$ alkyl and $C_1$ to $C_8$ heteroalkyl, wherein, each hetero atom, if present, is independently N, O or S, $R^c$ and $R^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In an eleventh embodiment, compounds have formula II and one or both of $R^e$ and $R^d$ or $R^e$ and $R^f$ are optionally joined to form a 4- to 8-membered heterocycle which is optionally fused to another 3- to 6-membered heterocycle.

In a twelfth embodiment $R^c$ and $R^d$ are joined and form a heterocyclic fused ring system selected from the group consisting of:

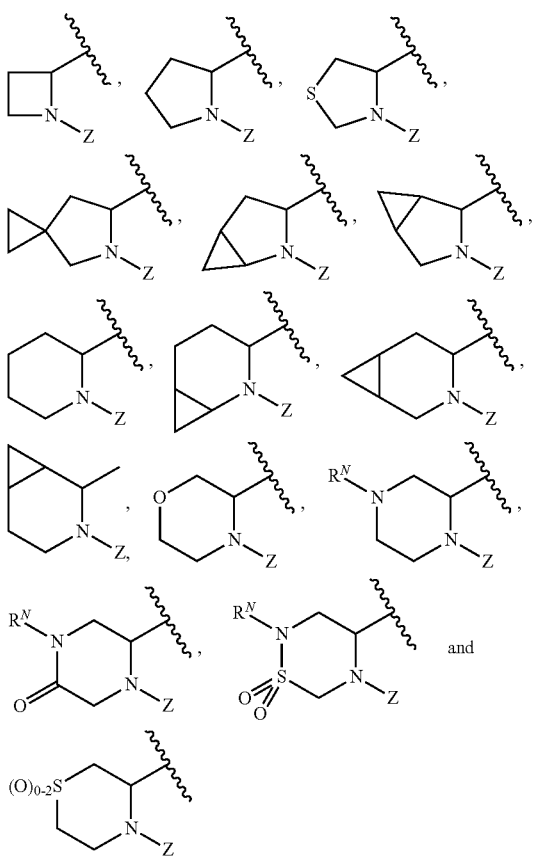

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a thirteenth embodiment, compounds have formula II and $R^e$ and $R^f$ are joined and form a heterocyclic fused ring system selected from the group consisting of:

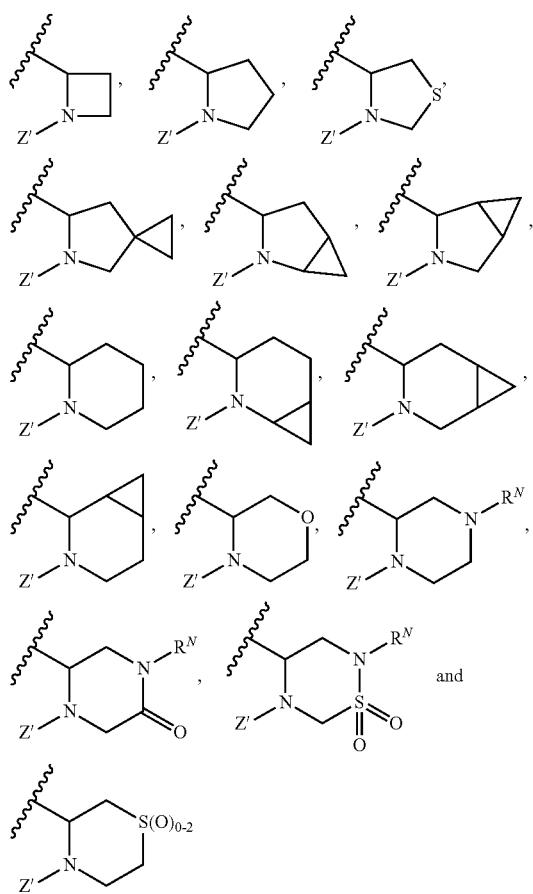

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds of formula III are provided:

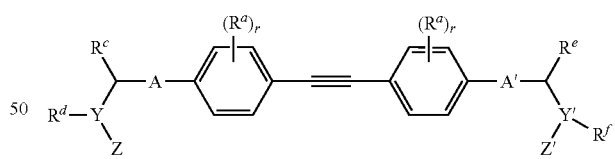

wherein

A and A' are independently selected from the group consisting of single bond,

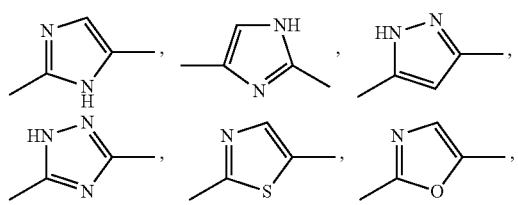

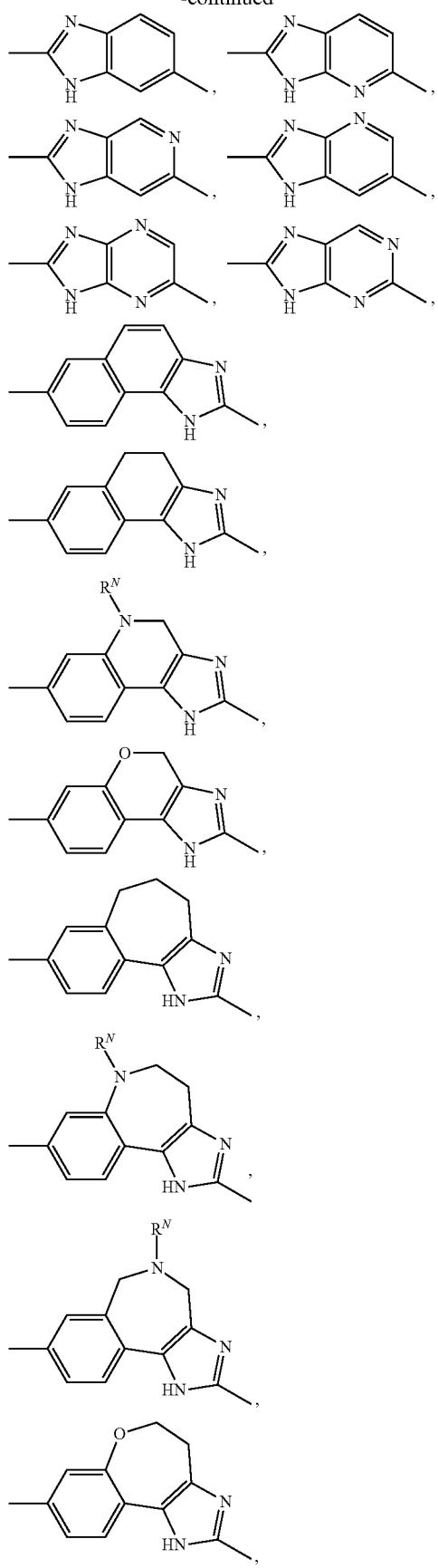

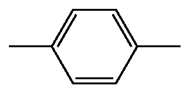

—(CR$_2$)$_n$—O—(CR$_2$)$_p$— and —(CR$_2$)$_n$—C(O)—N(R$^N$)—(CR$_2$)$_p$—;

each

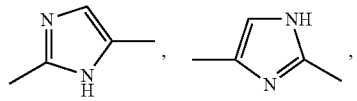

optionally independently includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each r is independently 0, 1, 2, 3 or 4.

The compounds of the present invention include pharmaceutically acceptable salts of III as well as an optically pure enantiomer, racemate or diastereomeric mixtures thereof.

In a first embodiment of the second aspect, A and A' are each independently

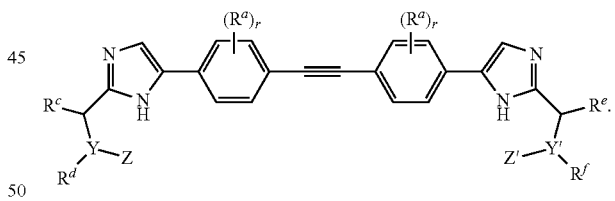

or —(CR$_2$)$_n$—C(O)N(R$^N$)—(CR$_2$)$_p$—.

In a second embodiment of the second aspect, the compound is of formula IIIa

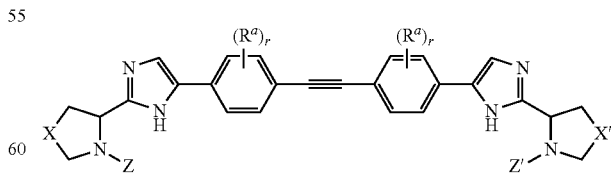

In a third embodiment of the second aspect, the compound is of formula IIIb:

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.
In a third aspect of the invention compounds of formula IV are disclosed:
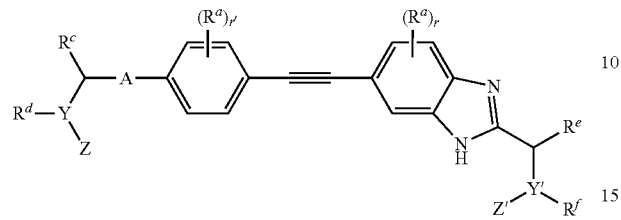
wherein:
A is selected from the group consisting of a single bond,
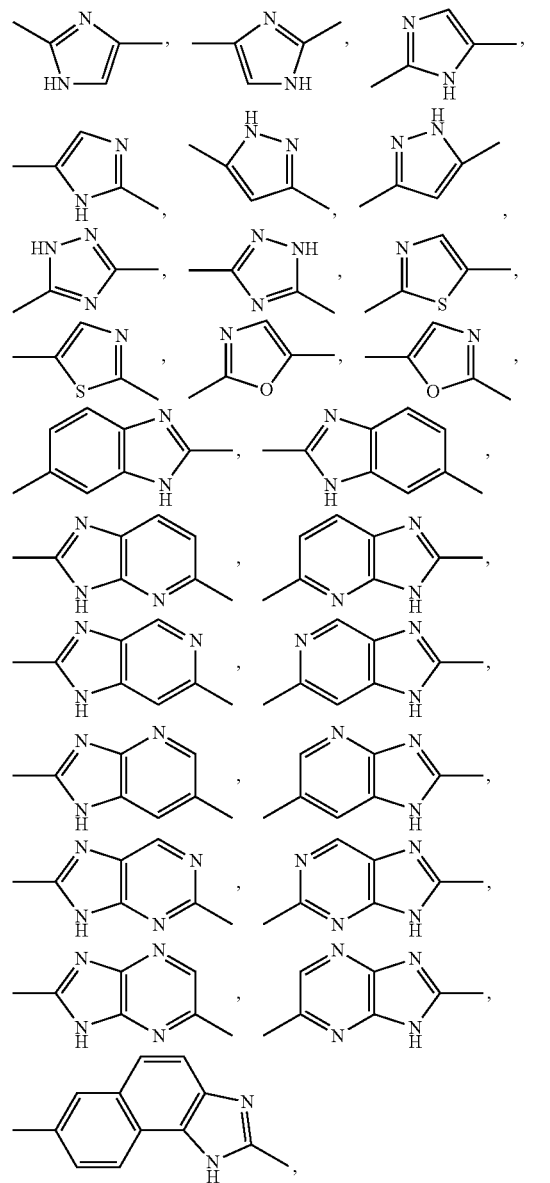
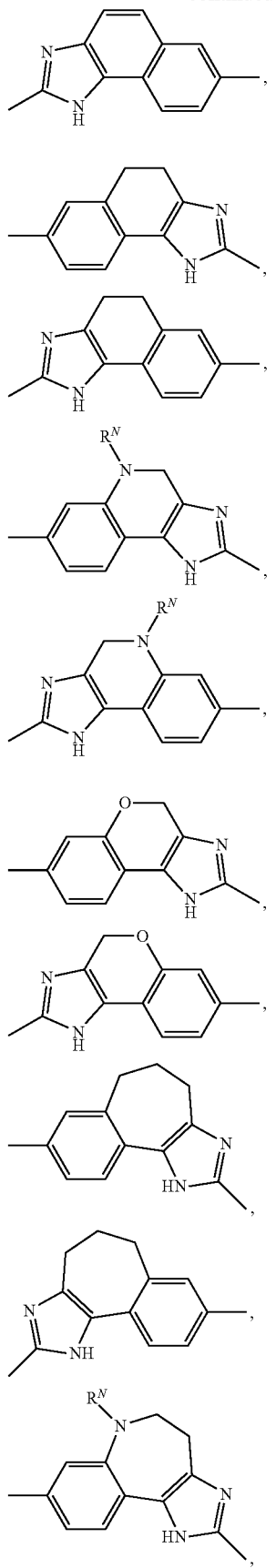

-continued

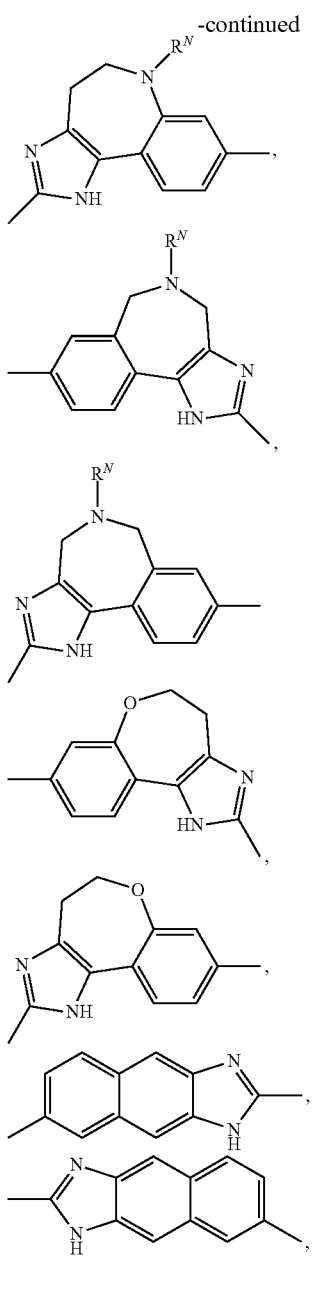

—(CR$_2$)$_n$—O—(CR$_2$)$_p$—, —(CR$_2$)$_n$—C(O)N(R$^N$)—(CR$_2$)$_p$— and —(CR$_2$)$_n$—N(R$^N$)C(O)—(CR$_2$)$_p$—;

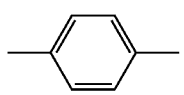

optionally includes 1 or 2 nitrogens as heteroatoms;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
r is 0, 1, 2, or 3; and
r' is 0, 1, 2, 3, or 4.

The compounds of the present invention include pharmaceutically acceptable salts of IV as well as an optically pure enantiomer, racemate or diastereomeric mixtures thereof.

In a first embodiment of the third aspect of the invention A is a single bond,

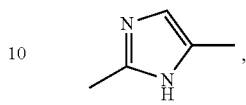

—(CR$_2$)$_n$—C(O)N(R$^N$)—(CR$_2$)$_p$—, or —(CR$_2$)$_n$—N(R$^N$)C(O)—(CR$_2$)$_p$—.

In a second embodiment of the third aspect the compounds are of formula IVa:

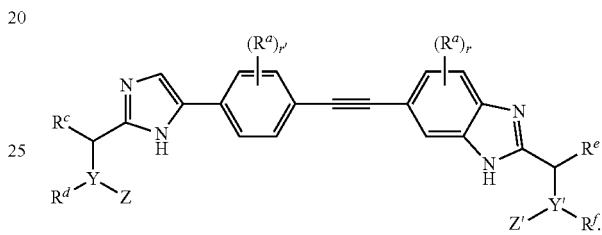

In a third embodiment of the third aspect the compounds are of formula IVb:

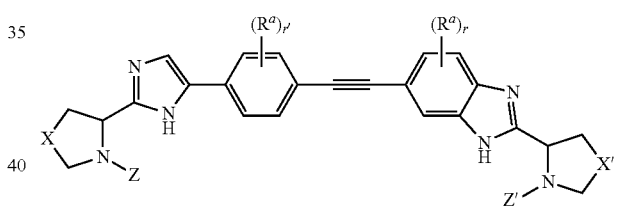

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth aspect of the invention, compounds are of formula V:

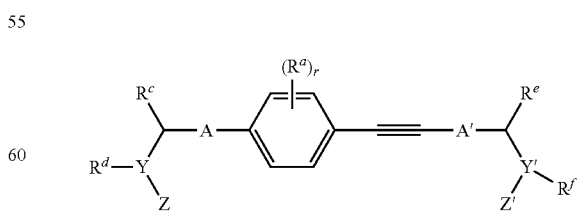

wherein
A and A' are independently selected from the group consisting of single bond,

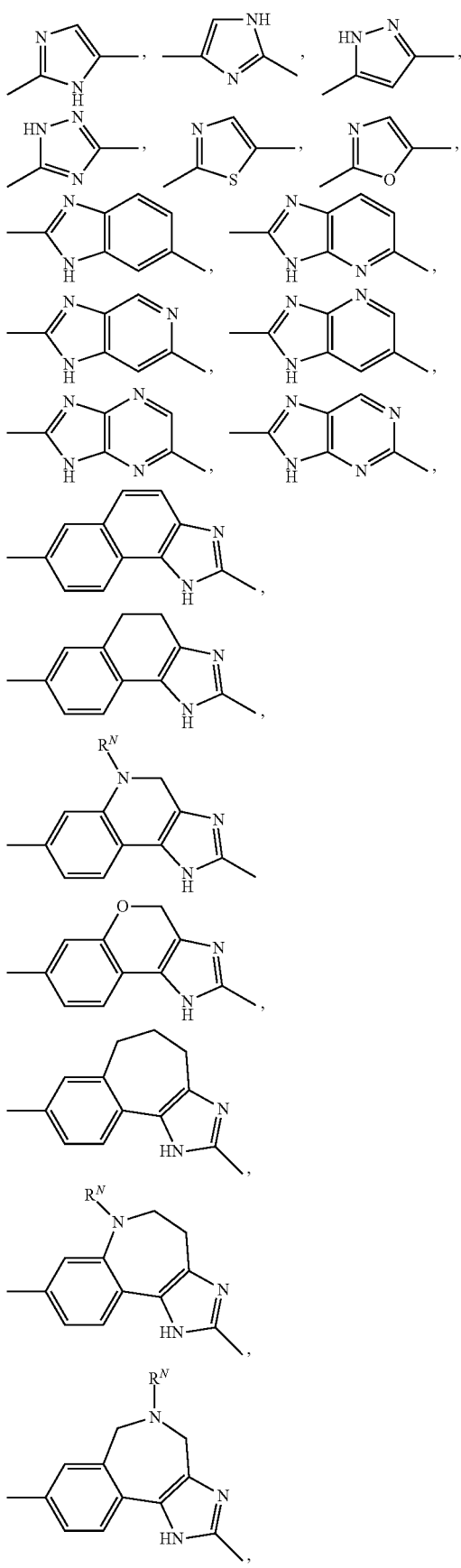

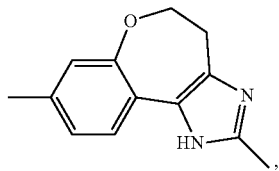

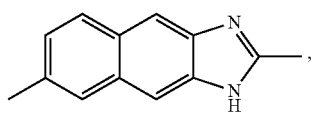

—(CR$_2$)$_n$—O—(CR$_2$)$_p$— and —(CR$_2$)$_n$—C(O)N(R$^N$)—(CR$_2$)$_p$—;

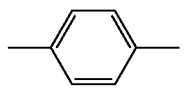

optionally includes 1 or 2 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is 0, 1, 2, 3, or 4.

The compounds of the present invention include pharmaceutically acceptable salts of V as well as an optically pure enantiomer, racemate or diastereomeric mixtures thereof.

In a first embodiment of the fourth aspect, compounds have formula V and A and A' are each independently

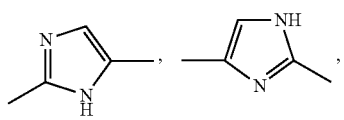

or —(CR$_2$)$_n$—C(O)N(R$^N$)—(CR$_2$)$_p$—.

In a second embodiment of the fourth aspect, compounds have formula Va:

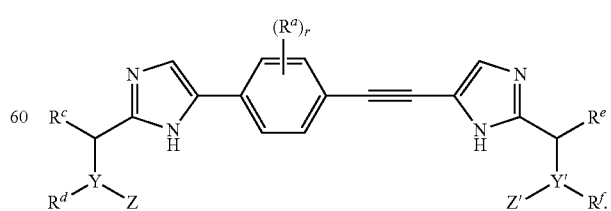

In a third embodiment of the fourth aspect, compounds have formula Vb:

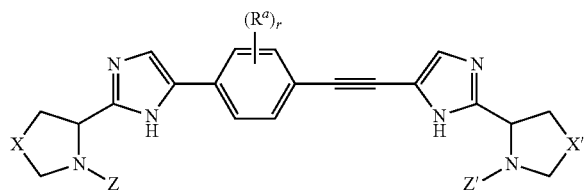

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth embodiment of the fourth aspect, compounds have formula V wherein:

A is selected from the group consisting of

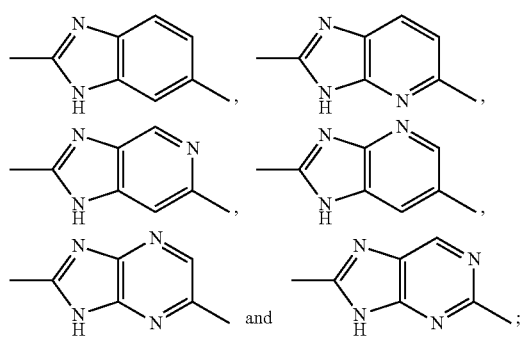

and

A' is selected from the group consisting of

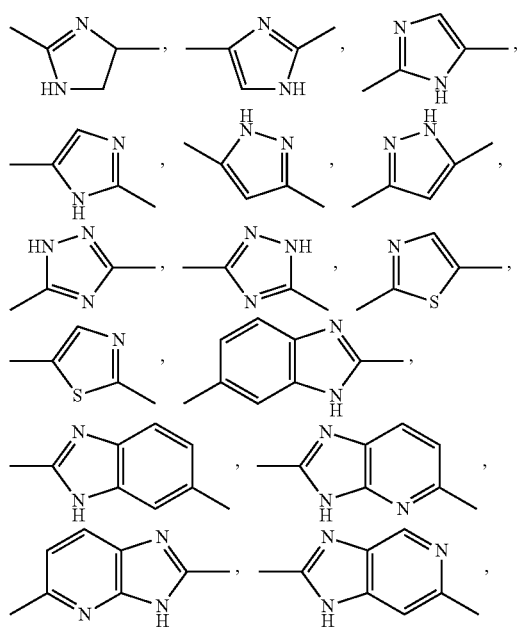

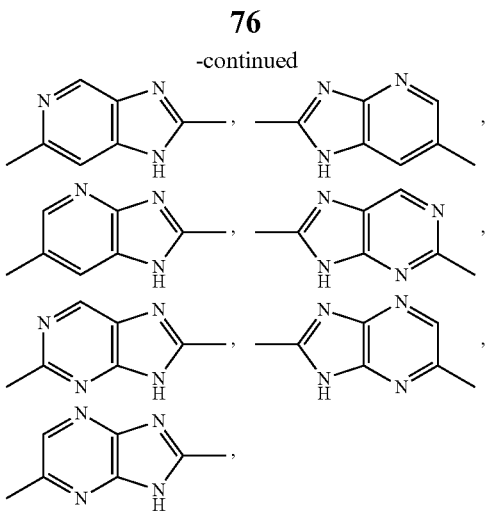

—(CR$_2$)$_n$—O—(CR$_2$)$_p$—, —(CR$_2$)$_n$—C(O)N(R$^N$)—(CR$_2$)$_n$— and —(CR$_2$)$_n$—N(R$^N$)C(O)—(CR$_2$)$_p$—.

In a fifth embodiment of the fourth aspect, compounds have formula V wherein:

A is selected from the group consisting of

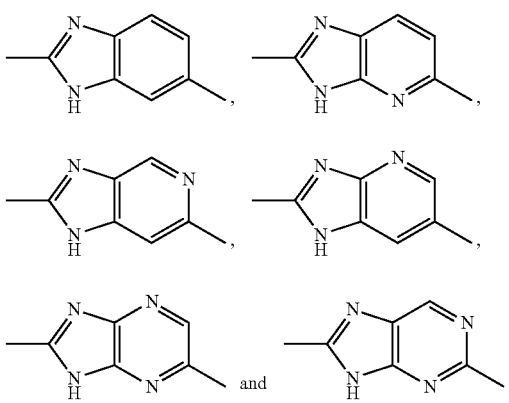

and

A' is

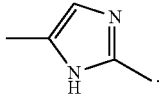.

In a sixth embodiment of the fourth aspect, the compounds have formula Vc:

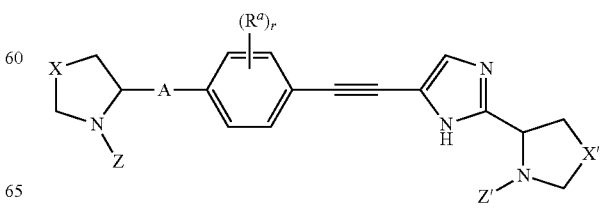

wherein:

A is selected from the group consisting of

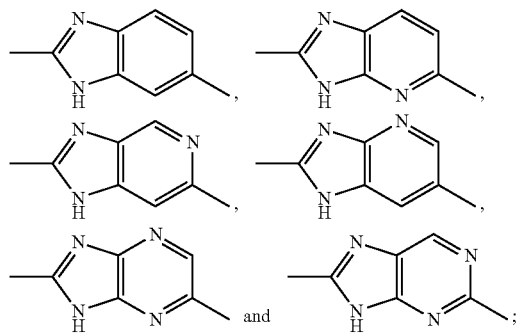

A' is

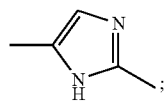

and

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a seventh embodiment of the fourth aspect, compounds have formula V wherein:

A is selected from the group consisting of

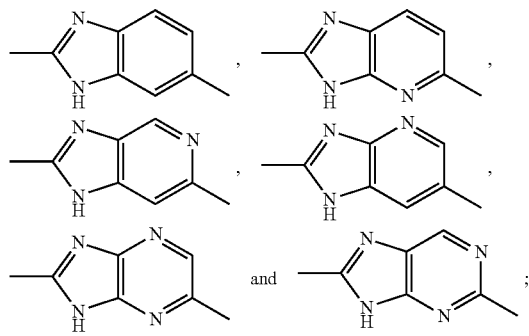

and

A' is selected from the group consisting of

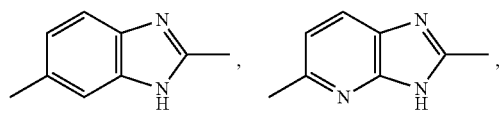

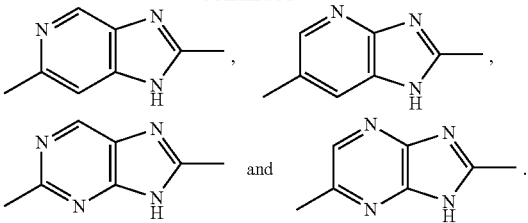

In a eighth embodiment of the fourth aspect, the compounds have formula Vd:

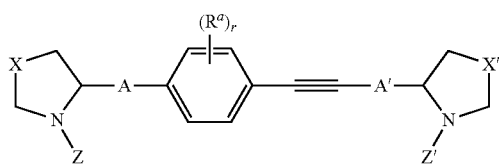

wherein:

A is selected from the group consisting of

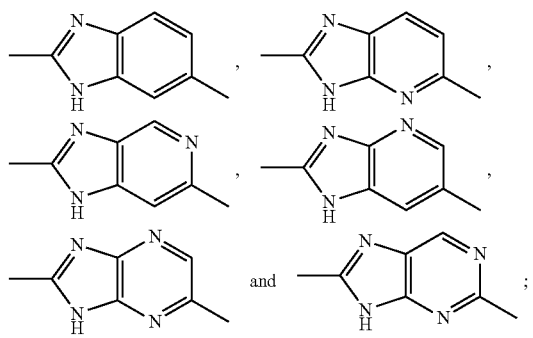

A' is selected from the group consisting of

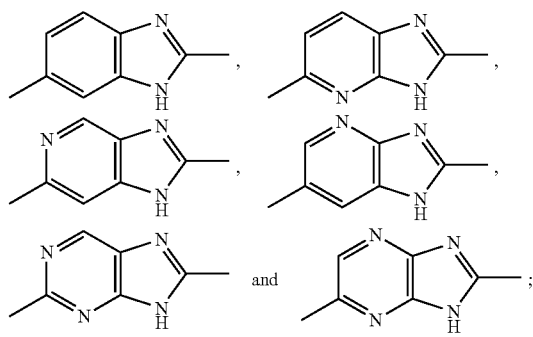

and

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifth aspect of the invention, compounds have formula VI:

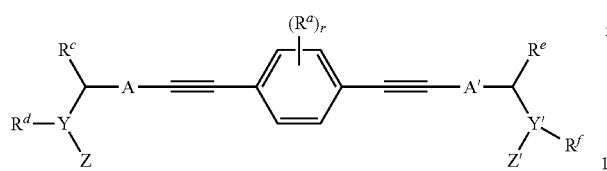

wherein
A and A' are independently selected from the group consisting of single bond,

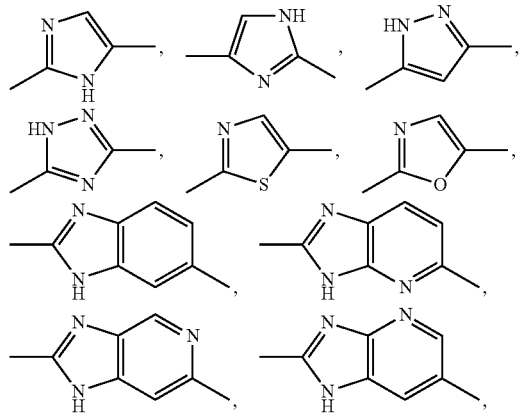

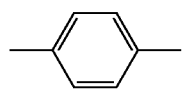

optionally includes 1 or 2 nitrogens as heteroatoms;
each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
r is 0, 1, 2, 3 or 4.

The compounds of the present invention include pharmaceutically acceptable salts of VI as well as an optically pure enantiomer, racemate or diastereomeric mixtures thereof.

In a first embodiment of the fifth aspect, A and A' are each independently

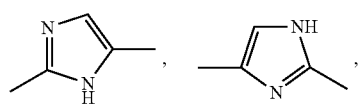

or —(CR$_2$)$_n$—C(O)N(R$^N$)—(CR$_2$)$_p$—.

In a second embodiment of the fifth aspect, compounds have formula VIa:

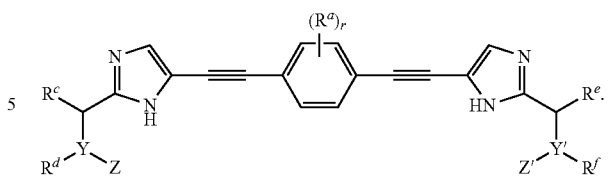

In a third embodiment of the fifth aspect, compounds have formula VIb:

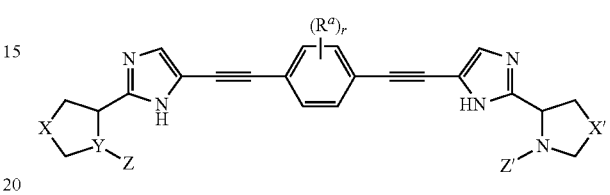

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a sixth aspect of the invention, compounds have formula VII:

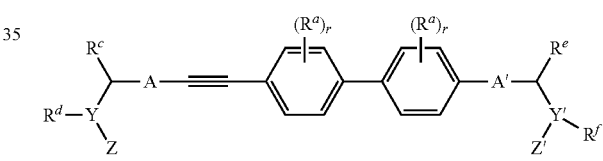

wherein,
A and A' are independently selected from the group consisting of single bond,

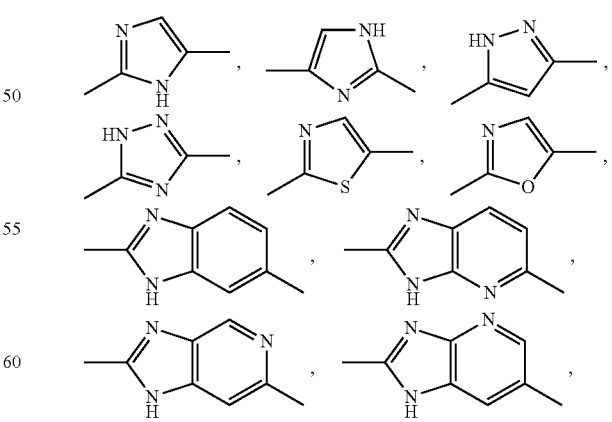

—(CR$_2$)$_n$—O—(CR$_2$)$_p$— and —(CR$_2$)$_n$—C(O)N(R$^N$)—(CR$_2$)$_p$—;
each

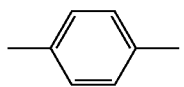

optionally independently includes 1 or 2 nitrogens as heteroatoms;

each $R^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each r is independently 0, 1, 2, 3 or 4.

The compounds of the present invention include pharmaceutically acceptable salts of VII as well as an optically pure enantiomer, racemate or diastereomeric mixtures thereof.

In a first embodiment of the sixth aspect, A and A' are each independently

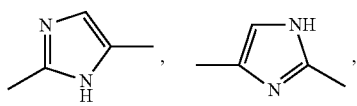

or —(CR$_2$)$_n$—C(O)N(R$^N$)—(CR$_2$)$_p$—.

In a second embodiment of the sixth aspect, compounds have formula VIIa:

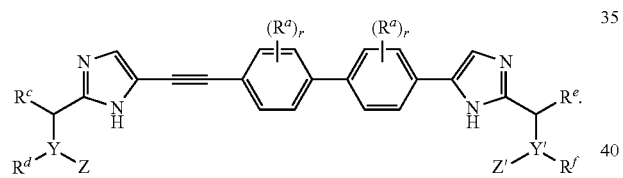

In a third embodiment of the sixth aspect, compounds have formula VIIb:

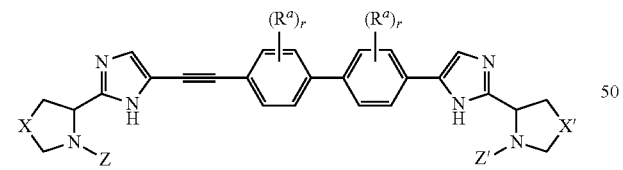

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a seventh aspect of the invention, compounds have formula VIII:

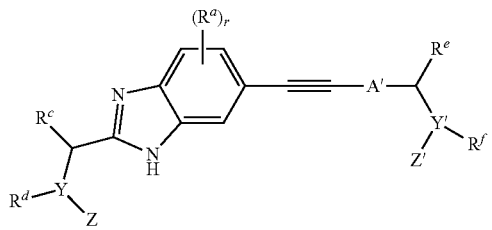

wherein
A' is selected from the group consisting of single bond,

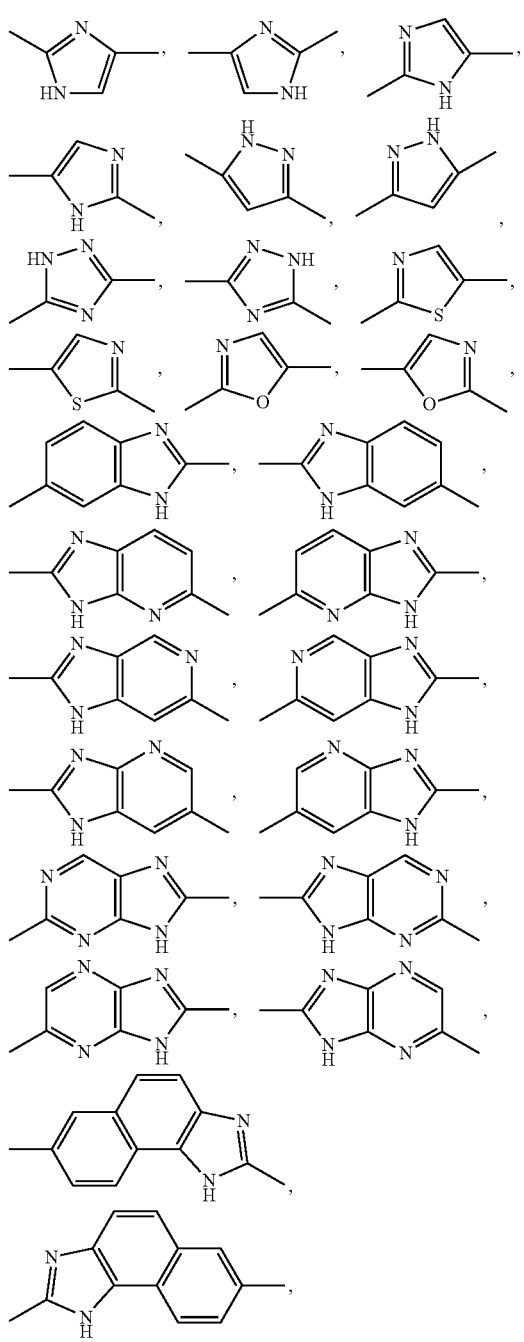

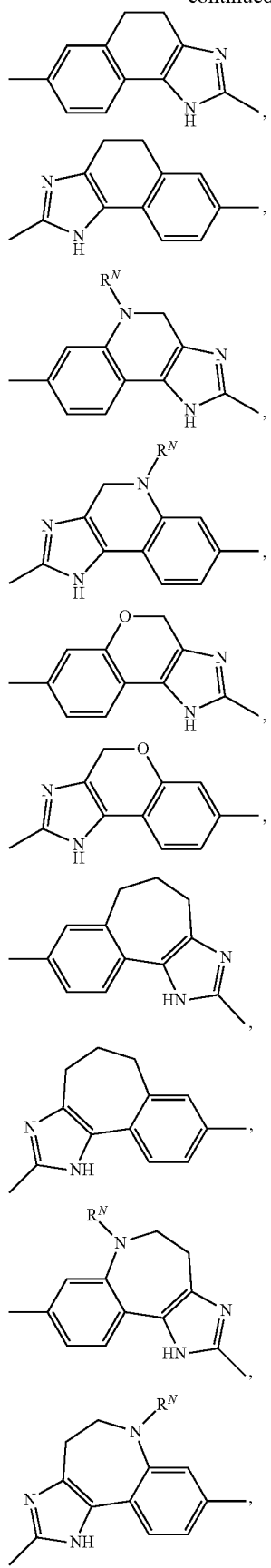

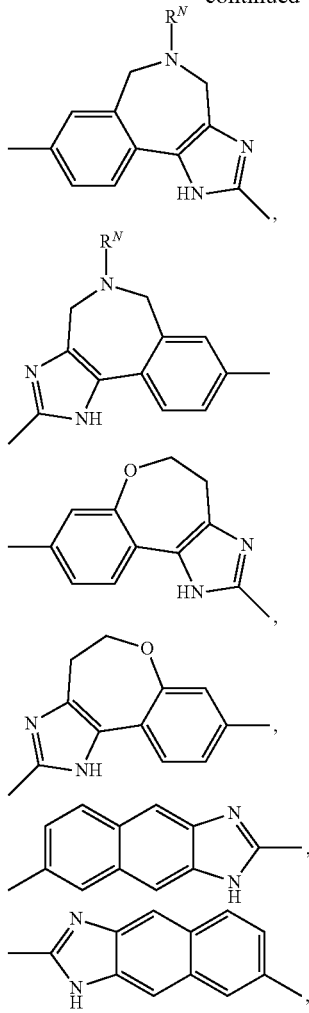

—(CR$_2$)$_n$—O—(CR$_2$)$_p$—, —(CR$_2$)$_n$—C(O)N(R$^N$)—(CR$_2$)$_p$— and —(CR$_2$)$_n$—N(R$^N$)C(O)—(CR$_2$)$_p$—;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is 0, 1, 2, or 3.

The compounds of the present invention include pharmaceutically acceptable salts of VIII as well as an optically pure enantiomer, racemate or diastereomeric mixtures thereof.

In a first embodiment of the seventh aspect, the compounds have formula VIII wherein A' is a single bond,

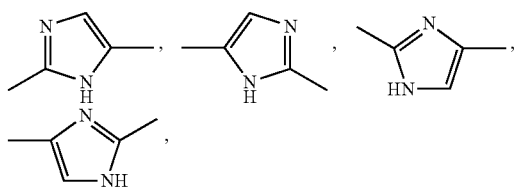

—(CR$_2$)$_n$—C(O)N(R$^N$)—(CR$_2$)$_p$—, or —(CR$_2$)$_n$—N(R$^N$)C(O)—(CR$_2$)$_p$—.

In a second embodiment of the seventh aspect, compounds have formula VIIIa:

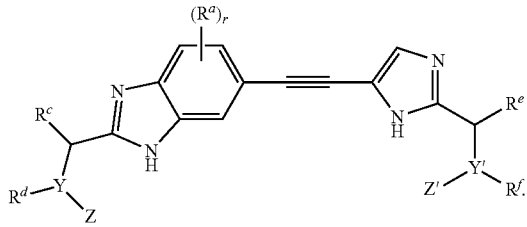

In a third embodiment of the seventh aspect, compounds have formula VIIIb:

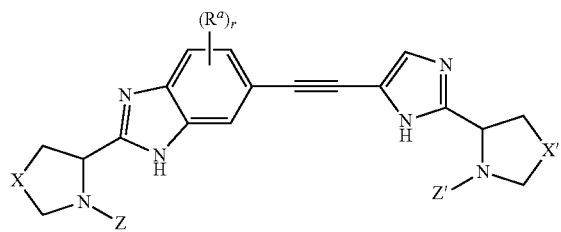

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In an eighth aspect of the invention, compounds have formula IX:

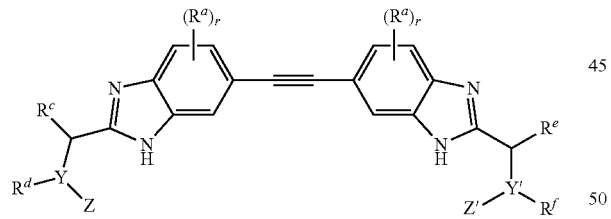

wherein
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
each r is independently 0, 1, 2, or 3.

The compounds of the present invention include pharmaceutically acceptable salts of 1x as well as an optically pure enantiomer, racemate or diastereomeric mixtures thereof.

In a first embodiment of the eighth aspect, compounds have formula IXa:

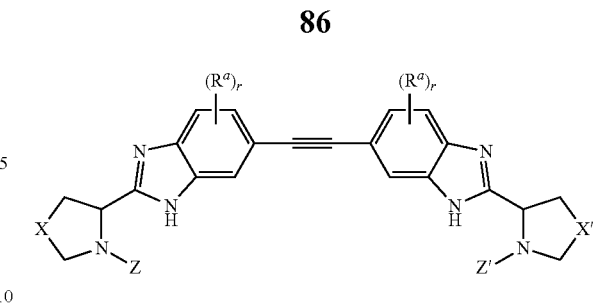

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In an ninth aspect of the invention, compounds have formula X:

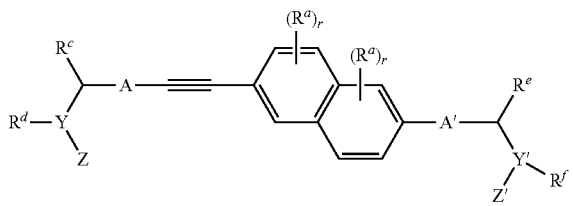

wherein
A and A' are independently selected from the group consisting of single bond,

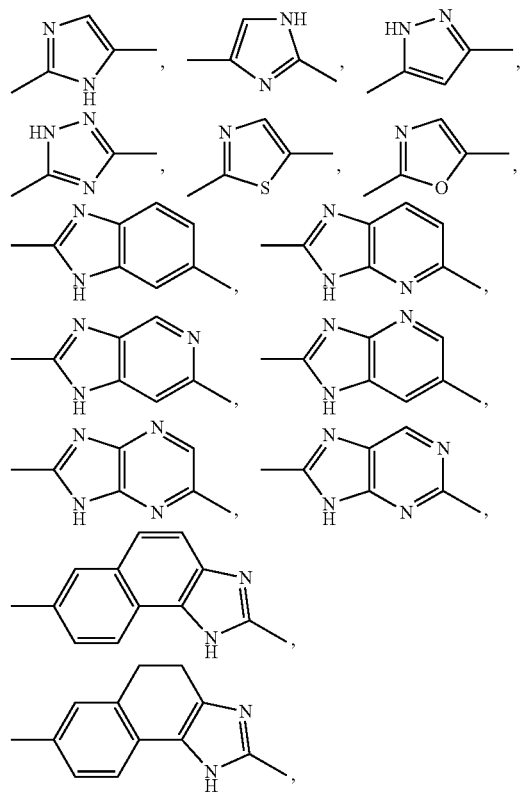

-continued

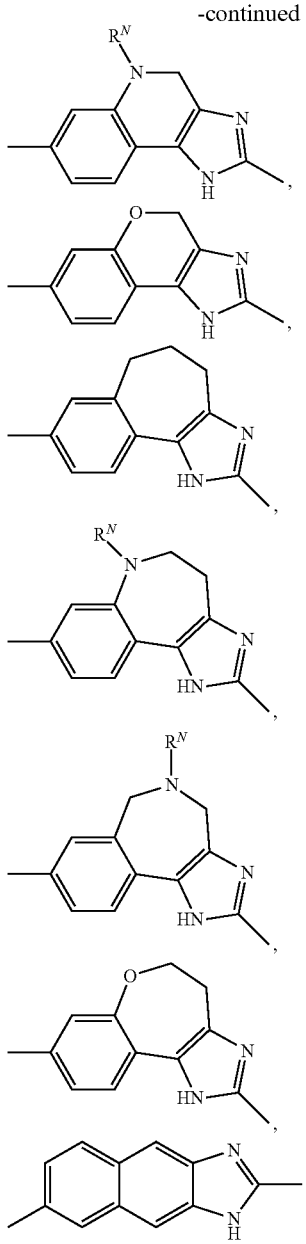

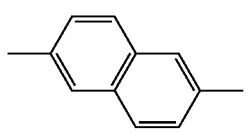

—(CR$_2$)$_n$—O—(CR$_2$)$_p$— and —(CR$_2$)$_n$—C(O)N(R$^N$)—(CR$_2$)$_p$—;

optionally includes 1, 2, 3 or 4 nitrogens as heteroatoms;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
each r is independently 0, 1, 2, or 3.

The compounds of the present invention include pharmaceutically acceptable salts of X as well as an optically pure enantiomer, racemate or diastereomeric mixtures thereof.

In a first embodiment of the ninth aspect, A and A' are each independently

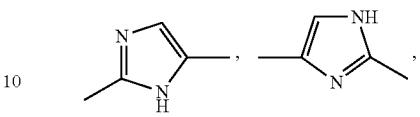

or —(CR$_2$)$_n$—C(O)N(R$^N$)—(CR$_2$)$_p$—.

In a second embodiment of the ninth aspect, compounds have formula Xa:

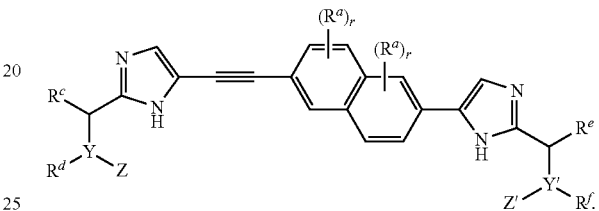

In a third embodiment of the ninth aspect, compounds have formula Xb:

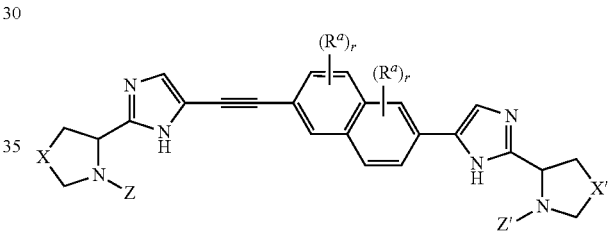

wherein X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fourth embodiment of the ninth aspect, compounds have formula X wherein:
A is selected from the group consisting of

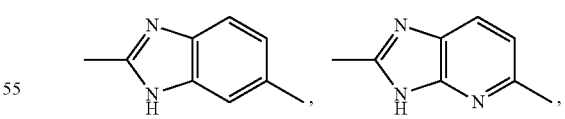

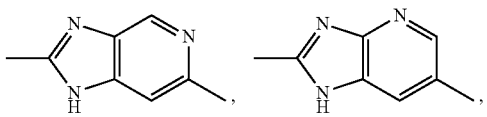

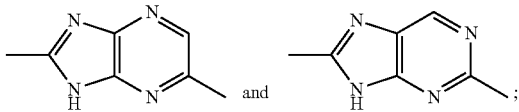

and

A' is

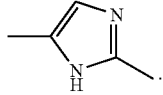

In a fifth embodiment of the ninth aspect, compounds have formula Xc:

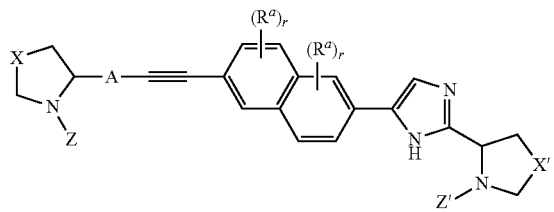

wherein:

A is selected from the group consisting of

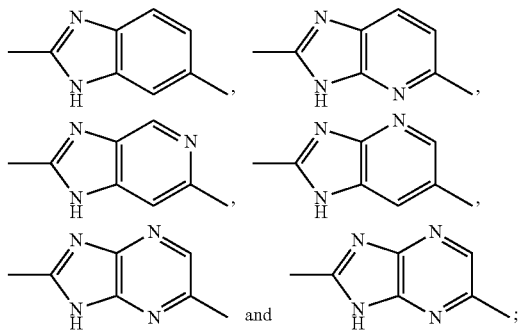

and

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^f$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a sixth embodiment of the ninth aspect, compounds have formula Xd:

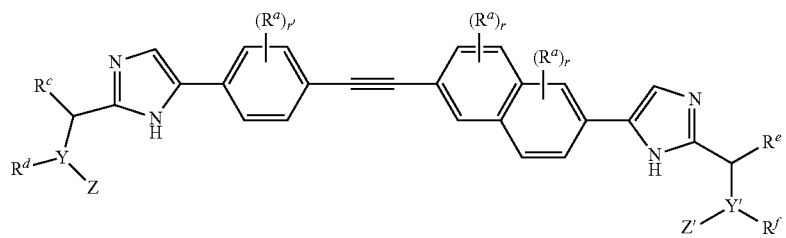

wherein:
r is 0, 1, 2, or 3; and
r' is 0, 1, 2, 3, or 4.

In a seventh embodiment of the ninth aspect, compounds have formula Xe:

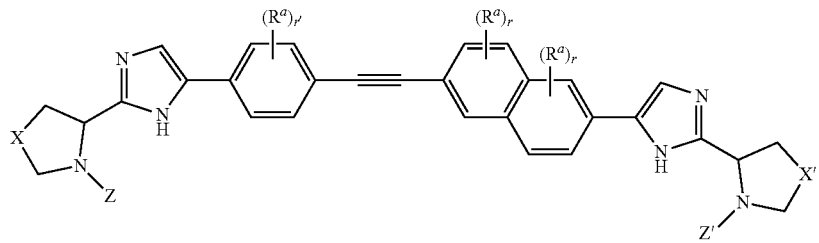

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^f$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a tenth aspect of the invention, compounds have formula XI:

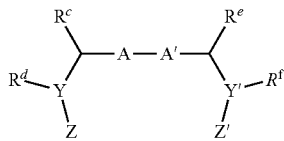

wherein A and A' are independently selected from the group consisting of

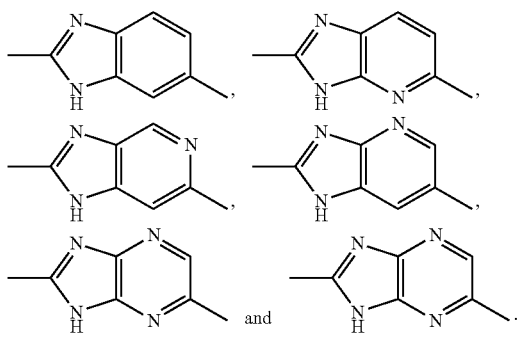

The compounds of the present invention include pharmaceutically acceptable salts of $X^1$ as well as an optically pure enantiomer, racemate or diastereomeric mixtures thereof.

In a first embodiment of the tenth aspect, compounds have formula XIa:

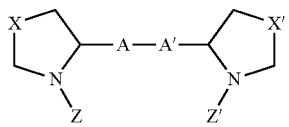

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In an eleventh aspect of the invention, compounds have formula XII:

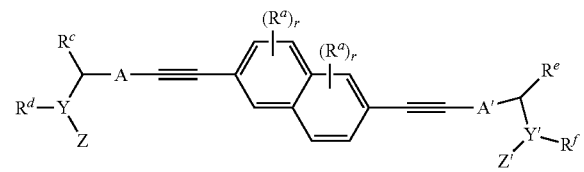

wherein:
A and A' are independently selected from the group consisting of single bond,

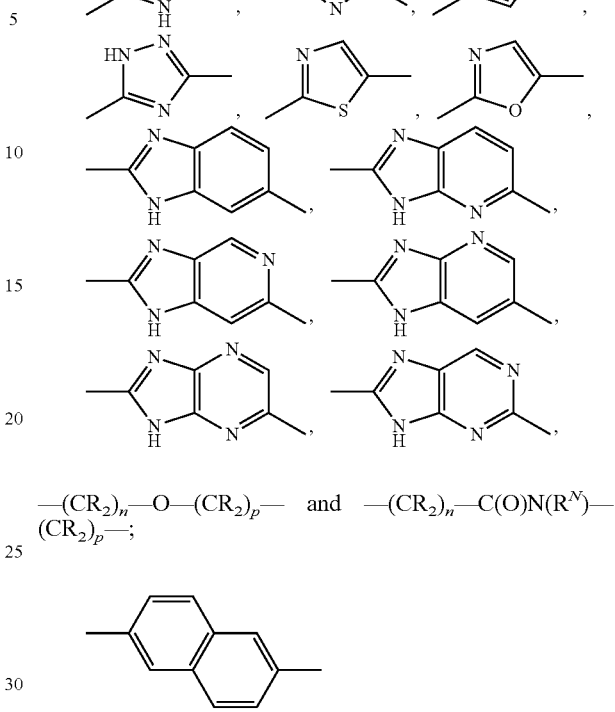

—(CR₂)ₙ—O—(CR₂)ₚ— and —(CR₂)ₙ—C(O)N(Rᴺ)—(CR₂)ₚ—;

optionally includes 1, 2, 3 or 4 nitrogens as heteroatoms;
each Rᵃ is independently selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
each r is independently 0, 1, 2, or 3.

The compounds of the present invention include pharmaceutically acceptable salts of XII as well as an optically pure enantiomer, racemate or diastereomeric mixtures thereof.

In a first embodiment of the eleventh aspect, A and A' are each independently

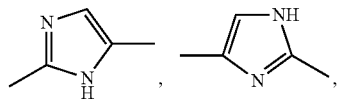

or —(CR₂)ₙ—C(O)N(Rᴺ)—(CR₂)ₚ—.

In a second embodiment of the eleventh aspect, compounds have formula XIIa:

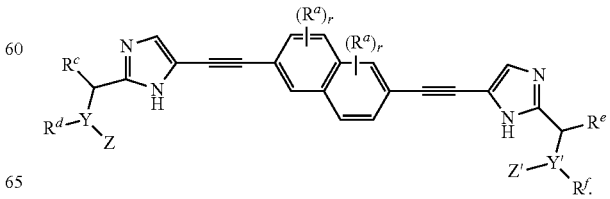

In a third embodiment of the eleventh aspect, compounds have formula XIIb:

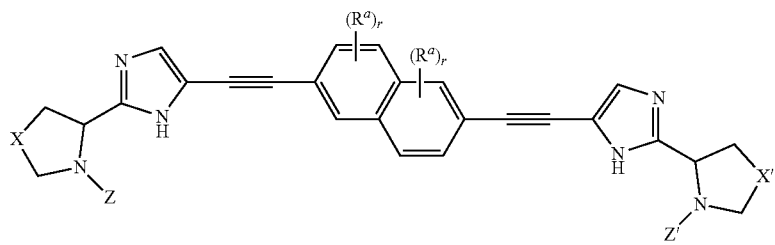

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a twelfth aspect of the invention, compounds have formula XIII:

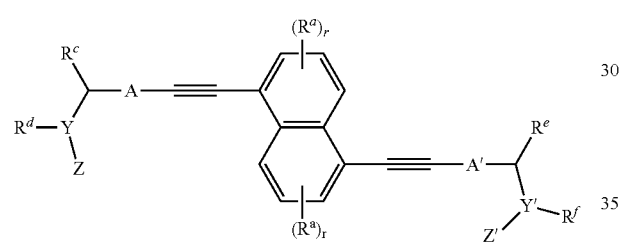

wherein

A and A' are independently selected from the group consisting of single bond,

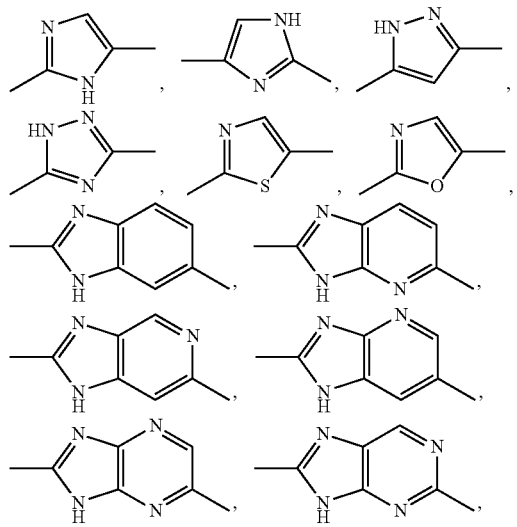

—(CR$_2$)$_n$—O—(CR$_2$)$_p$— and —(CR$_2$)$_n$—C(O)N(R$^N$)—(CR$_2$)$_p$—;

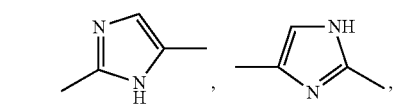

optionally includes 1, 2, 3 or 4 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and each r is independently 0, 1, 2, or 3.

The compounds of the present invention include pharmaceutically acceptable salts of XIII as well as an optically pure enantiomer, racemate or diastereomeric mixtures thereof.

In a first embodiment of the twelfth aspect, A and A' are each independently

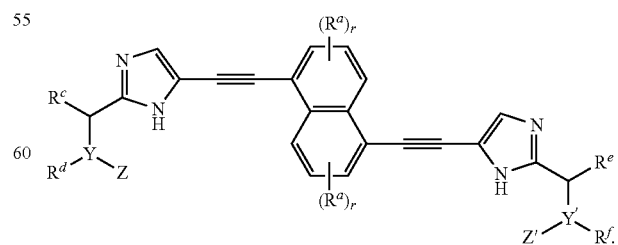

or —(CR$_2$)$_n$—C(O)N(R$^N$)—(CR$_2$)$_p$—.

In a second embodiment of the twelfth aspect, compounds have formula XIIIa:

In a third embodiment of the twelfth aspect, compounds have formula XIIIb:

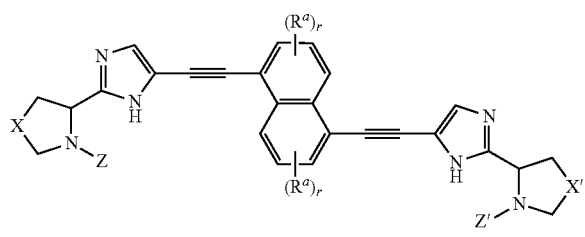

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In an thirteenth aspect of the invention, compounds have formula XIV:

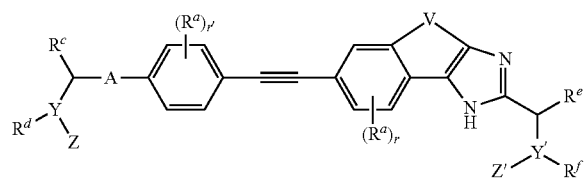

wherein:
A is selected from the group consisting of a single bond,

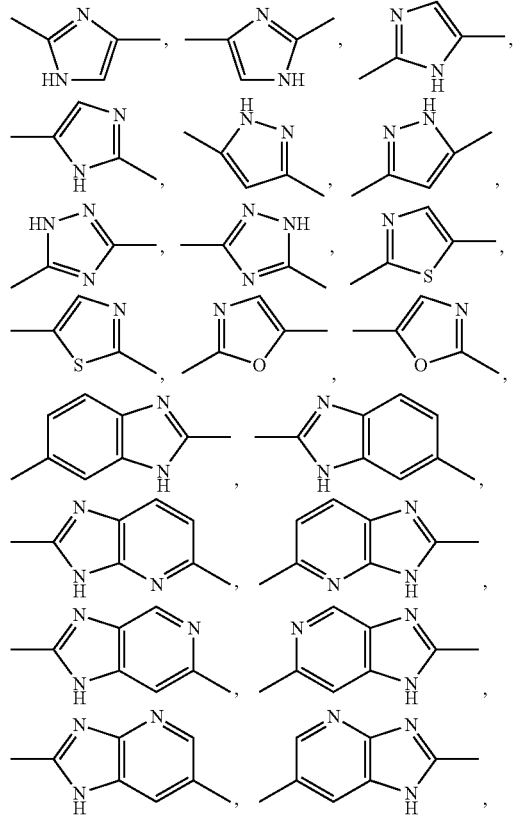

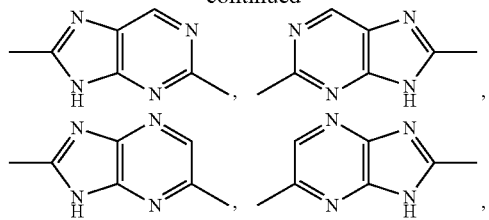

—(CR₂)ₙ—O—(CR₂)ₚ—, —(CR₂)—C(O)N(Rᴺ)—(CR₂)ₚ— and —(CR₂)ₙ—N(Rᴺ)C(O)—(CR₂)ₚ—;

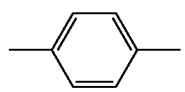

optionally includes 1 or 2 nitrogens as heteroatoms;
each IV is independently selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
r is 0, 1, 2, or 3; and
r' is 0, 1, 2, 3, or 4.

The compounds of the present invention include pharmaceutically acceptable salts of XIV as well as an optically pure enantiomer, racemate or diastereomeric mixtures thereof.

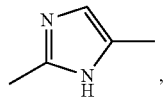

In a first embodiment of the thirteenth aspect, A is a single bond, —(CR₂)—C(O)N(Rᴺ)—(CR₂)ₚ—, or —(CR₂)ₙ—N(Rᴺ)C(O)—(CR₂)ₚ—.

In a second embodiment of the thirteenth aspect, compounds have formula XIVa:

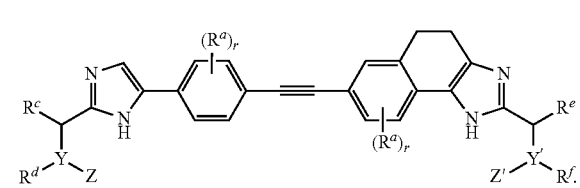

In a third embodiment of the thirteenth aspect, compounds have formula XIVb:

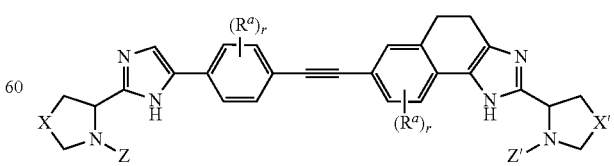

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a fourth embodiment of the thirteenth aspect, compounds have XIVc:

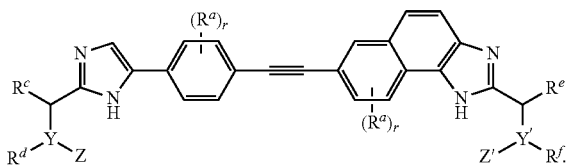

In a fifth embodiment of the thirteenth aspect, compounds have formula XIVd:

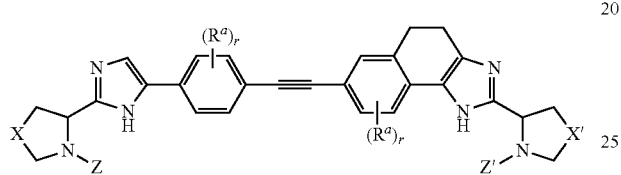

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a sixth embodiment of the thirteenth aspect, compounds have formula XIVe:

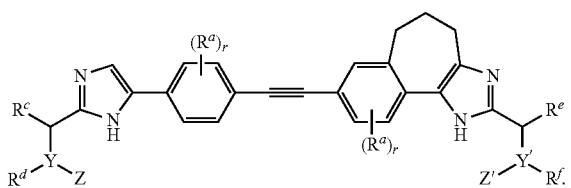

In a seventh embodiment of the thirteenth aspect, compounds have formula XIVf:

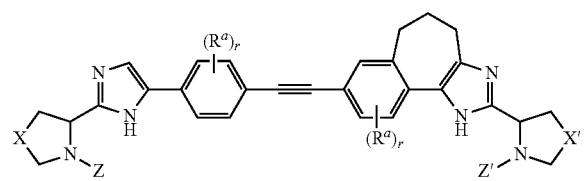

wherein X and X' are each independently selected from the group consisting of a bond, —CH₂—, —CH₂—CH₂—, —CH=CH—, —O—, —S—, —S(O)₁₋₂—, —CH₂O—, —CH₂S—, —CH₂S(O)₁₋₂— and —CH₂N(R¹)—, wherein R¹ is chosen from the group consisting of hydrogen, C₁ to C₈ alkyl, C₁ to C₈ heteroalkyl, cycloalkyl, heterocycle, aryl, heteroaryl, aralkyl, alkanoyl, alkoxycarbonyl, carbamoyl and substituted sulfonyl.

In a fourteenth aspect of the invention, compounds have formula XV:

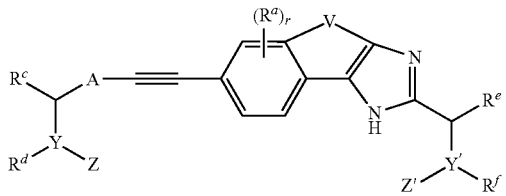

wherein:
A is selected from the group consisting of

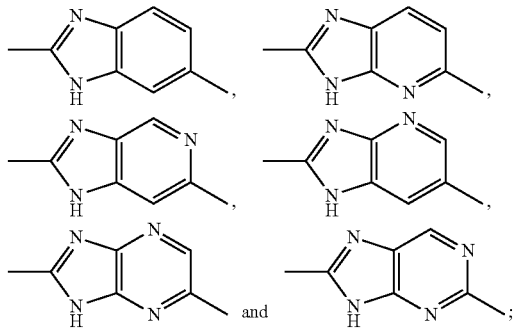

each $R^a$ is independently selected from the group consisting of —OH, —CN, —NO₂, halogen, C₁ to C₁₂ alkyl, C₁ to C₁₂ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and r is 0, 1, 2, or 3.

The compounds of the present invention include pharmaceutically acceptable salts of XV as well as an optically pure enantiomer, racemate or diastereomeric mixtures thereof.

In a first embodiment of the fourteenth aspect, compounds have formula XVa:

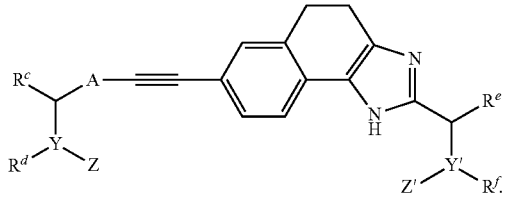

In a second embodiment of the fourteenth aspect, compounds have formula XVb:

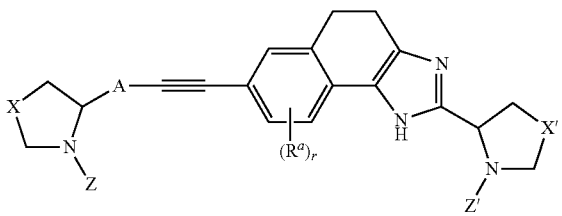

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a third embodiment of the fourteenth aspect, compounds have formula XVc:

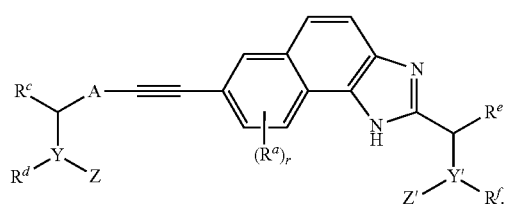

In a fourth embodiment of the fourteenth aspect, compounds have formula XVd:

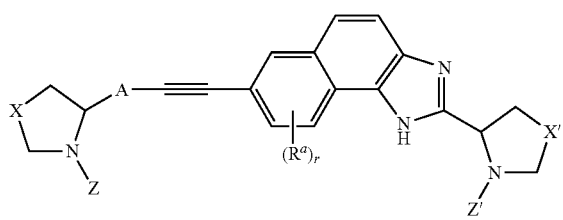

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifth embodiment of the fourteenth aspect, compounds have formula XVe:

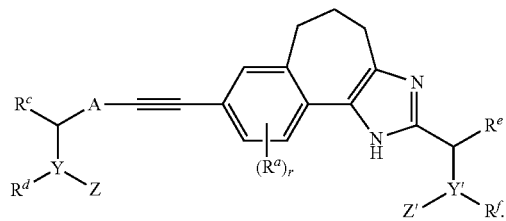

In a sixth embodiment of the fourteenth aspect, compounds have formula XVf:

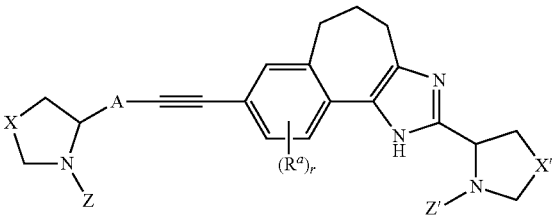

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

In a fifteenth aspect of the invention, in any compound of any of the second through fourteenth aspects, R$^c$, R$^d$, R$^e$ and R$^f$ are each independently selected from the group consisting of: hydrogen, C$_1$ to C$_8$ alkyl and C$_1$ to C$_8$ heteroalkyl, wherein, each hetero atom, if present, is independently N, O or S,
R$^c$ and R$^d$ are optionally joined to form a 4- to 8-membered heterocycle which is optionally fused to another 3- to 6-membered heterocycle, and
R$^e$ and R$^f$ are optionally joined to form a 4- to 8-membered heterocycle which is optionally fused to another 3- to 6-membered heterocycle.

In a first embodiment of the fifteenth aspect one of R$^c$ and R$^d$ or R$^e$ and R$^f$ are joined to form a 4- to 8-membered heterocycle which is optionally fused to another 3- to 6-membered heterocycle.

In a second embodiment of the fifteenth aspect both of R$^c$ and R$^d$ and R$^e$ and R$^f$ are joined to form a 4- to 8-membered heterocycle which is optionally fused to another 3- to 6-membered heterocycle.

In a sixteenth aspect of the invention, each R$^a$, if present in any of the second through fifteenth aspects, is independently —CN, —OCF$_3$, —OCHF$_2$, —CF$_3$, or —F.

In a seventeenth aspect of the invention, if present in any compound of any of the previous aspects, one of Y and Y' is N.

In a first embodiment of the seventeenth aspect, both Y and Y', if present, are N.

In an eighteenth aspect of the invention Z and Z' in any of the previous aspects are each 1-3 amino acids.

In a first embodiment of the eighteenth aspect, the amino acids are in the D configuration.

In a second embodiment of the eighteenth aspect, Z and Z' are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$.

In a third embodiment of the eighteenth aspect, one or both of Z and Z' are —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$.

In a fourth embodiment of the eighteenth aspect, one or both of Z and Z' are —U—(CR$^4_2$)$_t$—NR$^5$—(CR$^4_2$)$_t$—U—(CR$^4_2$)$_t$—NR$^7$—(CR$^4_2$)$_t$—R$^8$.

In a fifth embodiment of the eighteenth aspect, one or both of Z and Z' are —U—(CR$^4_2$)$_t$—NR$^5$—(CR$^4_2$)$_t$—R$^8$.

In a sixth embodiment of the eighteenth aspect, one or both of Z and Z' are —[C(O)—(CR$^4_2$)$_t$—NR$^5$—(CR$^4_2$)$_t$]—U—(CR$^4_2$)$_t$—NR$^7$—(CR$^4_2$)$_t$—R$^8$.

In a seventh embodiment of the eighteenth aspect, one or both of Z and Z' are —C(O)—(CR$^4_2$)$_t$—NR$^5$—(CR$^4_2$)$_t$—U—(CR$^4_2$)$_t$—NR$^7$—(CR$^4_2$)$_t$—R$^8$.

In an eighth embodiment of the eighteenth aspect, one or both of Z and Z' are —[C(O)—(CR$^4_2$)$_t$—NR$^5$—(CR$^4_2$)$_t$]$_u$—C(O)—(CR$^4_2$)$_t$—NR$^7$—(CR$^4_2$)$_t$—R$^8$.

In a ninth embodiment of the eighteenth aspect, one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

In a tenth embodiment of the eighteenth aspect, one or both of Z and Z' are —C(O)—(CR$^4_2$)$_t$—NR$^7$—(CR$^4_2$)$_t$—R$^8$.

In an eleventh embodiment of the eighteenth aspect, one or both of Z and Z' are —C(O)—(CR$^4_2$)$_n$—NR$^7$—(CR$^4_2$)$_n$—C(O)—R$^{81}$.

In a twelfth embodiment of the eighteenth aspect, one or both of Z and Z' are —C(O)—(CR$^4_2$)$_n$—NR$^7$—C(O)—R$^{81}$.

In a thirteenth embodiment of the eighteenth aspect, one or both of Z and Z' are —C(O)—(CR$^4_2$)$_n$—NR$^7$—(CR$^4_2$)$_n$—C(O)—O—R$^{81}$.

In a fourteenth embodiment of the eighteenth aspect, one or both of Z and Z' are —C(O)—(CR$^4_2$)$_n$—NR$^7$—C(O)—O—R$^{81}$.

In a fifteenth embodiment of the eighteenth aspect, one or both of Z and Z' are —U—(CR$^4_2$)$_t$—R$^8$.

In a sixteenth embodiment of the eighteenth aspect, one or both of Z and Z' are —C(O)—(CR$^4_2$)$_t$—R$^8$.

In a seventeenth embodiment of the eighteenth aspect, one or both of Z and Z' are —[U—(CR$^4_2$)$_t$—NR$^5$—(CR$^4_2$)$_t$]$_u$—U—(CR$^4_2$)$_t$—O—(CR$^4_2$)$_t$—R$^8$.

In an eighteenth embodiment of the eighteenth aspect, one or both of Z and Z' are —U—(CR$^4_2$)$_t$—NR$^5$—(CR$^4_2$)$_t$—U—(CR$^4_2$)$_t$—O—(CR$^4_2$)$_t$—R$^8$.

In a nineteenth embodiment of the eighteenth aspect, one or both of Z and Z' are —C(O)—(CR$^4_2$)$_t$—NR$^5$—(CR$^4_2$)$_t$—C(O)—(CR$^4_2$)$_t$—O—(CR$^4_2$)$_t$—R$^8$.

In a twentieth embodiment of the eighteenth aspect, one or both of Z and Z' are —U—(CR$^4_2$)$_t$—O—(CR$^4_2$)$_t$—R$^8$.

In a twenty-first embodiment of the eighteenth aspect, one or both of Z and Z' are —C(O)—(CR$^4_2$)$_t$—O—(CR$^4_2$)$_t$—R$^8$.

In a twenty-second embodiment of the eighteenth aspect, one or both of Z and Z' are —C(O)—(CR$^4_2$)$_n$—NR$^7$—R$^8$ wherein R$^7$ and R$^8$ together form a 4-7 membered ring.

In a nineteenth aspect of the invention, compounds have formula XVI:

wherein:
B' is selected from the group consisting of:

-continued wherein B' is optionally substituted with between 1 and 4 R$^a$;

optionally includes 1, 2, 3, or 4 nitrogens as heteroatoms;

each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;

each R$^8$ is independently chosen from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R" and —S(O)$_2$—N—R$^{81}_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl; and each R$^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

The compounds of the present invention include pharmaceutically acceptable salts of XVI as well as an optically pure enantiomer, racemate or diastereomeric mixtures thereof.

In a first embodiment of the nineteenth aspect, each R$^a$, if present, is selected from the group consisting of —CN, —OCF$_3$, —OCHF$_2$, —CF$_3$ and —F.

In a twentieth aspect of the invention, compounds have formula XVII:

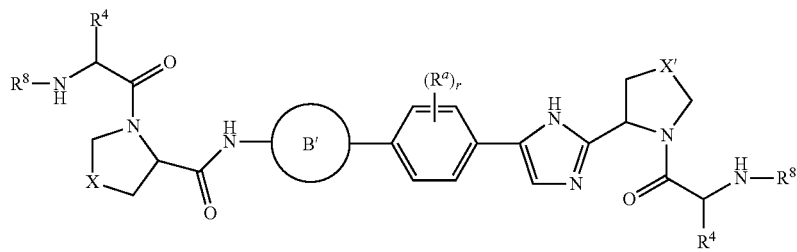

wherein:
B' is

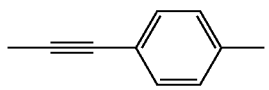

optionally substituted with between 1 and 4 R<sup>a</sup>;

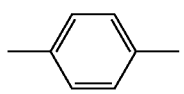

optionally includes 1, 2, 3, or 4 nitrogens as heteroatoms;
  each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
  r is 0, 1, 2, 3 or 4;
  X and X' are each independently selected from the group consisting of a bond, —CH$_2$—, —CH$_2$—CH$_2$—, —CH═CH—, —O—, —S—, —S(O)$_{1-2}$—, —CH$_2$O—, —CH$_2$S—, —CH$_2$S(O)$_{1-2}$— and —CH$_2$N (R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl;
  each R$^8$ is independently chosen from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}$$_2$, —S(O)$_2$—R$^{81}$ and —S(O)$_2$—N—R$^{81}$$_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl; and
  each R$^4$ is independently selected from the group consisting of hydrogen, C$_1$ to C$_8$ alkyl, C$_1$ to C$_8$ heteroalkyl, cycloalkyl, heterocycle, aryl, heteroaryl and aralkyl.

The compounds of the present invention include pharmaceutically acceptable salts of XVII as well as an optically pure enantiomer, racemate or diastereomeric mixtures thereof.

In a first embodiment of the twentieth aspect, each R$^a$, if present, is selected from the group consisting of —CN, —OCF$_3$, —OCHF$_2$, —CF$_3$ and —F.

In a twenty-first aspect of the invention, compounds have formula XVIII:

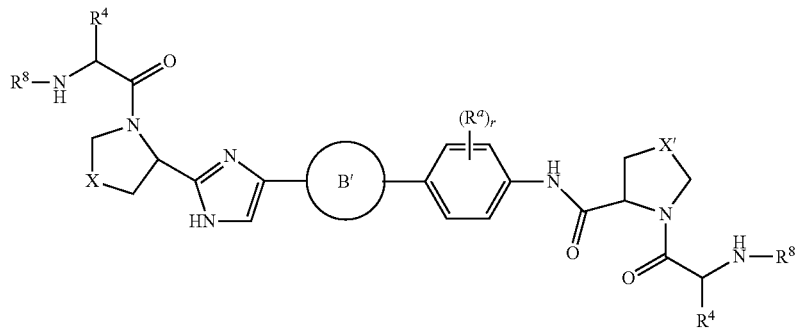

wherein:
B' is selected from the group consisting of:

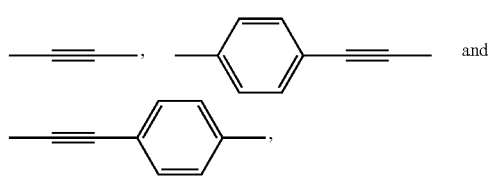

wherein B' is optionally substituted with between 1 and 4 R$^a$;

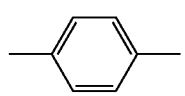

optionally includes 1, 2, 3, or 4 nitrogens as heteroatoms;

each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, 3 or 4;

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl;

each $R^8$ is independently chosen from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each R$^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl; and each $R^4$ is independently selected from the group consisting of hydrogen, $C_1$ to $C_8$ alkyl, $C_1$ to $C_8$ heteroalkyl, cycloalkyl, heterocycle, aryl, heteroaryl and aralkyl.

The compounds of the present invention include pharmaceutically acceptable salts of XVIII as well as an optically pure enantiomer, racemate or diastereomeric mixtures thereof.

In a first embodiment of the twenty-first aspect, each $R^a$, if present, is selected from the group consisting of —CN, —OCF$_3$, —OCHF$_2$, —CF$_3$ and —F.

General Synthesis

The compounds of the invention are prepared by a variety of synthetic techniques as they are illustrated in the various synthetic schemes outlined below. In general, the synthesis of central scaffold cores employs crossing coupling techniques such as, Sonogashira, Suzuki-Miayura, or Stille couplings for connecting carbon-carbon bonds. For scaffold cores linked via a carbon-nitrogen bond, their syntheses typically utilize a nucleophilic aromatic substitution reaction, a Buchwald cross coupling and Ma cross coupling reaction. The functional groups, typically amines and carboxyl groups on either ends of the cores are generally orthogonally protected to allow for selective further manipulations as needed.

The following abbreviations are used throughout this application:

ACN Acetonitrile
aq Aqueous
Bn Benzyl
BnOH Benzyl alcohol
Boc t-butoxycarbonyl
DCE Dichloroethane
DCM Dichloromethane
DIEA(DIPEA) Diisopropylethylamine
DMA N,N-Dimethylacetamide
DME 1,2-Dimethoxyethane
DMF N,N-Dimethylformamide
DMSO Dimethylsulfoxide
DMTMM 4-(4,6-Dimethoxy-1,3,5-triazin-2-yl)-4-methylmorpholinium chloride
DPPA Diphenylphosphoryl azide
DTT Dithiothreitol
EDC Ethylcarbodiimide hydrochloride
EDCl 1-Ethyl-3-[3-(dimethylamino) propyl]carbodiimide hydrochloride
EDTA Ethylene diamine tetraacetic acid
ESI Electrospray Ionization
Et$_3$N, TEA Triethylamine
EtOAc, EtAc Ethyl acetate
EtOH Ethanol
g Gram(s)
h Hour(s)
HBTU O-Benzotriazol-1-yl-N,N,N',N'-tetramethyluronium hexafluorophosphate
HOBt 1-Hydroxybenzotriazole
IC$_{50}$ The concentration of an inhibitor that causes a 50% reduction in a measured activity
LAH Lithium aluminum hydride
LDA Lithium diisopropylamide
LCMS Liquid Chromatography Mass Spectrometry
MeI Methyl Iodide
MeOH Methanol
min Minute(s)
mmol Millimole(s)
NMM 4-Methylmorpholine
NMP N-methylpyrrolidinone
PG Protective Group
PTT Phenyl trimethyl tribromide
Py Pyridine
rt Room temperature
TEA Triethylamine
Tf Trifluoromethanesulfonate
TFA Trifluoroacetic acid
TFAA Trifluoroacetic anhydride
THF Tetrahydrofuran
TLC Thin Layer Chromatography Reagents and solvents used below can be obtained from commercial sources such as Aldrich Chemical Co. (Milwaukee, Wis., USA). $^1$H-NMR spectra were recorded on a Bruker 400 MHz or 500 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electrospray spray ionization (ESI) mass spectrometry analysis was conducted on a Hewlett-Packard 1100 MSD electrospray mass spectrometer using the HP1 100 HPLC for sample delivery. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Normally the analyte was dissolved in methanol at 0.1 mg/mL and 5 microliter was infused with the delivery solvent into the mass spectrometer, which scanned from 100 to 1500 daltons. All compounds could be analyzed in the positive ESI mode, using an acetonitrile/water gradient (10%-90%) acetonitrile in water with 0.1% formic acid as delivery solvent. The compounds provided below could also be analyzed in the negative ESI mode, using 2 mM NH$_4$OAc in acetonitrile/water as delivery solvent. Enantiomeric purity was determined using a Hewlett-Packard Series 1050 system equipped with a chiral HLPC column (ChiralPak AD, 4.6 mm×150 mm) and isocratic elution using 5:95 isopropanol-hexane as a mobile phase.

The compounds were named using ChemDraw program from Cambridge Soft Inc.

Scheme 1-1
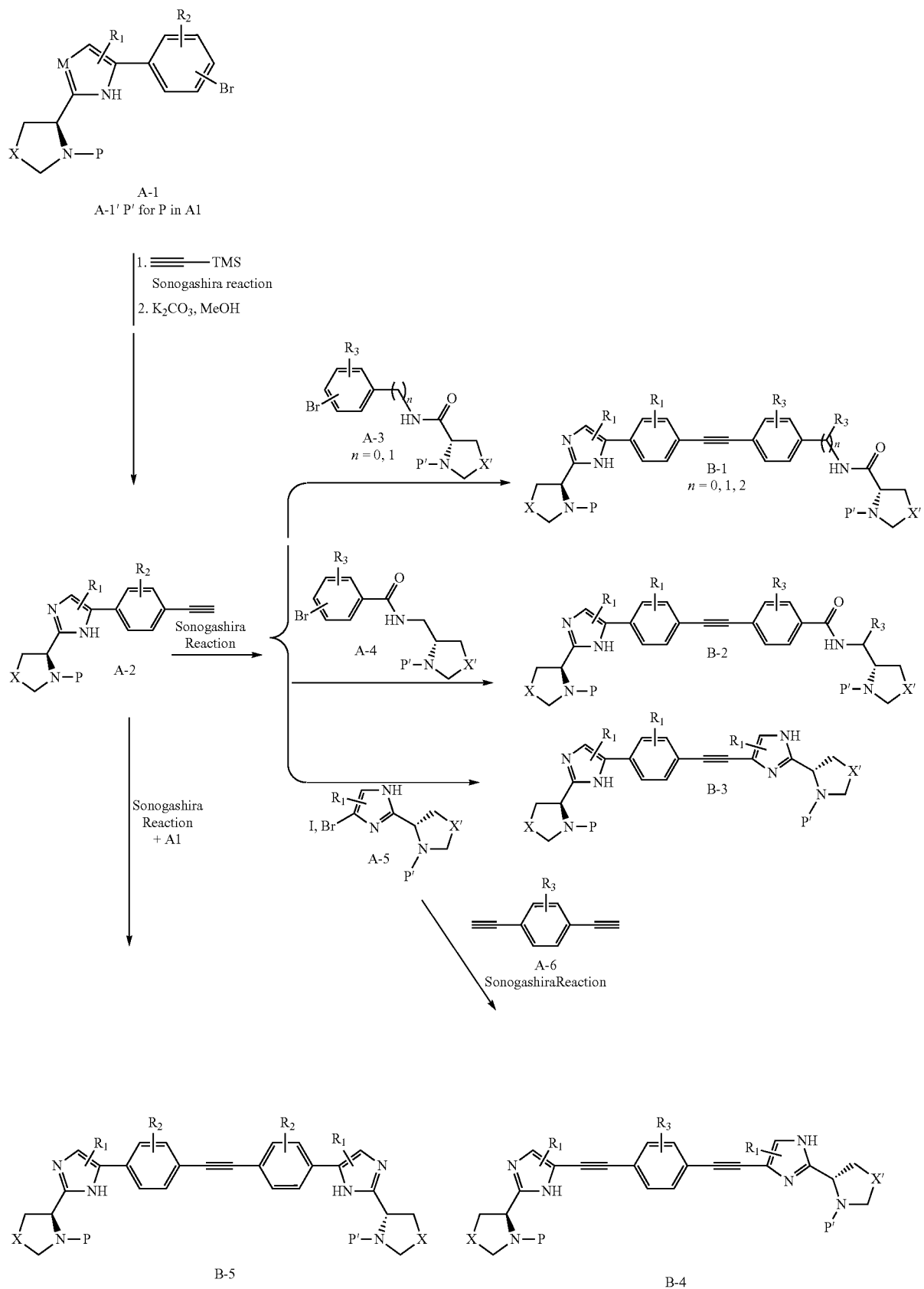

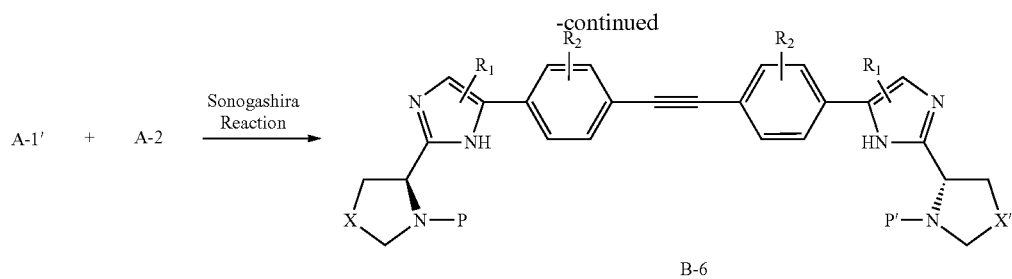

EXAMPLE 1

Scheme 1-1 depicts the general synthesis of scaffolds that contain an aryl-alkynyl moiety. For illustrative purposes, a substituted phenyl ring is used to represent an aryl group. The phenylimidazole intermediate A-1 can be prepared by following reported procedures. When A-1 (with a 4-bromo-substitutent) reacts with trimethylsilylacetylene in the presence of a palladium catalyst, typically Pd (PPh$_3$)$_2$Cl$_2$, CuI and a base such as triethylamine, the trimethylsilylacetylenyl substituted intermediate is formed, which upon treatment with K$_2$CO$_3$ in methanol affords compound A-2.

Under similar Sonogoshira conditions, compound A-2 reacts with A-1 to give cross coupled product B-5. By starting with a differentially protected analog A-1', compound B-6 is obtained. In similar fashion, acetylene intermediate A-2 couples with A-3, A-4, or A-5 to produce the cross coupled product B-1, B-2, or B-3, respectively. The cross coupling of diacetylyene A-6 with between two molecules of halide A-5 yields compound B-4.

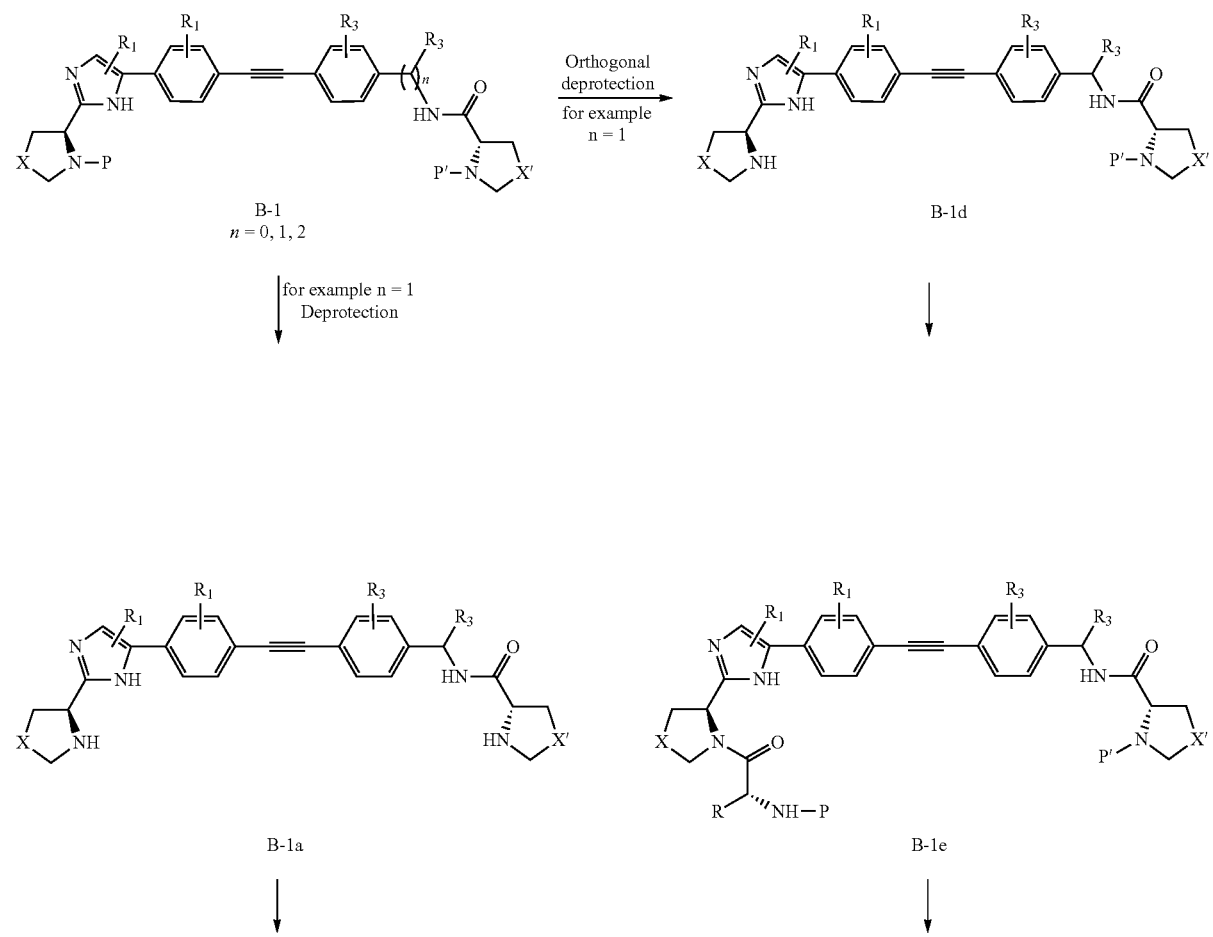

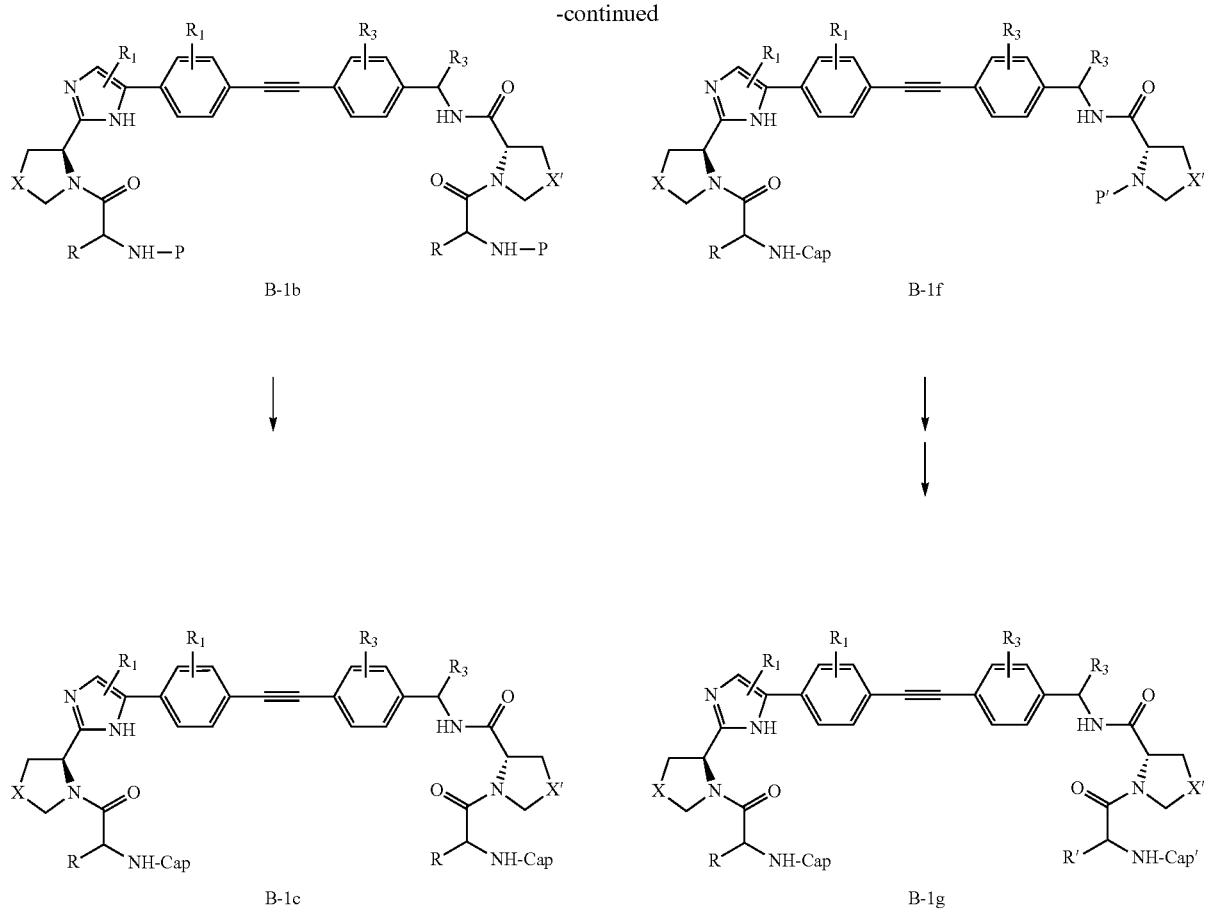

EXAMPLE 2

Scheme 2-1 illustrates the preparation of compounds by utilizing a variety of functional group manipulations. Scaffold B-1 is used here as an example. Starting from a properly protected B-1, the nitrogen protecting groups P and P' can be removed simultaneously to give B-1a. When B-1a is treated with a properly protected amino acid under standard peptide coupling conditions, such as HATU, Hunig's base, the doubly coupled product B-1b is obtained. The P group typically refers to a protecting group such as -Boc, Cbz, Troc, etc., P can also represent other alkyl, acyl, alkoxylcarbonyl, alkylaminocarbonyl groups that will be not removed. When P represents one of the removable protecting groups, it is removed to free the amino group for further derivatization to B-1c. The definition of Cap group is P and P'.

The protecting groups P and P' can be removed selectively to free one of the two amino groups in B-1 as in the B-1 to B-1d transformation. Those skilled in the art will understand that the P' group can be deprotected while the P group is preserved to give an alternative form such as B-1d. The free amino group of B-1d is coupled with another properly functionalized amino acid to give B-1e. When this process of selective deprotection and functionalization is repeated, compound B-1f is obtained. The newly introduced amino acid in B-1f can be either the same as the residue on the left-hand side of the molecule or can be different. From B-1f, a variety of compounds (with a general formula of B-1g) with differentially functionalized end pieces can be synthesized.

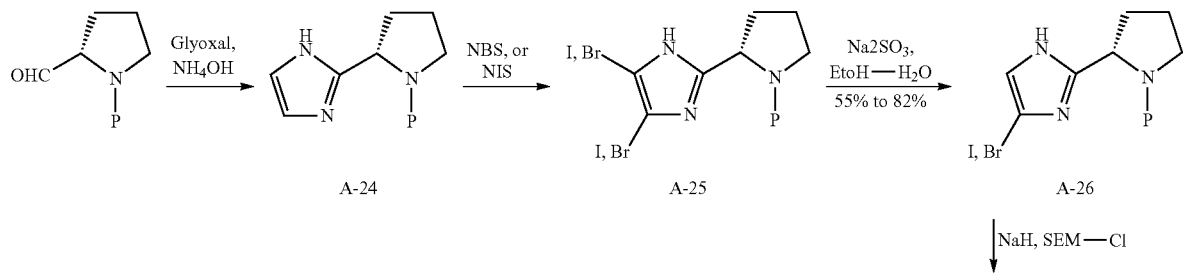

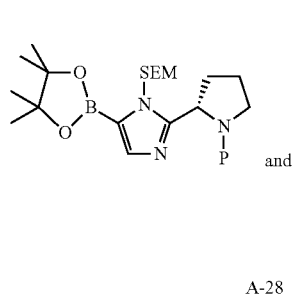
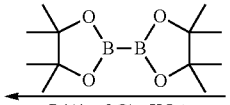
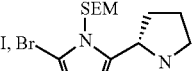
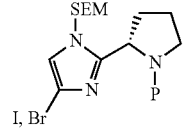

A-28 and A-27

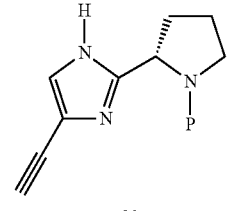
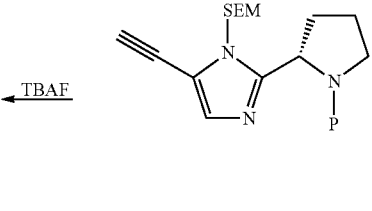

A-30     A-29

References:
1. *Polyhedron* 2005, 24, 2625
2. WO2008/021927

EXAMPLE 3

Scheme 3-1 using an L-proline-based structure as an example describes the synthesis of several key imidazole intermediates that are used for the construction of various more advanced intermediates in this invention. The commercially available L-prolinaldehyde is converted to imidazole A-24 by reacting with glyoxal in the presence of ammonium hydroxide.

The selective monohalogenation (bromination or iodination) is best achieved via a two-step sequence, i.e. non-selective dihalogenation followed by a selective removal of one of the two halogen atoms to A-26.

To facilitate the further functionalization, the imidazole moiety is preferably protected with SEM or other protecting groups. The protection process does generate a mixture of regioisomers of the protecting group. However, such a mixture does not usually affect the reactivity of the intermediates toward further reaction and will become one compound upon the removal of the protecting group.

The iodo- or bromo-imidazole intermediate A-27 is used converted to the corresponding borate A-28 under the conditions shown, or using conditions that are known to promote similar transformations. When the same intermediate A-27 is subjected to Sonogoshira coupling conditions, the acetylene compound A-28 is obtained after subsequent treatment with base.

The use of such an intermediate as an alternative way of synthesizing arylimidazole intermediates such as A-1 and B-3 is illustrated in Scheme 1-1. These versatile building blocks are used in many other manners as will be shown in the schemes to follow.

EXAMPLE 4

Synthesis of Compounds of Formula Vd

Compounds of formula Vd having structure Vd(i):

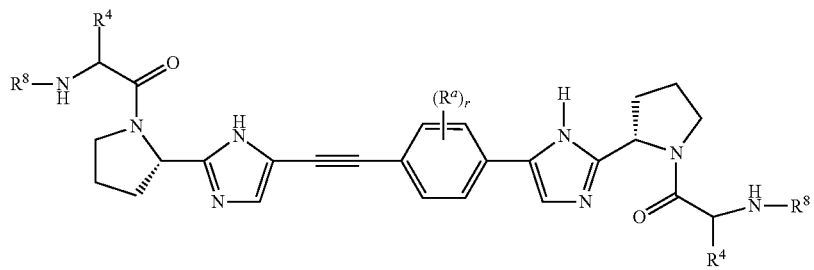

are made as in the following scheme.
Synthesis of Intermediate 8

Scheme 4-1

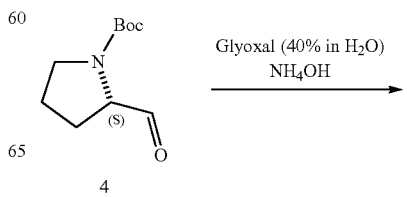

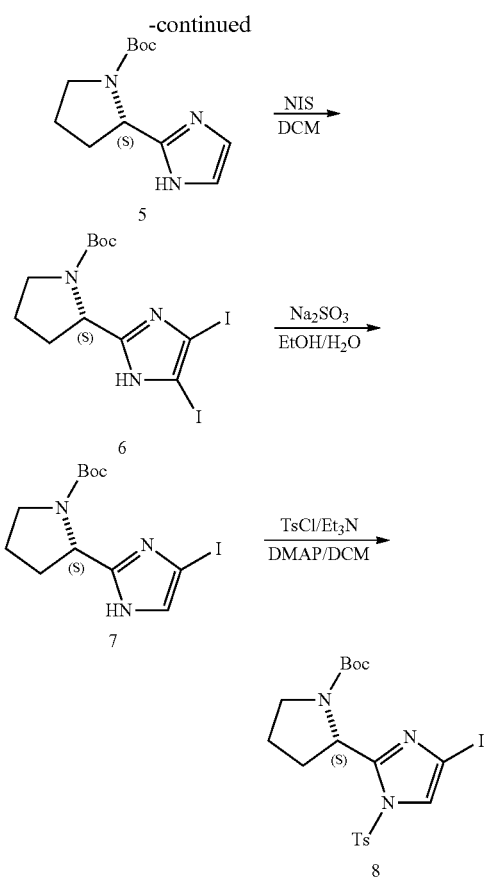

Step a.

Referring to Scheme 4-1, to a solution of N-Boc-L-prolinaldehyde (4) (20.0 g, 0.10 mol) in MeOH (200 mL) glyoxal (20.0 g, 0.34 mol) and NH$_4$OH (68.0 g, 1.90 mol) were added and the mixture was stirred at rt overnight. The organic solvent was removed under reduced pressure and the residue was purified by silica gel column chromatography (PE/EtOAc=1:1 (v/v)) to afford 5 (10.7 g, 45% yield) as a white solid. $^1$H NMR (500 MHz, CDCl$_3$) δ 1.48 (s, 9H), 1.96-2.12 (m, 3H), 2.91-2.92 (m, 1H), 3.38 (m, 2H), 4.93 (d, 1H, J=7.0 Hz), 6.96 (s, 2H) ppm. LC-MS (ESI): m/z 238.2 (M+H)$^+$.

Step b.

To a solution of (S)-tert-butyl 2-(1H-imidazol-2-yl)pyrrolidine-1-carboxylate (5) (10.0 g, 42.2 mmol) in DCM (300 mL) was added NIS (19.0 g, 84.4 mmol) slowly at 0° C. The reaction mixture was stirred 1 h at this temperature. The organic solvent was removed and the residue purified by silica gel column chromatography (PE/EtOAc=3:1 (v/v)) to afford 6 (18.2 g, 88% yield) as a yellow solid. LC-MS (ESI): m/z 490 (M+H)$^+$.

Step c.

To a suspension of (S)-tert-butyl 2-(4,5-diiodo-1H-imidazol-2-yl)pyrrolidine-1-carboxylate (6) (18.0 g, 36.8 mmol) in 800 mL EtOH/H$_2$O (v/v=30:70) solution was added Na$_2$SO$_3$ (39.4 g, 312.9 mmol). The mixture was refluxed for 17 h. EtOH was evaporated under reduced pressure and the residue was diluted with EtOAc. The organic layer was washed with brine and dried over Na$_2$SO$_4$ and then concentrated to dryness. The residue was purified by silica gel column chromatography (PE/EtOAc=3:1 (v/v)) to afford (S)-tert-butyl 2-(4-iodo-1H-imidazol-2-yl)pyrrolidine-1-carboxylate (7), (10.5 g, 80% yield) as a white solid. $^1$H NMR (500 MHz, DMSO) δ 1.16 (s, 5H), 1.38 (s, 4H), 1.80-1.91 (m, 3H), 2.08-2.18 (m, 1H), 3.30-3.46 (m, 2H), 4.66-4.76 (m, 1H), 7.16 (d, 1H, J=14 Hz), 12.04-12.09 (m, 1H) ppm; LC-MS (ESI): m/z calcd 364.0 (M+H)$^+$.

Step d.

To a solution of (S)-tert-butyl 2-(4-iodo-1H-imidazol-2-yl)pyrrolidine-1-carboxylate (7) (10.5 g, 28.9 mmol) in DCM (500 mL) was added TsCl (8.30 g, 43.4 mmol), Et$_3$N (8.76 g, 86.8 mmol) and DMAP (0.35 g, 2.90 mmol). The reaction mixture was stirred at rt for 2 h, and then concentrated under reduced pressure. The residue was treated with water and extracted with EtOAc (3×400 mL). The organic phase was washed with brine, dried, filtered, and concentrated to afford a crude product, which was purified by silica gel column chromatography (PE/EtOAc=5:1 (v/v)) and re-crystallization to afford 8 (10.0 g, 67% yield) as a white solid. LC-MS (ESI): m/z 518 (M+H)$^+$.

Synthesis of Intermediate 14

Scheme 4-2

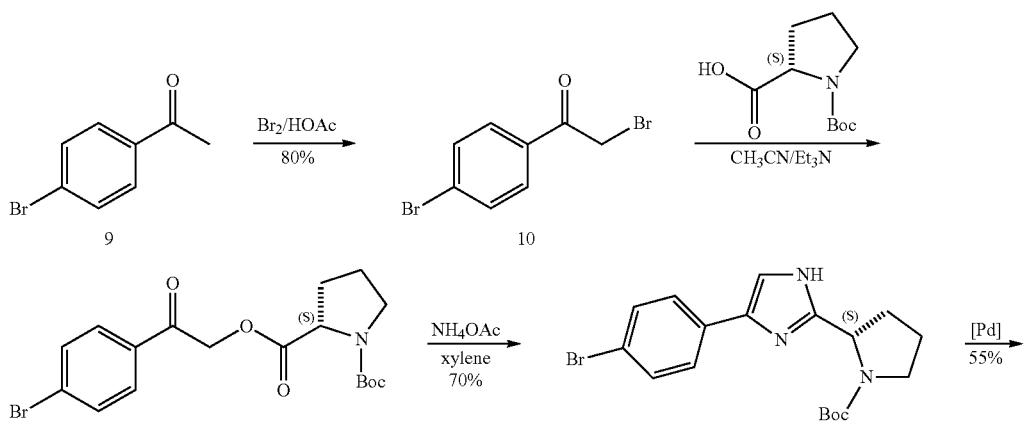

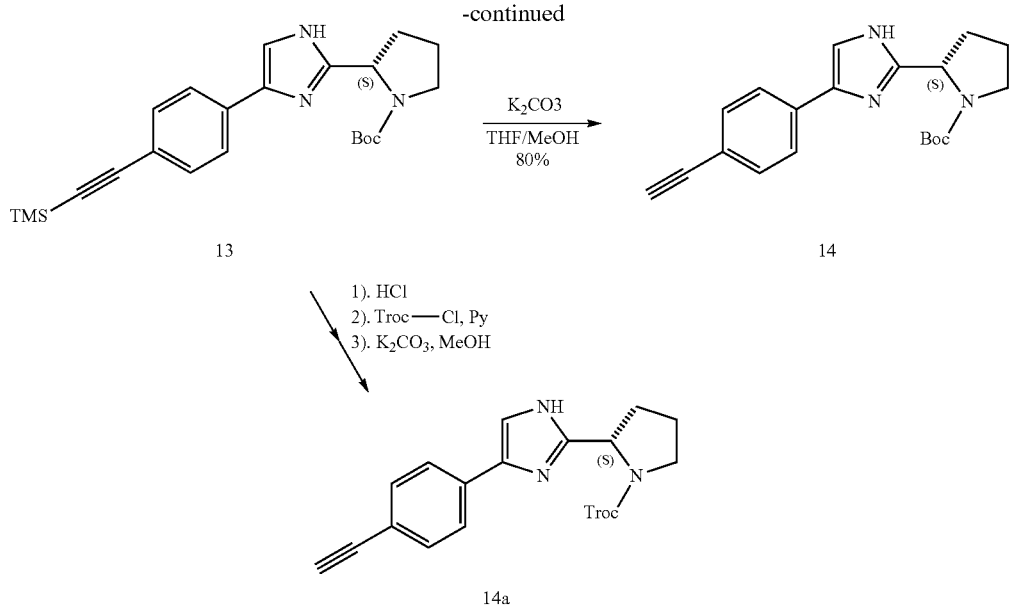

Step a.

Referring to Scheme 4-2, to a solution of 9 (115 g, 0.58 mol) in HOAc (200 mL) was added Br$_2$ (92.0 g, 0.58 mol) slowly, the mixture was stirred at rt for 2 h. The mixture was concentrated under reduced pressure and the residue was treated with water and extracted with EtOAc (3×400 mL). The organic phase was washed with saturated NaHCO$_3$, dried over anhydrous Na$_2$SO$_4$, filtered, and concentrated to afford a crude product, which was purified by recrystallization from PE/EtOAc (10/1 (v/v)) mixture to afford 10 (128 g, 80% yield) as a white solid.

Step b.

To a solution of 10 (120 g, 0.43 mol) in CH$_3$CN (300 mL) was added (S)— Boc-Pro-OH (97.0 g, 0.45 mol) and Et$_3$N (130 g, 1.29 mol) and the mixture was stirred at rt for 2 h. The mixture was concentrated under reduced pressure to afford 11. The crude product was used for next step without further purification.

Step c.

To a solution of 11 (159 g, 0.39 mol) in xylene (250 mL) was added NH$_4$OAc (300 g, 3.90 mol), the mixture was stirred at 140° C. for overnight. The mixture was concentrated under reduced pressure, the residue was purified by silica gel column chromatography (petroleum ether/EtOAc=10/1 (v/v)) to afford 12 (105 g, 70% yield) as a white solid. $^1$H NMR (500 MHz, CDCl$_3$) δ 1.48 (s, 9H), 1.96 (m, 1H), 2.16 (m, 2H), 3.01 (m, 1H), 3.42 (m, 2H), 4.96 (d, 1H, J=5.5 Hz), 7.22 (s, 1H), 7.46-7.55 (m, 4H) ppm; LC-MS (ESI): m/z 392 (M+H)$^+$.

Step d.

To a solution of 12 (10.0 g, 25.5 mmol) in anhydrous THF (100 mL) was added PPh$_3$ (1.34 g, 5.11 mmol), Pd (PPh$_3$)$_2$Cl$_2$ (1.79 g, 2.56 mmol), CuI (0.24 g, 1.28 mmol), DIPEA (7.75 g, 76.8 mmol), and TMS-acetylene (5.02 g, 51.2 mmol), the mixture was refluxed under argon for overnight. The organic solvent was removed under reduced pressure and residue was treated with water, extracted with EtOAc (2×100 mL), the combined organic phase was dried, filtered, and concentrated in vacuo to give a residue, which was purified by silica gel column chromatography (petroleum ether/EtOAc=3/1 (v/v)) to afford 13 (5.80 g, 55% yield) as a yellow solid. $^1$H NMR (500 MHz, CDCl$_3$) δ 0.21 (s, 9H), 1.49 (s, 9H), 1.97 (m, 1H), 2.16 (m, 2H), 2.40 (brs, 1H), 3.41 (m, 2H), 4.98 (d, 1H, J=7.0 Hz), 6.78 (s, 1H), 7.61-8.01 (m, 4H) ppm; LC-MS (ESI): m/z calcd. for C$_{23}$H$_{31}$N$_3$O$_2$Si 409.22. found 410.3 (M+H)$^+$.

Step e.

To a solution of 13 (5.80 g, 14.1 mmol) in THF (100 mL) and MeOH (100 mL) was added K$_2$CO$_3$ (5.85 g, 42.4 mmol), the mixture was stirred at rt for 3 h. The solvent was removed under reduced pressure and the residue was purified by silica gel column chromatography (DCM/MeOH=40:1 (v/v)) to afford 14 (3.80 g, 80%) as a yellow solid. $^1$H NMR (500 MHz, CDCl$_3$) δ 1.49 (s, 9H), 1.97 (m, 1H), 2.15 (m, 2H), 3.01 (brs, 1H), 3.40 (m, 2H), 4.96 (d, 1H, J=5.0 Hz), 7.24 (s, 1H), 7.47-7.52 (m, 4H) ppm.

Synthesis of Intermediate 14a

Referring still to Scheme 4-2, 50 mL 4N HCl/dioxane was added to a solution of 13 (14 g, 34.0 mmol) in dioxane (10 mL), and stirred at rt for 2.0 h. The mixture was concentrated to dryness to obtain a yellow solid, which was used directly for the next step.

Pyridine (8.2 mL, 102 mmol) was added to a hydrochloride salt of 13 in 150 mL DCM. After the mixture turned clear, TrocCl (7.1 mL, 68 mmol) was added drop-wise and stirred for 2.0 h. The reaction mixture was transferred to a separatory funnel and washed with H$_2$O and brine, dried over anhydrous Na$_2$SO$_4$, filtered and concentrated to obtain the Troc-protected compound (20 g) as a yellow solid. LC-MS (ESI): m/z calcd. for C$_{24}$H$_{25}$Cl$_6$N$_3$O$_4$Si 658.97. found 659.7 (M+H)$^+$, Ret. Time: 2.57 min. and calcd. for [M+H]$^+$ C$_{21}$H$_{24}$Cl$_3$N$_3$O$_2$Si 485.07. found 485.9, Ret. Time: 1.71 min.

Compound obtained from above (500 mg, 1.22 mmol) was dissolved in 30 mL THF/MeOH (1/1 (v/v)), K$_2$CO$_3$ (506 mg, 3.66 mmol) was added, the mixture stirred at rt for 2 h, and then concentrated to dryness. The residue was partitioned between H$_2$O and ethyl acetate. The organic layer was washed with brine, dried over anhydrous Na$_2$SO$_4$, filtered and concentrated in vacuo. The residue was purified by preparative HPLC to obtain 14a (320 mg, yield 64%). $^1$H NMR (500 MHz, DMSO) δ 1.91-2.10 (m, 4H), 2.22-2.28 (m, 1H), 3.46-

3.56 (m, 1H), 3.65-3.70 (m, 1H), 4.03 (s, 1H), 4.71 (s, 2H), 4.87-5.02 (m, 1H), 7.40-7.75 (m, 5H) ppm. LC-MS (ESI): m/z. (M+H)⁺412.

Synthesis of Compound 15 residue, which was neutralized by saturated NaHCO₃ and then extracted with DCM (4×50 mL). The combined organic phase was dried, filtered and concentrated in vacuo to afford 16 (0.50 g, 92% yield) as yellow solid, which was used for the

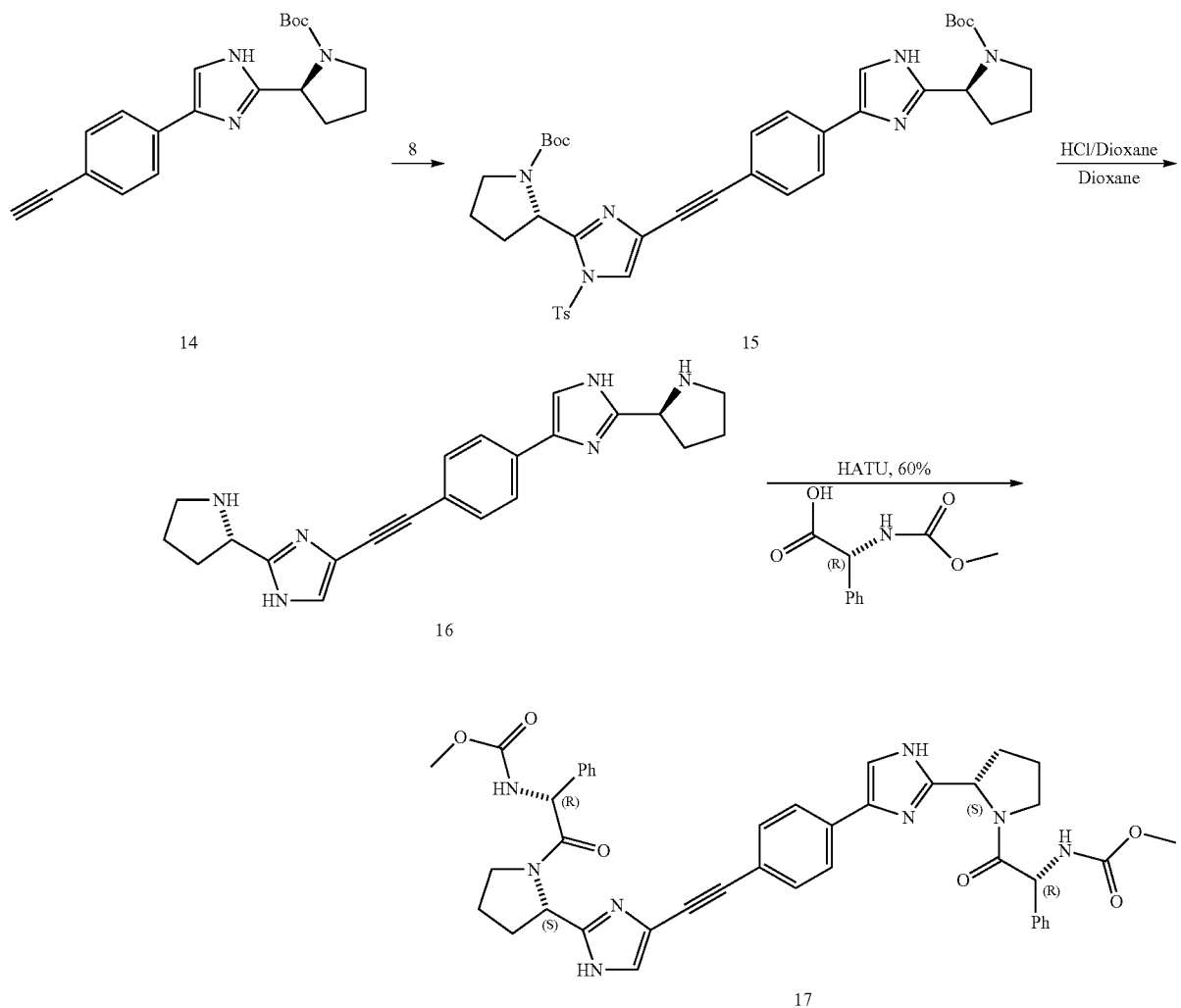

Step a.

Referring to Scheme 4-3, to a solution of 8 (1.0 g, 1.93 mmol) and 14 (0.65 g, 1.93 mmol) in 10 mL DMF was added Pd(PPh₃)₄ (0.22 g, 0.19 mmol), Et₃N (0.78 g, 7.74 mmol), the mixture was stirred at 120° C. in a microwave equipments (argon atmosphere) for 1 h. After cooling to rt, H₂O was added. The mixture was extracted with EtOAc (2×100 mL) and the combined organic phase was washed with H₂O and brine. Organic phase was then dried over anhydrous Na₂SO₄, filtered and concentrated in vacuo to give a residue. The residue as purified by silica gel column chromatography (DCM/MeOH=50/1 (v/v)) to afford 15 (0.7 g, 50% yield) as a yellow solid. LC-MS (ESI): m/z. calcd. for $C_{39}H_{46}N_6O_6S$ 726.32. found 727.3 (M+H)⁺.

Step b.

To a solution of 15 (0.70 g, 0.96 mmol) in 4 mL dioxane was added 4N HCl/dioxane (2.0 mL, 8 mmol). The mixture was stirred at rt for 2 h, then concentrated in vacuo to give a next step without further purification. LC-MS (ESI): m/z calcd. for $C_{22}H_{24}N_6$ 372.21. found 373.2 (M+H)⁺.

Step c.

To a solution of 16 (100 mg, 0.19 mmol) in 10 mL DMF was added (R)-2-(methoxycarbonylamino)-2-phenylacetic acid (89 mg, 0.43 mmol) and HATU (161 mg, 0.43 mmol). The mixture was stirred at rt for 1.5 h, then concentrated to remove the solvent. The residue obtained was purified by silica gel column chromatography (DCM/MeOH=40:1) to afford 17 (80 mg, 60% yield) as a yellow solid: ¹H NMR (500 MHz, CDCl₃) δ 1.91-2.23 (m, 7H), 2.86-2.91 (m, 2H), 3.18-3.23 (m, 2H), 3.65-3.75 (s+m, 8H), 5.22-5.30 (m, 2H), 5.32 (t, 2H, J=7.0 Hz), 6.06-6.07 (m, 2H), 7.24 (s, 1H), 7.39-7.52 (m, 12H), 7.62-7.68 (m, 2H) ppm; LC-MS (ESI): m/z calcd. for $C_{42}H_{42}N_8O_6$ 754.32. found 755.0 (M+H)⁺; HPLC showed >90% purity. Retention time=13.31 min 214 nm (detection wavelength).

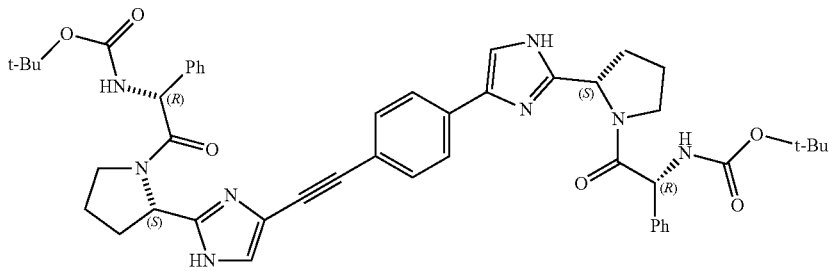

18

To a solution of compound 16 from Scheme 4-3 (0.10 g, 0.27 mmol) in DCM (4 mL) was added N-Boc-D-Phg-OH (0.16 g, 0.65 mmol). After several min, HATU (0.25 g, 0.65 mmol) was added, the reaction mixture was stirred at rt for 1.5 h, and then concentrated under reduced pressure. The residue obtained was purified by silica gel column chromatography (DCM/MeOH=40:1) to afford 18 (0.14 g, 60% yield) as a yellow solid. $^1$H NMR (500 MHz, CD$_3$OD) δ 1.46 (2 s, 18H), 1.98-2.18 (m, 6H), 2.38-2.48 (m, 2H), 4.02-4.08 (m, 2H), 5.22-5.32 (m, 2H), 5.46 (d, 2H, J=5.0 Hz), 7.12-7.48 (m, 1H), 7.40-7.45 (m, 10H), 7.66-7.70 (m, 2H), 7.84-7.85 (m, 2H), 7.92 (s, 1H) ppm; LC-MS (ESI): m/z calcd. for C$_{48}$H$_{54}$N$_8$O$_6$ 838.42. found 839.5 (M+H)$^+$; HPLC showed >97% purity. Retention time=16.62 min 214 nm (detection wavelength).

Preparation of Compound 19

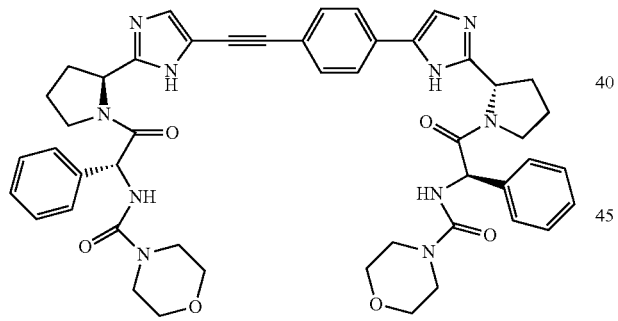

19

To a solution of compound 18 (0.20 g, 0.24 mmol) in dioxane (4 mL) was added 4 N HCl/dioxane (1.00 mL, 4.00 mmol). The mixture was stirred at rt for 2 h, then concentrated under reduced pressure. The residue was neutralized by addition of saturated NaHCO$_3$ and then extracted with DCM (4×50 mL). The combined organic phase was dried, filtered and concentrated in vacuo to afford the free amine. The free amine was dissolved in DCM (6 mL). The solution was cooled to 0° C. and morpholine carbonyl chloride (0.07 g, 0.48 mmol) was added. The solution was stirred for 0.5 h. The reaction mixture was concentrated under reduced pressure, and the resulting residue was purified by silica gel column chromatography (DCM/Hexane/MeOH=20/20/1 (v/v/v) followed by preparative HPLC to afford the deprotected compound (40 mg, 20% yield) as a white solid. $^1$H NMR (500 MHz, CDCl$_3$) δ 1.92-2.12 (m, 8H), 2.56-2.68 (m, 2H), 3.27-3.43 (m, 10H), 3.58-3.66 (m, 8H), 3.90 (t, 2H, J=7.5 Hz), 5.31-5.38 (m, 2H), 5.46-5.53 (m, 2H), 6.74 (brs, 1H), 7.21 (brs, 1H), 7.22-7.27 (m, 2H), 7.38-7.47 (m, 11H), 7.67 (d, 2H, J=8.0 Hz) ppm; LC-MS (ESI): m/z calcd. for C$_{48}$H$_{52}$N$_{10}$O$_6$ 864.41. found 865.3 (M+H)$^+$; HPLC showed >98% purity. Retention time=13.63 min 214 nm (detection wavelength).

Preparation of Compound 74

Scheme 4-4

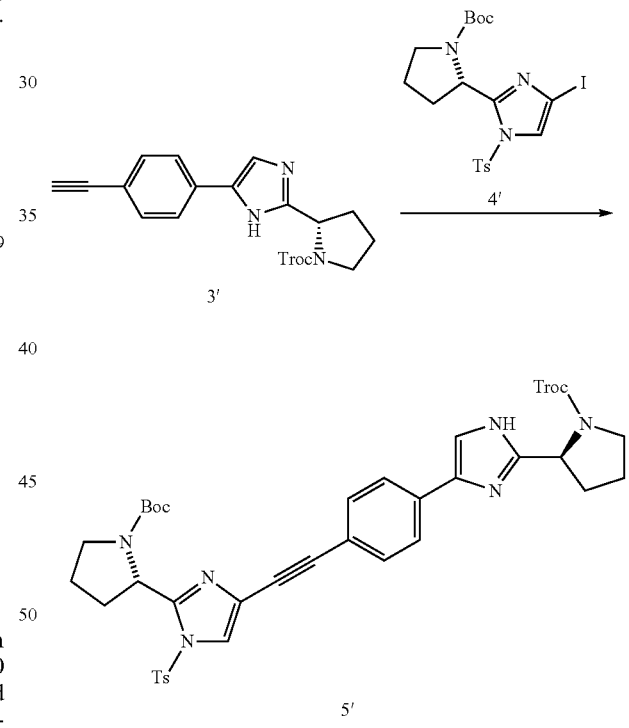

Referring to Scheme 4-4, a mixture of 4' (11.0 g, 21.3 mmol), 3' (12.0 g, 21.3 mmol), Pd (PPh$_3$)$_2$ Cl$_2$ (1.5 g, 2.1 mmol) and CuI (2.0 g, 1.05 mmol), DIPA (8 mL, 63.0 mmol) in 300 mL THF was stirred at rt for 2 h and then concentrated. The solution partitioned between H$_2$O and DCM and the organic layer was washed with H$_2$O (3×15 mL) and brine (15 mL), then dried over anhydrous Na$_2$SO$_4$ and filtered and concentrated in vacuo. The residue was purified by silica gel chromatography to obtain 5' (12.0 g, 68% yield). LC-MS (ESI): m/z calcd. for C$_{37}$H$_{39}$Cl$_3$N$_6$O$_6$S 800.17. found 801.9 (M+H)$^+$.

Scheme 4-5

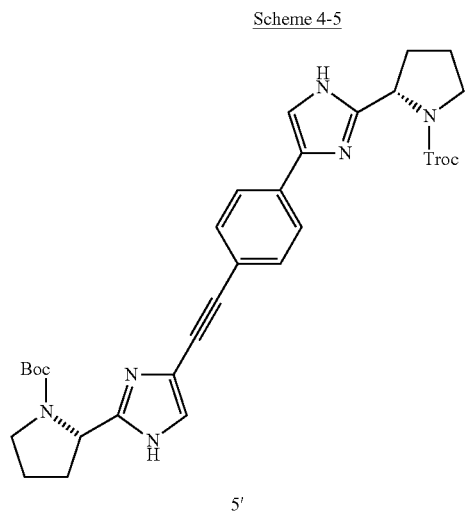

5'

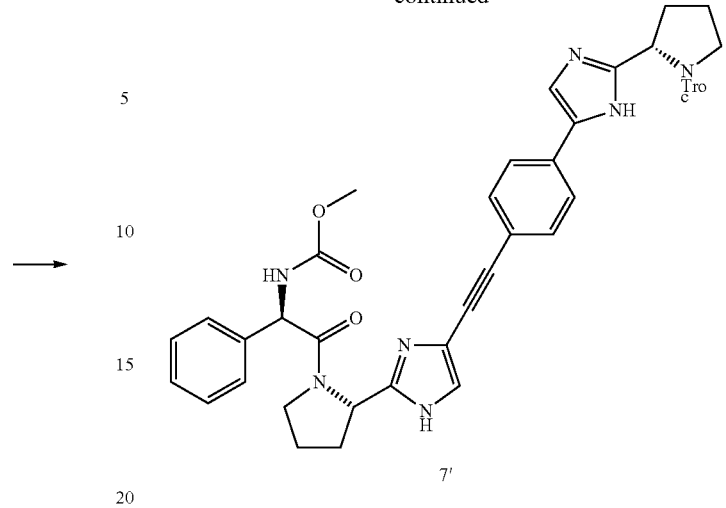

7'

Step a.
Referring to Scheme 4-5, compound 5' (1.1 g, 1.37 mmol) was dissolved in 5 mL dioxane. 4 N HCl/dioxane (5 mL) was added and stirred at rt for 3 h. The solvent was removed and the residue was washed with EtOAc. The residue was then filtered and dried in vacuo to obtain 6' (750 mg, 95% yield), which was used directly for the next step.

Step b.
To a solution of 6' (150 mg, 0.23 mmol) in 2 mL DMF was added DIPEA (0.3 mL, 1.15 mmol) followed by N-Moc-D-Phg-OH (58 mg, 0.27 mmol) and HATU (100 mg, 0.27 mmol). The mixture was stirred at rt for 1 h and then partitioned between H$_2$O and DCM. The organic phase was washed successively with H$_2$O (4×2 mL), dried over anhydrous Na$_2$SO$_4$, and concentrated in vacuo to obtain a crude residue. The residue was purified by Prep-TLC to give 7' (100 mg, 59% yield). $^1$H NMR (500 MHz, CDCl$_3$) δ 1.65-1.95 (m, 4H), 2.05-2.23 (m, 4H), 3.01-3.06 (m, 1H), 3.15-3.23 (m, 1H), 3.61-3.78 (s+m, 7H), 4.79-4.82 (m, 2H), 5.03-5.42 (m, 3H), 6.01 (d, 1H), 7.21-7.71 (m, 14H) ppm; LC-MS (ESI): m/z calcd. for C$_{35}$H$_{34}$Cl$_3$N$_7$O$_5$ 737.17. found 737.8.

To a solution of 7' (400 mg, 0.54 mmol) in 6 mL HOAc was added Zn dust (100 mg, 2.2 mmol), the mixture was heated to 50° C., and stirred for 4 h, then concentrated in vacuo, the residue was dissolved in THF and neutralized with aqueous NaHCO$_3$ till pH=8, the aqueous layer was washed 5% NaHCO$_3$, saturated NaCl solution and dried over Na$_2$SO$_4$, filtered and concentrated in vacuo to obtain 8' (240 mg, 64% yield). LC-MS (ESI): m/z calcd. for C$_{32}$H$_{33}$N$_7$O$_3$ 563.26. found 564.1 (M+H)$^+$.

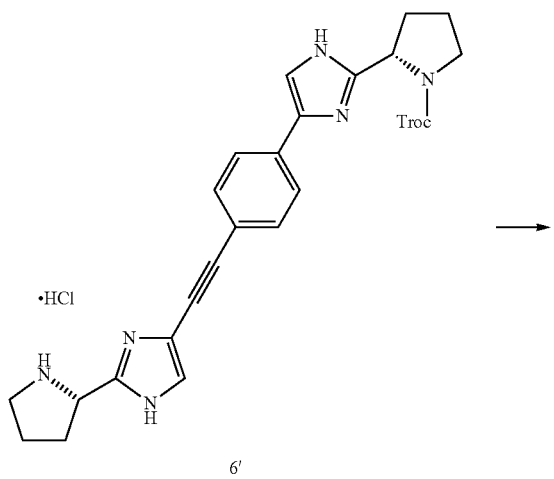

6'

Scheme 4-6

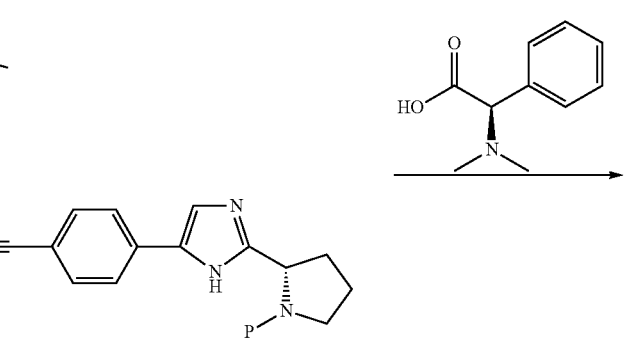

8' P = Troc
9' P = H

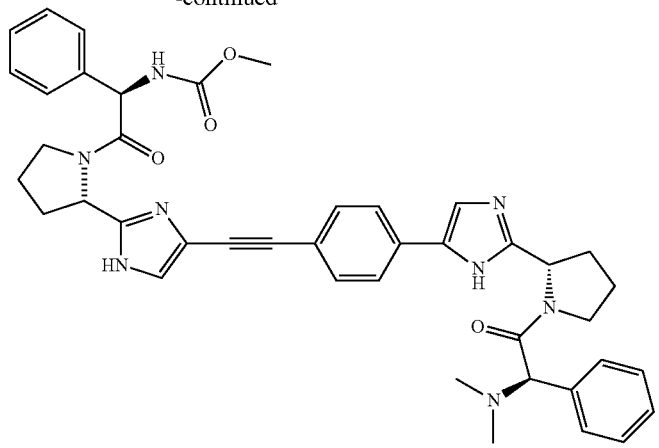

74

Referring to Scheme 4-6, to a solution of 8' (90 mg, 0.16 mmol) in 4 mL DMF was added Et$_3$N (0.11 mL, 0.8 mmol) at rt, followed by N,N-dimethyl-D-Phg-OH (34 mg, 0.19 mmol) and HATU (72 mg, 0.19 mmol). The mixture was stirred at rt for 1 h, then partitioned between H$_2$O and DCM. The organic phase was washed with H$_2$O (4×2 mL), dried over anhydrous Na$_2$SO$_4$, and concentrated in vacuo. The residue was purified by silica gel chromatography and preparative HPLC to give compound 74 (24 mg, 21% yield). $^1$H NMR (500 MHz, CDCl$_3$) δ 1.90-2.00 (m, 6H), 2.22-2.35 (s+m, 7H), 2.95-3.01 (m, 2H), 3.21 (m, 1H), 3.45 (m, 1H), 3.65-3.91 (s+m, 5H), 4.01 (s, 1H), 5.19-5.23 (m, 2H), 5.41-5.43 (m, 1H), 6.08 (brs, 1H), 7.22-7.70 (m, 16H), 10.53 (brs, 1H) ppm; LC-MS (ESI): m/z calcd. for C$_{42}$H$_{44}$N$_8$O$_4$ 724.35. found 725.0 [M+H]$^+$; HPLC showed 100% purity. Retention time=11.37 min 214 nm and 254 nm (detection wavelength).

Analogous compounds where the alkynyl-phenyl portion of the molecule is replaced by an alkynyl-phenyl-phenyl substructure such as in the compounds of formula VIIb, alkynyl-phenyl-benzimidazoyl structure such as the compounds of formulae Vc and Vd, or alkynyl-(1,5)-naphthyl structures were made using similar procedures to those for making 74.

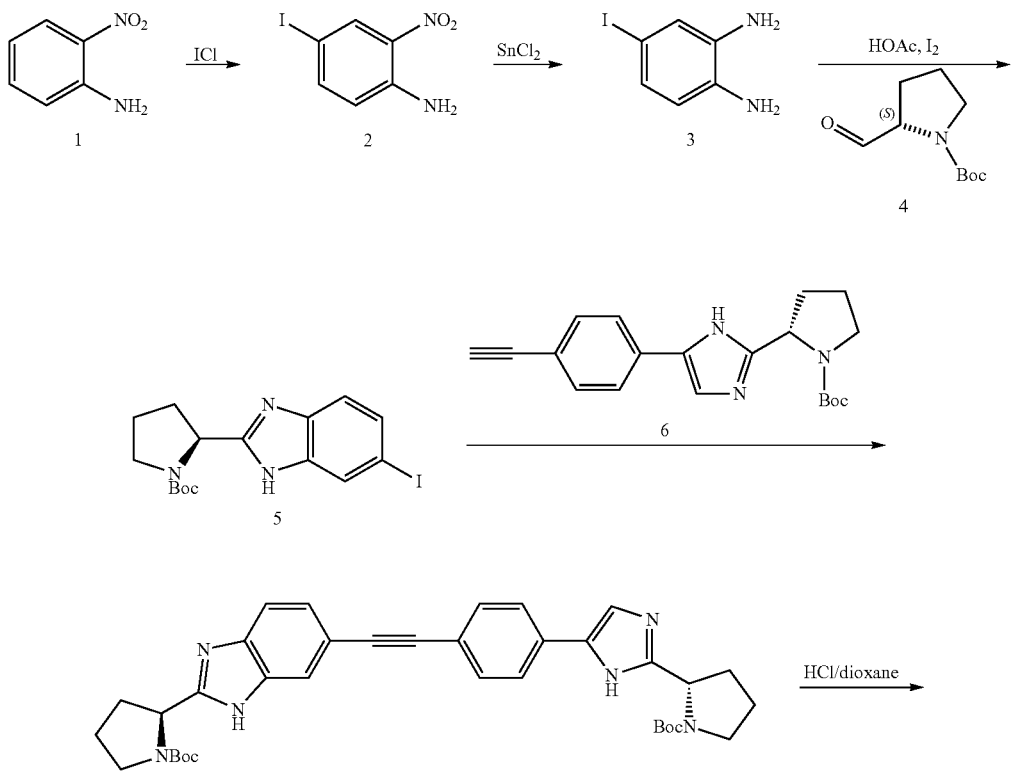

Scheme 5-1

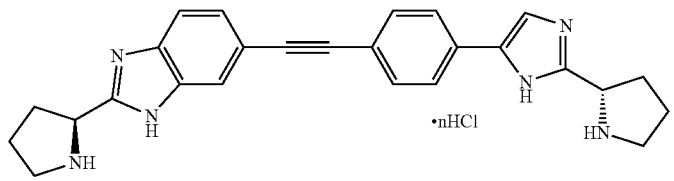
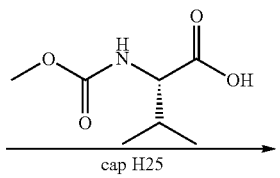

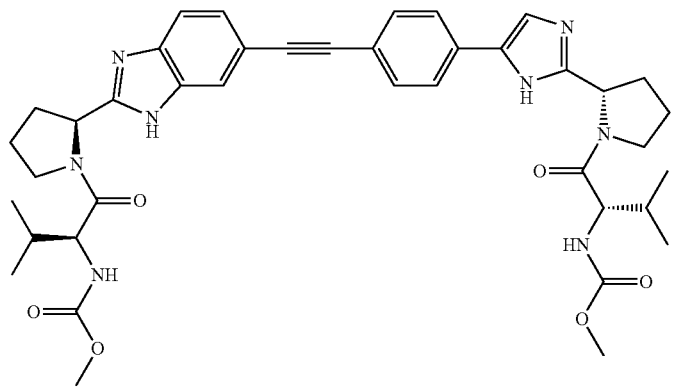

104

EXAMPLE 5

Synthesis of Compounds of Formula IVb

Step a.

Referring to Scheme 5-1, to a stirred solution of 1 (18.8 g, 137 mmol) and NaOAc (12.7 g, 155 mmol) in AcOH (70 mL) was added ICl (25.0 g, 155 mmol) in AcOH (40 mL) slowly over 30 min. The mixture was heated at 50° C. for 30 min and stirred at rt for additional 30 min. The reaction mixture was poured slowly into $H_2O$ (150 mL) while vigorous stirring and the stirring was continued for 17 h. The resulting precipitate was collected by filtration, washed with water (100 mL), dried under vacuum to give 2 (35 g, 95% yield) as a red powder. LC-MS (ESI) m/z 264.9 $(M+H)^+$.

Step b.

To a stirred solution of $SnCl_2$ (78.0 g, 346 mmol) in concentrated HCl (150 mL) was added 2 (25.4 g, 92.0 mmol) in three portions over 30 min at rt. The reaction mixture was heated at 70° C. for 1 h and then stirred at 0° C. overnight. The mixture was treated with $H_2O$ (150 mL) and stirred for 2 h. The precipitate was collected by filtration and dried under vacuum to afford 3 (17 g, 81% yield) as a grey solid. LC-MS (ESI) m/z 235.0 $(M+H)^+$.

Step c.

A mixture of 3 (1.05 g, 4.4 mmol), (S)-tert-butyl 2-formylpyrrolidine-1-carboxylate (4) (1.01 g, 4.4 mmol) and iodine (0.11 g, 0.44 mmol) in AcOH (5 mL) was stirred at rt in open air overnight, then neutralized with aqueous $NaHCO_3$, extracted with EtOAc (3×100 mL). The organic layer was washed with brine, dried over anhydrous $Na_2SO_4$, filtered and concentrated in vacuo. The residue was purified by silica gel chromatography (Petroleum ether/EtOAc=4/1 (v/v)) to afford 5 (500 mg, 30% yield) as a yellow solid. LC-MS (ESI) m/z 414.1 $(M+H)^+$.

Step d.

A mixture of 5 (630 mg, 1.53 mmol), 6 (520 mg, 1.53 mmol), Pd $(PPh_3)_2Cl_2$ (56 mg, 0.080 mmol) and CuI (8 mg, 0.04 mmol), P(t-Bu)$_3$ (1.1 mL, 0.31 mmol), piperidine (1.05 mL, 4.60 mmol) in DMF (20 mL) was stirred at 40° C. for 12 h. The reaction mixture was partitioned between $H_2O$ and DCM. The organic layer was washed with $H_2O$ (4×50 mL) and brine (15 mL), dried over anhydrous $Na_2SO_4$, filtered and then concentrated in vacuo. The residue was purified by silica gel chromatography (DCM/MeOH=50/1 (v/v)) to afford 7 (550 mg, 50% yield) as a pale yellow solid. LC-MS (ESI) m/z 623.3 $(M+H)^+$.

To a stirred solution of 7 (200 mg, 0.32 mmol) in dioxane (3 mL) was added 4 N HCl/dioxane (3 mL) and the mixture was stirred at rt for 3 h. The solvent was removed in vacuo to yield 8 (220 mg), which was used directly for the next step.

To a solution of 8 (220 mg, 0.320 mmol) in DMF (2 mL) was added $Et_3N$ (0.34 mL, 3.2 mmol), followed by N-methoxycarbonyl-L-Val-OH (140 mg, 0.800 mmol) and HATU (306 mg, 0.800 mmol). After stirring for 1 h at rt, the solution was partitioned between $H_2O$ and DCM. The organic phase was washed successively with $H_2O$ and brine, dried over anhydrous $Na_2SO_4$, filtered and concentrated in vacuo. The residue was purified by prep-HPLC to give target molecule, 104 (40 mg, 28% yield) as a white powder. $^1H$ NMR (500 MHz, $CDCl_3$) δ 7.80-7.10 (m, 8H), 5.51-5.49 (m, 2H), 5.42-5.40 (m, 1H), 5.26-5.25 (m, 1H), 4.36-4.34 (m, 2H), 3.88-3.85 (m, 2H), 3.77-3.75 (m, 2H), 3.71-3.70 (m, 6H), 2.98 (s, 2H), 2.50-2.00 (m, 9H), 0.89 (s, 12H) ppm; LC-MS (ESI) m/z 737.4 $(M+H)^+$ Scheme 5-2

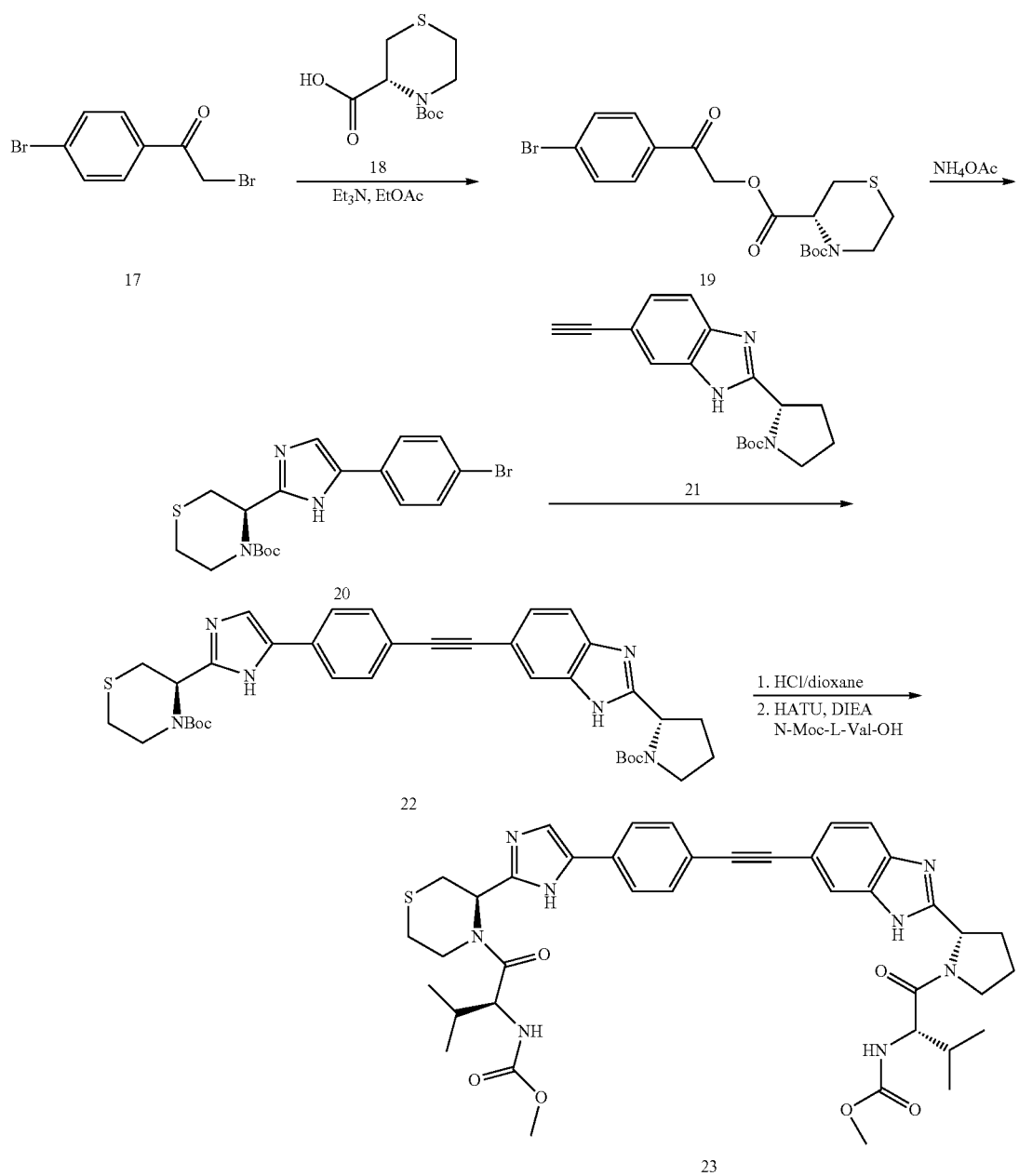

Step a.

Referring to Scheme 5-2, a mixture of compound 17 (667 mg, 2.4 mmol), (R)—N-Boc-thiomorpholine-3-carboxylic acid (594 mg, 2.4 mmol) and Et$_3$N (486 mg, 4.8 mmol) in EtOAc (20 mL) was stirred at rt for 2 h. Subsequently, the reaction mixture was concentrated and the residue was dried in vacuo to give crude compound 19, which was used for the next step without further purification. LC-MS (ESI): m/z 466.0 (M+Na)$^+$.

Step b.

A mixture of compound 19 obtained from the reaction above and NH$_4$OAc (1.85 g, 24 mmol) in toluene (15 mL) was refluxed overnight. The solvent was removed and the residue was purified by silica gel column chromatography (Petroleum ether/EtOAc=3/1 (v/v)) to give compound 20 (856 mg, 84% yield) as a yellow solid. LCMS (ESI): m/z 424.1 (M+H)$^+$.

Step c.

To a mixture of compound 20 (361 mg, 0.85 mmol), compound 21 (290 mg, 0.93 mmol), CuI (16 mg, 0.085 mmol), P(t-Bu)$_3$ (35 mg, 0.17 mmol), and piperidine (289 mg, 3.4 mmol) in 5 mL of DMF was added Pd(PPh$_3$)$_2$Cl$_2$ (60 mg, 0.085 mmol). After stirring at 80'C overnight under an atmosphere of N$_2$, the reaction mixture was poured into H$_2$O (100 mL) and the resulting suspension was extracted with EtOAc several times (20 mL×3). The extracts were combined, washed with brine, and dried with anhydrous Na$_2$SO$_4$. The solvent was removed and the residue was purified by silica gel column chromatography (Petroleum ether/acetone=2/1

(v/v)) to give compound 22 (95 mg, 17% yield) as an off-white solid. LC-MS (ESI): m/z 655.3 (M+H)⁺.

Step d.

A mixture of compound 22 (80 mg, 0.12 mmol) in 4N HCl in dioxane (3 mL) was stirred at rt several hours. The mixture was concentrated and the residue was dried in vacuo to give an HCl salt, which was used without further purification. LC-MS (ESI): m/z 455.2 (M+H)⁺.

Step e.

Subsequently, the HCl salt was dissolved in DMF (2 mL) and the resulting mixture was sequentially added DIPEA (155 mg, 1.2 mmol), N-Moc-L-Val-OH (44 mg, 0.25 mmol), and HATU (127 mg, 0.36 mmol). After stirring at rt for 30 min, the reaction mixture was slowly added into water (20 mL). The resulting suspension was filtered and the solid was purified by preparative HPLC to give compound 23. LC-MS (ESI): m/z 769.3 (M+H)⁺.

Scheme 5-3

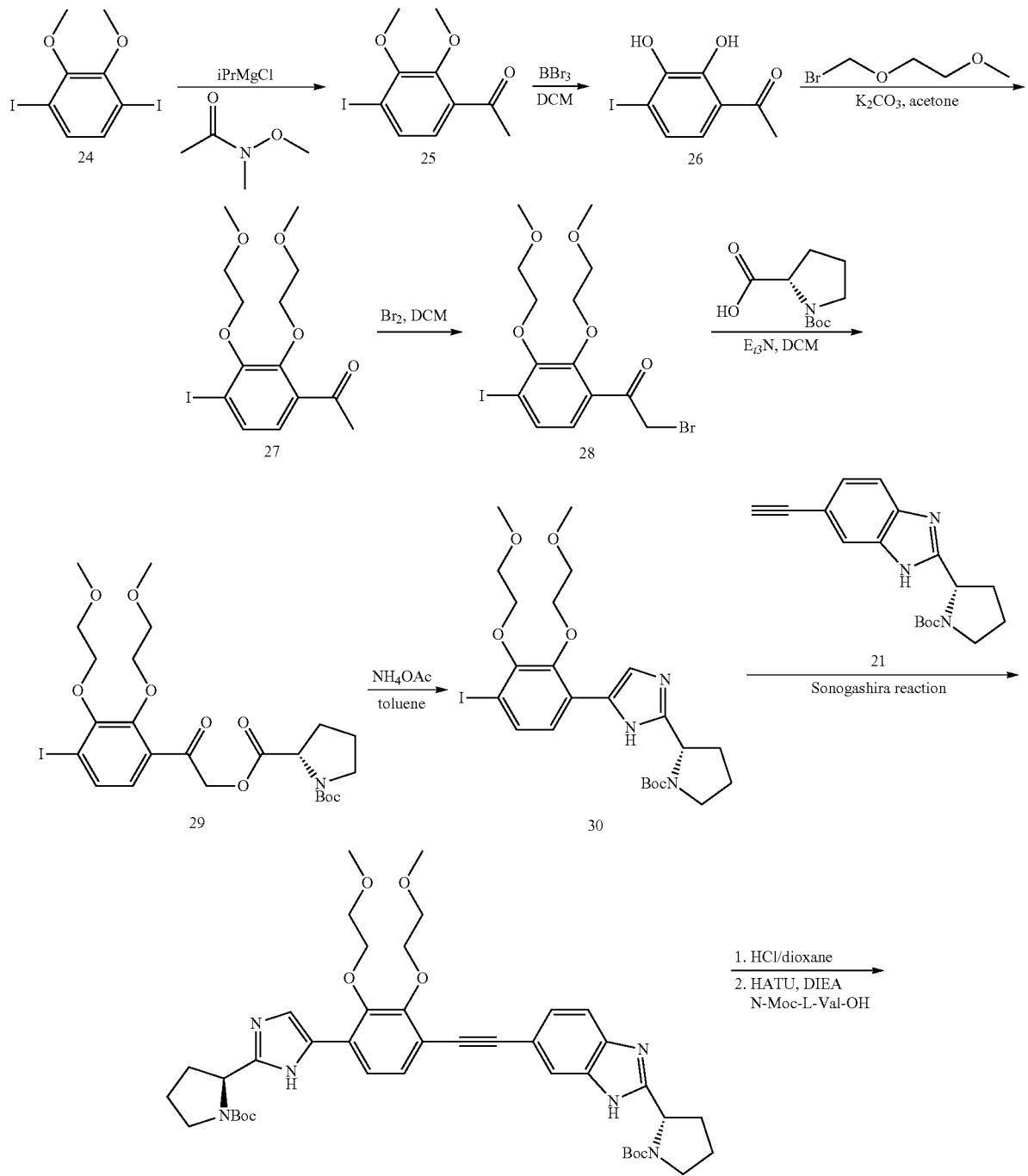

-continued

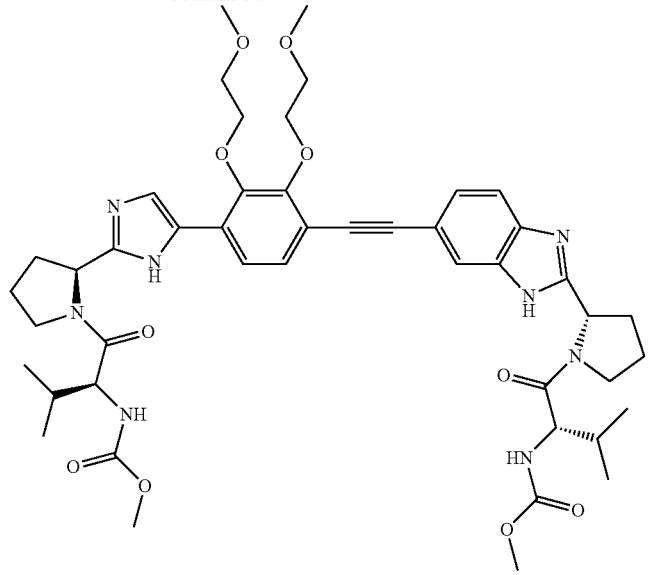

32

Step a.

Referring to scheme 5-3, to a solution of compound 24 (2.45 g, 6.3 mmol) in THF (20 mL) was slowly added 2.0M i-PrMgCl in Et$_2$O (3.2 mL) at −78° C. After stirring at −78° C. for 1 h, the reaction mixture was added N-methoxy-N-methylacetamide (779 mg, 7.6 mmol). Subsequently, the mixture was slowly warmed up to rt and diluted with EtOAc (100 mL). The mixture was washed with H$_2$O (20 mL×3) and dried with anhydrous Na$_2$SO$_4$. The solvent was removed and the residue was purified by silica gel column chromatography (Petroleum ether/EtOAc=10/1 (v/v)) to give compound 25 (1.25 g, 65% yield). $^1$H NMR (CDCl$_3$, 500 MHz): δ 7.56 (d, 1H, J=10.0 Hz), 7.16 (d, 1H, J=10.5 Hz), 3.95 (s, 3H), 3.88 (s, 3H), 2.61 (s, 3H) ppm; LC-MS (ESI): m/z 307.0 (M+H)$^+$.

Step b.

To a solution of compound 25 (1.0 g, 3.3 mmol) in dichloromethane (20 mL) was slowly added 4N BBr$_3$ in DCM (4.9 mL) at 0° C. After stirring at rt for 30 min, the reaction was quenched by adding H$_2$O (20 mL). The organic layer was separated and dried with anhydrous MgSO$_4$. The solvent was removed and the residue was purified by silica gel column chromatography (PE/acetone=10/1 (v/v)) to give compound 26 (800 mg, 88% yield). $^1$H NMR (DMSO, 500 MHz): 612.52 (s, 1H), 9.96 (s, 1H), 7.30 (d, 1H, J=8.5 Hz), 7.19 (d, 1H, J=9.0 Hz), 2.62 (s, 3H) ppm; LC-MS (ESI): m/z 278.9 (M+H)$^+$.

Step c.

To a solution of compound 26 (800 mg, 2.9 mmol) in acetone (30 mL) was added K$_2$CO$_3$ (4.0 g, 29 mmol), 1-bromo-2-methoxyethane (1.9 g, 11.5 mmol), and KI (1.4 g, 8.7 mmol) at rt. After refluxing for 12 h, the reaction mixture was filtered through CELITE™ 545 and the filter cake was washed with EtOAc several times (100 mL×3). The filtrate was washed with brine and dried with anhydrous Na$_2$SO$_4$. The solvent was removed and the residue was purified by silica gel column chromatography (Petroleum ether/acetone=2/1 (v/v)) to give compound 27 (651 mg, 57% yield). $^1$H NMR (CDCl$_3$, 500 MHz): δ 7.57 (d, 1H, J=8.0 Hz), 7.21 (d, 1H, J=8.0 Hz), 4.28 (t, 2H, J=5.0 Hz), 4.19 (t, 2H, J=4.0 Hz), 3.80 (t, 2H, J=5.0 Hz), 3.63 (t, 2H, J=4.5 Hz), 3.47 (s, 3H), 3.35 (s, 3H), 2.65 (s, 3H) ppm; LC-MS (ESI): m/z 395.0 (M+H)$^+$.

Step d.

To a solution of compound 27 (210 mg, 0.53 mmol) in DCM (5 mL) was added Br$_2$ (85 mg, 0.53 mmol) at rt. After stirring at rt for 2 h, the reaction mixture was concentrated and the residue was dried in vacuo to give crude compound 28, which was used for the next step without further purification. LC-MS (ESI): m/z 472.9 (M+H)$^+$.

Step e.

A mixture of compound 28 obtained from the reaction above, N-Boc-L-Pro-OH (114 mg, 0.53 mmol), and Et$_3$N (162 mg, 1.6 mmol) in EtOAc (5 mL) was stirred at rt for 2 h. Subsequently, the reaction mixture was concentrated and the residue was dried in vacuo to give crude compound 29, which was used for the next step without further purification. LC-MS (ESI): m/z 608.1 (M+H)$^+$.

Step f.

A mixture of compound 29 obtained from the reaction above and NH$_4$OAc (409 mg, 5.3 mmol) in toluene (10 mL) was stirred at 110° C. overnight. Subsequently, the reaction mixture was concentrated and the residue was purified by silica gel column chromatography (Petroleum ether/acetone=2/1 (v/v)) to give compound 30 (110 mg, 35% yield, three steps from compound 27). LC-MS (ESI): m/z 588.1 (M+H)$^+$.

Step g.

A mixture of compound 21 (63 mg, 0.20 mmol), compound 30 (110 mg, 0.19 mmol), Pd(PPh$_3$)$_2$Cl$_2$ (13 mg, 0.019 mmol), CuI (3.6 mg, 0.019 mmol), P(t-Bu)$_3$ (7.7 mg, 0.038 mmol), and piperidine (77 mg, 0.9 mmol) in DMF (5 mL) was stirred at 80° C. overnight under an atmosphere of N$_2$. Subsequently, the reaction mixture was diluted with H$_2$O (50 mL) and the aqueous layer was extracted with DCM several times (20 mL×3). The extracts were combined, washed with brine, and dried with anhydrous Na$_2$SO$_4$. The solvent was removed and the residue was purified by silica gel column chromatography (PE/acetone=2/1 (v/v) to give compound 31 (67 mg, 46% yield). LC-MS (ESI): m/z 771.4 (M+H)$^+$.

Step h.

A mixture of compound 31 (60 mg, 0.08 mmol) in 4N HCl/dioxane (3 mL) was stirred at rt for 2 h. The reaction mixture was concentrated and the residue was dried in vacuo to give an HCl salt, which was used for the next step without further purification. LC-MS (ESI): m/z 571.3 (M+H)$^+$.

Step i.

To a mixture of the HCl salt in DMF (3 mL) was added DIPEA (103 mg, 0.8 mmol), followed by N-Moc-L-Val-OH (35 mg, 0.2 mmol) and HATU (76 mg, 0.2 mmol). After stirring at rt for 30 min, the reaction mixture was poured into water. The solid was collected by filtration and purified by preparative HPLC to give compound 32. LC-MS (ESI): m/z 885.4 (M+H)$^+$.

Scheme 5-4

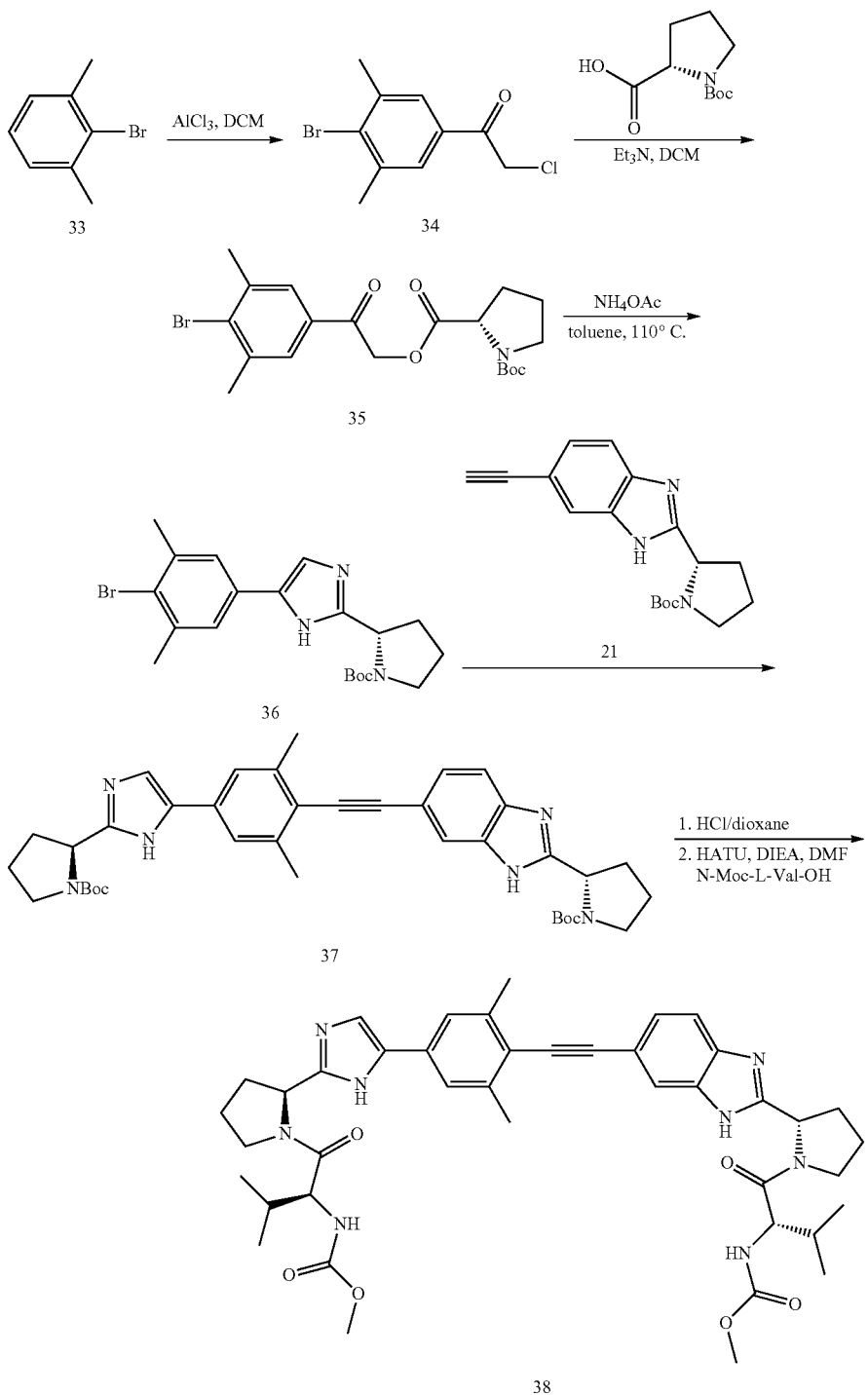

Step a.

Referring to Scheme 5-4, to a solution of compound 33 (20 g, 0.11 mol) in DCM (1000 mL) was added anhydrous $AlCl_3$ (16 g, 0.12 mol), followed by 2-chloroacetyl chloride (12.4 g, 0.11 mol) at 0° C. After stirring at 0° C. for 1 h, the reaction was quenched by adding $H_2O$ (400 mL) and the resulting mixture was extracted with DCM several times (50 mL×3). The extracts were combined, washed with brine, and dried with anhydrous $Na_2SO_4$. The solvent was removed and the residue was purified by silica gel column chromatography, followed by re-crystallization from a solution of Petroleum ether/EtOAc (9/1 (v/v)) to give compound 34 (20 g, 70% yield). LC-MS (ESI): m/z 261.0 $(M+H)^+$.

Step b.

To a solution of compound 34 (18.2 g, 70 mmol) in DCM (500 mL) was added N-Boc-L-Pro-OH (15.1 g, 70 mmol), followed by $Et_3N$ (77.9 g, 77 mmol) at rt. After stirring at rt for 2 h, the reaction mixture was concentrated and the residue was dried in vacuo to give crude compound 35, which was used for the next step without further purification. LC-MS (ESI): m/z 440.1 $(M+H)^+$.

Step c.

A mixture of compound 35 obtained from the reaction above and $NH_4OAc$ (54 g, 0.7 mol) in toluene (350 mL) was stirred at 110° C. overnight. Subsequently, the reaction mixture was concentrated and the residue was purified by silica gel column chromatography (PE/EtOAc=10/1 (v/v)) to give compound 36 (17.6 g, 60% yield, two steps from compound 34). LC-MS (ESI): m/z 420.1 $(M+H)^+$.

Step d.

To a mixture of compound 21 (342 mg, 1.1 mmol), compound 36 (420 mg, 1.0 mmol), CuI (19 mg, 0.1 mmol), tris(2-methoxyphenyl)phosphine (70 mg, 0.2 mmol), and piperidine (255 mg, 3.0 mmol) in DMF (10 mL) was added $Pd(OAc)_2$ (22 mg, 0.10 mmol) under an atmosphere of $N_2$. After stirring at 80° C. under an atmosphere of $N_2$ overnight, the reaction mixture was poured into ice $H_2O$ (50 mL). The solid was collected and purified by silica gel column chromatography (PE/EtOAc=2/1 (v/v)) to give compound 37 (220 mg, 34% yield) as an off-white solid. LC-MS (ESI): m/z 651.4 $(M+H)^+$.

Step e.

A mixture of compound 37 (120 mg, 0.18 mmol) in 4N HCl/dioxane (4 mL) was stirred at rt for 3 h. Subsequently, the reaction mixture was concentrated and the residue was dried in vacuo to give an HCl salt, which was used for the next step without further purification. LC-MS (ESI): m/z 451.3 $(M+H)^+$.

Step f.

To the HCl salt in DMF (2 mL) was added DIPEA (233 mg, 1.8 mmol), followed by N-Moc-L-Val-OH (70 mg, 0.4 mmol), and HATU (152 mg, 0.4 mmol). After stirring at rt for 10 min, the reaction mixture was slowly added into water. The solid was collected by filtration and purified by preparative HPLC to give compound 38. LC-MS (ESI): m/z 765.4 $(M+H)^+$.

EXAMPLE 6

Synthesis of Compounds of Formula Mb

Synthesis of Example Compounds 38 and 49

Scheme 6-1

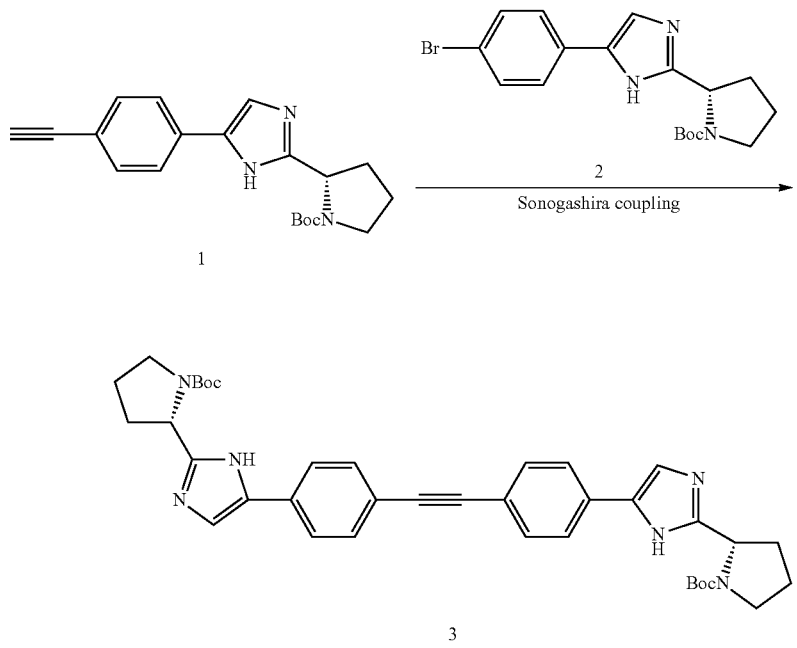

Referring to Scheme 6-1, to a solution of the compound 1 (402 mg, 1.19 mmol), 2 (390 mg, 1.0 mmol), CuI (4.8 mg, 0.025 mmol), $PPh_3$ (51 mg, 0.17 mmol), DIPA (0.46 ml, 3.0 mmol), Pd $(PPh_3)_2Cl_2$ (36 mg, 0.1 mmol) in DMF (1 mL) was added. The mixture was heated to 120° C. for 35 min under an atmosphere of Ar in a microwave reactor and then cooled to rt. The mixture was poured into $H_2O$, extracted with EtOAc, washed with brine, dried over $MgSO_4$, filtered and concentrated in vacuo. The residue was purified by silica gel column chromatography to provide 3 (324 mg, 50% yield). LC-MS (ESI): m/z calcd. for $C_{38}H_{44}N_6O_4$ 648.34. found 649.0 $[M+H]^+$.

Scheme 6-2
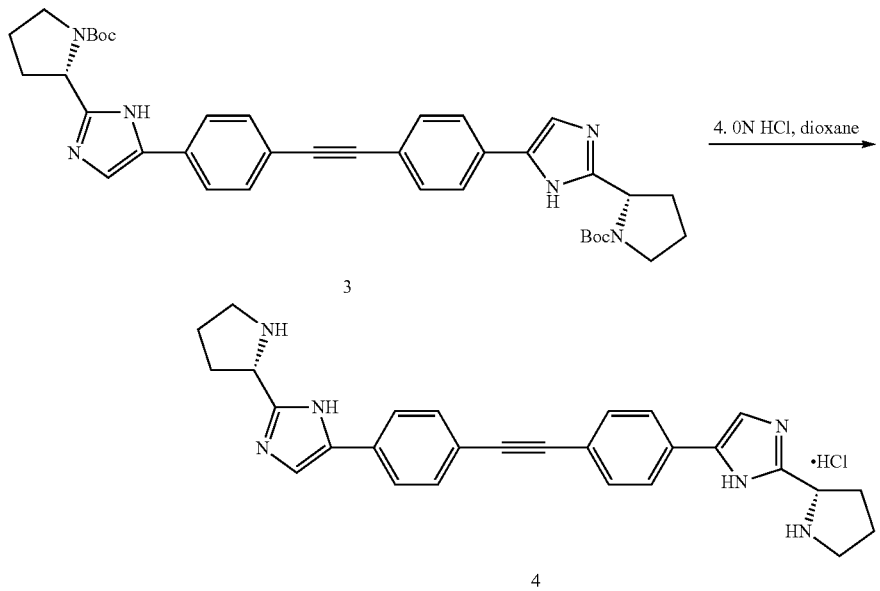
Referring to Scheme 6-2, to a solution of 3 (400 mg, 0.62 mmol) in 4 mL dioxane was added 4 mL 4.0 N HCl in dioxane. The reaction mixture was stirred at rt for 6 h and then the volatile component was removed in vacuo. The residue was washed with DCM, filtered to provide 4 (HCl salt) as a white solid (336 mg, 80% yield). LC-MS (ESI): m/z calcd. for $C_{28}H_{28}N_6$ 448.24. found 449.1 (M+H)$^+$.
Scheme 6-3
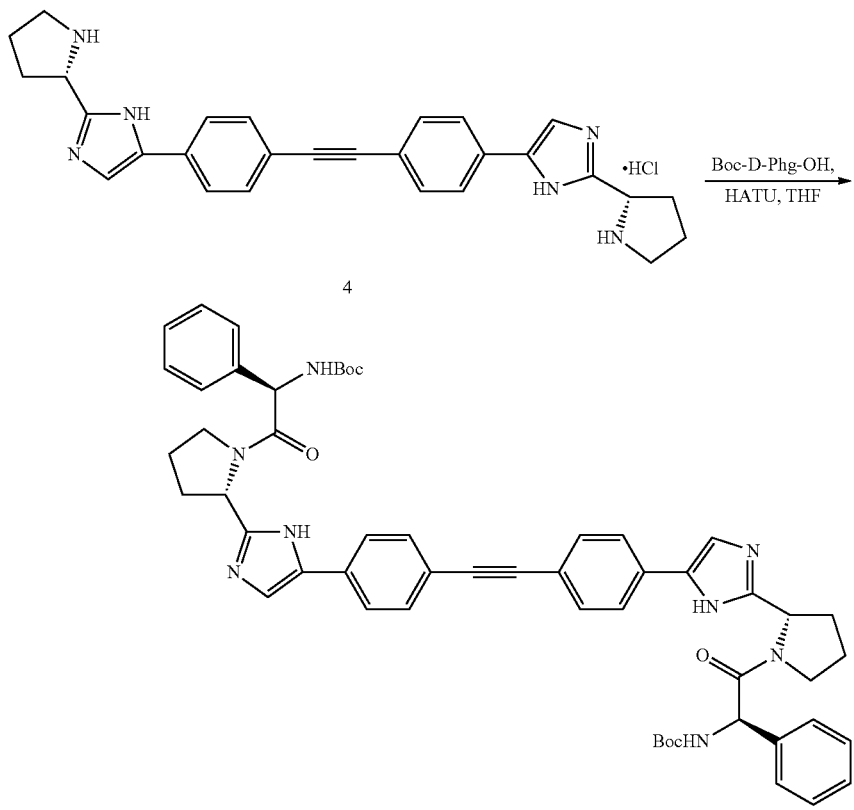

Referring to Scheme 6-3, to a mixture of 4 (160 mg, 0.24 mmol) and N-Boc-D-Phg-OH (155 mg, 0.6 mmol) in 10 ml DCM was added successively with DIPEA (0.44 ml, 2.40 mmol), HATU (235 mg, 0.6 mmol). The reaction mixture was stirred at rt for 1.5 h, then washed with water, dried over MgSO$_4$, filtered and concentrated in vacuo. The residue was purified by prep-HPLC to provide compound 38 as a white solid (300 mg, 54% yield). $^1$H NMR (500 MHz, CDCl$_3$) δ 1.44 (s, 18H), 1.92-2.16 (m, 8H), 2.90 (m, 2H), 3.24 (m, 2H), 3.80 (t, 2H, J=7.5 Hz), 5.33-5.37 (m, 4H), 5.65 (m, 2H), 7.38-7.71 (m, 20H) ppm; LC-MS (ESI): m/z calcd. for C$_{58}$H$_{58}$N$_8$O$_6$ 914.45. found 915.1 (M+H)$^+$, 937.2 [M+Na]$^+$; HPLC showed >94% purity. Retention time=17.87 min 214 and 254 nm (detection wavelength).

Scheme 6-4

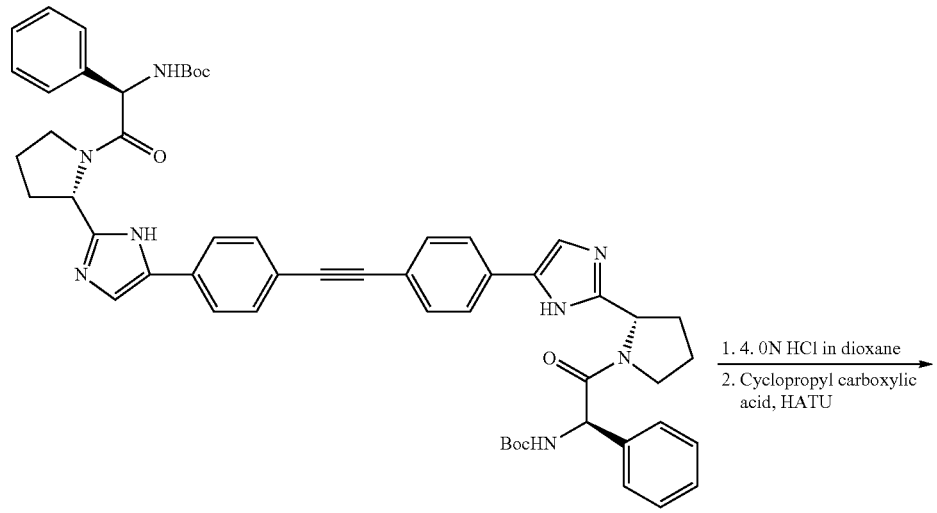

38

1. 4.0N HCl in dioxane
2. Cyclopropyl carboxylic acid, HATU

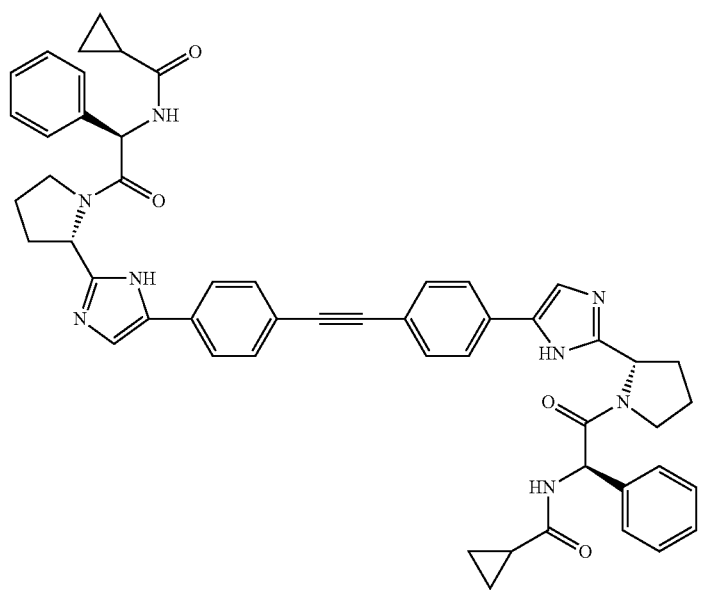

49

Step a.

Referring to Scheme 6-4, to a solution of 38 (160 mg, 0.17 mmol) in dioxane (2 mL) was added 2 mL 4.0 N HCl in dioxane. The reaction mixture was stirred at rt overnight and then the volatile component was removed in vacuo. The residue was used directly for the next step without further purification Step b.

To a mixture of solution of above HCl salt (0.17 mmol), DIPEA (0.41 ml, 1.7 mmol) and cyclopropanecarboxylic acid (0.056 mL, 0.43 mmol) in 4 ml DCM was added HATU (207 mg, 0.43 mmol). The reaction mixture was stirred at rt for 1.5 h, then transferred to a separatory funnel and washed with H$_2$O, dried over MgSO$_4$, filtered and concentrated in vacuo. The residue was purified by preparative HPLC to provide 49 as a white solid (40 mg, 28% yield for 2 steps). $^1$H NMR (500 MHz, CDCl$_3$) δ 0.76-0.78 (m, 4H), 0.94-0.99 (m, 4H), 1.43-1.47 (m, 2H), 1.90-1.92 (m, 3H), 2.04-2.08 (m, 5H), 2.79 (m, 2H), 3.26 (m, 2H), 5.33 (d, 2H, J=7.0 Hz), 5.60 (d, 2H, J=6.0 Hz) 6.93 (m, 2H), 7.24-7.77 (m, 20H) ppm; LC-MS (ESI): m/z calcd. for C$_{52}$H$_{50}$N$_8$O$_4$ 850.40. found 851.7 (M+H)$^+$; HPLC showed >95% purity. Retention time=15.64 min 214 and 254 nm (detection wavelength).

Synthesis of Example Compounds 48 and 51

Synthesis of 48 and 51 follows the same procedure as from 4 to 38 and then to 49 as described previously in reference to Schemes 6-3 to 6-4.

Compound 48: $^1$H NMR (500 MHz, CDCl$_3$) δ 1.03 (d, 12H), 1.40 (s, 18H), 2.01-2.19 (m, 8H), 2.81 (m, 2H), 3.58 (m, 2H), 3.91 (m, 1H), 4.12 (m, 2H), 5.14 (d, 2H, J=7.0 Hz), 5.34 (s, 2H), 7.18 (s, 2H), 7.53-7.76 (m, 8H) ppm; LC-MS (ESI): m/z calcd. for C$_{48}$H$_{62}$N$_8$O$_6$ 846.48. found 847.3 (M+H)$^+$; HPLC showed >96% purity. Retention time=17.33 min 214 nm (detection wavelength).

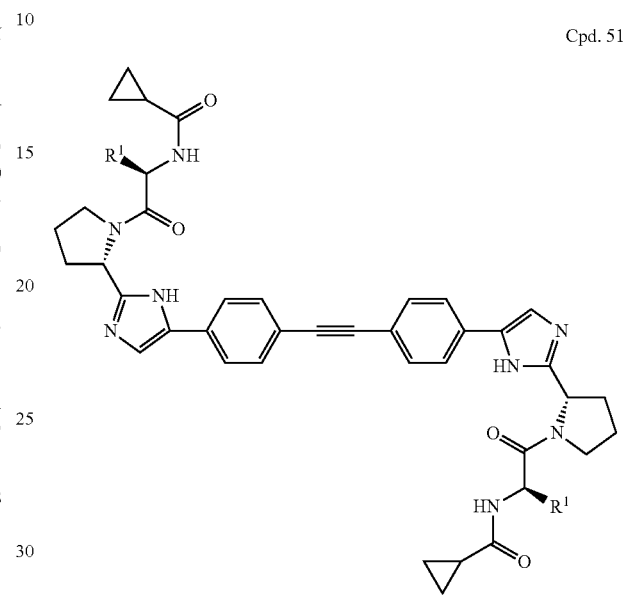

Cpd. 51

R$^1$ = isopropyl,

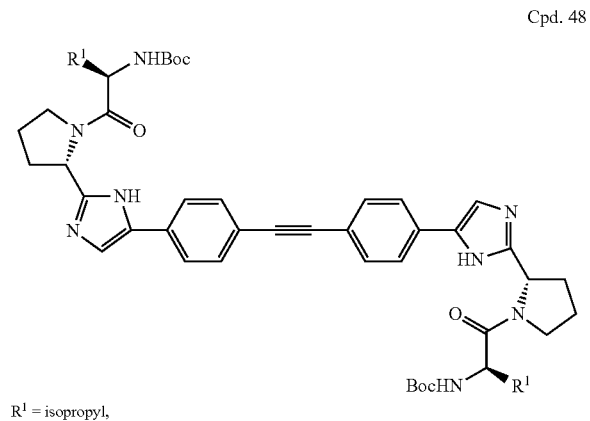

Cpd. 48

R$^1$ = isopropyl,

Compound 51: $^1$H NMR (500 MHz, CDCl$_3$) δ 0.23-0.89 (m, 8H), 0.98-1.06 (m, 12H), 1.98-2.50 (m, 13H), 3.62 (m, 2H), 4.06-4.42 (m, 4H), 5.49 (m, 2H), 6.82-7.06 (m, 1H), 7.50-7.72 (m, 8H), 8.25 (brs, 1H), 8.63 (brs, 1H), 10.49-10.52 (m, 2H) ppm; LC-MS (ESI): m/z calcd. for C$_{46}$H$_{54}$N$_8$O$_4$ 782.43. found 783.2 (M+H)$^+$; HPLC showed >99% purity. Retention time=15.17 min 214 nm (detection wavelength).

Synthesis of Compound 80

Scheme 6-5

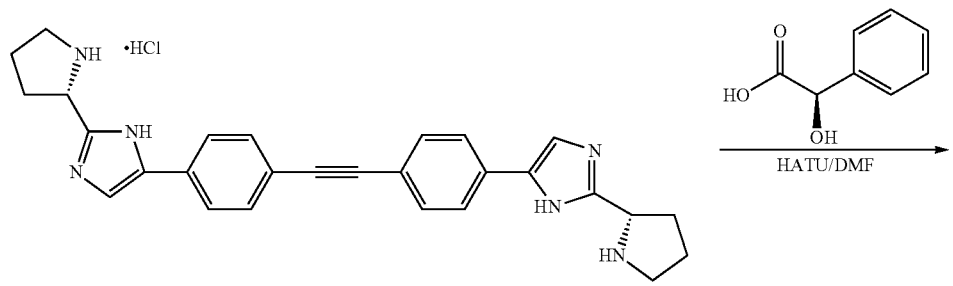

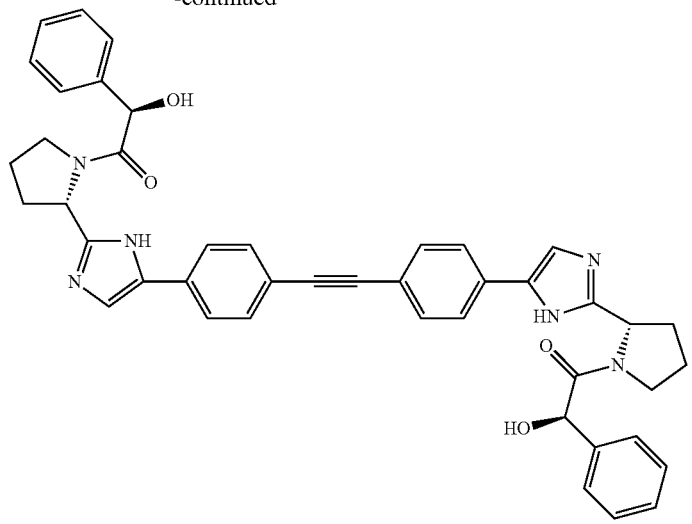

80

Referring to Scheme 6-5, to a solution of 4 (40 mg, 0.067 mmol) in 10 ml DMF was added (R)-2-hydroxy-2-phenylacetic acid (25 mg, 0.161 mmol), HATU (61 mg, 0.16 mmol) and TEA (41 mg, 0.40 mmol) at rt. The mixture was then stirred for 1.0 h and concentrated to remove the solvent. The residue obtained was purified by silica gel column chromatography (DCM/MeOH=40/1 (v/v)) to afford 80 (19 mg, 40% yield) as white solid: $^1$H NMR (500 MHz, CDCl$_3$) δ 1.28-1.32 (m, 2H), 1.78-2.02 (m, 4H), 2.27 (m, 2H), 2.82-3.06 (m, 4H), 3.53 (m, 2H), 5.28 (m, 2H), 5.52 (m, 2H), 7.15-7.61 (m, 20H) ppm; LC-MS (ESI): m/z calcd. for C$_{44}$H$_{40}$N$_6$O$_4$ 716.31. found 717.1 (M+H)$^+$; HPLC showed >92% purity. Retention time=13.02 min 214 nm (detection wavelength).

EXAMPLE 7

Synthesis of Compounds of Formula IIIa

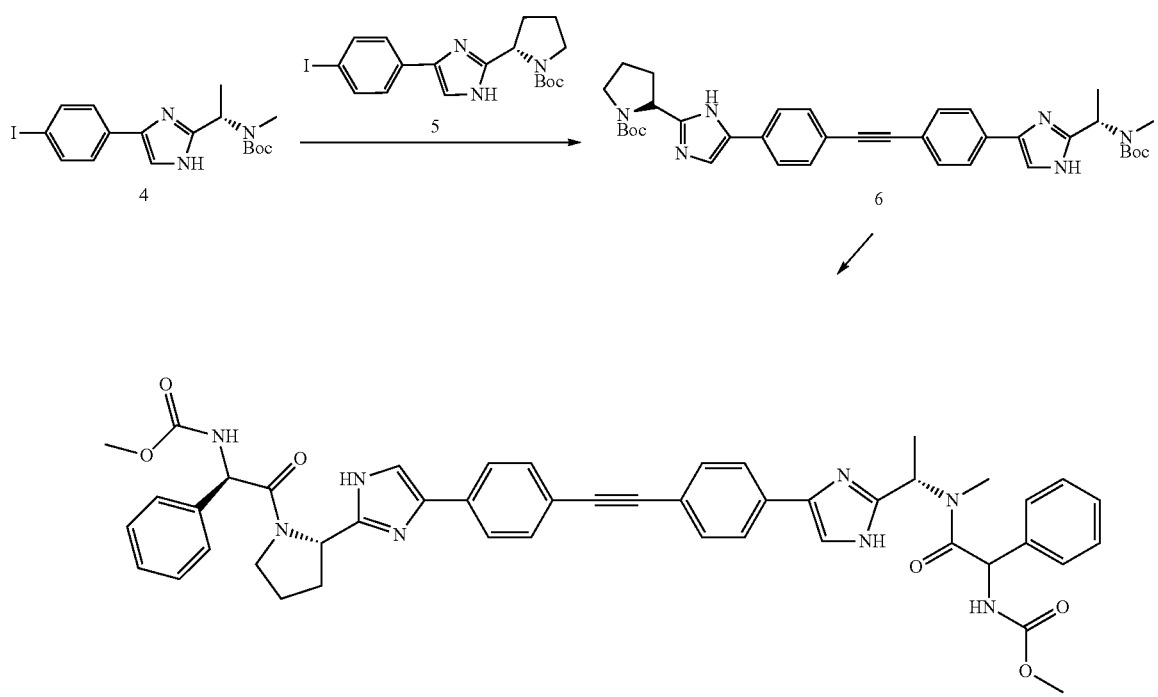

Step a.

Referring to Scheme 7-1, compound 4, (5)-tert-butyl 1-(4-(4-iodophenyl)-1H-imidazol-2-yl)ethyl(methyl)carbamate, was prepared from N-Methyl-(S)-Boc-Ala-OH (2.23 g, 11.0 mmol) and 2-chloro-1-(4-iodophenyl)ethanone.

Step b.

To a solution of iodo-precursor 4 (1.55 g, 3.60 mmol), alkyne 5 (1.35 g, 4.00 mmol), CuI (34 mg, 0.18 mmol), P(t-Bu)$_3$ (145 mg, 0.720 mmol) and piperidine (1.4 mL, 14 mmol) in DMF (150 mL) was added PdCl$_2$(PPh$_3$)$_2$ (253 mg, 0.360 mmol). The mixture was stirred at 40° C. under Ar atmosphere overnight. The resulting solution was added dropwise to H$_2$O (200 mL). The mixture was filtered and crude product was collected as a yellow solid, which was purified by silica gel column chromatography to obtain (R)-tert-butyl 2-(5-(4-((4-(2-((S)-1-(tert-butoxycarbonyl(methyl)amino)ethyl)-1H-imidazol-4-yl)phenyl)ethynyl)phenyl)-1H-imidazol-2-yl)pyrrolidine-1-carboxylate 6 (1.45 g, 67%): $^1$H NMR (500 MHz, CDC$_{l3}$) δ ppm 7.69-7.65 (m, 3H), 7.54-7.53 (m, 5H), 7.27 (s, 2H), 5.29 (m, 1H), 4.97 (m, 1H), 3.41 (m, 2H), 3.02 (m, 1H), 2.78 (s, 3H), 2.16 (m, 2H), 1.97 (m, 1H), 1.67 (d, J=6.5 Hz, 3H), 1.50 (s, 18H); LCMS (ESI) m/z 637 (M+H)$^+$.

Step c.

To a stirred solution of 6 (150 mg, 0.240 mmol) in dioxane (3 mL) was added dropwise 4.0 N HCl in dioxane (3 mL). The solution was stirred at rt for 4 h, and then concentrated to yield a yellowish solid (132 mg), which was used directly for the next step. The residue (132 mg, 0.240 mmol) was then suspended in THF (5 mL) and DIPEA (0.26 mL) was added, followed by addition of N-Methoxycarbonyl-D-Phg-OH (123 mg, 0.590 mmol). After stirred for 15 min, HATU (123 mg, 0.590 mmol) was added in several portions to the mixture. This reaction mixture was stirred at rt for 2 hours and then concentrated to yield a residue which was purified by prep-HPLC to obtain compound 7 (40 mg, 21%): $^1$H NMR (500 MHz, CDCl$_3$) δ ppm 7.75-7.65 (m, 4H), 7.52-7.50 (m, 5H), 7.45-7.44 (m, 2H), 7.40-7.38 (m, 7H), 7.26-7.25 (m, 1H), 6.15-6.05 (m, 1H), 6.01-5.86 (m, 1H), 5.53-5.52 (m, 1H), 5.43-5.41 (m, 1H), 5.30-5.29 (m, 1H), 3.72-3.68 (m, 2H), 3.68 (s, 2H), 3.66-3.65 (m, 4H), 3.24-3.20 (m, 1H), 2.87-2.78 (m, 3H), 2.24-2.13 (m, 2H), 2.10-2.00 (m, 2H), 1.93-1.90 (m, 8H), 1.58-1.57 (m, 2H); LCMS (ESI) m/z 818 (M+H)$^+$.

Starting from the same Boc-deprotected intermediate of compound 6, the following four compounds are prepared using the same procedure as described above.

| Number | Structure |
|---|---|
| 7a | 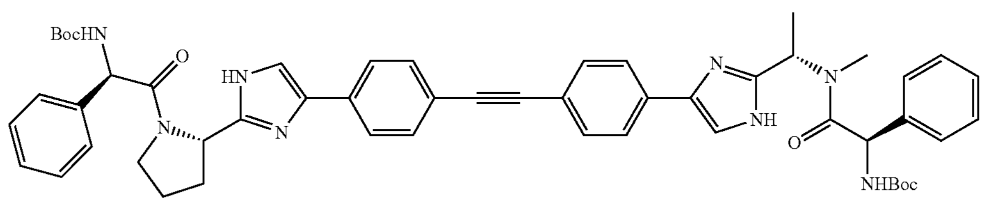 [SMILES: C[C@@H](c1nc(-c2ccc(C#Cc3ccc(-c4c[nH]c([C@@H]5CCCN5C(=O)[C@H](NC(=O)OC(C)(C)C)c5ccccc5)n4)cc3)cc2)c[nH]1)N(C)C(=O)[C@H](NC(=O)OC(C)(C)C)c1ccccc1] |
| 7b | 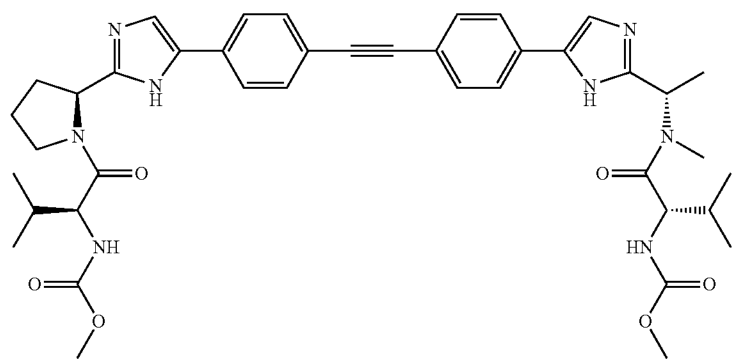 [SMILES: COC(=O)N[C@H](C(=O)N(C)[C@@H](C)c1ncc(-c2ccc(C#Cc3ccc(-c4cnc([C@@H]5CCCN5C(=O)[C@@H](NC(=O)OC)C(C)C)[nH]4)cc3)cc2)[nH]1)C(C)C] |
| 7c | 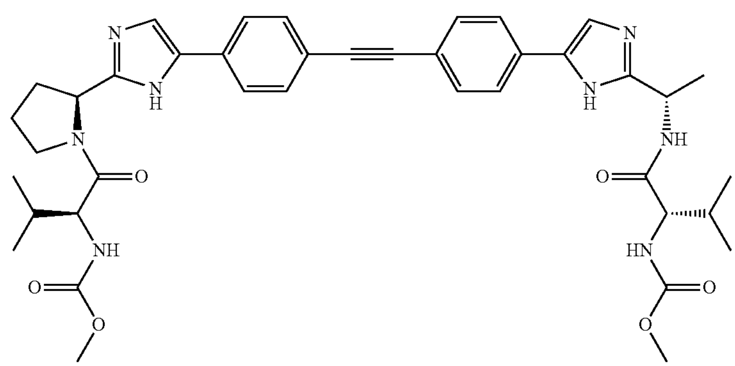 [SMILES: COC(=O)N[C@H](C(=O)N[C@@H](C)c1ncc(-c2ccc(C#Cc3ccc(-c4cnc([C@@H]5CCCN5C(=O)[C@@H](NC(=O)OC)C(C)C)[nH]4)cc3)cc2)[nH]1)C(C)C] |

| Number | Structure |
|---|---|
| 7d | 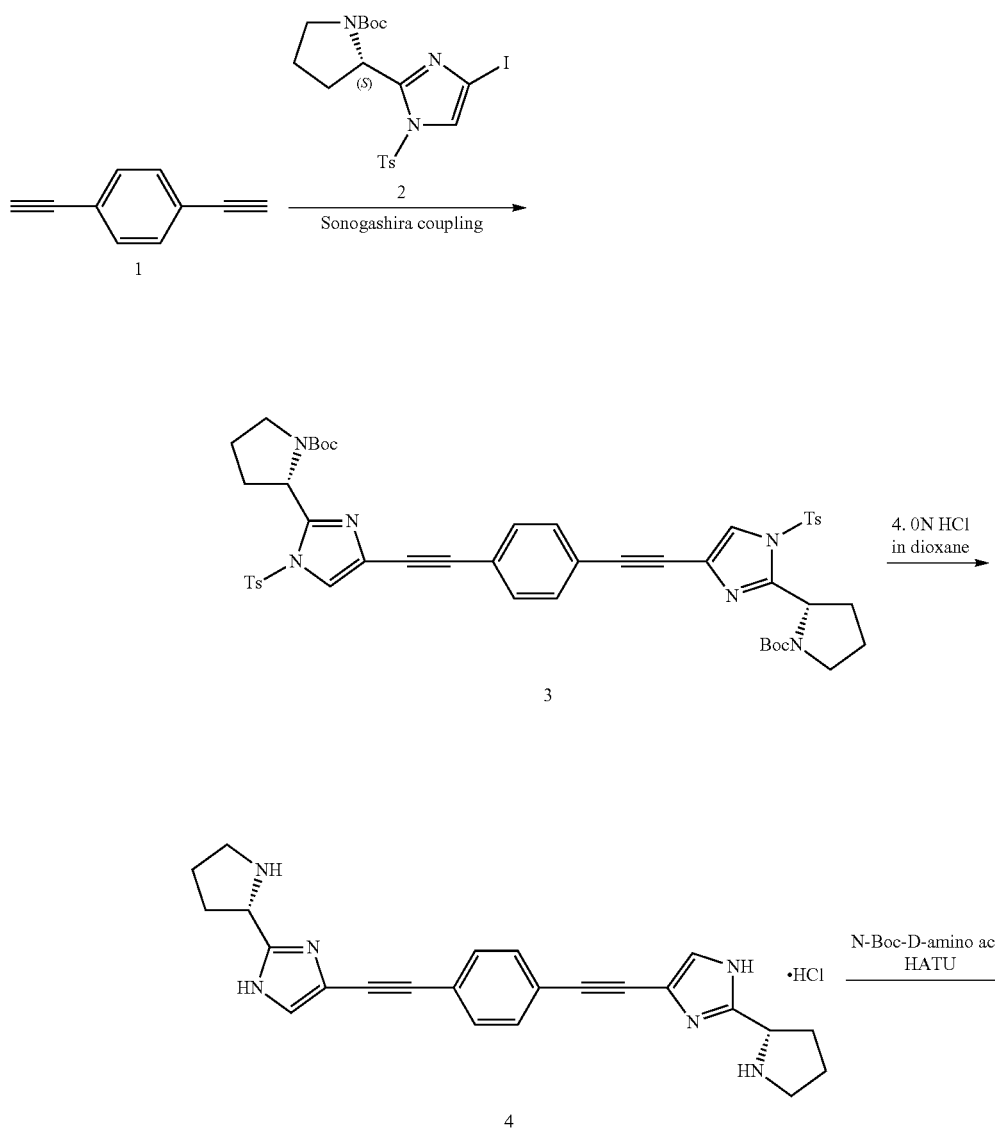 |

-continued

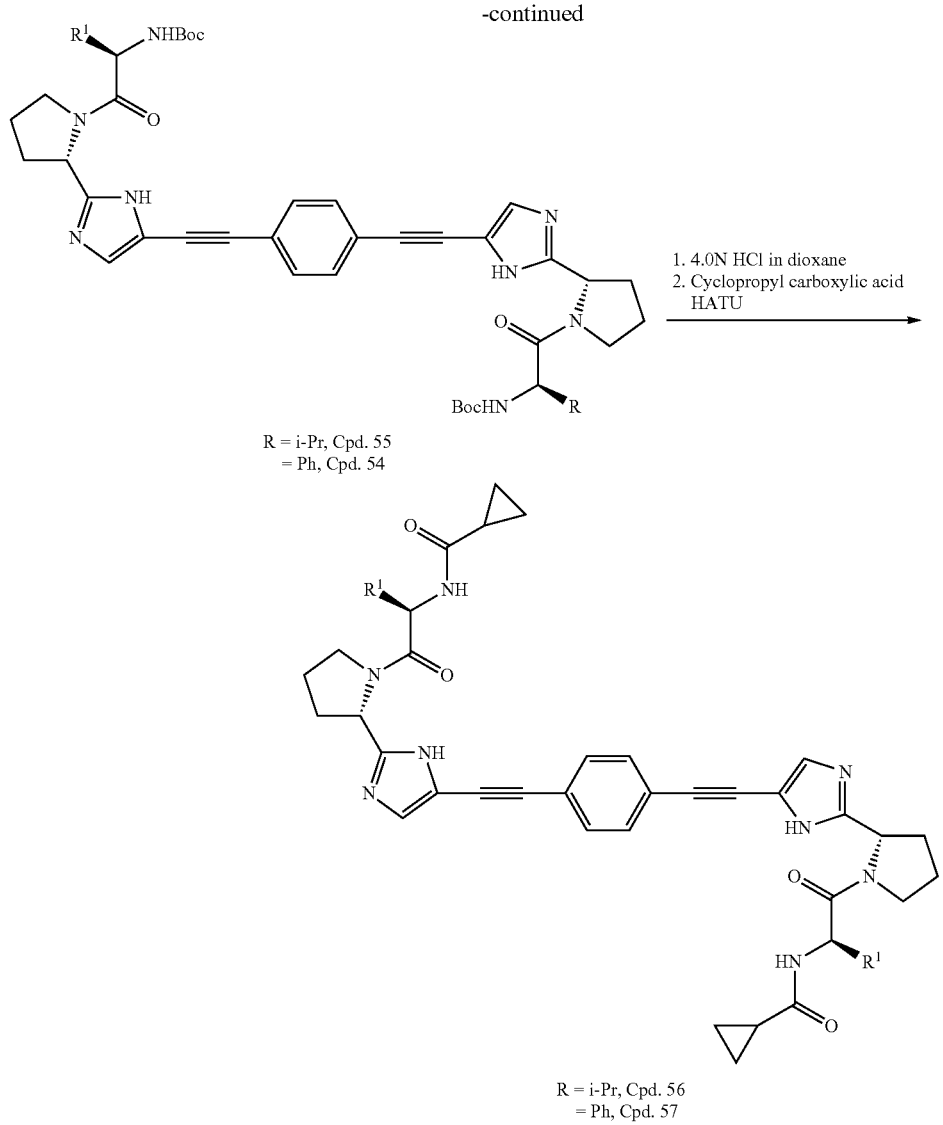

R = i-Pr, Cpd. 55
= Ph, Cpd. 54

1. 4.0N HCl in dioxane
2. Cyclopropyl carboxylic acid
   HATU

R = i-Pr, Cpd. 56
= Ph, Cpd. 57

EXAMPLE 8

Synthesis of Compounds of Formula VIb

Step a.

Referring to Scheme 8-1, Pd(PPh$_3$)$_2$Cl$_2$ (140 mg, 0.2 mmol) was added to a mixture of 1 (304 mg, 2.4 mmol), 2 (2.07 g, 4 mmol), CuI (20 mg, 0.1 mmol), PPh$_3$ (208 mg, 0.8 mmol) and DIPA (2.24 mL, 16 mmol) in 8 mL DMF. The reaction mixture was flushed with nitrogen, heated with microwave at 120° C. for 30 min, and then cooled to rt. The mixture was added to H$_2$O, extracted with EtOAc, washed with brine, dried over MgSO$_4$, filtered and concentrated in vacuo. The residue was purified by silica gel column chromatography to provide 3 (1.37 g, 62.8% yield) as an off-white solid. LC-MS (ESI): m/z calcd. for C$_{48}$H$_{52}$N$_6$O$_8$S$_2$ 904.33. found 905.0 (M+H)$^+$.

Step b.

To a solution of 3 (1.36 g, 1.5 mol) in dioxane (5 mL) was added 5 mL 4.0 N HCl in dioxane, the reaction mixture was stirred at rt for overnight, then the volatile component was removed in vacuo. The residue was washed with DCM, filtered to provide 4 (HCl salt) as a white solid (620 mg, 76% yield). LC-MS (ESI): m/z calcd. for C$_{24}$H$_{24}$N$_6$ 396.2. found 397.0 (M+H)$^+$.

Step c.

HATU (526 mg, 1.38 mmol) was added to a mixture of 4 (300 mg, 0.55 mmol), DIPEA (0.97 ml, 5.57 mmol) and N-Boc-D-Phg-OH (348 mg, 1.38 mmol) in 10 mL DCM. The reaction mixture was stirred at rt for 1.5 h, then washed with water, dried over MgSO$_4$, filtered and concentrated in vacuo. The residue was purified by prep-HPLC to provide Cpd. 54 as a white solid (250 mg, 52% yield). $^1$H NMR (500 MHz, CDCl$_3$) δ ppm 1.48 (s, 18H), 1.97-2.08 (m, 6H), 2.78-2.88 (m, 2H), 3.22 (m, 2H), 3.62-3.67 (m, 2H), 5.22-5.48 (m, 4H), 5.62 (s, 2H), 7.31-7.52 (m, 16H), 10.6 (brs, 1H); LCMS: Anal. Calcd. for C$_{50}$H$_{54}$N$_8$O$_6$ 862.42. found 863.2 (M+H)$^+$; HPLC showed >98% purity. Retention time=17.46 min 214 nm (detection wavelength).

Step d.

To a solution of Cpd. 54 (250 mg, 0.29 mmol) in dioxane (2 mL) was added 4.0 N HCl in dioxane (2 mL), the reaction mixture was stirred at rt overnight. The volatile component was removed in vacuo and the residue was used directly for the next step without further purification.

Step e.

HATU (165 mg, 0.43 mmol) was added to a mixture of HCl salt (140 mg, 0.17 mmol), DIPEA (0.3 ml, 1.7 mmol) and cyclopropanecarboxylic acid (36 mg, 0.4 mmol) in DCM (10 mL). The reaction mixture was stirred at rt for 1.5 h, then transferred to a separatory funnel and washed with H$_2$O, dried over MgSO$_4$, filtered and concentrated in vacuo. The residue was purified by prep-HPLC to provide 57 as a white solid (24 mg, 17% yield). $^1$H NMR (500 MHz, CDCl$_3$) δ 0.73-0.76 (m, 4H), 0.98-1.04 (m, 4H), 1.43-1.48 (m, 2H), 1.62-2.11 (m, 7H), 2.75 (m, 2H), 3.24 (m, 2H), 3.77 (m, 2H), 5.24 (s, 2H), 5.61 (s, 2H), 6.92 (m, 2H), 7.25-7.51 (m, 16H), 10.7 (brs, 1H) ppm; LC-MS (ESI): m/z calcd. for C$_{48}$H$_{46}$N$_8$O$_4$ 798.36. found 799.1 (M+H)$^+$; HPLC showed 2 peaks, 85.9% and 13.6% purity. Retention time=14.99 and 14.65 min 214 nm (detection wavelength).

Using a same procedure described for the preparation of compound 54 and compound 57 starting from compound 4, target molecules compound 55 and compound 56 were synthesized Cpd. 55

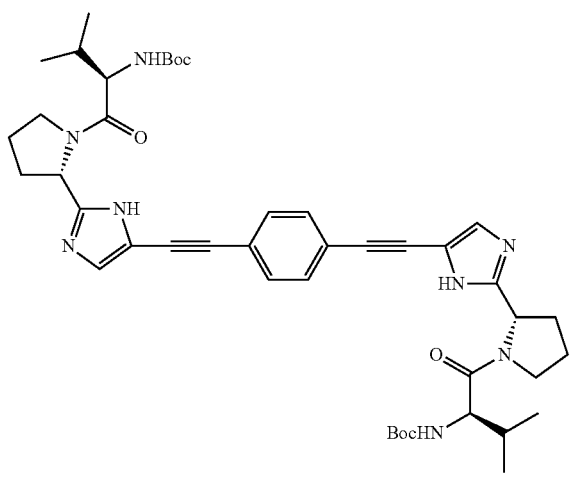

-continued

Cpd. 56

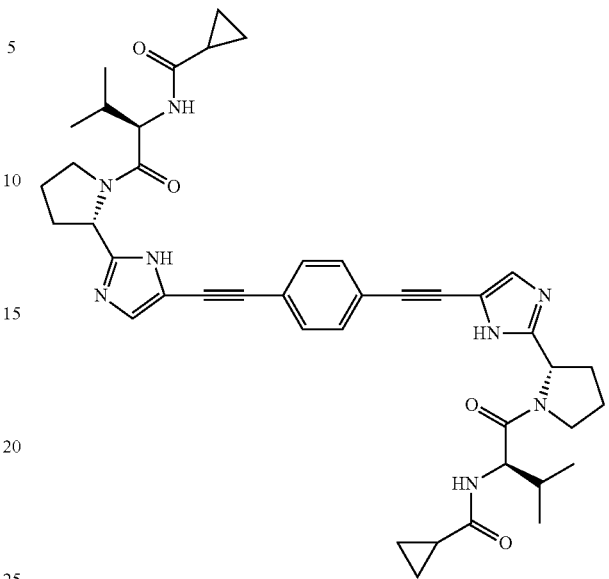

Compound 55: $^1$H NMR (500 MHz, CDCl$_3$) δ 1.01 (s, 12H), 1.47 (s, 18H), 1.99-2.10 (m, 8H), 2.75 (m, 2H), 3.22 (m, 2H), 3.56 (m, 2H), 3.74-4.10 (m, 4H), 5.18 (m, 2H), 5.24 (s, 2H), 7.24 (s, 2H), 7.96 (s, 4H), 10.6 (brs, 1H) ppm; LC-MS (ESI): m/z calcd. for C$_{44}$H$_{58}$N$_8$O$_6$ 794.45. found 795.2 (M+H)$^+$; HPLC showed >94% purity. Retention time=16.75 min 214 and 254 nm (detection wavelength).

Compound 56: $^1$H NMR (500 MHz, CDCl$_3$) δ 0.47-0.94 (m, 7H), 1.01 (s, 6H), 1.08 (s, 6H), 1.76-2.12 (m, 9H), 3.58 (m, 2H), 3.98-4.38 (m, 4H), 5.48 (s, 2H), 7.22-7.48 (m, 6H), 9.0 (brs, 1H), 10.6 (brs, 1H) ppm; LC-MS (ESI): m/z calcd. for C$_{42}$H$_{50}$N$_8$O$_4$ 730.40. found 731.2 (M+H)$^+$; HPLC showed 100% purity. Retention time=14.48 min 214 and 254 nm (detection wavelength).

Scheme 9-1

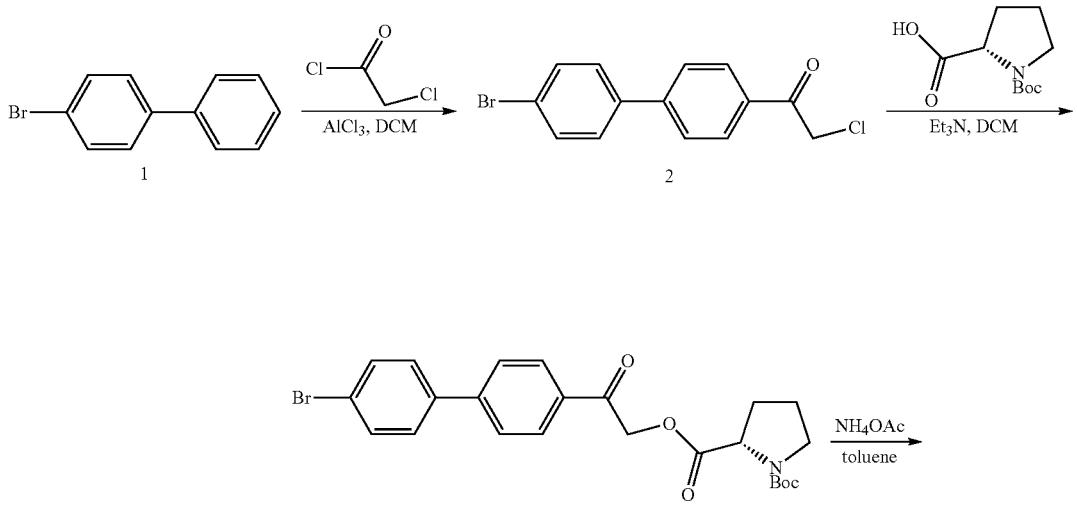

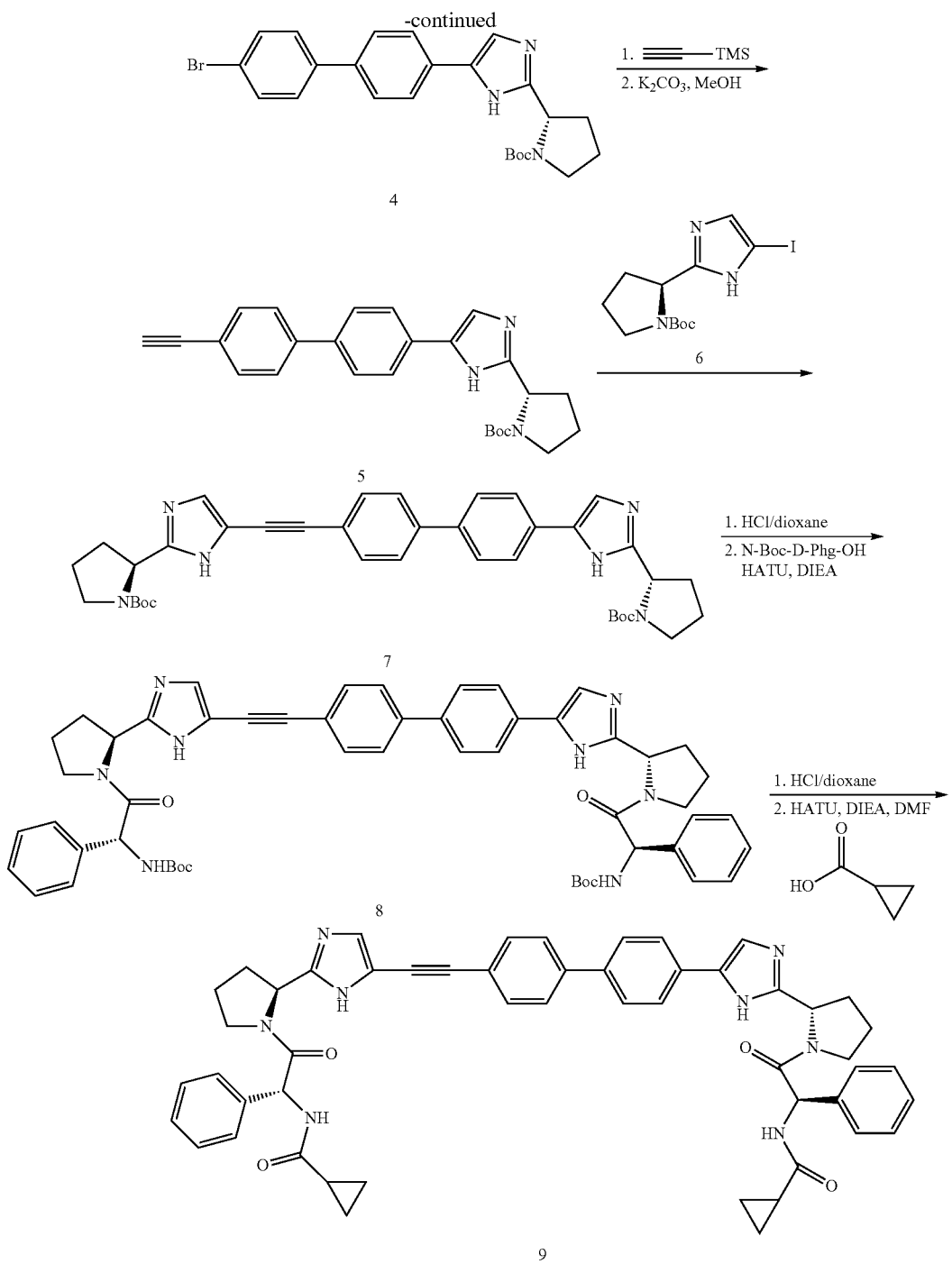

EXAMPLE 9

Synthesis of Compounds of Formula VIIb

Step a.

Referring to Scheme 9-1, to a solution of 1 (10.0 g, 43 mmol) in DCM (160 mL) was added AlCl₃ (8.6 g, 65 mmol), followed by 2-chloroacetyl chloride (5.9 g, 52 mmol) at 0° C. After stirring at rt for 1 h, the reaction was quenched by adding H₂O (500 mL). The resulting mixture was extracted with DCM several times (200 mL×3). The organic extracts were combined, washed with H₂O several times (100 mL×3), and dried with anhydrous Na₂SO₄ The solvent was removed and the residue purified by silica gel chromatography to give compound 2 (12 g, 90% yield) as a white solid. ¹H NMR (500 MHz, CDCl₃) δ 7.98 (d, J=8.5 Hz, 2H), 7.68 (d, J=8.5 Hz, 2H), 7.60 (d, J=8.0 Hz, 2H), 7.50 (d, J=8.0 Hz, 2H), 4.79 (s, 2H) ppm; LC-MS (ESI): m/z 309.0 (M+H)⁺.

Step b.

A mixture of compound 2 (8.7 g, 28 mmol), N-Boc-L-Pro-OH (6.0 g, 28 mmol), and Et₃N (8.4 g, 83 mmol) in DCM (100 mL) was stirred at rt for 2 h. Subsequently, the solvent was removed and the residue was dried in vacuo to give crude compound 3, which was used for the next step without further purification. LC-MS (ESI): m/z 488.1 (M+H)$^+$.

Step c.

A mixture of crude compound 3 obtained from the reaction above and NH$_4$OAc (17.5 g, 0.22 mol) in toluene (100 mL) was stirred at 110° C. overnight. Subsequently, the reaction mixture was concentrated and the residue was purified by silica gel column chromatography (Petroleum ether/EtOAc=1/1 (v/v)) to give compound 4 (4.7 g, 36% yield, two steps from compound 2) as a yellow solid. $^1$H NMR (500 MHz, CDCl$_3$) δ 7.57-7.55 (m, 4H), 7.48 (d, J=8.5 Hz, 4H), 7.27 (s, 1H), 4.98 (d, J=5.5 Hz, 1H), 3.42 (m, 2H), 3.04 (m, 1H), 2.17 (m, 2H), 1.99-1.96 (m, 1H), 1.51 (s, 9H) ppm; LC-MS (ESI): m/z 468.1 (M+H)$^+$.

Step d.

A mixture of compound 4 (4.0 g, 8.5 mmol), PPh$_3$ (465 mg, 1.8 mmol), Pd(PPh$_3$)$_2$Cl$_2$ (630 mg, 0.9 mmol), CuI (85 mg, 0.45 mmol), DIEA (3.5 g, 27 mmol), and trimethylsilylacetylene (1.8 g, 18.3 mmol) in anhydrous THF (200 mL) was refluxed overnight under an atmosphere of N$_2$. The reaction mixture was concentrated and the residue was diluted with EtOAc (200 mL). The resulting mixture was washed with brine and dried with anhydrous Na$_2$SO$_4$. The solvent was removed and the residue was purified by silica gel column chromatography (Petroleum ether/EtOAc=3/1 (v/v)) to give an intermediate (3.7 g, 90% yield) as a yellow solid. $^1$H NMR (500 MHz, CDCl$_3$) δ 7.60-7.51 (m, 8H), 7.25 (s, 1H), 4.98 (d, J=5.5 Hz, 1H), 3.42 (m, 2H), 3.02 (m, 1H), 2.16 (m, 2H), 1.98-1.97 (m, 1H), 1.50 (s, 9H) ppm; LC-MS (ESI): m/z 486.2 (M+H)$^+$.

Step e.

Subsequently, a mixture of the intermediate from Step d (3.5 g, 7.2 mmol) and K$_2$CO$_3$ (5.0 g, 36 mmol) in THF (100 mL) and MeOH (100 mL) was stirred at rt for 3 h. The reaction mixture was concentrated and the residue was purified by silica gel column chromatography (PE/acetone=2/1 (v/v)) to give compound 5 (2.8 g, 94% yield) as a yellow solid. LC-MS (ESI): m/z 414.2 (M+H)$^+$.

Step f.

To a solution of compound 5 (2.1 g, 5.0 mmol), compound 6 (2.2 g, 6.0 mmol), CuI (47 mg, 0.25 mmol), P(t-Bu)$_3$ (202 mg, 1.0 mmol), and piperidine (1.7 g, 20 mmol) in DMF (50 mL) was added Pd(PPh$_3$)$_2$Cl$_2$ (351 mg, 0.5 mmol) under an atmosphere of N$_2$. After stirring at 40° C. overnight under an atmosphere of N$_2$, the reaction mixture was added to H$_2$O (150 mL) drop-wise. The resulting suspension was filtered and the solid was purified by silica gel column chromatography to give compound 7 (2.4 g, 75% yield). LC-MS (ESI): m/z 693.3 (M+H)$^+$.

Step g.

A mixture of compound 7 (500 mg, 0.77 mmol) in 4.0 N HCl in dioxane (10 mL) was stirred at rt overnight. The reaction mixture was concentrated and the residue was dried in vacuo to give an HCl salt, which was used for the next step without further purification. LC-MS (ESI): m/z 449.2 (M+H)$^+$.

Step h.

Subsequently, the residue was dissolved in DMF (10 mL) and the resulting mixture was sequentially added DIPEA (814 mg, 6.3 mmol), N-Boc-D-Phg-OH (427 mg, 1.7 mmol), and HATU (646 mg, 1.7 mmol). After stirring at rt for 1.5 h, the reaction mixture was poured into H$_2$O (100 mL) and the resulting suspension was extracted with DCM several times (30 mL×3). The extracts were combined, washed with brine, and dried with anhydrous MgSO$_4$. The solvent was removed and the residue was purified by silica gel column chromatography (EtOAc/PE/MeOH=2/1/0.2 (v/v/v)) to give compound 8 (430 mg, 61% yield) as an off-white solid. $^1$H NMR (500 MHz, CDCl$_3$) δ 7.77 (s, 2H), 7.64-7.60 (m, 6H), 7.46-7.38 (m, 10H), 7.27 (s, 1H), 7.26 (s, 1H), 5.66-5.63 (m, 2H), 5.38-5.29 (m, 4H), 3.83-3.78 (m, 2H), 3.23-2.35 (m, 2H), 2.85 (br, 2H), 2.12-1.93 (m, 8H), 1.46 (s, 9H), 1.44 (s, 9H) ppm; LC-MS (ESI): m/z 915.4 (M+H)$^+$.

Step i.

A mixture of compound 8 (100 mg, 0.11 mmol) in 4.0 N HCl in dioxane (3 mL) was stirred at rt overnight. The solvent was removed and the residue was dried in vacuo to give an HCl salt, which was used for the next step without further purification. LC-MS (ESI): m/z 715.3 (M+H)$^+$.

Step j.

Subsequently, the HCl salt was dissolved in DMF (3 mL) and the resulting mixture was sequentially added to DIPEA (129 mg, 1.0 mmol), cyclopropanecarboxylic acid (24 mg, 0.28 mmol), and HATU (106 mg, 0.28 mmol). After stirring at rt for 2 h, the reaction mixture was poured into H$_2$O (50 mL) and the resulting suspension was extracted with DCM several times (20 mL×3). The extracts were combined, washed with brine, and dried with anhydrous MgSO$_4$. The solvent was removed and the residue was purified by preparative HPLC and to give compound 9. $^1$H NMR (500 MHz, CD$_3$OD) δ 7.88-7.77 (m, 8H), 7.68-7.67 (m, 2H), 7.49-7.47 (m, 4H), 7.41-7.39 (m, 6H), 5.65 (d, 2H, J=7.5 Hz), 5.32 (d, J=5.0 Hz, 1H), 5.27-5.26 (d, J=6.5 Hz, 1H), 4.01 (s, 1H), 3.35-3.31 (m, 2H), 2.39-2.38 (m, 2H), 2.15-1.99 (m, 6H), 1.70-1.66 (m, 2H), 0.91-0.85 (m, 3H), 0.75-0.68 (m, 5H) ppm; LC-MS (ESI): m/z 851.4 (M+H)$^+$.

Scheme 10-1

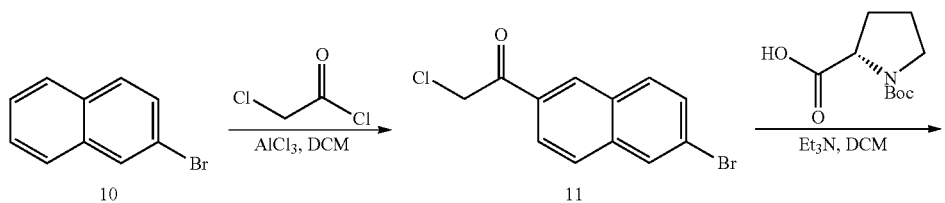

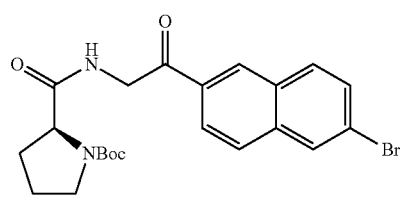
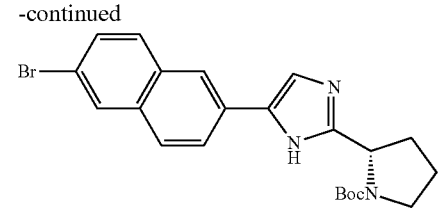

12 → 13

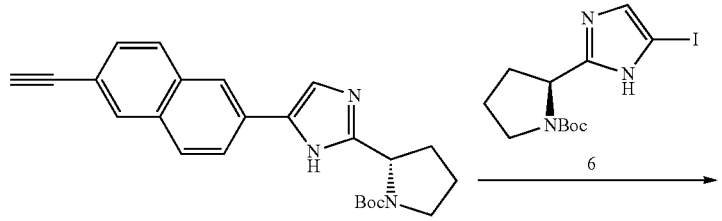

14

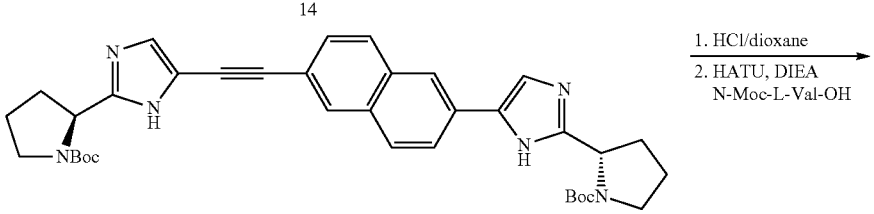

15

1. HCl/dioxane
2. HATU, DIEA
   N-Moc-L-Val-OH

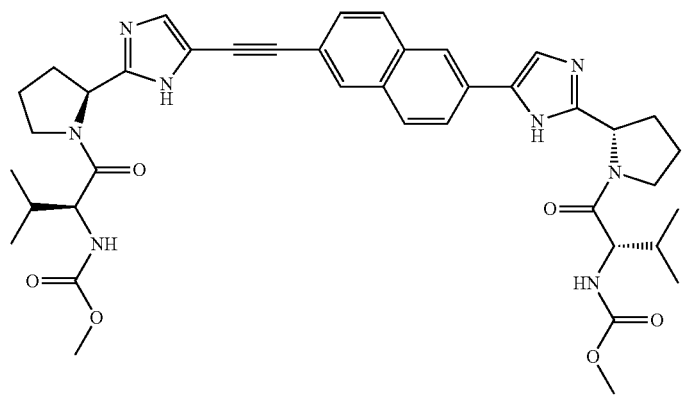

16

EXAMPLE 10

Synthesis of Compounds of Formula Xb

Step a.

Referring to scheme 10-1, to a solution of compound 10 (62 g, 0.3 mol) in DCM (1000 mL) was added $AlCl_3$ (44 g, 0.33 mol), followed by 2-chloroacetyl chloride (34 g, 0.3 mmol) at 0° C. After stirring at 0° C. for 1 h, the reaction mixture was quenched by adding $H_2O$ (500 mL). The organic layer was separated, washed with brine, and dried with anhydrous $Na_2SO_4$ The solvent was removed and the residue was re-crystallized in 10% of EtOAc in hexane to give compound 11 (28 g, 33% yield) as a white solid. $^1H$ NMR (500 MHz, $CDCl_3$) δ 8.44 (s, 1H), 8.07 (s, 1H), 8.04 (d, J=11.0 Hz, 1H), 7.84 (d, J=8.5 Hz, 2H), 7.66 (d, J=8.5 Hz, 1H), 4.81 (s, 2H) ppm; LC-MS (ESI): m/z 282.9 $(M+H)^+$.

Step b.

A mixture of compound 11 (28 g, 99 mmol), N-Boc-L-Pro-OH (23.4 g, 109 mmol), and $Et_3N$ (50 g, 495 mmol) in DCM (500 mL) was stirred at rt for 2 h. Subsequently, the reaction mixture was concentrated and the residue was dried in vacuo to give crude compound 12, which was used for the next without further purification. LC-MS (ESI): m/z 461.1 $(M+H)^+$.

Step c.

A mixture of compound 12 obtained from the reaction above and $NH_4OAc$ (77 g, 1.0 mol) in toluene (500 mL) was stirred at 110° C. overnight. The reaction mixture was concentrated and the residue was purified by silica gel column chromatography (Petroleum ether/EtOAc=1/1 (v/v)) to give compound 13 (30 g, 68% yield, two steps from compound 11) as a yellow solid. LC-MS (ESI): m/z 442.1 $(M+H)^+$.

Step d.

A mixture of compound 13 (10.0 g, 22.6 mmol), trimethylsilylacetylene (4.5 g, 45.8 mmol), DIPEA (7.0 g, 54.2 mmol), CuI (220 mg, 1.15 mmol), $PPh_3$ (1.2 g, 4.6 mmol), and $Pd(PPh_3)_2Cl_2$ (1.6 g, 2.3 mmol) in anhydrous THF (200 mL) was refluxed overnight under an atmosphere of $N_2$. The reaction mixture was concentrated and the residue was diluted with EtOAc (250 mL). The mixture was washed with brine and dried with anhydrous $Na_2SO_4$. The solvent was removed and the residue was purified by silica gel column chromatography (Petroleum ether/EtOAc=3/1 (v/v)) to give an intermediate (10 g, 96% yield) as a yellow solid. LC-MS (ESI): m/z 460.2 (M+H)+.

Step e.

Subsequently, the intermediate from step d (2.0 g, 4.4 mmol) was treated with K$_2$CO$_3$ (1.8 g, 13.1 mmol) in THF (25 mL) and MeOH (25 mL). After stirring at rt for 3 h, the reaction mixture was concentrated and the residue was purified by silica gel column chromatography (PE/acetone=2/1 (v/v)) to give compound 14 (1.3 g, 77% yield) as a yellow solid: LC-MS (ESI): m/z 388.2 (M+H)+.

Step f.

To a solution of compound 6 (1.1 g, 3.4 mmol), compound 14 (1.3 g, 3.4 mmol), CuI (54 mg, 0.34 mmol), PPh$_3$ (178 mg, 0.68 mmol), and DIPEA (879 mg, 6.8 mmol) in DMF (40 mL) was added Pd(PPh$_3$)$_2$Cl$_2$ (239 mg, 0.34 mmol) under an atmosphere of N$_2$. After stirring at 40° C. overnight under an atmosphere of N$_2$, the reaction mixture was poured into ice H$_2$O (200 mL). The solid was collected by filtration and purified by silica gel column chromatography to give compound 15 (1.3 g, 61% yield) as a pale solid. LC-MS (ESI): m/z 623.3 (M+H)+.

Step g.

A mixture of compound 15 (150 mg, 0.24 mmol) in 4.0 N HCl in dioxane (3 mL) was stirred at rt for 4 h. The reaction mixture was concentrated and the residue was dried in vacuo to give an HCl salt, which was used for the next step without further purification. LC-MS (ESI): m/z 423.2 (M+H)+.

Step h.

Subsequently, the residue was dissolved in THF (5 mL) and the resulting mixture was sequentially added DIPEA (194 mg, 1.5 mmol), N-Moc-L-Val-OH (84 mg, 0.48 mmol), and HATU (182 mg, 0.48 mmol). After stirring at rt for 2 h, the reaction mixture was concentrated and the residue was purified by preparative HPLC to give compound 16. $^1$H NMR (500 MHz, CDCl$_3$) δ 8.20-8.00 (m, 1H), 7.90-7.60 (m, 4H), 7.55-7.45 (m, 1H), 7.31-7.27 (m, 1H), 7.24-7.21 (m, 1H), 5.82 (s, 2H), 5.23-5.22 (m, 2H), 4.35-4.32 (m, 2H), 3.88-3.84 (m, 2H), 3.70 (s, 8H), 3.14-2.72 (m, 2H), 2.39-2.35 (m, 2H), 2.30-1.90 (m, 8H), 1.08-1.04 (m, 1H), 0.89 (s, 12H) ppm; LC-MS (ESI): m/z 737.4 (M+H)+.

Scheme 10-2

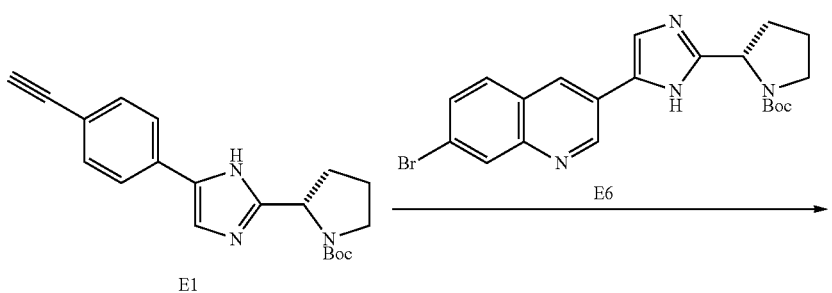

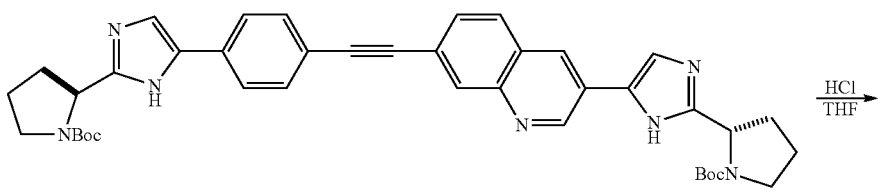

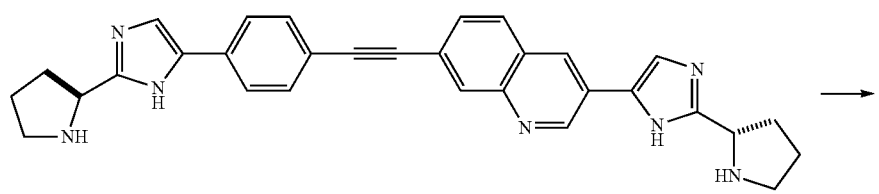

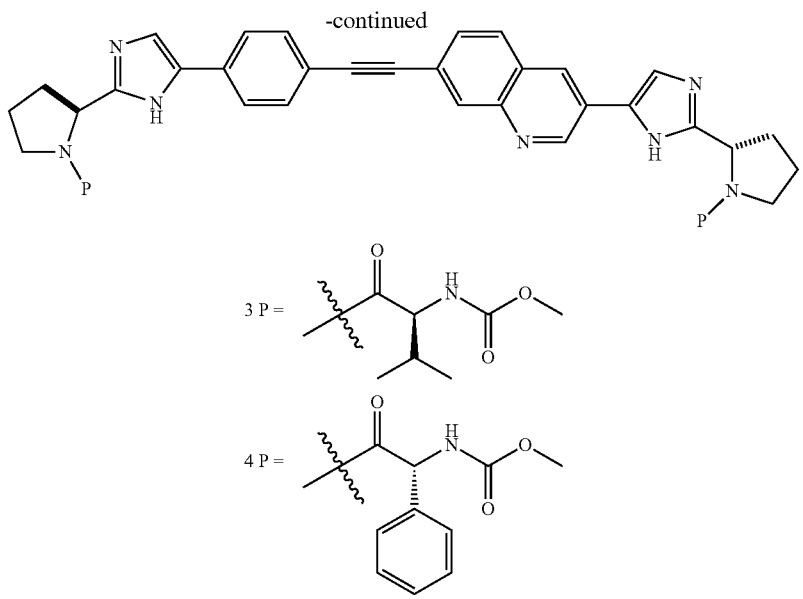

Step a.

Referring to Scheme 10-2, a mixture of 2-[5-(4-ethynyl-phenyl)-1H-imidazol-2-yl]-pyrrolidine-1-carboxylic acid tert-butyl ester (E1) (34 mg, 0.1 mmol), 2-[5-(7-Bromo-quinolin-3-yl)-1H-imidazol-2-yl]-pyrrolidine-1-carboxylic acid tert-butyl ester (E6) (49 mg, 0.11 mmol, prepared as described in the front), Pd(PCy$_3$)$_2$Cl$_2$ (3.7 mg, 5 μmol), and Cs$_2$CO$_3$ (39 mg, 0.12 mmol) in DMSO (1.0 mL) was purged with N$_2$. The resulting mixture was heated at 95° C. for 15 h. The reaction was quenched with H$_2$O, and then extracted with DCM (3×10 mL). Combined organic layers were washed with H$_2$O and brine, dried over Na$_2$SO$_4$, filtered, and concentrated on a rotary evaporator. The crude mixture was purified by prep-HPLC to give the desired Intermediate 1 as yellow solid (66.7 mg, 87% yield).

Step b.

To a mixture of bis-imidazole 1 (99 mg, 0.141 mmol) in THF (2.0 mL) was added HCl (4.0 M in dioxane, 4.0 mL) followed by stirring at rt for 15 h. All volatile was removed on a rotary evaporator to give brown solid, which was washed with Et$_2$O. The organic solvent was carefully removed and then the solid was further dried on a rotary evaporator to give yellow solid. The crude product 2 was used for the next step without further purification.

Step c.

To a crude solution of 2 (50 mg, —0.1 mmol), N-Moc-L-Val-OH (35 mg, 0.2 mmol), and HATU (76 mg, 0.2 mmol) in CH$_3$CN (1.0 mL) was added DIPEA (78 mg, 97 μL, 0.6 mmol). The resulting mixture was stirred at rt for 4 h. Based on LCMS analysis the reaction mixture was a mixture of the desired product and over acylated products. All solvent of the reaction mixture was removed on a rotary evaporator, and then dissolved in a mixture of MeOH (3.0 mL) and 10% HCl (1.0 mL). The mixture was heated at 45° C. for 25 min, and all solvent was removed on a rotary evaporator to give crude product. The crude product was purified by prep-HPLC eluting H$_2$O to CH$_3$CN. Compound 3 was obtained as pale yellow solid (6.4 mg). $^1$H NMR (300 MHz, CDCl$_3$) δ 9.23 (Brs, 2H), 7.38-8.60 (m, 11H), 5.20-5.42 (m, 4H), 4.22-4.50 (m, 4H), 3.56-3.78 (m, 6H), 1.40-2.50 (m, 10H), 0.8-1.0 (m, 12H). LC-MS (ESI): m/z 814.4 [M+H]$^+$.

Step d.

To a crude solution of 2 (50 mg, —0.1 mmol), N-Moc-D-Phg-OH (42 mg, 0.2 mmol), and HATU (76 mg, 0.2 mmol) in CH$_3$CN (1.0 mL) was added DIPEA (78 mg, 97 μL, 0.6 mmol). After stirring at rt for 4 h, the reaction mixture was concentrated and the residue was purified by preparative HPLC to give compound 4 (7.4 mg). as pale yellow solid. $^1$H NMR (300 MHz, CD$_3$OD) δ 9.31-9.28 (m, 1H), 8.42-8.60 (m, 1H), 8.09-8.15 (m, 2H), 7.92-7.96 (m, 1H), 7.53-7.78 (m, 7H), 7.32-7.50 (m, 9H), 6.96-7.10 (m, 2H), 5.50-5.64 (m, 2H), 5.20-5.30 (m, 2H), 3.88-4.04 (m, 1H), 3.54-3.72 (m, 6H), 3.18-3.40 (m, 3H), 1.90-2.24 (m, 8H) ppm. LC-MS (ESI): m/z 882.4 [M+H]$^+$.

EXAMPLE 11

Synthesis of Compounds of Formula V

Scheme 11-1

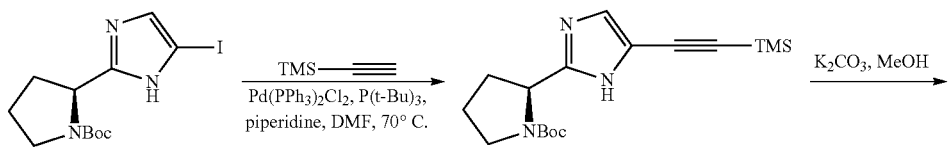

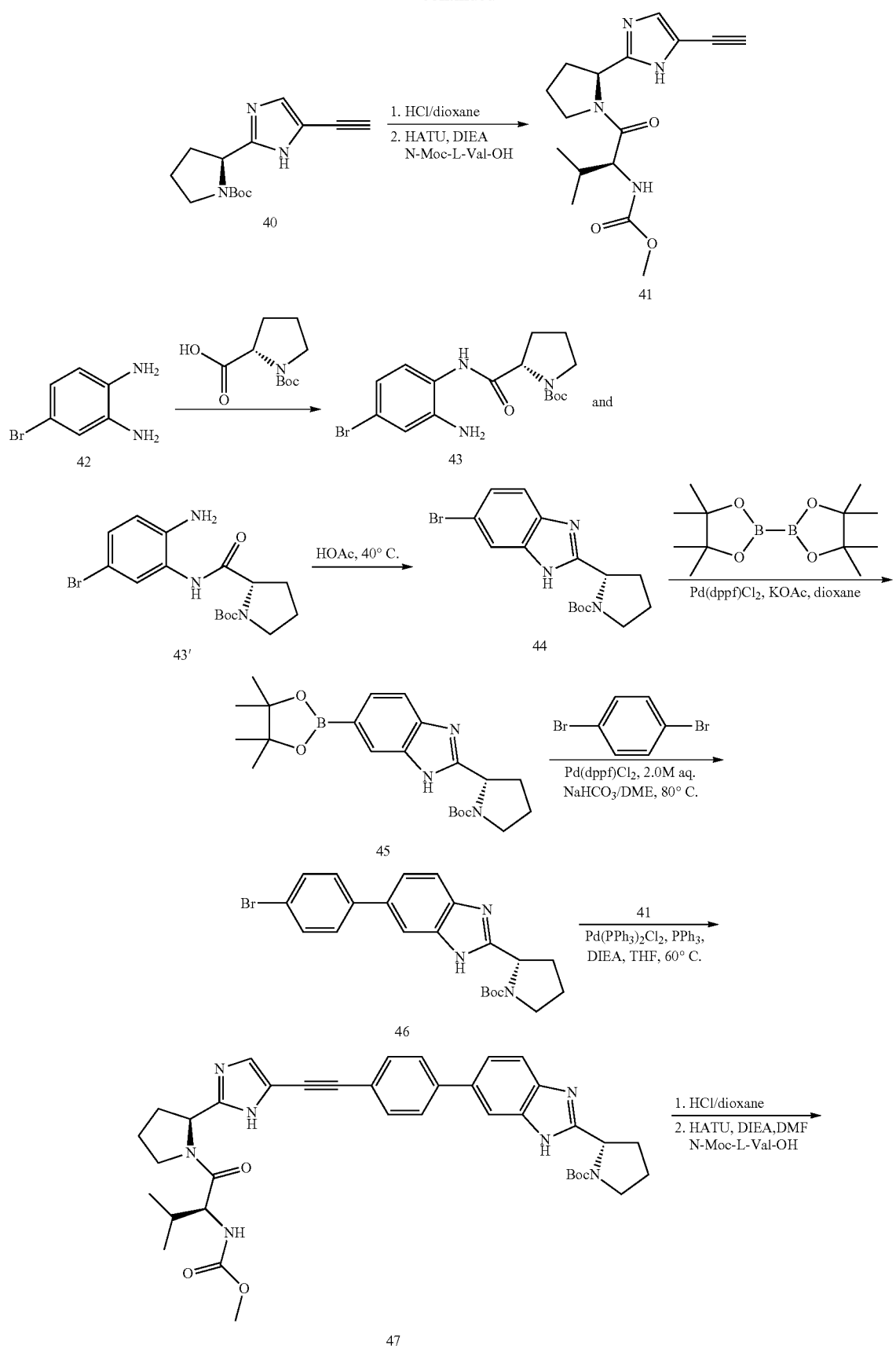

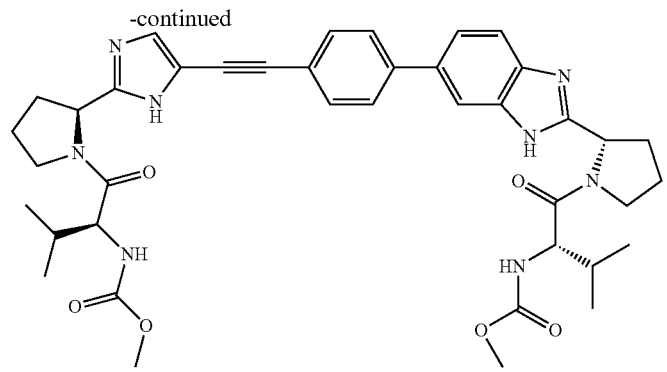

48

Step a.

Referring to Scheme 11-1, a mixture of compound 6 (54.5 g, 0.15 mol), trimethylsilylacetylene (17.7 g, 0.18 mol), P(t-Bu)₃ (121.4 g, 0.6 mol), piperidine (51.0 g, 0.6 mol), and Pd(PPh₃)₂Cl₂ (10.5 g, 15 mmol) in DMF (300 mL) was stirred at 70° C. overnight under an atmosphere of N₂. Subsequently, the reaction mixture was concentrated and the residue was diluted with EtOAc (500 mL). The resulting mixture was washed with water several times (100 mL×3) and dried with anhydrous Na₂SO₄. The solvent was removed and the residue was purified by silica gel column chromatography to give compound 39 (27.5 g, 55% yield). LC-MS (ESI): m/z 334.2 (M+H)⁺.

Step b.

A mixture of compound 39 (25 g, 75 mmol) and K₂CO₃ (41.5 g, 300 mmol) in MeOH (250 mL) and THF (250 mL) was stirred at rt for 2 h. Subsequently, the reaction mixture was filtered through CELITE™ 545 and the filter cake was washed with EtOAc several times (100 mL×3). The filtrate was concentrated and the residue was diluted with EtOAc (500 mL). The resulting mixture was washed with water several times (100 mL×3) and dried with anhydrous Na₂SO₄. The solvent was removed and the residue was purified by silica gel column chromatography to give compound 40 (12.3 g, 63% yield). LC-MS (ESI): m/z 262.1 (M+H)⁺.

Step c.

A mixture of compound 40 (10 g, 38.3 mmol) in 4N HCl/dioxane (100 mL) was stirred at rt for 2 h. The reaction mixture was concentrated and the residue was dried in vacuo to give an HCl salt, which was used for the next step without further purification. LC-MS (ESI): m/z 162.1 (M+H)⁺.

Step d.

Subsequently, the HCl salt was dissolved in DMF (120 mL) and the resulting mixture was sequentially added Et₃N (19.3 g, 191 mmol), N-Moc-L-Val-OH (7.4 g, 42 mmol), and HATU (16 g, 42 mmol). After stirring at rt for 1 h, the reaction mixture was concentrated and the residue was diluted with DCM (150 mL). The resulting mixture was washed with water several times (100 mL×3) and dried with anhydrous Na₂SO₄. The solvent was removed and the residue was purified by silica gel column chromatography (DCM/EtOAc=4/1 (v/v)) to give compound 41 (7.0 g, 57%). LC-MS (ESI): m/z 319.2 (M+H)⁺.

Step e.

To a solution of N-Boc-L-Pro-OH (29 g, 135 mmol) and DIPEA (29 g, 225 mmol) in THF (500 mL) was added HATU (51 g, 135 mmol) at rt. After stirring at rt for 10 min, compound 42 (25 g, 135 mmol) was added and the resulting solution was stirred at rt for another several hours. Subsequently, the reaction mixture was concentrated and the residue was diluted with EtOAc (500 mL). The resulting mixture was washed with H₂O several times (100 mL×3) and dried with anhydrous Na₂SO₄. The solvent was removed and the residue was dried in vacuo to give a mixture of crude compounds 43 and 43', which were used for the next step without further purification. LC-MS (ESI): m/z 384.1 (M+H)⁺.

Step f.

A mixture of crude compounds 43 and 43' obtained from the reaction above in AcOH (1000 mL) was stirred at 40° C. for 12 h. Subsequently, the reaction mixture was carefully neutralized by adding saturated aqueous sodium bicarbonate solution to adjust the pH value to 8. The resulting mixture was extracted with EtOAc several times (250 mL×3). The extracts were combined, washed with water, and dried with anhydrous Na₂SO₄. The solvent was removed and the residue was purified by silica gel chromatography (Petroleum ether/EtOAc=4/1 (v/v)) to give compound 44 (35 g, 71% yield, two steps from compound 42) as a yellow solid. LC-MS (ESI): m/z 366.1 (M+H)⁺.

Step g.

To a mixture of compound 44 (5.0 g, 13.7 mmol), bis(pinacolato)diboron (10.4 g, 41.1 mmol), potassium acetate (4.0 g, 41.1 mmol) in 1,4-dioxane (100 mL) was added Pd(dppf) Cl₂.CH₂Cl₂ (680 mg, 0.7 mmol) at rt under an atmosphere of N₂. After stirring at 80° C. for 3 h under an atmosphere of N₂, the reaction mixture was filtered through CELITE™ 545 and the filter cake was washed with EtOAc several times (50 mL×3). The filtrate was washed with brine and dried with anhydrous Na₂SO₄. The solvent was removed and the residue was purified by silica gel column chromatography (Petroleum ether/EtOAc=2/1 (v/v)) to give compound 45 (3.3 g, 58% yield). LC-MS (ESI): m/z 414.2 (M+H)⁺.

Step h.

A mixture of compound 45 (2.1 g, 5.0 mmol), 1,4-dibromobenzene (1.2 g, 5.0 mmol), and Pd(dppf)Cl₂.CH₂Cl₂ (243 mg, 0.25 mmol) in 2 N aqueous NaHCO₃ (7.5 mL) and DME (22.5 mL) was stirred at 80° C. overnight under an atmosphere of N₂. Subsequently, the reaction mixture was concentrated and the residue was diluted with EtOAc (100 mL). The resulting mixture was washed with H₂O several times (20 mL×3) and dried with anhydrous Na₂SO₄. The solvent was removed and the residue was purified by silica gel column chromatography to give compound 46 (1.3 g, 60% yield). LC-MS (ESI): m/z 442.1 (M+H)⁺.

Step i.

A mixture of compound 41 (150 mg, 0.47 mmol), compound 46 (162 mg, 0.37 mmol), Pd(PPh₃)₂Cl₂ (35 mg, 0.05 mmol), CuI (10 mg, 0.05 mmol), PPh₃ (26 mg, 0.10 mmol), and DIPEA (245 mg, 1.9 mmol) in DMF (5 mL) was stirred at 80° C. overnight under an atmosphere of N₂. Subsequently, the reaction mixture was concentrated and the residue was diluted with DCM (100 mL). The resulting mixture was washed with H₂O several times (20 mL×3) and dried with anhydrous Na₂SO₄. The solvent was removed and the residue was purified by silica gel column chromatography (Petroleum ether/EtOAc=2/1 (v/v)) to give compound 47 (150 mg, 60% yield). LC-MS (ESI): m/z 680.3 (M+H)⁺.

Step j.

A mixture of compound 47 (120 mg, 0.18 mmol) in 4N HCl/dioxane (3 mL) was stirred at rt for 2 h. The reaction mixture was concentrated and the residue was dried in vacuo to give an HCl salt, which was used for the next step without further purification. LC-MS (ESI): m/z 580.3 (M+H)⁺.

Step k.

Subsequently, the HCl salt was dissolved in DMF (3 mL) and the resulting mixture was sequentially added Et₃N (182 mg, 1.8 mmol), N-Moc-L-Val-OH (35 mg, 0.2 mmol), and HATU (76 mg, 0.2 mmol). After stirred at rt for 10 min, the reaction mixture was concentrated and the residue was purified by preparative HPLC to give compound 48. LC-MS (ESI): m/z 737.4 (M+H)⁺.

EXAMPLE 12

Synthesis of Compounds of Formula XI

Scheme 12-1

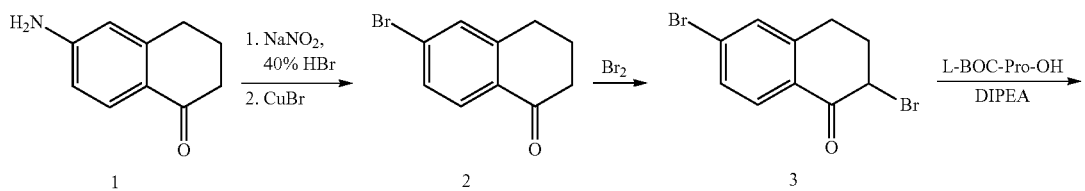

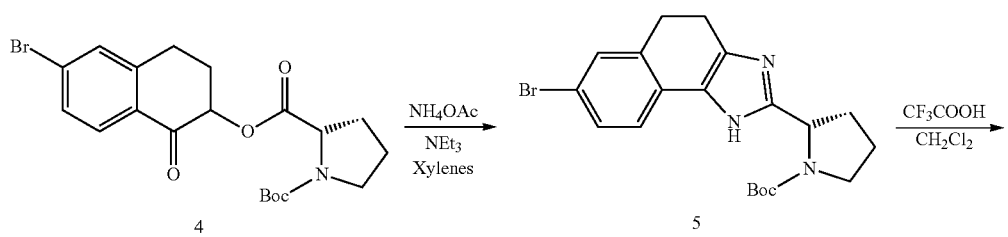

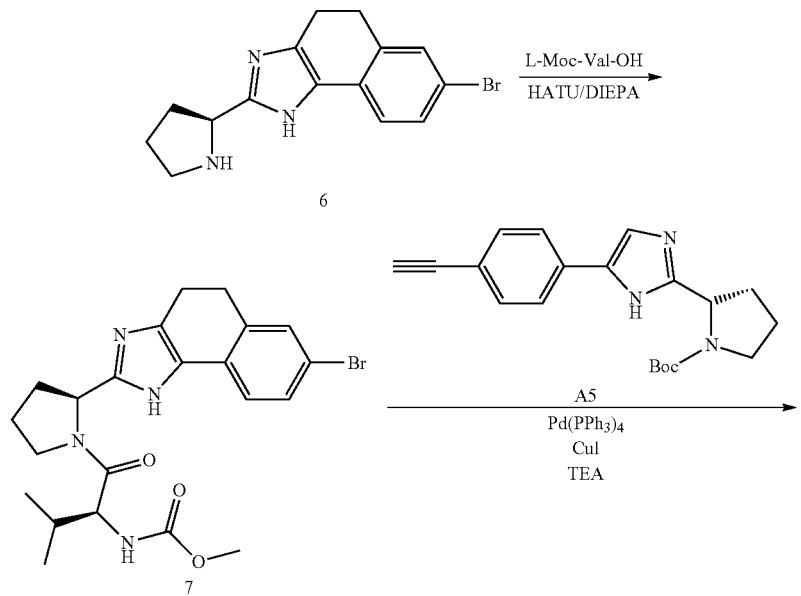

-continued

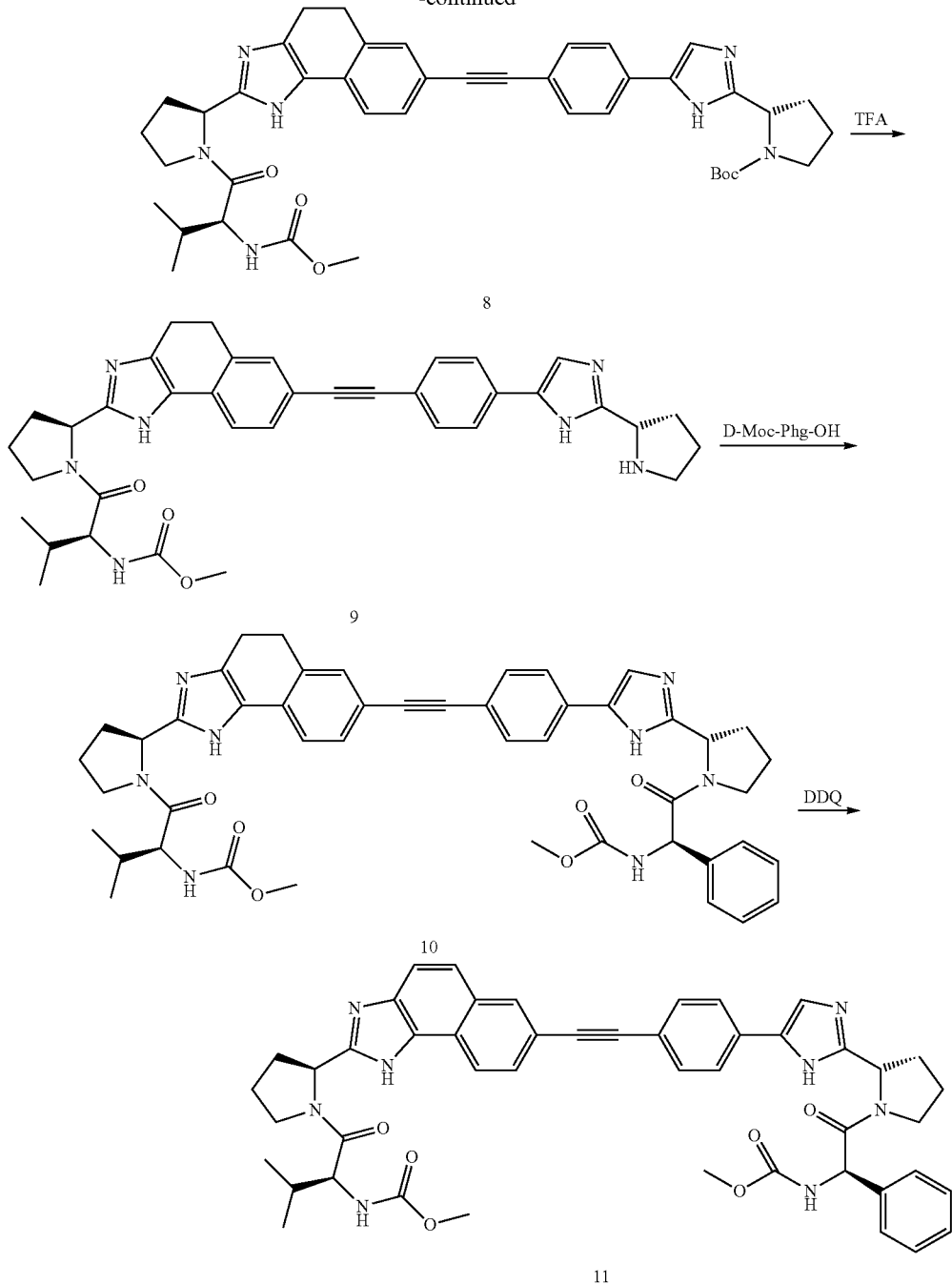

Step a.

Referring to Scheme 12-1, to a solution of 1 (20.60 g, 0.128 mol) in 45 mL of 48% hydrobromic acid and 10 mL of H$_2$O was added a solution of 9.72 g (0.141 mol) of sodium nitrite in 18 mL of water, maintaining a temperature below 5° C. After stirring at 5° C. for 1 h, CuBr (0.128 mol) was added and the resulting mixture was stirred at rt for 3 h. Subsequently, the mixture was extracted with EtOAc (2×200 mL). The extracts were combined, washed with brine, and dried with anhydrous Na$_2$SO$_4$. The solvent was removed and the residue was purified by silica gel column chromatography (Hexane/EtOAc=12/1 (v/v)) to afford 2 (13.3 g, 46% yield) as a powder. $^1$H NMR (CDCl$_3$, 400 MHz) δ 7.90 (d, 1H), 7.44 (m, 2H), 2.96 (t, 2H), 2.64 (t, 2H), 2.15 (m, 2H) ppm.

Step b.

To a solution of the ketone 2 (12.49 g, 55.5 mmol) in 300 mL of methylene chloride and 0.30 mL of 48% hydrobromic acid was slowly added 3.1 mL of bromine at 0° C. The reaction mixture was gradually warmed up to rt and kept stirring for 2 h. The organic solution was washed with saturated NaHCO$_3$ twice, and then with H$_2$O. The crude product was purified by FCC to afford 3 (11.9 g, 71%). $^1$H NMR (CDCl$_3$) δ 7.94 (d, 2H), 7.52 (m, 2H), 4.72 (t, 1H), 3.32 (m, 1H), 2.92 (m, 1H), 2.48 (m, 2H).

Step c.

A mixture of 3 (11.80 g, 38.8 mmol), N-Boc-L-Pro-OH (10.02 g, 46.6 mmol), and diisopropylethylamine (7.02 g, 54.3 mmol) in acetonitrile (200 mL) was stirred at 50° C. for 10 h. The solvent was evaporated and the residue was partitioned between methylene chloride and $H_2O$. The organic layer was separated and concentrated to dryness. The crude product was purified by silica gel column chromatography (hexanes/ethyl acetate=1/7 to 1/4 (v/v)) to provide 4 (11.53 g, 68% yield) as a white solid. $^1$H NMR (CDCl$_3$, 400 MHz) δ 7.84 (m, 1H), 7.48 (m, 2H), 5.58 (m, 1H), 4.40 (m, 1H), 3.60 (m, 1H), 3.40 (m, 1H), 3.18 (m, 1H), 3.04 (m, 1H), 2.37 (m, 2H), 2.04 (m, 1H), 1.96 (m, 1H), 1.46 (ds, 9H) ppm.

Step d.

A mixture of 4 (11.09 g, 25.3 mmol), ammonium acetate (29.25 g, 38.0 mmol) and triethylamine (38.45 g, 38.0 mmol) in xylenes (600 mL) in a sealed tube was stirred at 140° C. for 2 h. After being cooled, the reaction mixture was transferred into a flask and concentrated to dryness. The residue was partitioned between chloroform and $H_2O$, and the organic layer was washed with $H_2O$ and concentrated. The crude product was purified by silica gel column chromatography (NH$_4$OH/acetonitrile/ethyl acetate: 1/8/100=(v/v/v)) to afford 5 (8.22 g, 75% yield) as a white solid. LC-MS (ESI): m/z 420.1 (M+H)$^+$.

Step e.

Trifluoroacetic acid (20 mL) was slowly added into a solution of 5 (4.80 g, 11.4 mmol) in methylene chloride (40 mL) at rt. After stirring at rt for 2 h, the reaction mixture was concentrated and the residue was dried in vacuo to give a TFA salt, which was used for the next step without further purification. LC-MS (ESI): m/z 318.1 (M+H)$^+$.

Step f.

To a mixture of the TFA salt (6.28 g, 11.5 mmol) in DMF (23 mL) was added DIPEA (22.8 mL, 138 mmol), followed by N-Moc-L-Val-OH (2.42 g, 13.8 mmol) and HATU (5.25 g, 13.8 mmol). After stirring at rt for 2 h, the reaction mixture was slowly dropped into water while stirring. The resulting precipitate was collected by filtration. The crude product was purified by silica gel column chromatography (Hexane/Ethyl Acetate=1/4 to 0/1 (v/v)) to afford 7 (4.43 g, 81% yield). LC-MS (ESI): m/z 475.3 (M+H)$^+$.

Step g.

To a solution of 7 (0.78 g, 1.7 mmol), acetylene (0.56 g, 1.7 mmol), CuI (63 mg, 0.33 mmol), and Et$_3$N (0.67 mL, 5.0 mmol) in DMF (20 mL) was added Pd(PPh$_3$)$_4$ (2.95 g, 4.20 mmol). The resulting mixture was degassed with N$_2$, and then stirred at 110° C. overnight in a sealed tube. The reaction mixture was slowly dropped into H$_2$O (100 mL). The precipitate was collected and then dissolved in EtOAc. The organic phase was dried, filtered, and concentrated in vacuo to give a residue, which was purified by silica gel column chromatography (NH$_4$OH/acetonitrile/EtOAc=1/8/10 (v/v/v)) to afford 8 (0.38 g, 31% yield). LC-MS (ESI): m/z 732.8 (M+H)$^+$.

Step h.

Trifluoroacetic acid (5 mL) was slowly added into a solution of the imidazole 8 (0.38 g, 0.52 mmol) in methylene chloride (10 mL) at rt. The resulting mixture was stirred at rt for 2 h, and then concentrated to dryness. The crude product was further dried in vacuo overnight, which was directly used for the next reaction without further purification. LC-MS (ESI): m/z 632.3 (M+H)$^+$.

Step i.

To a mixture of the TFA salt (200 mg, 0.17 mmol) in DMF (2 mL) and THF (1 mL) was added DIPEA (0.23 mL, 1.38 mmol), followed by N-Moc-D-Phg-OH (47 mg, 0.23 mmol) and DMTMM (72 mg, 0.26 mmol). After stirring at rt for 2 h, the reaction mixture was slowly dropped into H$_2$O while stirring. The resulting precipitate was collected by filtration. The crude product was purified by prep-HPLC to afford 10 (65 mg, 46% yield). $^1$H NMR (CDCl$_3$, 400 MHz) δ 7.70-7.20 (m, 13H), 6.06 (d, 1H), 5.44 (m, 2H), 5.28 (m, 3H), 4.38 (m, 1H), 3.90-3.64 (m, 10H), 3.22 (m, 1H), 3.04 (m, 1H), 2.90 (m, 2H), 2.74 (m, 4H), 2.40-1.90 (m, 6H), 1.10-0.92 (m, 6H) ppm. LC-MS (ESI): m/z 823.4 (M+H)$^+$.

Step j.

A solution of 10 (45.3 mg, 0.055 mmol), DDQ (13.1 mg, 0.058 mmol) in 6 mL of benzene was refluxed for 2.5 h. After removal of the solvent, the crude product was purified by prep-HPLC to afford 11 (12 mg) as light yellow powder. $^1$H NMR (CDCl$_3$, 400 MHz) δ 8.00 (s, 1H, NH), 7.70-7.38 (m, 13H), 7.26 (s, 1H), 7.18 (s, 1H), 6.08 (d, 1H), 5.48 (m, 3H), 5.30 (m, 1H), 4.40 (m, 1H), 3.96-3.64 (m, 10H), 3.22 (m, 1H), 2.94 (m, 1H), 2.68 (m, 2H), 2.50-1.90 (m, 6H), 1.10-0.92 (m, 6H) ppm. LC-MS (ESI): m/z 821.4 (M+H)$^+$.

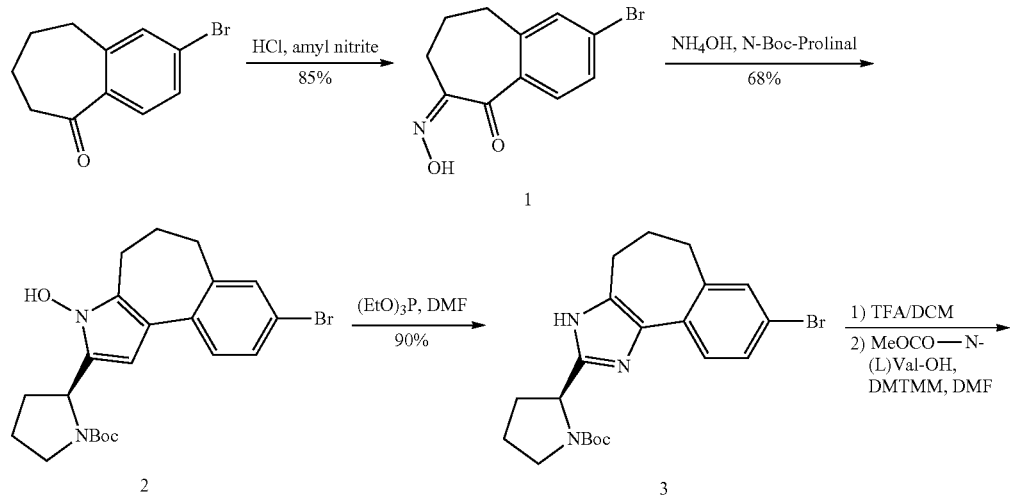

Scheme 12-2

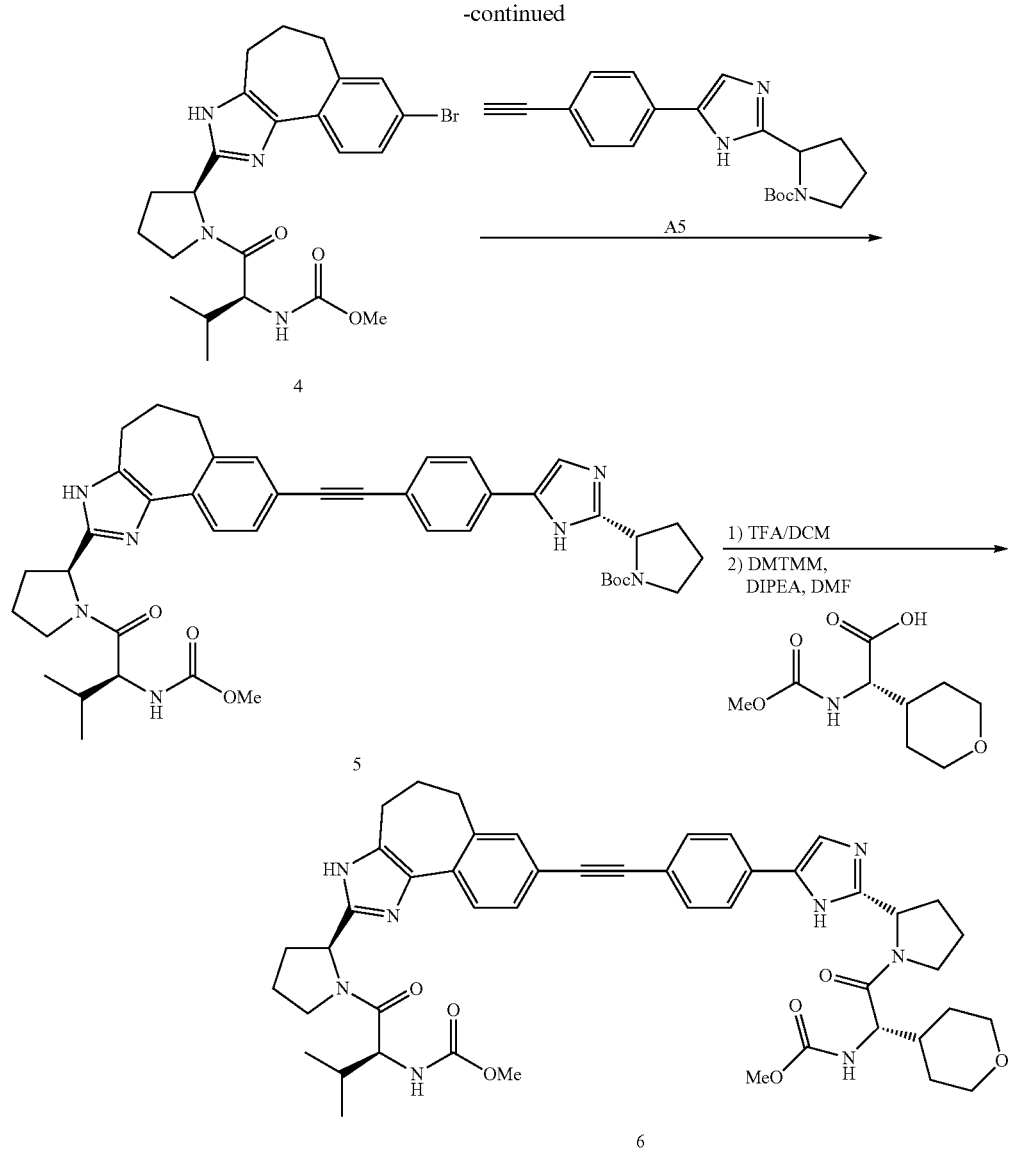

Step a.

Referring to Scheme 12-2, to a solution of 2-bromo-6,7,8,9-tetrahydro-5H-benzo[7]annulen-5-one (21 g, synthesized from the commercial starting materials following the procedures in J. Med. Chem. 2005, 48, 7351) in THF (350 mL) and Et$_2$O (700 mL) was added 4N HCl in dioxane (32 mL) at 0° C. followed by amyl nitrite (16.8 mL). The reaction was slowly warmed up to rt and stirred overnight under nitrogen gas protection and concentrated under vacuum to remove most of the solvent. The residue was purified by silica gel flash column chromatography (EtOAc/Hexanes=1/4 (v/v)) to provide compound 1 (19 g, 81% yield). LC-MS (ESI): m/z 268.0 (M+H)$^+$.

Step b.

To a suspension of compound 1 (19 g) and N-Boc-L-Prolinal (15 g) in methanol (800 mL) was added 28% NH$_4$OH at rt. The reaction stirred overnight under nitrogen gas protection and concentrated under vacuum to remove most of the methanol. The residue was then diluted with ethyl acetate and was extracted with ethyl acetate. The organic phase was washed with H$_2$O, dried over sodium sulfate and concentrated in vacuo to give the crude product, which was purified by silica gel flash column chromatography (EtOAc/Hexanes=4/1 (v/v)) to provide 2 (23 g, 73% yield). LC-MS (ESI): m/z 448.1 (M+H)$^+$.

Step c.

To a solution of compound 2 from above (23 g) in DMF (70 mL) was added triethyl phosphite at rt under N$_2$ atmosphere. The reaction mixture was stirred at 80° C. overnight and cooled to rt, diluted with ethyl acetate, extracted with ethyl acetate, the organic phase was washed with H$_2$O, dried over sodium sulfate and concentrated in vacuo to give a crude product, which was purified by silica gel flash column chromatography (EtOAc) to provide 3 (21 g, 93% yield). LC-MS (ESI): m/z 432.1 (M+H)$^+$.

Step d.

To a stirred solution of 3 (6.0 g) in dichloromethane (100 mL) was added trifluoroacetic acid (10 mL). After three hours, the reaction was concentrated to dryness to provide an HCL salt. Subsequently, the HCl salt was dissolved in DMF (80 mL) and DIPEA (14 mL), N-Moc-L-Val-OH (2.85 g) and HATU (6.16 g) were added. After stirring at rt for 1 h, the reaction mixture was diluted with $H_2O$. The resulting suspension was filtered. The solid was collected by filtration and purified silica gel column chromatography (EtOAc/Hexane=4/1 (v/v)) to provide 4 (5.0 g, 76% yield). LC-MS (ESI): m/z 489.1 $(M+H)^+$.

Step e.

To a solution of 4 (0.78 g, 1.7 mmol), acetylene intermediate A5 (0.56 g, 1.7 mmol, synthesized as described in Scheme 1-1), CuI (63 mg, 0.33 mmol), and $Et_3N$ (0.67 mL, 5.0 mmol) in DMF (20 mL) was added $Pd(PPh_3)_4$ (0.19 g, 0.165 mmol). The resulting mixture was degassed with $N_2$, and then stirred at 100° C. overnight in a sealed tube. The reaction mixture was slowly dropped into $H_2O$ (100 mL). The precipitate was collected and then dissolved in EtOAc. The organic phase was dried, filtered, and concentrated in vacuo to give a residue, which was purified by silica gel column chromatography (EtOAc) to afford 5 (420 mg, 34% yield). LC-MS (ESI): m/z 746.4 $(M+H)^+$ Step f.

To a stirred solution of 5 (13 mg) in dichloromethane (2 mL) was added trifluoroacetic acid (0.2 mL). After stirring at rt for 3 h, the reaction mixture was concentrated to dryness to give a TFA salt. Subsequently, the TFA salt was dissolved in DMF (2 mL), and the resulting solution was added DIPEA (30 μL), N-methoxycarbonyl-L-4-tetrahydropyranylglycine (5.0 mg) and HATU (8.7 mg). After stirring at rt for 1 h, the reaction mixture was concentrated and the residue was purified by preparative HPLC (Phenomenex, C18-Luna column, $H_2O$-MeCN, 0.1% $HCO_2H$) to provide 6 (4.5 mg, 31% yield). $^1H$ NMR ($CD_3OD$, 300 MHz,) δ 8.17 (s, br. 1H), 7.75-7.62 (m, 2H), 7.50-7.42 (m, 2H), 7.41-7.30 (m, 3H), 7.20-7.05 (m, 1H), 5.19-5.10 (m, 2H), 4.32-4.20 (m, 2H), 4.09-4.00 (m, 1H), 3.92-3.80 (m, 4H), 3.65 (s, 6H), 2.95-2.80 (m, 6H), 2.40-1.90 (m, 12H), 1.65-1.30 (m, 4H), 1.03-0.86 (m, 6H) ppm; LC-MS (ESI): m/z 845.4 $(M+H)^+$ Biological Activity Biological activity of the compounds of the invention was determined using an HCV replicon assay. The HCV 1b_Huh-Luc/Neo-ET cell line persistently expressing a bicistronic genotype 1b replicon in Huh 7 cells was obtained from ReBLikon GMBH. This cell line was used to test compound inhibition using luciferase enzyme activity readout as a measurement of compound inhibition of replicon levels.

On Day 1 (the day after plating), each compound is added in triplicate to the cells. Plates incubated for 72 h prior to running the luciferase assay. Enzyme activity was measured using a Bright-Glo Kit (cat. number E2620) manufactured by Promega Corporation. The following equation was used to generate a percent control value for each compound.

% Control=(Average Compound Value/Average Control)*100

The $EC_{50}$ value was determined using GraphPad Prism and the following equation:

$$Y=Bottom+(Top-Bottom)/(1+10^{\wedge}((Log\ IC50-X)*HillSlope))$$

$EC_{50}$ values of compounds are determined several times in the replicon assay.

Example compounds of the disclosed invention are illustrated in Tables 1-14 attached as appendices. The tables show inhibitory activity of many of the example compounds with respect to HCV 1b. The biological activity is indicated as being *, , *, or ****, which corresponds to $EC_{50}$ ranges of >1000 nM, 999 nM to 10 nM, 9.9 nM to 1 nM, or <1 nM respectively. The tables further provide mass spectrometry results for the synthesized example compounds.

Pharmaceutical Compositions

A twenty-second aspect of the invention provides a pharmaceutical composition comprising the compounds of the invention. In a first embodiment, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, basic compounds such as free bases. A thorough discussion of pharmaceutically acceptable excipients and salts is available in Remington's Pharmaceutical Sciences, 18th Edition (Easton, Pa.: Mack Publishing Company, 1990).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

A twenty-third aspect of the invention provides use of the compounds of the invention in the manufacture of a medicament.

In a first embodiment of the twenty-third aspect the medicament is for the treatment of hepatitis C.

A twenty-fourth aspect of the invention provides a method of treating hepatitis C comprising administering to a subject in need thereof, a therapeutically effective amount of a compound of the invention, optionally in a pharmaceutical composition. A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject may be administered as many doses as is required to reduce and/or alleviate the signs, symptoms or causes of the disorder in question, or bring about any other desired alteration of a biological system. One of ordinary skill in the art of treating such diseases will be able, without undue experimentation and in reliance upon personal knowledge and the disclosure of this application, to ascertain a therapeutically effective amount of the compounds of this invention for a given disease.

Combination Therapy

The compounds of the present invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention may include, without limitation, all classes of HCV antivirals. For combination therapies, mechanistic classes of agents that may be useful when combined with the compounds of the present invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-813, PHX-1766, PHX2054, IDX-136, IDX-316, ABT-450 EP-013420 (and congeners) and VBY-376; the Nucleosidic HCV polymerase (replicase) inhibitors useful in the invention include, but are not limited to, R7128, PSI-7851, IDX-184, IDX-102, R1479, UNX-08189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nuclosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, NS5A inhibitors of the present invention may be used in combination with cyclophyllin and immunophyllin antagonists (eg, without limitation, DEBIO compounds, NM-811 as well as cyclosporine and its derivatives), kinase inhibitors, inhibitors of heat shock proteins (e.g., HSP90 and HSP70), other immunomodulatory agents that may include, without limitation, interferons (-alpha, -beta, -omega, -gamma, -lambda or synthetic) such as Intron A™, Roferon-A™, Canferon-A300™, Advaferon™, Infergen™, Humoferon™, Sumiferon MP™, Alfaferone™ IFN-β™, Feron™ and the like; polyethylene glycol derivatized (pegylated) interferon compounds, such as PEG interferon-α-2a (Pegasys™), PEG interferon-α-2b (PEGIntron™), pegylated IFN-α-con1 and the like; long acting formulations and derivatizations of interferon compounds such as the albumin-fused interferon, Albuferon™, Locteron™ and the like; interferons with various types of controlled delivery systems (e.g. ITCA-638, omega-interferon delivered by the DUROS™ subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL™, REMICADE™ and HUMIRA™.

In addition, NS5A inhibitors of the present invention may be used in combination with antiprotozoans and other antivirals thought to be effective in the treatment of HCV infection, such as, without limitation, the prodrug nitazoxanide. Nitazoxanide can be used as an agent in combination the compounds disclosed in this invention as well as in combination with other agents useful in treating HCV infection such as peginterferon alfa-2a and ribavarin (see, for example, Rossignol, J F and Keeffe, E B, *Future Microbiol.* 3:539-545, 2008).

NS5A inhibitors of the present invention may also be used with alternative forms of interferons and pegylated interferons, ribavirin or its analogs (e.g., tarabavarin, levoviron), microRNA, small interfering RNA compounds (e.g., SIR-PLEX-140-N and the like), nucleotide or nucleoside analogs, immunoglobulins, hepatoprotectants, anti-inflammatory agents and other inhibitors of NS5A Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE-02003002 and BIVN 401 and IMPDH inhibitors. Other illustrative HCV inhibitor compounds include those disclosed in the following publications: U.S. Pat. No. 5,807,876; U.S. Pat. No. 6,498,178; U.S. Pat. No. 6,344,465; U.S. Pat. No. 6,054,472; WO97/40028; WO98/40381; WO00/56331, WO 02/04425; WO 03/007945; WO 03/010141; WO 03/000254; WO 01/32153; WO 00/06529; WO 00/18231; WO 00/10573; WO 00/13708; WO 01/85172; WO 03/037893; WO 03/037894; WO 03/037895; WO 02/100851; WO 02/100846; EP 1256628; WO 99/01582; WO 00/09543; WO02/18369; WO98/17679, WO00/056331; WO 98/22496; WO 99/07734; WO 05/073216, WO 05/073195 and WO 08/021,927.

Additionally, combinations of, for example, ribavirin and interferon, may be administered as multiple combination therapy with at least one of the compounds of the present invention. The present invention is not limited to the aforementioned classes or compounds and contemplates known and new compounds and combinations of biologically active agents (see, Strader, D. B., Wright, T., Thomas, D. L. and Seeff, L. B., *AASLD Practice Guidelines.* 1-22, 2009 and Manns, M. P., Foster, G. R., Rockstroh, J. K., Zeuzem, S., Zoulim, F. and Houghton, M., *Nature Reviews Drug Discovery.* 6:991-1000, 2007, Pawlotsky, J-M., Chevaliez, S, and McHutchinson, J. G., *Gastroenterology.* 132:179-1998, 2007, Lindenbach, B. D. and Rice, C. M., *Nature* 436:933-938, 2005, Klebl, B. M., Kurtenbach, A., Salassidis, K., Daub, H. and Herget, T., *Antiviral Chemistry & Chemotherapy*. 16:69-90, 2005, Beaulieu, P. L., *Current Opinion in Investigational Drugs*. 8:614-634, 2007, Kim, S-J., Kim, J-H., Kim, Y-G., Lim, H-S, and Oh, W-J., *The Journal of Biological Chemistry*. 48:50031-50041, 2004, Okamoto, T., Nishimura, Y., Ichimura, T., Suzuki, K., Miyamura, T., Suzuki, T., Moriishi, K. and Matsuura, Y., *The EMBO Journal*. 1-11, 2006, Soriano, V., Peters, M. G. and Zeuzem, S. *Clinical Infectious Diseases*. 48:313-320, 2009, Huang, Z., Murray, M. G. and Secrist, J. A., *Antiviral Research*. 71:351-362, 2006 and Neyts, J., *Antiviral Research*. 71:363-371, 2006, each of which is incorporated by reference in their entirety herein). It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself.

Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the professional judgment of the person administering or supervising the administration of the combination therapy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

TABLE 1

| Compound # | Structure | Inhibition of HCV genotype 1b | MS (M + H⁺) |
|---|---|---|---|
| 99 | 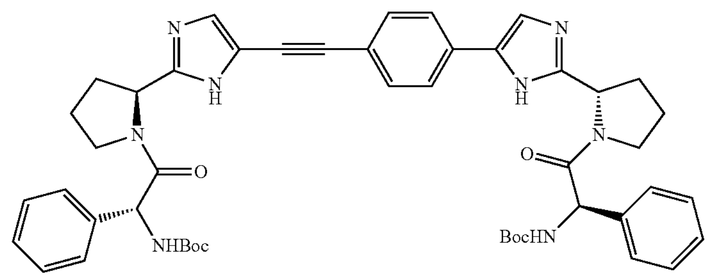 [SMILES: CC(C)(C)OC(=O)N[C@@H](C(=O)N1CCC[C@H]1c1ncc(C#Cc2ccc(-c3cnc([C@@H]4CCCN4C(=O)[C@H](NC(=O)OC(C)(C)C)c4ccccc4)[nH]3)cc2)[nH]1)c1ccccc1] | **** | 839.4 |
| 100 | 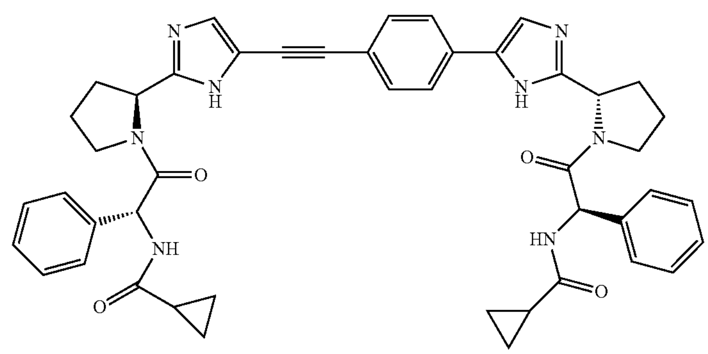 [SMILES: O=C(N[C@@H](C(=O)N1CCC[C@H]1c1ncc(C#Cc2ccc(-c3cnc([C@@H]4CCCN4C(=O)[C@H](NC(=O)C4CC4)c4ccccc4)[nH]3)cc2)[nH]1)c1ccccc1)C1CC1] | **** | 775.4 |
| 101 | 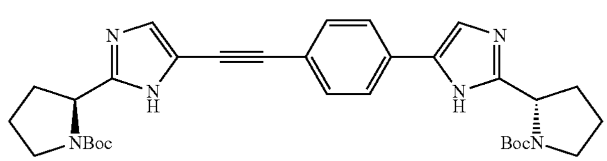 [SMILES: CC(C)(C)OC(=O)N1CCC[C@H]1c1ncc(C#Cc2ccc(-c3cnc([C@@H]4CCCN4C(=O)OC(C)(C)C)[nH]3)cc2)[nH]1] | ** | 573.3 |

TABLE 1-continued

| Compound # | Structure | Inhibition of HCV genotype 1b | MS (M + H+) |
|---|---|---|---|
| 102 | 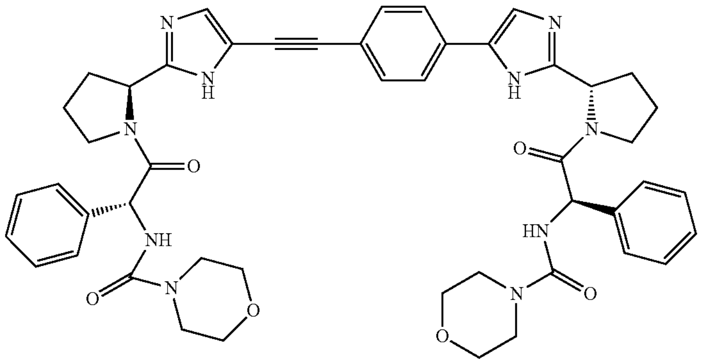 [SMILES: O=C(N[C@@H](C(=O)N1CCC[C@H]1c1ncc(C#Cc2ccc(-c3cnc([C@@H]4CCCN4C(=O)[C@H](NC(=O)N4CCOCC4)c4ccccc4)[nH]3)cc2)[nH]1)c1ccccc1)N1CCOCC1] | *** | 865.4 |
| 103 | 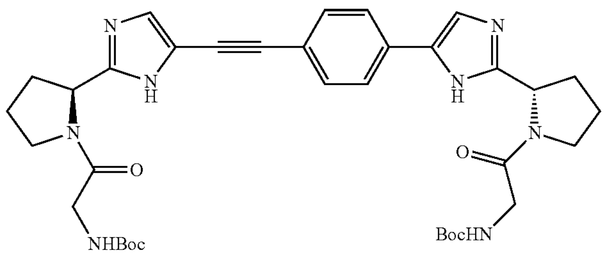 [SMILES: CC(C)(C)OC(=O)NCC(=O)N1CCC[C@H]1c1ncc(C#Cc2ccc(-c3cnc([C@@H]4CCCN4C(=O)CNC(=O)OC(C)(C)C)[nH]3)cc2)[nH]1] | ** | 687.4 |
| 104 | 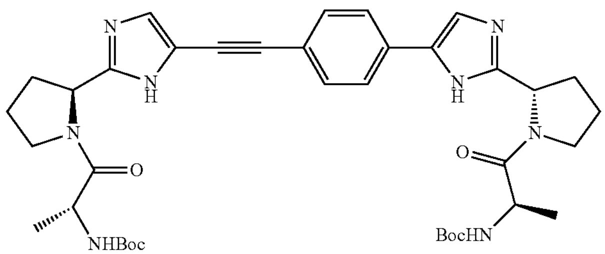 [SMILES: C[C@@H](NC(=O)OC(C)(C)C)C(=O)N1CCC[C@H]1c1ncc(C#Cc2ccc(-c3cnc([C@@H]4CCCN4C(=O)[C@@H](C)NC(=O)OC(C)(C)C)[nH]3)cc2)[nH]1] | *** | 715.4 |
| 105 | 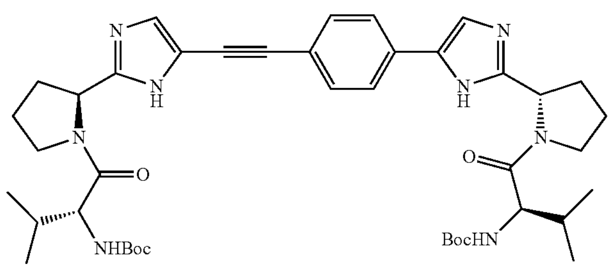 [SMILES: CC(C)[C@@H](NC(=O)OC(C)(C)C)C(=O)N1CCC[C@H]1c1ncc(C#Cc2ccc(-c3cnc([C@@H]4CCCN4C(=O)[C@H](NC(=O)OC(C)(C)C)C(C)C)[nH]3)cc2)[nH]1] | ** | 771.4 |
| 106 | 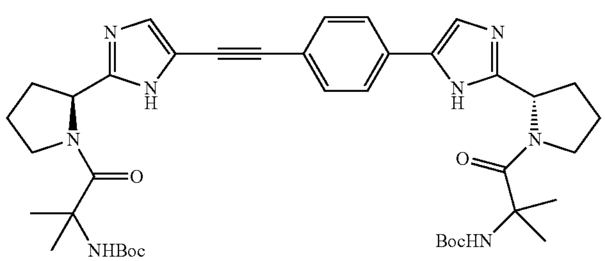 [SMILES: CC(C)(C)OC(=O)NC(C)(C)C(=O)N1CCC[C@H]1c1ncc(C#Cc2ccc(-c3cnc([C@@H]4CCCN4C(=O)C(C)(C)NC(=O)OC(C)(C)C)[nH]3)cc2)[nH]1] | * | 743.4 |

TABLE 1-continued

| Compound # | Structure | Inhibition of HCV genotype 1b | MS (M + H⁺) |
|---|---|---|---|
| 107 | 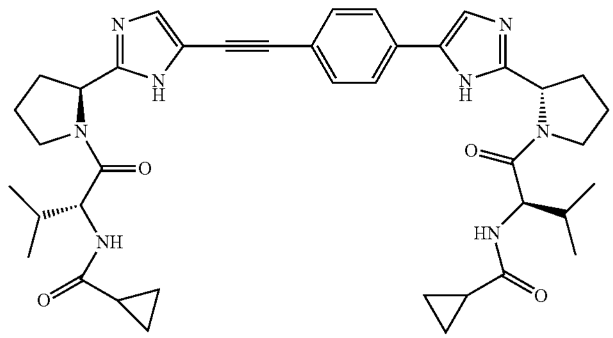 [SMILES: CC(C)[C@@H](NC(=O)C1CC1)C(=O)N1CCC[C@H]1c1ncc(C#Cc2ccc(-c3cnc([C@@H]4CCCN4C(=O)[C@H](NC(=O)C4CC4)C(C)C)[nH]3)cc2)[nH]1] | *** | 707.4 |
| 108 | 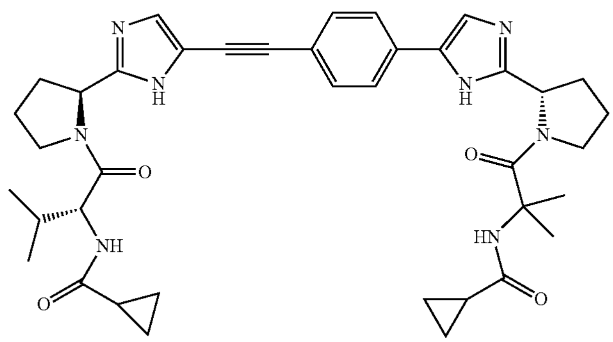 [SMILES: CC(C)[C@@H](NC(=O)C1CC1)C(=O)N1CCC[C@H]1c1ncc(C#Cc2ccc(-c3cnc([C@@H]4CCCN4C(=O)C(C)(C)NC(=O)C4CC4)[nH]3)cc2)[nH]1] | * | 679.4 |
| 109 | 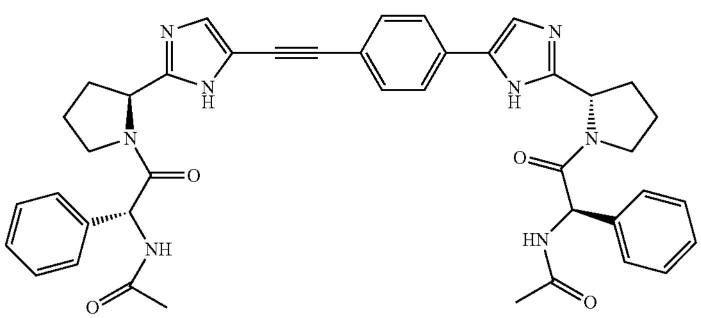 [SMILES: CC(=O)N[C@@H](C(=O)N1CCC[C@H]1c1ncc(C#Cc2ccc(-c3cnc([C@@H]4CCCN4C(=O)[C@H](NC(C)=O)c4ccccc4)[nH]3)cc2)[nH]1)c1ccccc1] | **** | 723.3 |
| 110 | 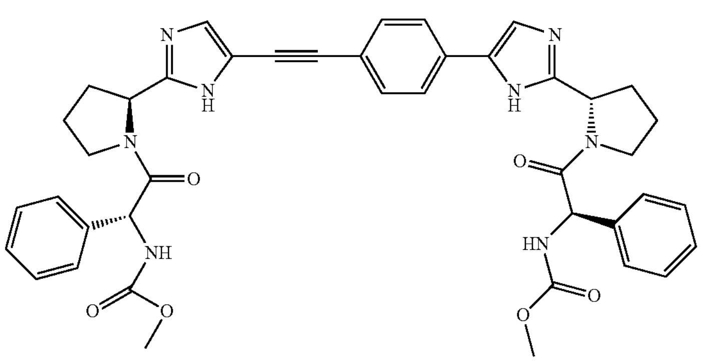 [SMILES: COC(=O)N[C@@H](C(=O)N1CCC[C@H]1c1ncc(C#Cc2ccc(-c3cnc([C@@H]4CCCN4C(=O)[C@H](NC(=O)OC)c4ccccc4)[nH]3)cc2)[nH]1)c1ccccc1] | **** | 755.3 |

TABLE 1-continued

| Compound # | Structure | Inhibition of HCV genotype 1b | MS (M + H⁺) |
|---|---|---|---|
| 111 | 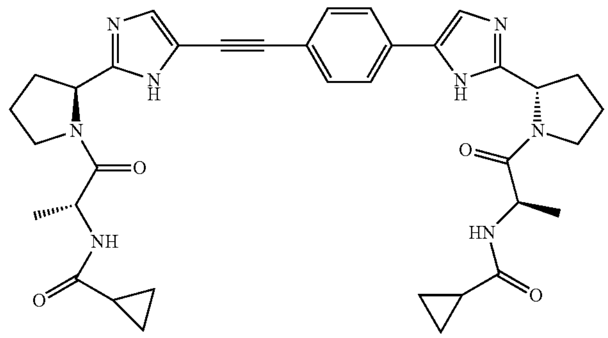 [SMILES: C[C@@H](NC(=O)C1CC1)C(=O)N1CCC[C@H]1c1ncc(C#Cc2ccc(-c3cnc([C@@H]4CCCN4C(=O)[C@@H](C)NC(=O)C4CC4)[nH]3)cc2)[nH]1] | *** | 651.3 |
| 112 | 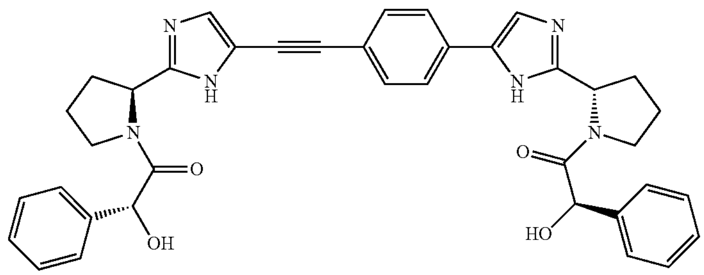 [SMILES: O=C([C@H](O)c1ccccc1)N1CCC[C@H]1c1ncc(C#Cc2ccc(-c3cnc([C@@H]4CCCN4C(=O)[C@H](O)c4ccccc4)[nH]3)cc2)[nH]1] | **** | 641.3 |
| 113 | 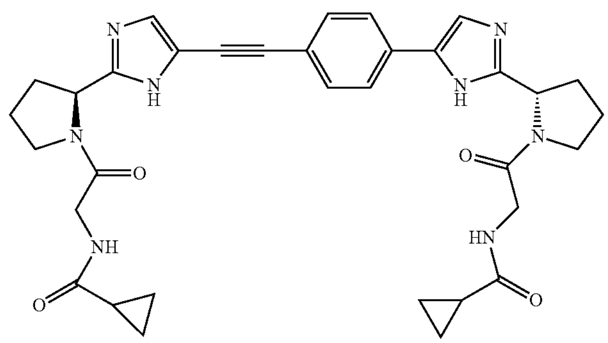 [SMILES: O=C(NCC(=O)N1CCC[C@H]1c1ncc(C#Cc2ccc(-c3cnc([C@@H]4CCCN4C(=O)CNC(=O)C4CC4)[nH]3)cc2)[nH]1)C1CC1] | ** | 623.3 |
| 114 | 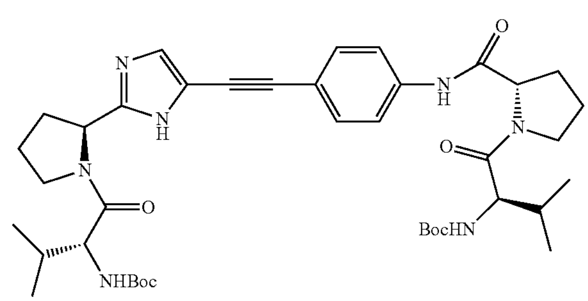 [SMILES: CC(C)[C@@H](NC(=O)OC(C)(C)C)C(=O)N1CCC[C@H]1C(=O)Nc1ccc(C#Cc2cnc([C@@H]3CCCN3C(=O)[C@H](NC(=O)OC(C)(C)C)C(C)C)[nH]2)cc1] | ** | 748.4 |
| 115 | 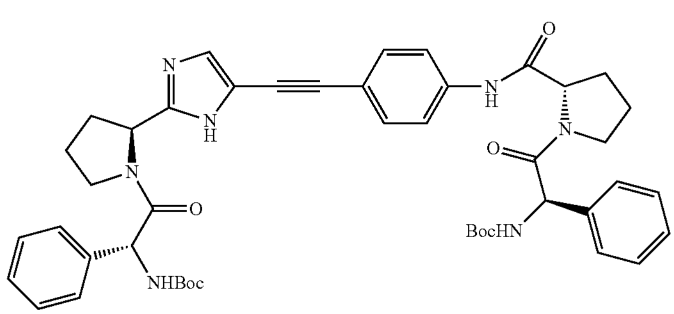 [SMILES: CC(C)(C)OC(=O)N[C@@H](C(=O)N1CCC[C@H]1C(=O)Nc1ccc(C#Cc2cnc([C@@H]3CCCN3C(=O)[C@H](NC(=O)OC(C)(C)C)c3ccccc3)[nH]2)cc1)c1ccccc1] | **** | 816.4 |

TABLE 1-continued

| Compound # | Structure | Inhibition of HCV genotype 1b | MS (M + H⁺) |
| --- | --- | --- | --- |
| 116 | 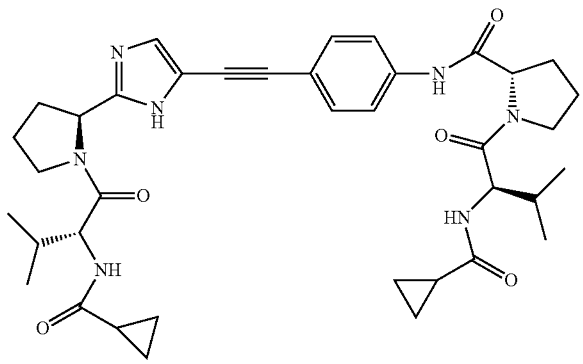 [SMILES: CC(C)[C@@H](NC(=O)C1CC1)C(=O)N1CCC[C@H]1C(=O)Nc1ccc(C#Cc2cnc([C@@H]3CCCN3C(=O)[C@H](NC(=O)C3CC3)C(C)C)[nH]2)cc1] | *** | 684.4 |
| 117 | 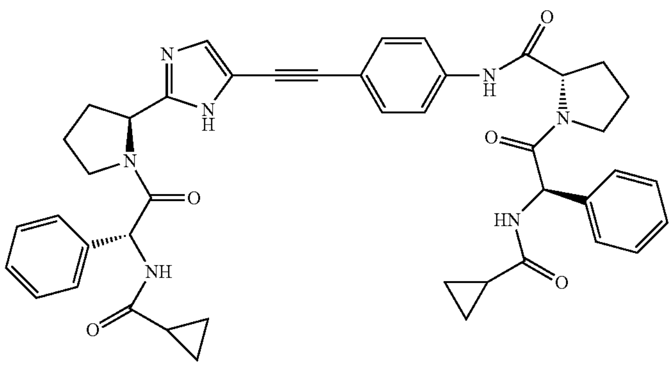 [SMILES: O=C(N[C@@H](C(=O)N1CCC[C@H]1C(=O)Nc1ccc(C#Cc2cnc([C@@H]3CCCN3C(=O)[C@H](NC(=O)C3CC3)c3ccccc3)[nH]2)cc1)c1ccccc1)C1CC1] | **** | 752.3 |
| 118 | 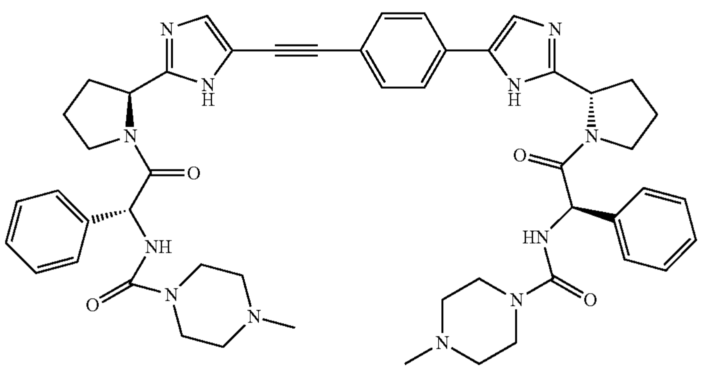 [SMILES: CN1CCN(C(=O)N[C@@H](C(=O)N2CCC[C@H]2c2ncc(C#Cc3ccc(-c4cnc([C@@H]5CCCN5C(=O)[C@H](NC(=O)N5CCN(C)CC5)c5ccccc5)[nH]4)cc3)[nH]2)c2ccccc2)CC1] | ** | 891.5 |
| 119 | 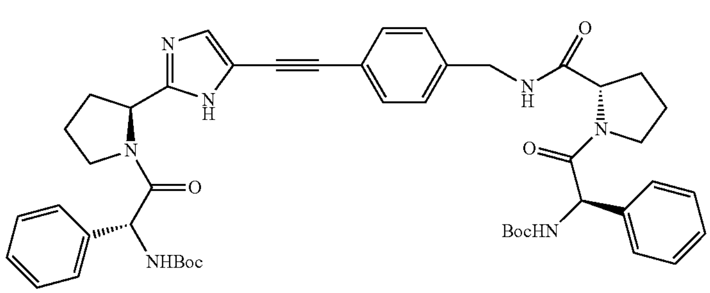 [SMILES: CC(C)(C)OC(=O)N[C@@H](C(=O)N1CCC[C@H]1C(=O)NCc1ccc(C#Cc2cnc([C@@H]3CCCN3C(=O)[C@H](NC(=O)OC(C)(C)C)c3ccccc3)[nH]2)cc1)c1ccccc1] | **** | 830.4 |

TABLE 1-continued

| Compound # | Structure | Inhibition of HCV genotype 1b | MS (M + H⁺) |
|---|---|---|---|
| 120 | 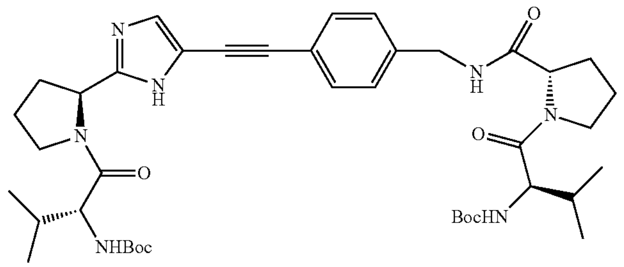 [SMILES: CC(C)[C@@H](NC(=O)OC(C)(C)C)C(=O)N1CCC[C@H]1C(=O)NCc1ccc(C#Cc2cnc([C@@H]3CCCN3C(=O)[C@H](NC(=O)OC(C)(C)C)C(C)C)[nH]2)cc1] | ** | 762.4 |
| 121 | 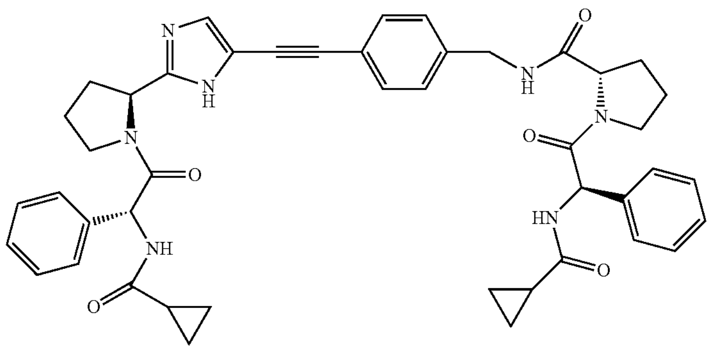 [SMILES: O=C(N[C@@H](C(=O)N1CCC[C@H]1C(=O)NCc1ccc(C#Cc2cnc([C@@H]3CCCN3C(=O)[C@H](NC(=O)C3CC3)c3ccccc3)[nH]2)cc1)c1ccccc1)C1CC1] | **** | 766.4 |
| 122 | 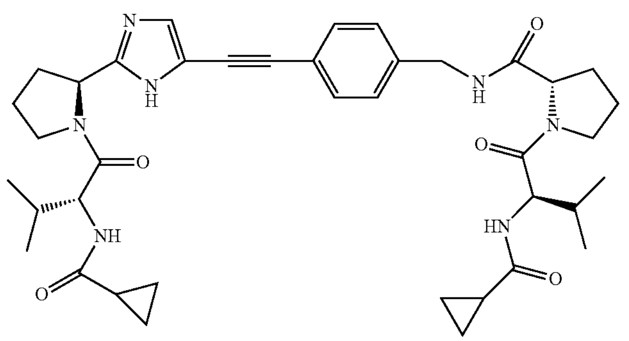 [SMILES: CC(C)[C@@H](NC(=O)C1CC1)C(=O)N1CCC[C@H]1C(=O)NCc1ccc(C#Cc2cnc([C@@H]3CCCN3C(=O)[C@H](NC(=O)C3CC3)C(C)C)[nH]2)cc1] | *** | 698.4 |
| 123 | 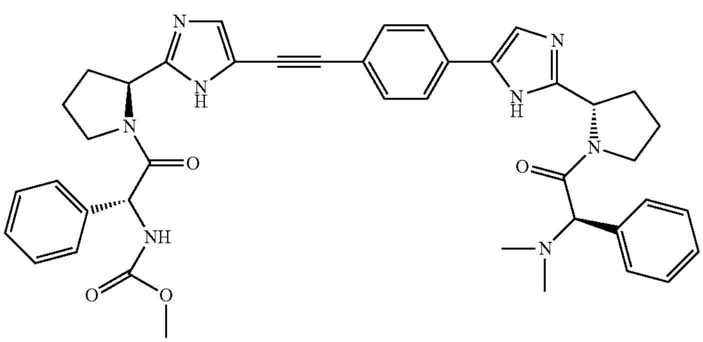 [SMILES: COC(=O)N[C@@H](C(=O)N1CCC[C@H]1c1ncc(C#Cc2ccc(-c3cnc([C@@H]4CCCN4C(=O)[C@@H](c4ccccc4)N(C)C)[nH]3)cc2)[nH]1)c1ccccc1] | **** | 725.3 |
| 124 | 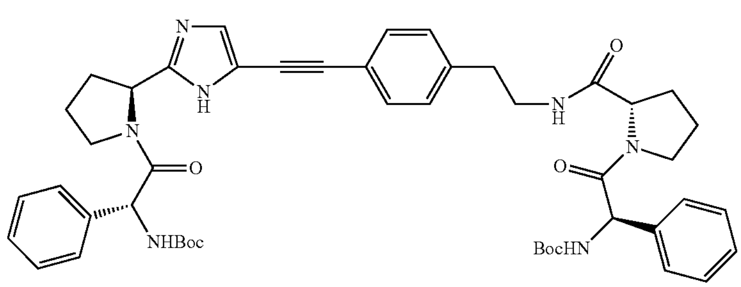 [SMILES: CC(C)(C)OC(=O)N[C@@H](C(=O)N1CCC[C@H]1C(=O)NCCc1ccc(C#Cc2cnc([C@@H]3CCCN3C(=O)[C@H](NC(=O)OC(C)(C)C)c3ccccc3)[nH]2)cc1)c1ccccc1] | **** | 844.4 |

TABLE 1-continued

| Compound # | Structure | Inhibition of HCV genotype 1b | MS (M + H⁺) |
|---|---|---|---|
| 125 | 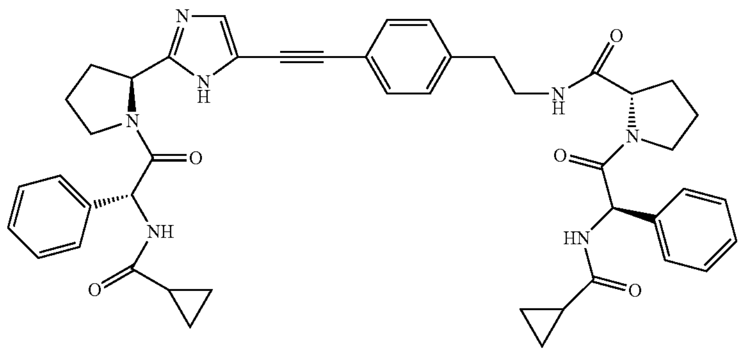 [SMILES: O=C(N[C@@H](C(=O)N1CCC[C@H]1C(=O)NCCc1ccc(C#Cc2cnc([C@@H]3CCCN3C(=O)[C@H](NC(=O)C3CC3)c3ccccc3)[nH]2)cc1)c1ccccc1)C1CC1] | **** | 780.4 |
| 126 | 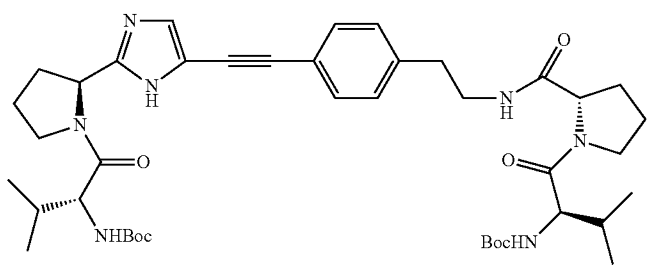 [SMILES: CC(C)[C@@H](NC(=O)OC(C)(C)C)C(=O)N1CCC[C@H]1C(=O)NCCc1ccc(C#Cc2cnc([C@@H]3CCCN3C(=O)[C@H](NC(=O)OC(C)(C)C)C(C)C)[nH]2)cc1] | ** | 776.5 |
| 127 | 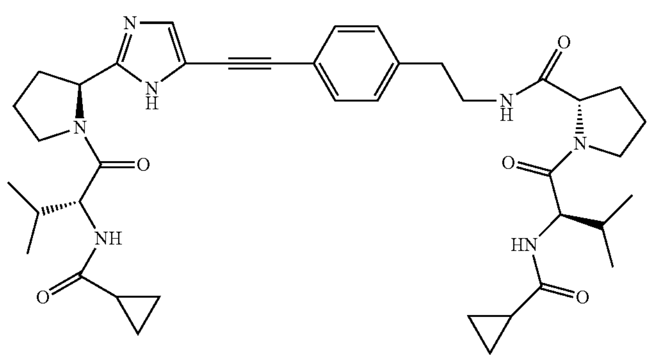 [SMILES: CC(C)[C@@H](NC(=O)C1CC1)C(=O)N1CCC[C@H]1C(=O)NCCc1ccc(C#Cc2cnc([C@@H]3CCCN3C(=O)[C@H](NC(=O)C3CC3)C(C)C)[nH]2)cc1] | ** | 712.4 |
| 128 | 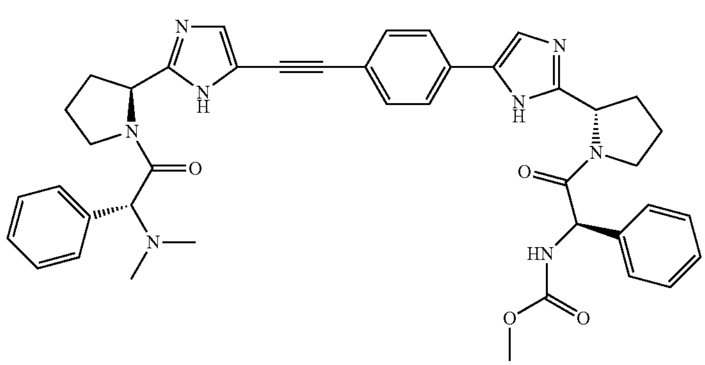 [SMILES: COC(=O)N[C@@H](C(=O)N1CCC[C@H]1c1ncc(-c2ccc(C#Cc3cnc([C@@H]4CCCN4C(=O)[C@@H](c4ccccc4)N(C)C)[nH]3)cc2)[nH]1)c1ccccc1] | **** | 725.3 |

TABLE 1-continued

| Compound # | Structure | Inhibition of HCV genotype 1b | MS (M + H+) |
|---|---|---|---|
| 129 | 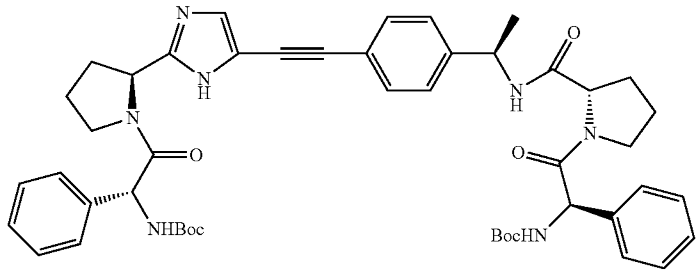 [SMILES: C[C@@H](NC(=O)[C@@H]1CCCN1C(=O)[C@H](NC(=O)OC(C)(C)C)c1ccccc1)c1ccc(C#Cc2cnc([C@@H]3CCCN3C(=O)[C@H](NC(=O)OC(C)(C)C)c3ccccc3)[nH]2)cc1] | ** | 844.4 |
| 130 | 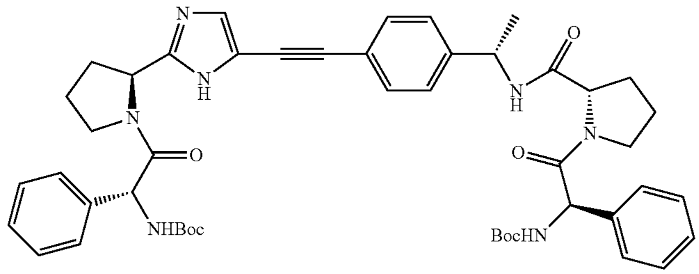 [SMILES: C[C@H](NC(=O)[C@@H]1CCCN1C(=O)[C@H](NC(=O)OC(C)(C)C)c1ccccc1)c1ccc(C#Cc2cnc([C@@H]3CCCN3C(=O)[C@H](NC(=O)OC(C)(C)C)c3ccccc3)[nH]2)cc1] | ** | 844.4 |
| 131 | 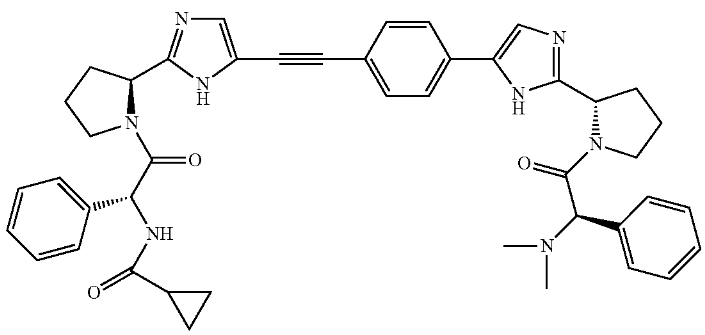 [SMILES: CN(C)[C@@H](C(=O)N1CCC[C@H]1c1ncc(-c2ccc(C#Cc3cnc([C@@H]4CCCN4C(=O)[C@H](NC(=O)C4CC4)c4ccccc4)[nH]3)cc2)[nH]1)c1ccccc1] | **** | 735.4 |
| 132 | 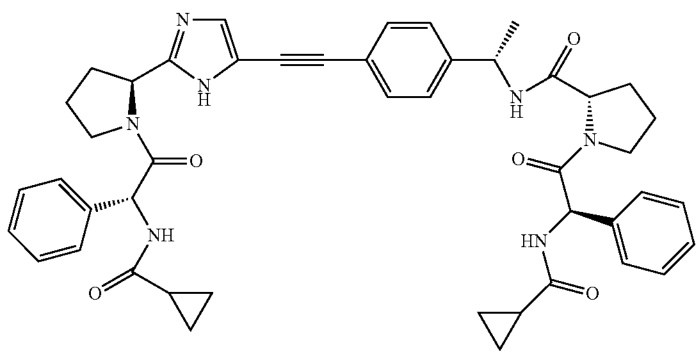 [SMILES: C[C@H](NC(=O)[C@@H]1CCCN1C(=O)[C@H](NC(=O)C1CC1)c1ccccc1)c1ccc(C#Cc2cnc([C@@H]3CCCN3C(=O)[C@H](NC(=O)C3CC3)c3ccccc3)[nH]2)cc1] | ** | 780.4 |
| 133 | 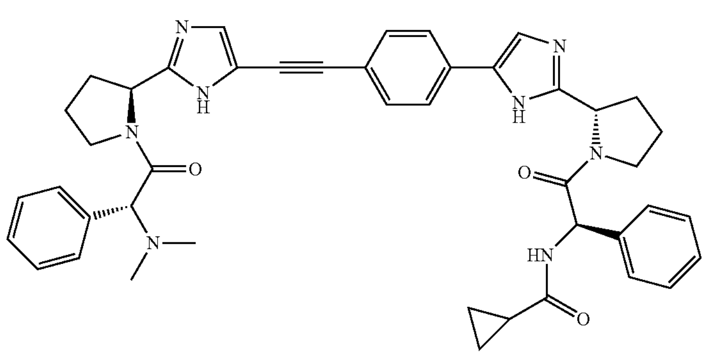 [SMILES: CN(C)[C@@H](C(=O)N1CCC[C@H]1c1ncc(C#Cc2ccc(-c3cnc([C@@H]4CCCN4C(=O)[C@H](NC(=O)C4CC4)c4ccccc4)[nH]3)cc2)[nH]1)c1ccccc1] | **** | 735.4 |

TABLE 1-continued
| Compound # | Structure | Inhibition of HCV genotype 1b | MS (M + H⁺) |
|---|---|---|---|
| 134 | 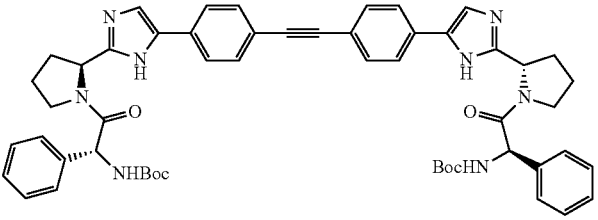 [SMILES: CC(C)(C)OC(=O)N[C@@H](C(=O)N1CCC[C@H]1c1ncc(-c2ccc(C#Cc3ccc(-c4cnc([C@@H]5CCCN5C(=O)[C@H](NC(=O)OC(C)(C)C)c5ccccc5)[nH]4)cc3)cc2)[nH]1)c1ccccc1] | **** | 687.4 |
| 135 | 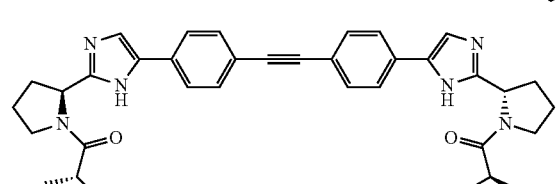 | * | 780.4 |
TABLE 2
| Compound # | Structure | Inhibition of HCV genotype 1b | MS (M + H⁺) |
|---|---|---|---|
| 150 | 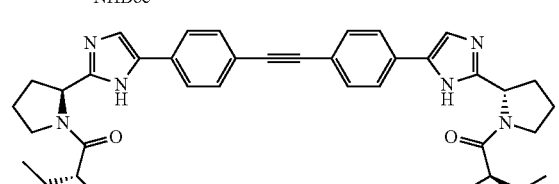 | **** | 915.4 |
| 151 | 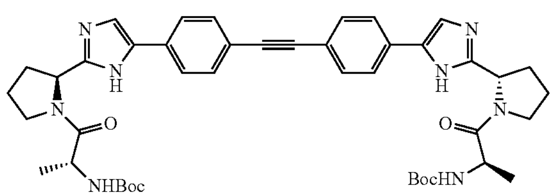 [SMILES: C[C@@H](NC(=O)OC(C)(C)C)C(=O)N1CCC[C@H]1c1ncc(-c2ccc(C#Cc3ccc(-c4cnc([C@@H]5CCCN5C(=O)[C@@H](C)NC(=O)OC(C)(C)C)[nH]4)cc3)cc2)[nH]1] | ** | 791.4 |
| 152 | 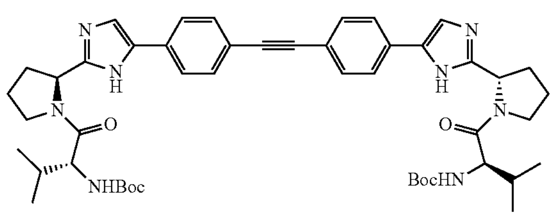 [SMILES: CC(C)[C@@H](NC(=O)OC(C)(C)C)C(=O)N1CCC[C@H]1c1ncc(-c2ccc(C#Cc3ccc(-c4cnc([C@@H]5CCCN5C(=O)[C@H](NC(=O)OC(C)(C)C)C(C)C)[nH]4)cc3)cc2)[nH]1] | ** | 847.5 |

TABLE 2-continued

| Compound # | Structure | Inhibition of HCV genotype 1b | MS (M + H⁺) |
|---|---|---|---|
| 153 | 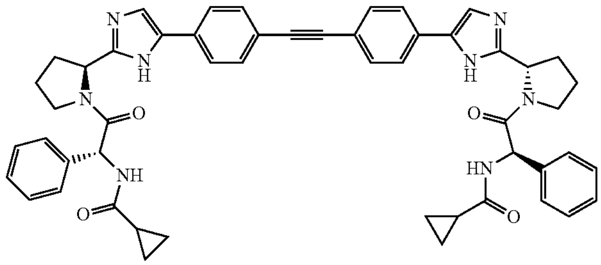 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)C5CC5)c5ccccc5)[nH]4)cc3)cc2)[nH]1)c1ccccc1)C1CC1] | **** | 851.4 |
| 154 | 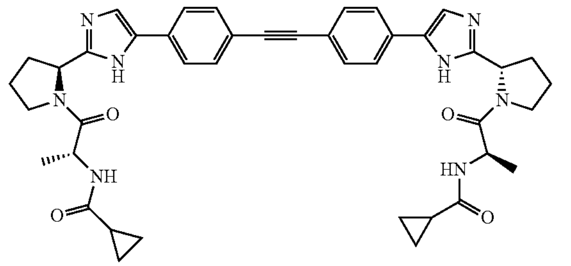 [SMILES: C[C@@H](NC(=O)C1CC1)C(=O)N1CCC[C@H]1c1ncc(-c2ccc(C#Cc3ccc(-c4cnc([C@@H]5CCCN5C(=O)[C@@H](C)NC(=O)C5CC5)[nH]4)cc3)cc2)[nH]1] | *** | 727.4 |
| 155 | 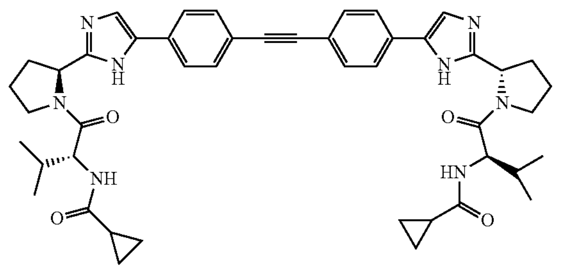 [SMILES: CC(C)[C@@H](NC(=O)C1CC1)C(=O)N1CCC[C@H]1c1ncc(-c2ccc(C#Cc3ccc(-c4cnc([C@@H]5CCCN5C(=O)[C@H](NC(=O)C5CC5)C(C)C)[nH]4)cc3)cc2)[nH]1] | *** | 783.4 |
| 156 | 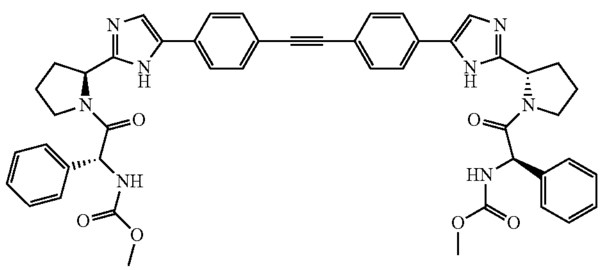 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cc3)cc2)[nH]1)c1ccccc1] | **** | 831.4 |
| 157 | 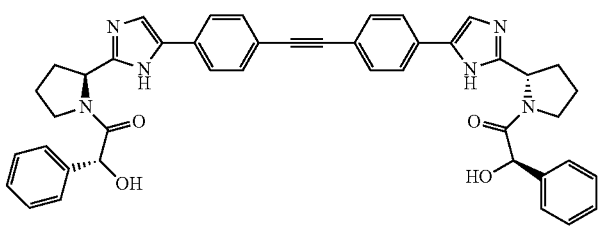 [SMILES: O=C([C@H](O)c1ccccc1)N1CCC[C@H]1c1ncc(-c2ccc(C#Cc3ccc(-c4cnc([C@@H]5CCCN5C(=O)[C@H](O)c5ccccc5)[nH]4)cc3)cc2)[nH]1] | **** | 717.3 |
| 158 | 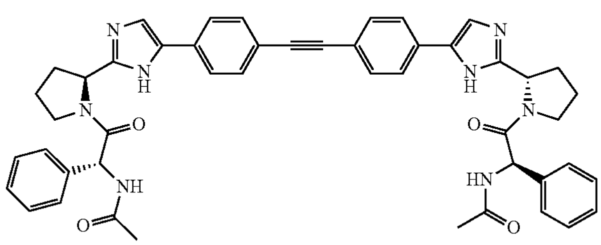 [SMILES: CC(=O)N[C@@H](C(=O)N1CCC[C@H]1c1ncc(-c2ccc(C#Cc3ccc(-c4cnc([C@@H]5CCCN5C(=O)[C@H](NC(C)=O)c5ccccc5)[nH]4)cc3)cc2)[nH]1)c1ccccc1] | **** | 799.4 |

TABLE 2-continued

| Compound # | Structure | Inhibition of HCV genotype 1b | MS (M + H⁺) |
| --- | --- | --- | --- |
| 159 | 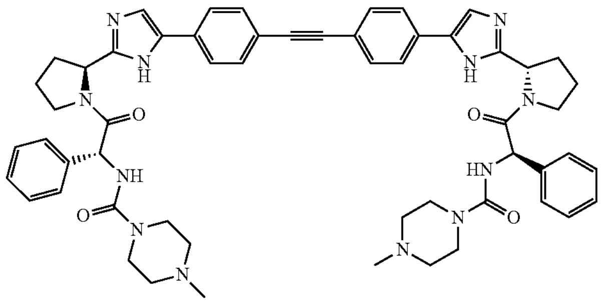 [SMILES: CN1CCN(C(=O)N[C@@H](C(=O)N2CCC[C@H]2c2ncc(-c3ccc(C#Cc4ccc(-c5cnc([C@@H]6CCCN6C(=O)[C@H](NC(=O)N6CCN(C)CC6)c6ccccc6)[nH]5)cc4)cc3)[nH]2)c2ccccc2)CC1] | **** | 967.5 |
| 160 | 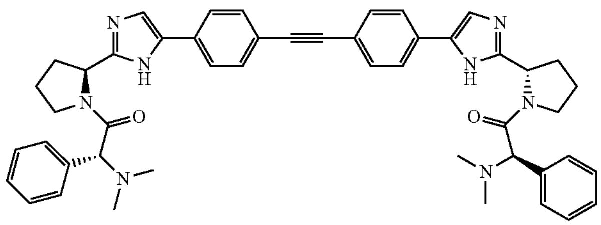 [SMILES: CN(C)[C@@H](C(=O)N1CCC[C@H]1c1ncc(-c2ccc(C#Cc3ccc(-c4cnc([C@@H]5CCCN5C(=O)[C@@H](c5ccccc5)N(C)C)[nH]4)cc3)cc2)[nH]1)c1ccccc1] | **** | 771.4 |
| 161 | 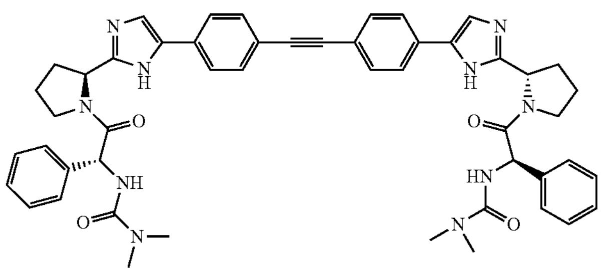 [SMILES: CN(C)C(=O)N[C@@H](C(=O)N1CCC[C@H]1c1ncc(-c2ccc(C#Cc3ccc(-c4cnc([C@@H]5CCCN5C(=O)[C@H](NC(=O)N(C)C)c5ccccc5)[nH]4)cc3)cc2)[nH]1)c1ccccc1] | **** | 857.4 |
| 162 | 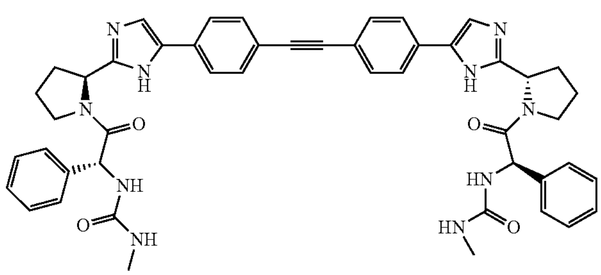 [SMILES: CNC(=O)N[C@@H](C(=O)N1CCC[C@H]1c1ncc(-c2ccc(C#Cc3ccc(-c4cnc([C@@H]5CCCN5C(=O)[C@H](NC(=O)NC)c5ccccc5)[nH]4)cc3)cc2)[nH]1)c1ccccc1] | **** | 829.4 |
| 163 | 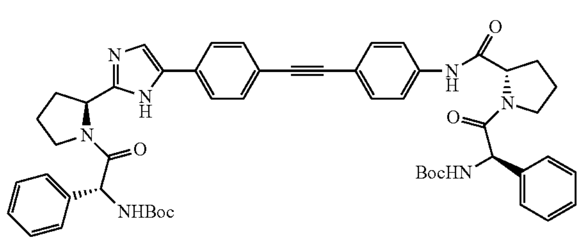 [SMILES: CC(C)(C)OC(=O)N[C@@H](C(=O)N1CCC[C@H]1C(=O)Nc1ccc(C#Cc2ccc(-c3cnc([C@@H]4CCCN4C(=O)[C@H](NC(=O)OC(C)(C)C)c4ccccc4)[nH]3)cc2)cc1)c1ccccc1] | **** | 892.4 |

TABLE 2-continued

| Compound # | Structure | Inhibition of HCV genotype 1b | MS (M + H⁺) |
| --- | --- | --- | --- |
| 164 | 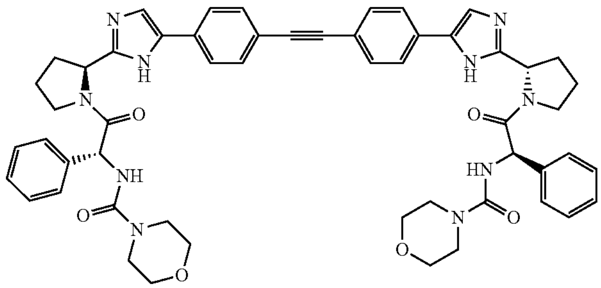 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)N5CCOCC5)c5ccccc5)[nH]4)cc3)cc2)[nH]1)c1ccccc1)N1CCOCC1] | **** | 941.4 |
| 165 | 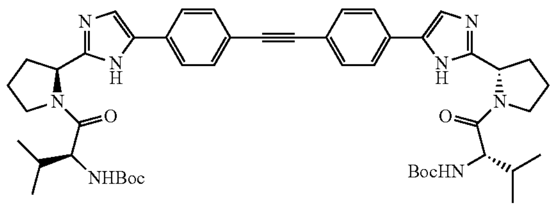 [SMILES: CC(C)[C@H](NC(=O)OC(C)(C)C)C(=O)N1CCC[C@H]1c1ncc(-c2ccc(C#Cc3ccc(-c4cnc([C@@H]5CCCN5C(=O)[C@@H](NC(=O)OC(C)(C)C)C(C)C)[nH]4)cc3)cc2)[nH]1] | ** | 847.5 |
| 166 | 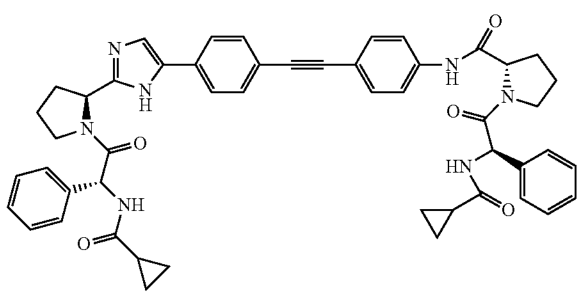 [SMILES: O=C(N[C@@H](C(=O)N1CCC[C@H]1C(=O)Nc1ccc(C#Cc2ccc(-c3cnc([C@@H]4CCCN4C(=O)[C@H](NC(=O)C4CC4)c4ccccc4)[nH]3)cc2)cc1)c1ccccc1)C1CC1] | **** | 828.4 |
| 167 | 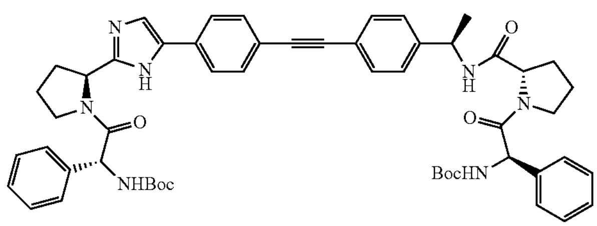 [SMILES: C[C@@H](NC(=O)[C@@H]1CCCN1C(=O)[C@H](NC(=O)OC(C)(C)C)c1ccccc1)c1ccc(C#Cc2ccc(-c3cnc([C@@H]4CCCN4C(=O)[C@H](NC(=O)OC(C)(C)C)c4ccccc4)[nH]3)cc2)cc1] | *** | 920.5 |
| 168 | 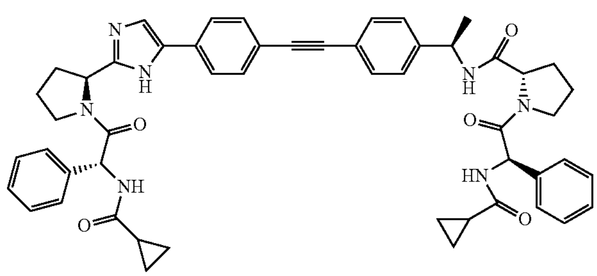 [SMILES: C[C@@H](NC(=O)[C@@H]1CCCN1C(=O)[C@H](NC(=O)C1CC1)c1ccccc1)c1ccc(C#Cc2ccc(-c3cnc([C@@H]4CCCN4C(=O)[C@H](NC(=O)C4CC4)c4ccccc4)[nH]3)cc2)cc1] | **** | 856.4 |
| 169 | 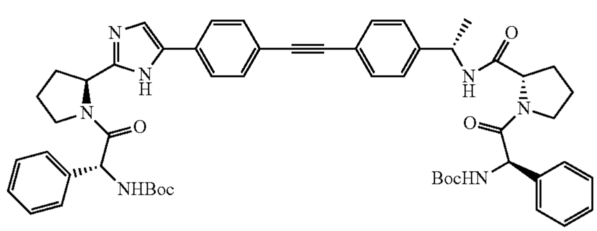 [SMILES: C[C@H](NC(=O)[C@@H]1CCCN1C(=O)[C@H](NC(=O)OC(C)(C)C)c1ccccc1)c1ccc(C#Cc2ccc(-c3cnc([C@@H]4CCCN4C(=O)[C@H](NC(=O)OC(C)(C)C)c4ccccc4)[nH]3)cc2)cc1] | *** | 920.5 |

TABLE 2-continued

| Compound # | Structure | Inhibition of HCV genotype 1b | MS (M + H+) |
|---|---|---|---|
| 170 | 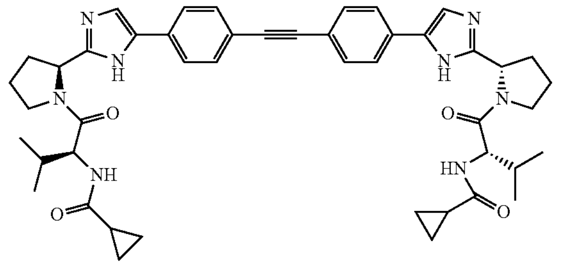 [SMILES: CC(C)[C@H](NC(=O)C1CC1)C(=O)N1CCC[C@H]1c1ncc(-c2ccc(C#Cc3ccc(-c4cnc([C@@H]5CCCN5C(=O)[C@@H](NC(=O)C5CC5)C(C)C)[nH]4)cc3)cc2)[nH]1] | *** | 783.4 |
| 171 | 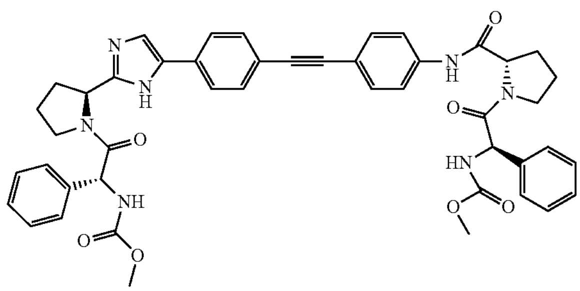 [SMILES: COC(=O)N[C@@H](C(=O)N1CCC[C@H]1C(=O)Nc1ccc(C#Cc2ccc(-c3cnc([C@@H]4CCCN4C(=O)[C@H](NC(=O)OC)c4ccccc4)[nH]3)cc2)cc1)c1ccccc1] | **** | 808.3 |
| 172 | 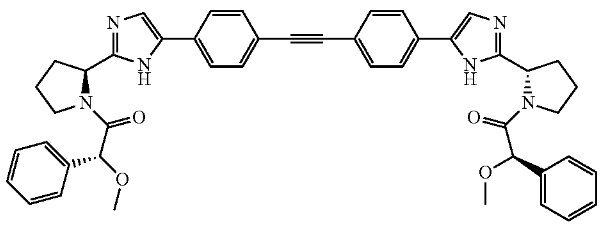 [SMILES: CO[C@@H](C(=O)N1CCC[C@H]1c1ncc(-c2ccc(C#Cc3ccc(-c4cnc([C@@H]5CCCN5C(=O)[C@H](OC)c5ccccc5)[nH]4)cc3)cc2)[nH]1)c1ccccc1] | **** | 745.3 |
| 173 | 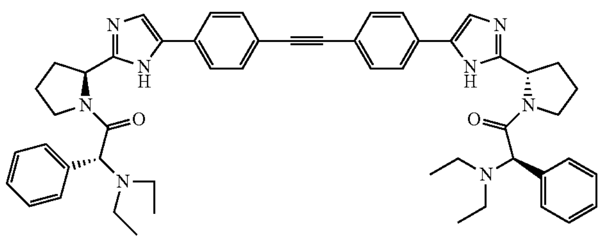 [SMILES: CCN(CC)[C@@H](C(=O)N1CCC[C@H]1c1ncc(-c2ccc(C#Cc3ccc(-c4cnc([C@@H]5CCCN5C(=O)[C@@H](c5ccccc5)N(CC)CC)[nH]4)cc3)cc2)[nH]1)c1ccccc1] | **** | 827.5 |
| 174 | 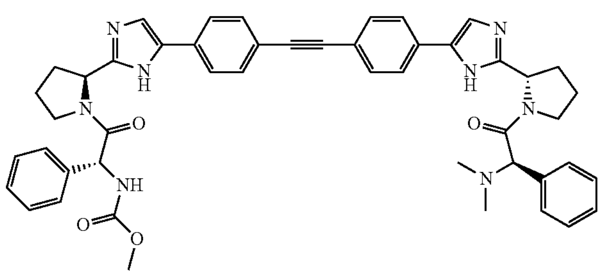 [SMILES: COC(=O)N[C@@H](C(=O)N1CCC[C@H]1c1ncc(-c2ccc(C#Cc3ccc(-c4cnc([C@@H]5CCCN5C(=O)[C@@H](c5ccccc5)N(C)C)[nH]4)cc3)cc2)[nH]1)c1ccccc1] | **** | 801.4 |
| 175 | 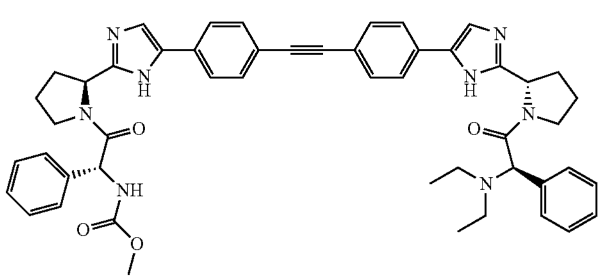 [SMILES: CCN(CC)[C@@H](C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cc3)cc2)[nH]1)c1ccccc1] | **** | 829.4 |

TABLE 2-continued

| Compound # | Structure | Inhibition of HCV genotype 1b | MS (M + H+) |
|---|---|---|---|
| 176 | 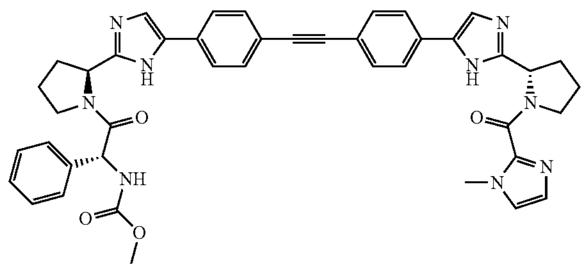 [SMILES: COC(=O)N[C@@H](C(=O)N1CCC[C@H]1c1ncc(-c2ccc(C#Cc3ccc(-c4cnc([C@@H]5CCCN5C(=O)c5nccn5C)[nH]4)cc3)cc2)[nH]1)c1ccccc1] | **** | 748.3 |
| 177 | 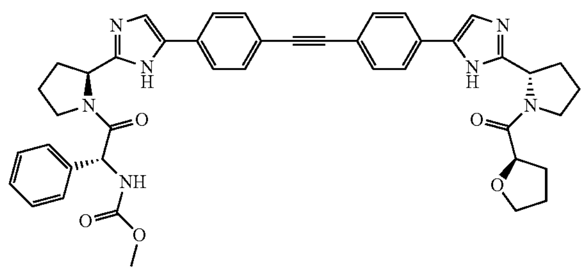 | **** | 738.4 |
| 178 | 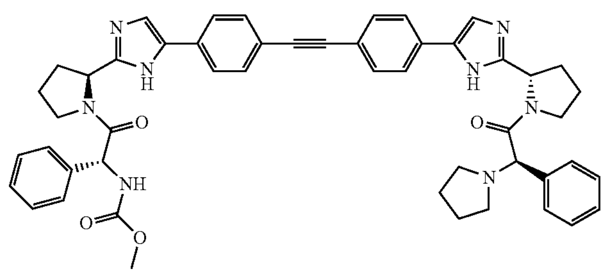 [SMILES: COC(=O)N[C@@H](C(=O)N1CCC[C@H]1c1ncc(-c2ccc(C#Cc3ccc(-c4cnc([C@@H]5CCCN5C(=O)[C@@H](c5ccccc5)N5CCCC5)[nH]4)cc3)cc2)[nH]1)c1ccccc1] | **** | 827.4 |
| 179 | 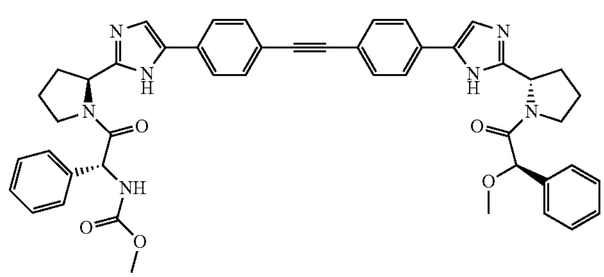 [SMILES: COC(=O)N[C@@H](C(=O)N1CCC[C@H]1c1ncc(-c2ccc(C#Cc3ccc(-c4cnc([C@@H]5CCCN5C(=O)[C@H](OC)c5ccccc5)[nH]4)cc3)cc2)[nH]1)c1ccccc1] | **** | 788.3 |
| 180 | 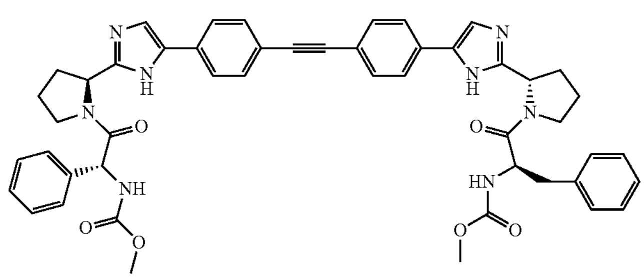 [SMILES: COC(=O)N[C@H](Cc1ccccc1)C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cc3)cc2)[nH]1] | **** | 845.4 |

TABLE 2-continued

| Compound # | Structure | Inhibition of HCV genotype 1b | MS (M + H+) |
|---|---|---|---|
| 181 | 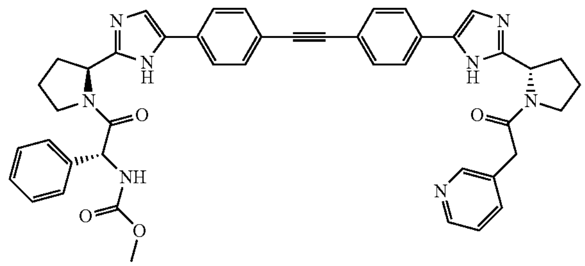 [SMILES: COC(=O)N[C@@H](C(=O)N1CCC[C@H]1c1ncc(-c2ccc(C#Cc3ccc(-c4cnc([C@@H]5CCCN5C(=O)Cc5cccnc5)[nH]4)cc3)cc2)[nH]1)c1ccccc1] | **** | 759.3 |
| 182 | 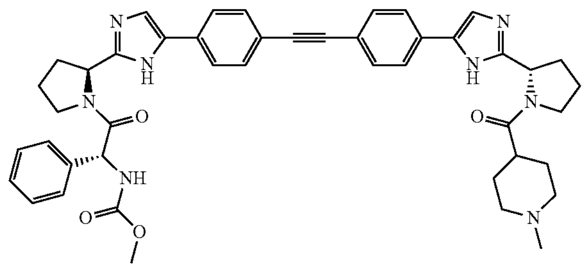 | **** | 765.4 |
| 183 | 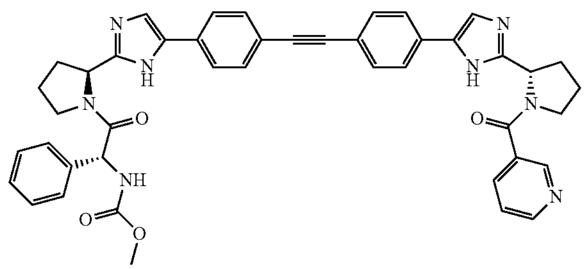 [SMILES: COC(=O)N[C@@H](C(=O)N1CCC[C@H]1c1ncc(-c2ccc(C#Cc3ccc(-c4cnc([C@@H]5CCCN5C(=O)c5cccnc5)[nH]4)cc3)cc2)[nH]1)c1ccccc1] | **** | 745.3 |
| 184 | 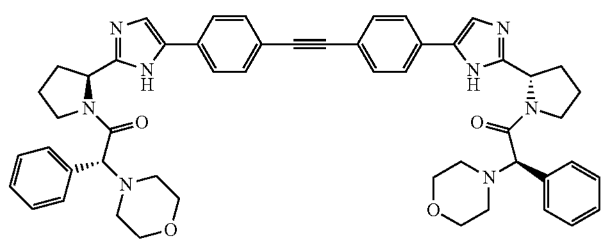 [SMILES: O=C([C@@H](c1ccccc1)N1CCOCC1)N1CCC[C@H]1c1ncc(-c2ccc(C#Cc3ccc(-c4cnc([C@@H]5CCCN5C(=O)[C@@H](c5ccccc5)N5CCOCC5)[nH]4)cc3)cc2)[nH]1] | **** | 855.4 |
| 185 | 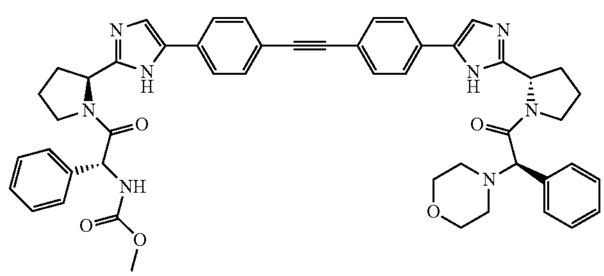 [SMILES: COC(=O)N[C@@H](C(=O)N1CCC[C@H]1c1ncc(-c2ccc(C#Cc3ccc(-c4cnc([C@@H]5CCCN5C(=O)[C@@H](c5ccccc5)N5CCOCC5)[nH]4)cc3)cc2)[nH]1)c1ccccc1] | **** | 843.4 |
| 186 | 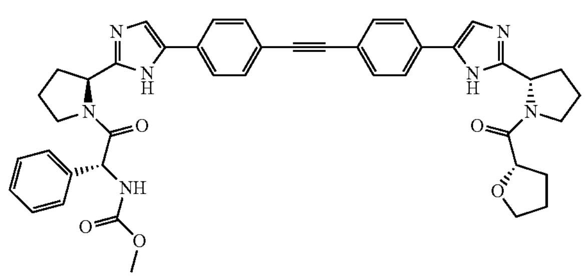 [SMILES: COC(=O)N[C@@H](C(=O)N1CCC[C@H]1c1ncc(-c2ccc(C#Cc3ccc(-c4cnc([C@@H]5CCCN5C(=O)[C@@H]5CCCO5)[nH]4)cc3)cc2)[nH]1)c1ccccc1] | **** | 738.3 |

TABLE 2-continued

| Compound # | Structure | Inhibition of HCV genotype 1b | MS (M + H+) |
|---|---|---|---|
| 187 | 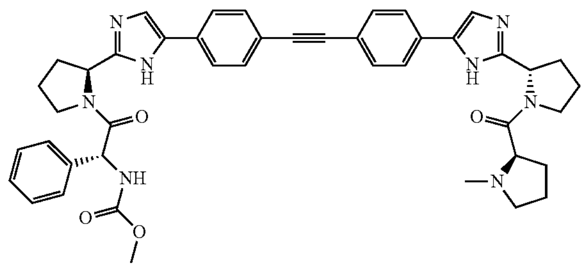 [SMILES: COC(=O)N[C@@H](C(=O)N1CCC[C@H]1c1ncc(-c2ccc(C#Cc3ccc(-c4cnc([C@@H]5CCCN5C(=O)[C@H]5CCCN5C)[nH]4)cc3)cc2)[nH]1)c1ccccc1] | **** | 751.4 |
| 188 | 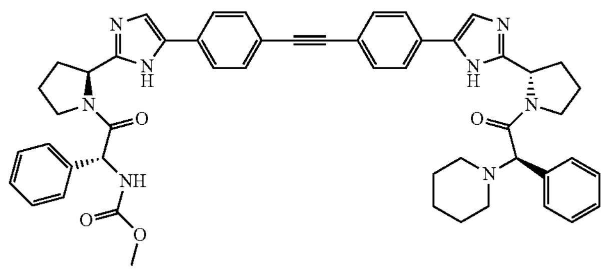 [SMILES: COC(=O)N[C@@H](C(=O)N1CCC[C@H]1c1ncc(-c2ccc(C#Cc3ccc(-c4cnc([C@@H]5CCCN5C(=O)[C@@H](c5ccccc5)N5CCCCC5)[nH]4)cc3)cc2)[nH]1)c1ccccc1] | **** | 841.4 |
| 189 | 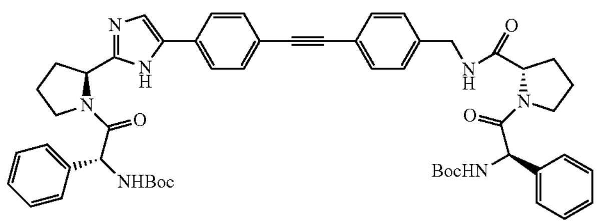 [SMILES: CC(C)(C)OC(=O)N[C@@H](C(=O)N1CCC[C@H]1C(=O)NCc1ccc(C#Cc2ccc(-c3cnc([C@@H]4CCCN4C(=O)[C@H](NC(=O)OC(C)(C)C)c4ccccc4)[nH]3)cc2)cc1)c1ccccc1] | **** | 906.4 |
| 190 | 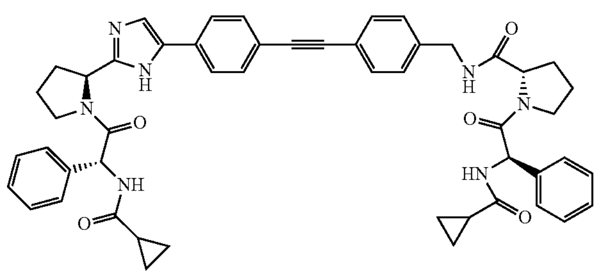 [SMILES: O=C(N[C@@H](C(=O)N1CCC[C@H]1C(=O)NCc1ccc(C#Cc2ccc(-c3cnc([C@@H]4CCCN4C(=O)[C@H](NC(=O)C4CC4)c4ccccc4)[nH]3)cc2)cc1)c1ccccc1)C1CC1] | **** | 842.4 |
| 191 | 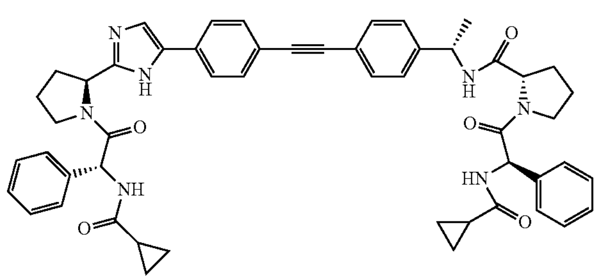 [SMILES: C[C@H](NC(=O)[C@@H]1CCCN1C(=O)[C@H](NC(=O)C1CC1)c1ccccc1)c1ccc(C#Cc2ccc(-c3cnc([C@@H]4CCCN4C(=O)[C@H](NC(=O)C4CC4)c4ccccc4)[nH]3)cc2)cc1] | **** | 856.4 |
| 192 | 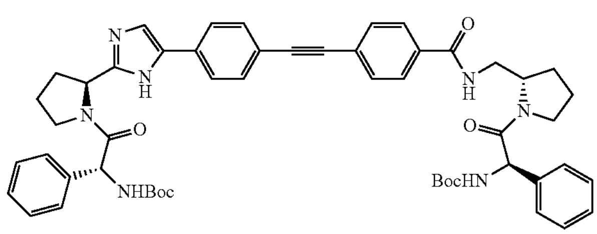 [SMILES: CC(C)(C)OC(=O)N[C@@H](C(=O)N1CCC[C@H]1CNC(=O)c1ccc(C#Cc2ccc(-c3cnc([C@@H]4CCCN4C(=O)[C@H](NC(=O)OC(C)(C)C)c4ccccc4)[nH]3)cc2)cc1)c1ccccc1] | *** | 906.4 |

TABLE 2-continued
| Compound # | Structure | Inhibition of HCV genotype 1b | MS (M + H⁺) |
|---|---|---|---|
| 193 | 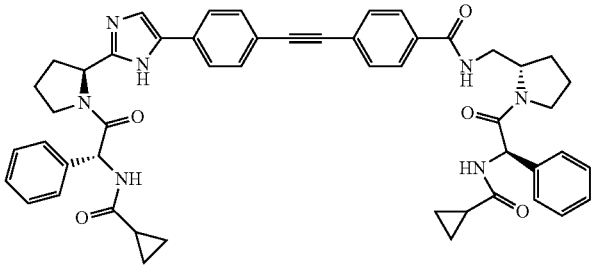 [SMILES: O=C(NC[C@@H]1CCCN1C(=O)[C@H](NC(=O)C1CC1)c1ccccc1)c1ccc(C#Cc2ccc(-c3cnc([C@@H]4CCCN4C(=O)[C@H](NC(=O)C4CC4)c4ccccc4)[nH]3)cc2)cc1] | **** | 842.4 |
| 194 | 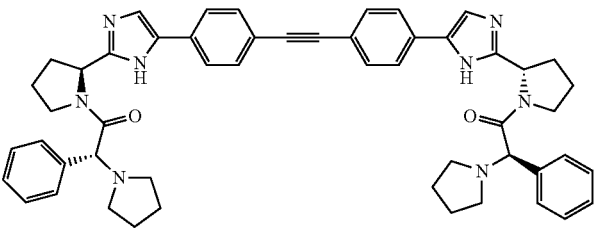 [SMILES: O=C([C@@H](c1ccccc1)N1CCCC1)N1CCC[C@H]1c1ncc(-c2ccc(C#Cc3ccc(-c4cnc([C@@H]5CCCN5C(=O)[C@@H](c5ccccc5)N5CCCC5)[nH]4)cc3)cc2)[nH]1] | **** | 823.4 |
| 195 | 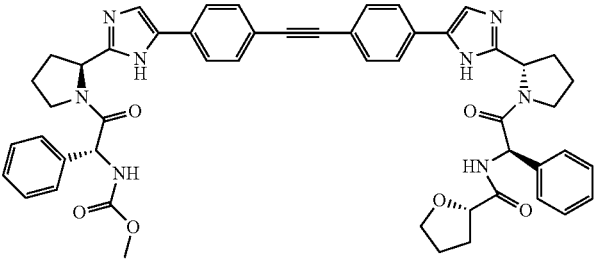 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)[C@@H]5CCCO5)c5ccccc5)[nH]4)cc3)cc2)[nH]1)c1ccccc1] | **** | 871.4 |
| 196 | 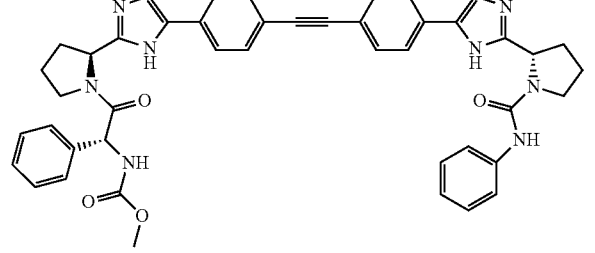 | *** | 759.3 |
| 197 | 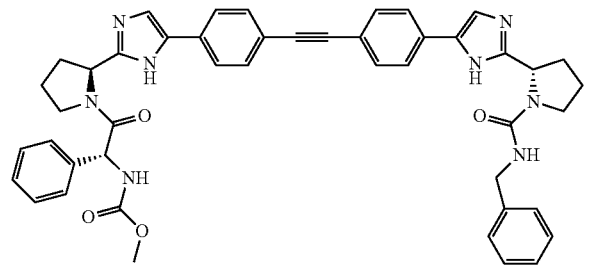 [SMILES: COC(=O)N[C@@H](C(=O)N1CCC[C@H]1c1ncc(-c2ccc(C#Cc3ccc(-c4cnc([C@@H]5CCCN5C(=O)NCc5ccccc5)[nH]4)cc3)cc2)[nH]1)c1ccccc1] | **** | 773.3 |

TABLE 2-continued

| Compound # | Structure | Inhibition of HCV genotype 1b | MS (M + H+) |
|---|---|---|---|
| 198 | 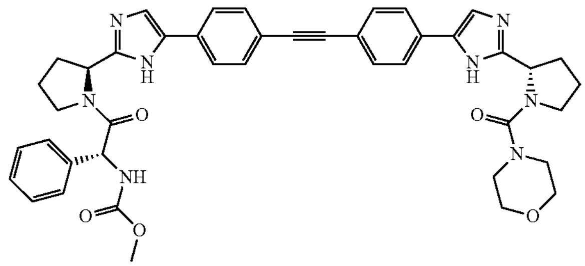 [SMILES: COC(=O)N[C@@H](C(=O)N1CCC[C@H]1c1ncc(-c2ccc(C#Cc3ccc(-c4cnc([C@@H]5CCCN5C(=O)N5CCOCC5)[nH]4)cc3)cc2)[nH]1)c1ccccc1] | **** | 753.3 |
| 199 | 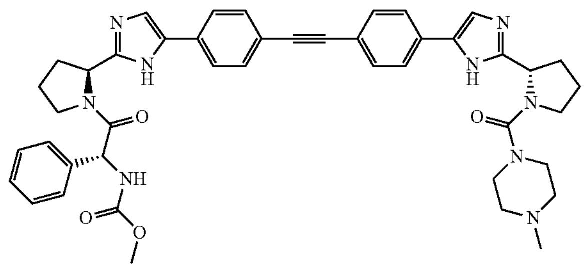 | **** | 776.4 |
| 200 | 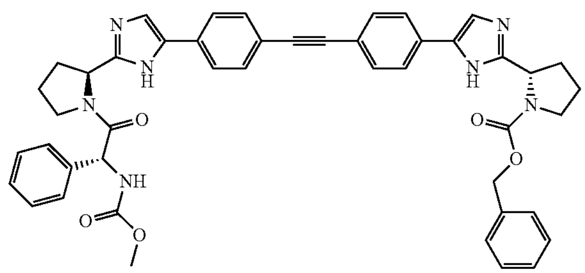 [SMILES: COC(=O)N[C@@H](C(=O)N1CCC[C@H]1c1ncc(-c2ccc(C#Cc3ccc(-c4cnc([C@@H]5CCCN5C(=O)OCc5ccccc5)[nH]4)cc3)cc2)[nH]1)c1ccccc1] | **** | 774.3 |
| 201 | 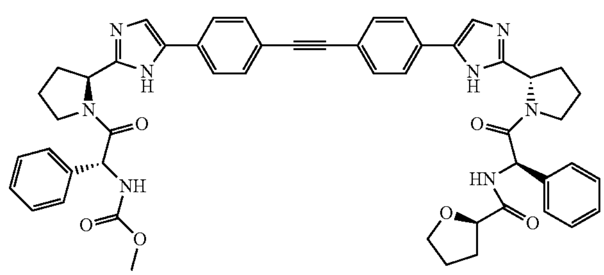 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)[C@H]5CCCO5)c5ccccc5)[nH]4)cc3)cc2)[nH]1)c1ccccc1] | **** | 871.4 |
| 202 | 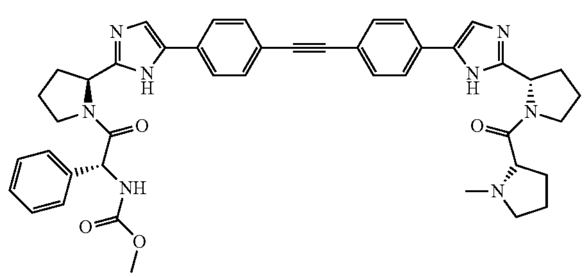 | **** | 751.4 |

TABLE 2-continued

| Compound # | Structure | Inhibition of HCV genotype 1b | MS (M + H+) |
|---|---|---|---|
| 203 | 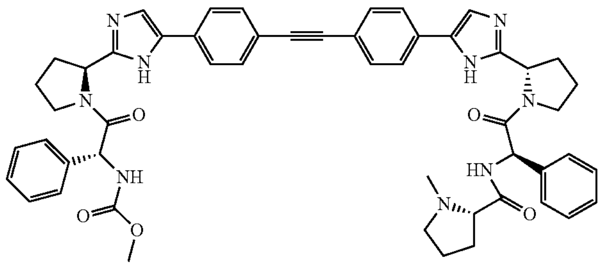 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)[C@@H]5CCCN5C)c5ccccc5)[nH]4)cc3)cc2)[nH]1)c1ccccc1] | **** | 884.4 |
| 204 | 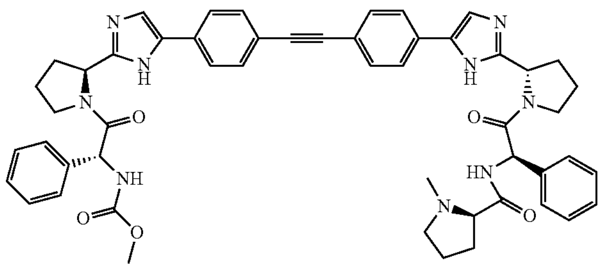 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)[C@H]5CCCN5C)c5ccccc5)[nH]4)cc3)cc2)[nH]1)c1ccccc1] | **** | 884.4 |
| 205 | 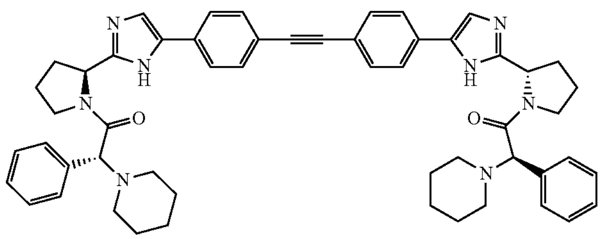 [SMILES: O=C([C@@H](c1ccccc1)N1CCCCC1)N1CCC[C@H]1c1ncc(-c2ccc(C#Cc3ccc(-c4cnc([C@@H]5CCCN5C(=O)[C@@H](c5ccccc5)N5CCCCC5)[nH]4)cc3)cc2)[nH]1] | **** | 851.5 |
| 206 | 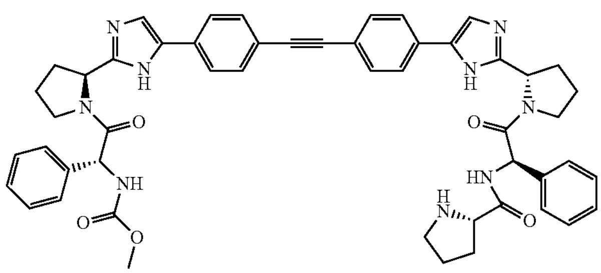 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)[C@@H]5CCCN5)c5ccccc5)[nH]4)cc3)cc2)[nH]1)c1ccccc1] | **** | 870.4 |
| 207 | 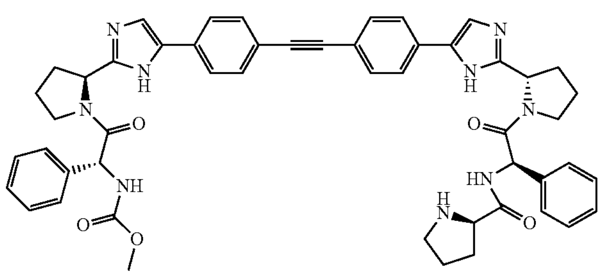 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)[C@H]5CCCN5)c5ccccc5)[nH]4)cc3)cc2)[nH]1)c1ccccc1] | **** | 870.4 |
| 208 | 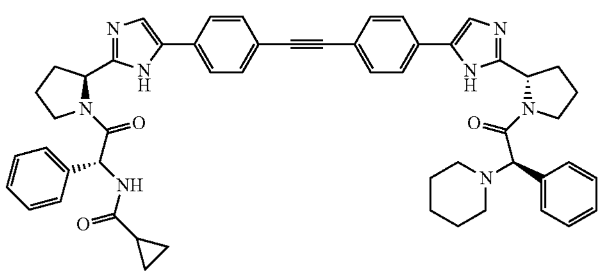 | **** | 851.4 |

TABLE 2-continued

| Compound # | Structure | Inhibition of HCV genotype 1b | MS (M + H⁺) |
|---|---|---|---|
| 209 | 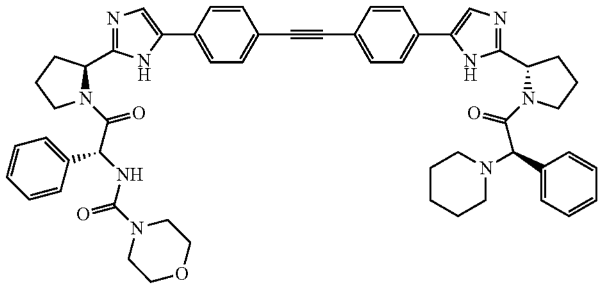 [SMILES: O=C(N[C@@H](C(=O)N1CCC[C@H]1c1ncc(-c2ccc(C#Cc3ccc(-c4cnc([C@@H]5CCCN5C(=O)[C@@H](c5ccccc5)N5CCCCC5)[nH]4)cc3)cc2)[nH]1)c1ccccc1)N1CCOCC1] | **** | 896.5 |
| 210 | 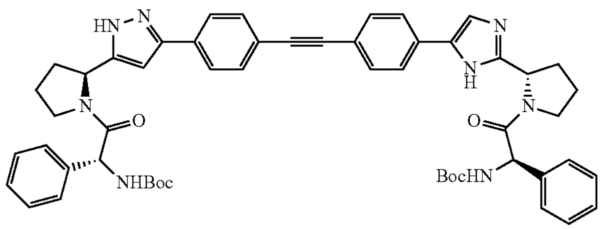 | **** | 915.4 |
| 211 | 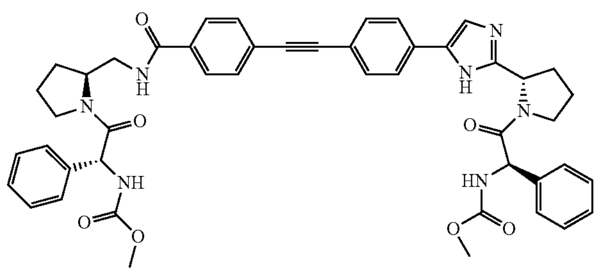 [SMILES: COC(=O)N[C@@H](C(=O)N1CCC[C@H]1CNC(=O)c1ccc(C#Cc2ccc(-c3cnc([C@@H]4CCCN4C(=O)[C@H](NC(=O)OC)c4ccccc4)[nH]3)cc2)cc1)c1ccccc1] | **** | 822.4 |
| 212 | 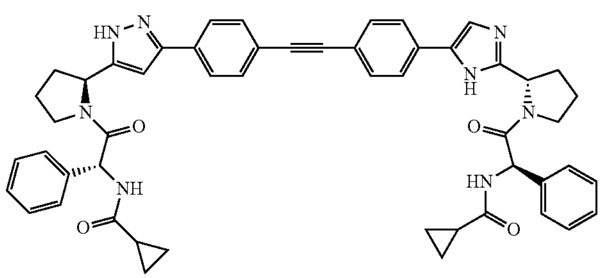 [SMILES: O=C(N[C@@H](C(=O)N1CCC[C@H]1c1cc(-c2ccc(C#Cc3ccc(-c4cnc([C@@H]5CCCN5C(=O)[C@H](NC(=O)C5CC5)c5ccccc5)[nH]4)cc3)cc2)n[nH]1)c1ccccc1)C1CC1] | **** | 851.4 |
| 213 | 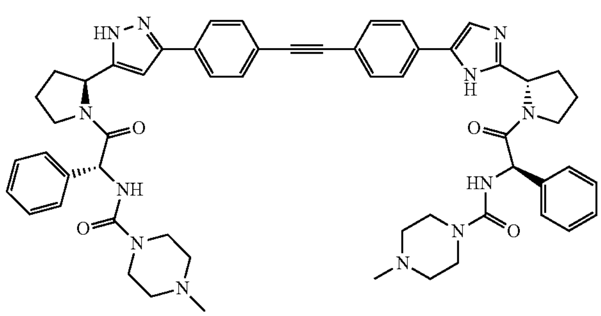 [SMILES: CN1CCN(C(=O)N[C@@H](C(=O)N2CCC[C@H]2c2cc(-c3ccc(C#Cc4ccc(-c5cnc([C@@H]6CCCN6C(=O)[C@H](NC(=O)N6CCN(C)CC6)c6ccccc6)[nH]5)cc4)cc3)n[nH]2)c2ccccc2)CC1] | **** | 967.5 |

TABLE 2-continued

| Compound # | Structure | Inhibition of HCV genotype 1b | MS (M + H+) |
|---|---|---|---|
| 214 | 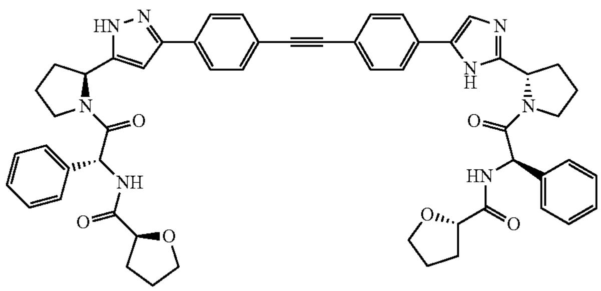 [SMILES: O=C(N[C@@H](C(=O)N1CCC[C@H]1c1cc(-c2ccc(C#Cc3ccc(-c4cnc([C@@H]5CCCN5C(=O)[C@H](NC(=O)[C@@H]5CCCO5)c5ccccc5)[nH]4)cc3)cc2)n[nH]1)c1ccccc1)[C@@H]1CCCO1] | **** | 911.4 |
| 215 | 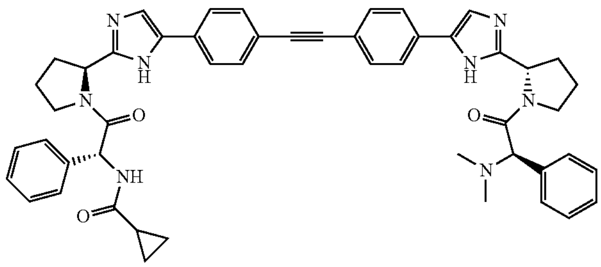 [SMILES: CN(C)[C@@H](C(=O)N1CCC[C@H]1c1ncc(-c2ccc(C#Cc3ccc(-c4cnc([C@@H]5CCCN5C(=O)[C@H](NC(=O)C5CC5)c5ccccc5)[nH]4)cc3)cc2)[nH]1)c1ccccc1] | **** | 811.4 |
| 216 | 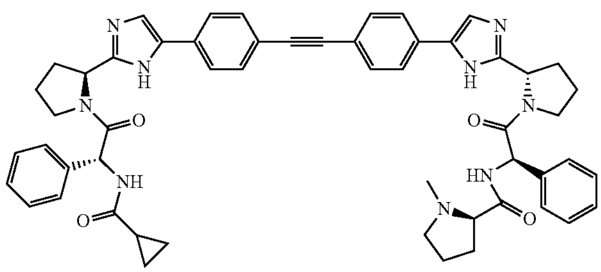 [SMILES: CN1CCC[C@@H]1C(=O)N[C@@H](C(=O)N1CCC[C@H]1c1ncc(-c2ccc(C#Cc3ccc(-c4cnc([C@@H]5CCCN5C(=O)[C@H](NC(=O)C5CC5)c5ccccc5)[nH]4)cc3)cc2)[nH]1)c1ccccc1] | **** | 894.4 |
| 217 | 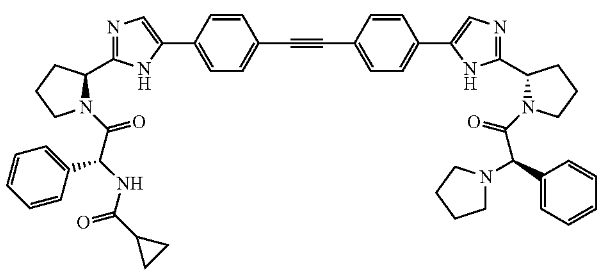 [SMILES: O=C(N[C@@H](C(=O)N1CCC[C@H]1c1ncc(-c2ccc(C#Cc3ccc(-c4cnc([C@@H]5CCCN5C(=O)[C@@H](c5ccccc5)N5CCCC5)[nH]4)cc3)cc2)[nH]1)c1ccccc1)C1CC1] | **** | 837.4 |
| 218 | 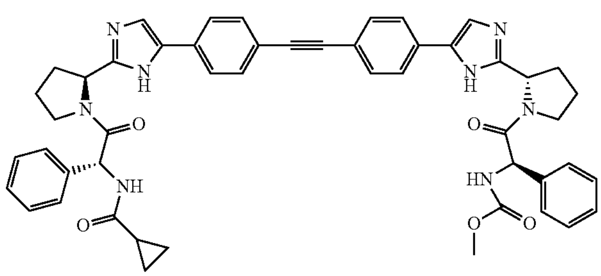 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)C5CC5)c5ccccc5)[nH]4)cc3)cc2)[nH]1)c1ccccc1] | **** | 841.4 |

TABLE 2-continued

| Compound # | Structure | Inhibition of HCV genotype 1b | MS (M + H+) |
|---|---|---|---|
| 219 | 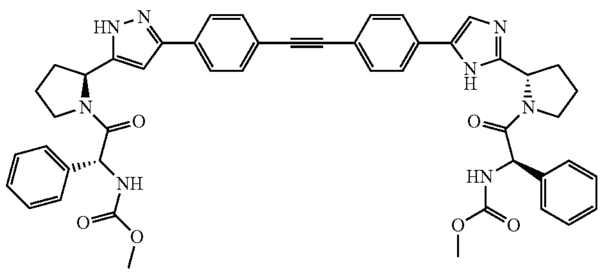 [SMILES: COC(=O)N[C@@H](C(=O)N1CCC[C@H]1c1cc(-c2ccc(C#Cc3ccc(-c4cnc([C@@H]5CCCN5C(=O)[C@H](NC(=O)OC)c5ccccc5)[nH]4)cc3)cc2)n[nH]1)c1ccccc1] | **** | 831.4 |
| 220 | 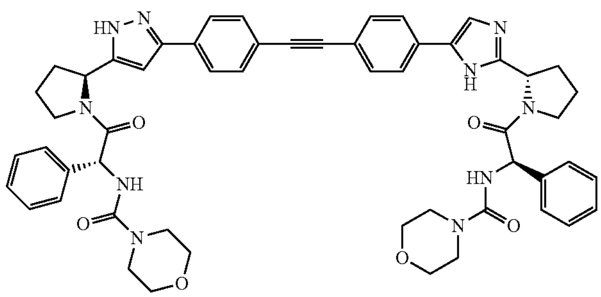 [SMILES: O=C(N[C@@H](C(=O)N1CCC[C@H]1c1cc(-c2ccc(C#Cc3ccc(-c4cnc([C@@H]5CCCN5C(=O)[C@H](NC(=O)N5CCOCC5)c5ccccc5)[nH]4)cc3)cc2)n[nH]1)c1ccccc1)N1CCOCC1] | **** | 941.4 |
| 221 | 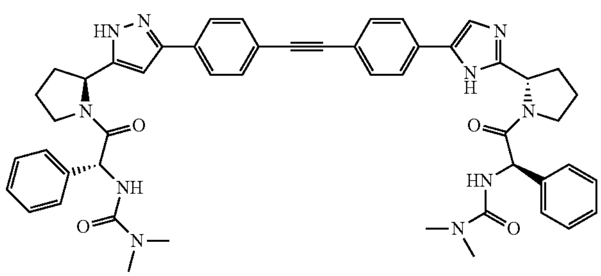 [SMILES: CN(C)C(=O)N[C@@H](C(=O)N1CCC[C@H]1c1cc(-c2ccc(C#Cc3ccc(-c4cnc([C@@H]5CCCN5C(=O)[C@H](NC(=O)N(C)C)c5ccccc5)[nH]4)cc3)cc2)n[nH]1)c1ccccc1] | **** | 857.4 |
| 222 | 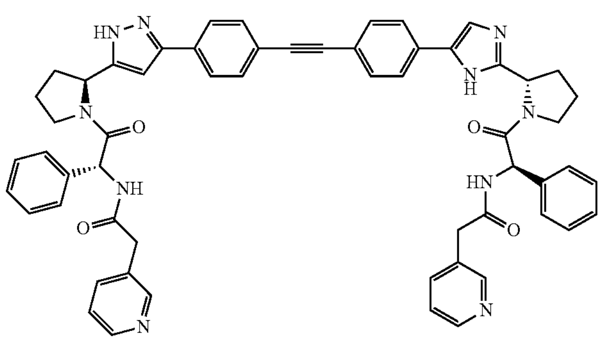 [SMILES: O=C(Cc1cccnc1)N[C@@H](C(=O)N1CCC[C@H]1c1cc(-c2ccc(C#Cc3ccc(-c4cnc([C@@H]5CCCN5C(=O)[C@H](NC(=O)Cc5cccnc5)c5ccccc5)[nH]4)cc3)cc2)n[nH]1)c1ccccc1] | **** | 953.4 |
| 223 | 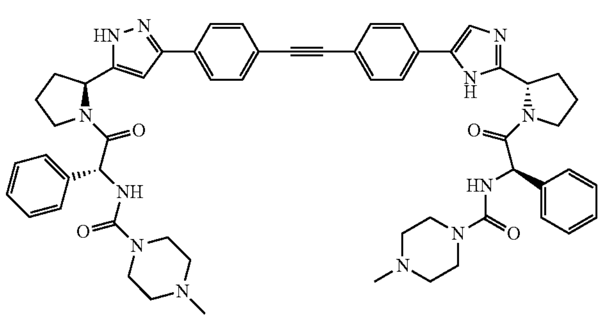 [SMILES: CN1CCN(C(=O)N[C@@H](C(=O)N2CCC[C@H]2c2cc(-c3ccc(C#Cc4ccc(-c5cnc([C@@H]6CCCN6C(=O)[C@H](NC(=O)N6CCN(C)CC6)c6ccccc6)[nH]5)cc4)cc3)n[nH]2)c2ccccc2)CC1] | **** | 967.5 |

TABLE 2-continued

| Compound # | Structure | Inhibition of HCV genotype 1b | MS (M + H+) |
|---|---|---|---|
| 224 | 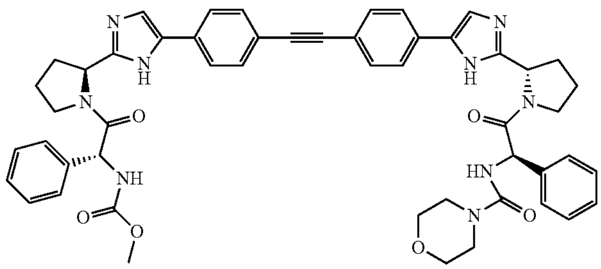 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCOCC5)c5ccccc5)[nH]4)cc3)cc2)[nH]1)c1ccccc1] | **** | 886.4 |
| 225 | 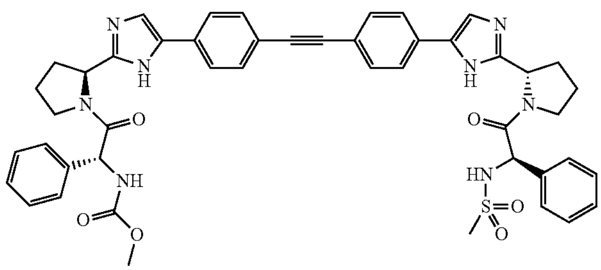 [SMILES: COC(=O)N[C@@H](C(=O)N1CCC[C@H]1c1ncc(-c2ccc(C#Cc3ccc(-c4cnc([C@@H]5CCCN5C(=O)[C@H](NS(C)(=O)=O)c5ccccc5)[nH]4)cc3)cc2)[nH]1)c1ccccc1] | **** | 851.3 |
| 226 | 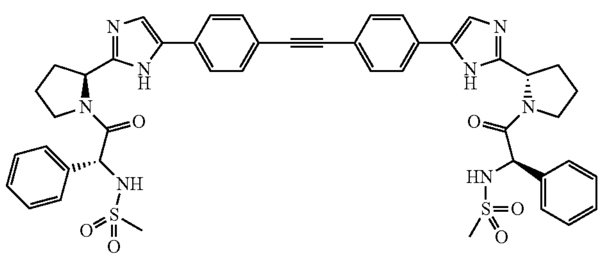 [SMILES: CS(=O)(=O)N[C@@H](C(=O)N1CCC[C@H]1c1ncc(-c2ccc(C#Cc3ccc(-c4cnc([C@@H]5CCCN5C(=O)[C@H](NS(C)(=O)=O)c5ccccc5)[nH]4)cc3)cc2)[nH]1)c1ccccc1] | **** | 871.3 |
| 227 | 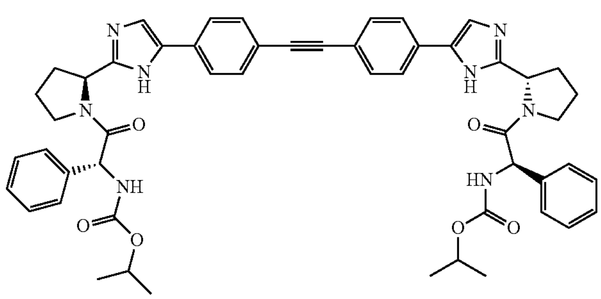 [SMILES: CC(C)OC(=O)N[C@@H](C(=O)N1CCC[C@H]1c1ncc(-c2ccc(C#Cc3ccc(-c4cnc([C@@H]5CCCN5C(=O)[C@H](NC(=O)OC(C)C)c5ccccc5)[nH]4)cc3)cc2)[nH]1)c1ccccc1] | **** | 887.4 |
| 228 | 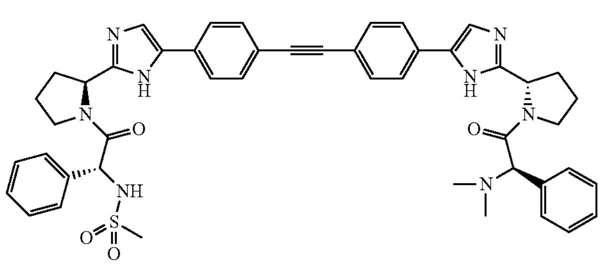 [SMILES: CN(C)[C@@H](C(=O)N1CCC[C@H]1c1ncc(-c2ccc(C#Cc3ccc(-c4cnc([C@@H]5CCCN5C(=O)[C@H](NS(C)(=O)=O)c5ccccc5)[nH]4)cc3)cc2)[nH]1)c1ccccc1] | **** | 821.4 |

TABLE 2-continued

| Compound # | Structure | Inhibition of HCV genotype 1b | MS (M + H+) |
|---|---|---|---|
| 229 | 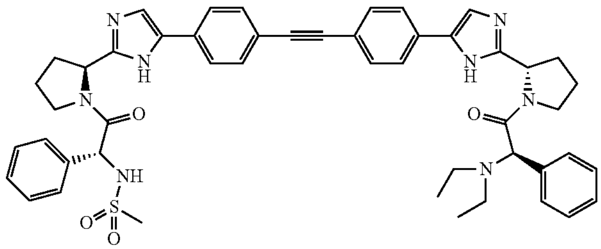 [SMILES: CCN(CC)[C@@H](C(=O)N1CCC[C@H]1c1ncc(-c2ccc(C#Cc3ccc(-c4cnc([C@@H]5CCCN5C(=O)[C@H](NS(C)(=O)=O)c5ccccc5)[nH]4)cc3)cc2)[nH]1)c1ccccc1] | **** | 849.4 |
| 230 | 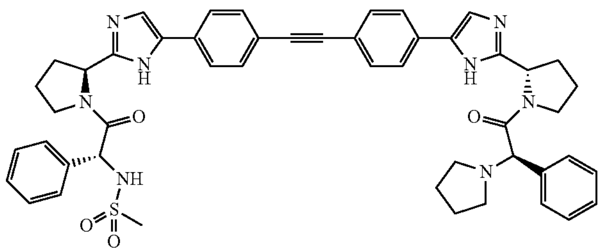 [SMILES: CS(=O)(=O)N[C@@H](C(=O)N1CCC[C@H]1c1ncc(-c2ccc(C#Cc3ccc(-c4cnc([C@@H]5CCCN5C(=O)[C@@H](c5ccccc5)N5CCCC5)[nH]4)cc3)cc2)[nH]1)c1ccccc1] | **** | 847.4 |
| 231 | 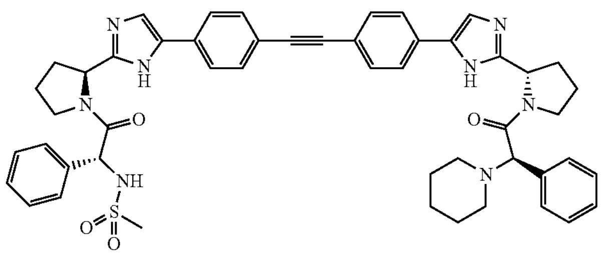 [SMILES: CS(=O)(=O)N[C@@H](C(=O)N1CCC[C@H]1c1ncc(-c2ccc(C#Cc3ccc(-c4cnc([C@@H]5CCCN5C(=O)[C@@H](c5ccccc5)N5CCCCC5)[nH]4)cc3)cc2)[nH]1)c1ccccc1] | **** | 861.4 |
| 232 | 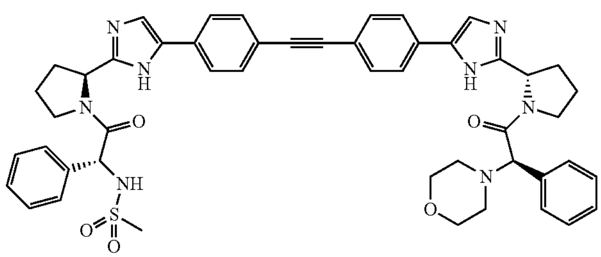 [SMILES: CS(=O)(=O)N[C@@H](C(=O)N1CCC[C@H]1c1ncc(-c2ccc(C#Cc3ccc(-c4cnc([C@@H]5CCCN5C(=O)[C@@H](c5ccccc5)N5CCOCC5)[nH]4)cc3)cc2)[nH]1)c1ccccc1] | **** | 863.4 |
| 233 | 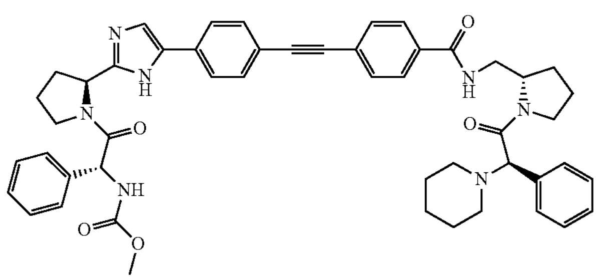 [SMILES: COC(=O)N[C@@H](C(=O)N1CCC[C@H]1c1ncc(-c2ccc(C#Cc3ccc(C(=O)NC[C@@H]4CCCN4C(=O)[C@@H](c4ccccc4)N4CCCCC4)cc3)cc2)[nH]1)c1ccccc1] | **** | 832.4 |
| 234 | 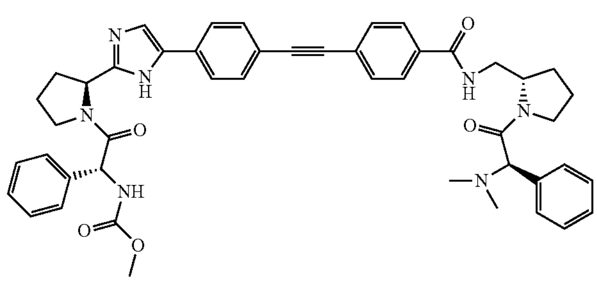 [SMILES: COC(=O)N[C@@H](C(=O)N1CCC[C@H]1c1ncc(-c2ccc(C#Cc3ccc(C(=O)NC[C@@H]4CCCN4C(=O)[C@@H](c4ccccc4)N(C)C)cc3)cc2)[nH]1)c1ccccc1] | **** | 792.4 |

TABLE 2-continued
| Compound # | Structure | Inhibition of HCV genotype 1b | MS (M + H+) |
|---|---|---|---|
| 235 | 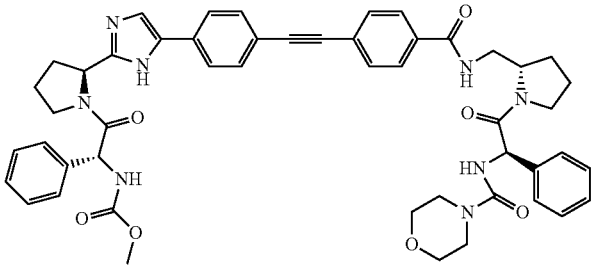 [SMILES: COC(=O)N[C@@H](C(=O)N1CCC[C@H]1c1ncc(-c2ccc(C#Cc3ccc(C(=O)NC[C@@H]4CCCN4C(=O)[C@H](NC(=O)N4CCOCC4)c4ccccc4)cc3)cc2)[nH]1)c1ccccc1] | **** | 877.4 |
| 236 | 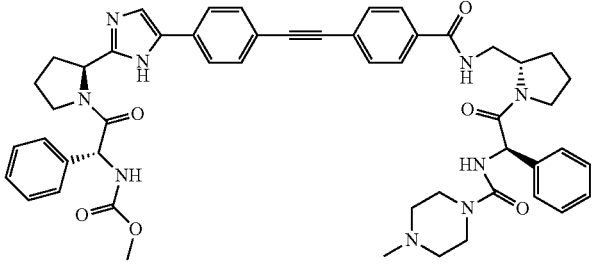 [SMILES: COC(=O)N[C@@H](C(=O)N1CCC[C@H]1c1ncc(-c2ccc(C#Cc3ccc(C(=O)NC[C@@H]4CCCN4C(=O)[C@H](NC(=O)N4CCN(C)CC4)c4ccccc4)cc3)cc2)[nH]1)c1ccccc1] | **** | 890.4 |
| 237 | 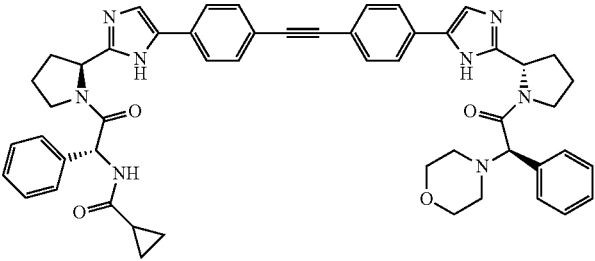 | **** | 853.4 |
| 238 | 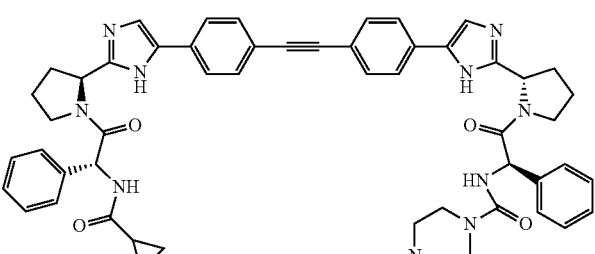 | **** | 909.4 |
| 239 | 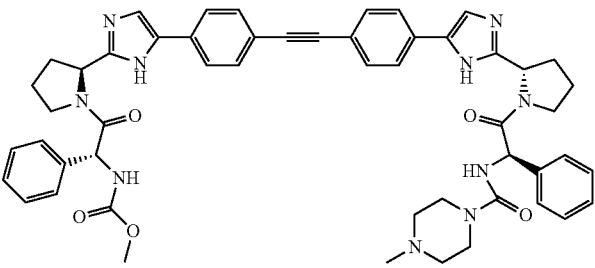 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCN(C)CC5)c5ccccc5)[nH]4)cc3)cc2)[nH]1)c1ccccc1] | **** | 896.4 |

TABLE 2-continued

| Compound # | Structure | Inhibition of HCV genotype 1b | MS (M + H⁺) |
|---|---|---|---|
| 240 | 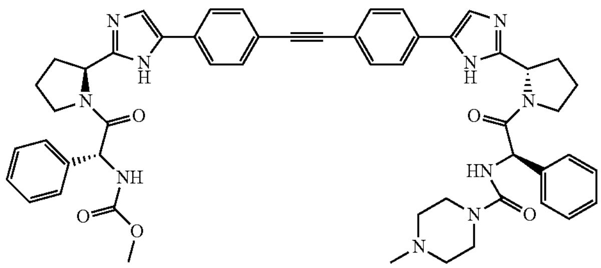 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCN(C)CC5)c5ccccc5)[nH]4)cc3)cc2)[nH]1)c1ccccc1] | **** | 899.4 |
| 241 | 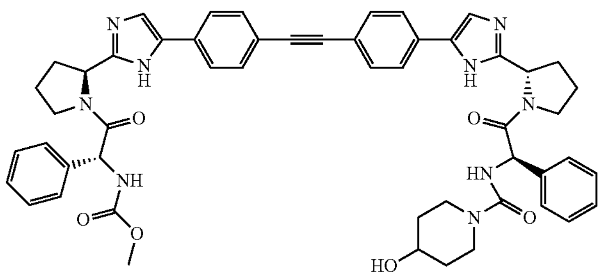 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC(O)CC5)c5ccccc5)[nH]4)cc3)cc2)[nH]1)c1ccccc1] | **** | 900.4 |
| 242 | 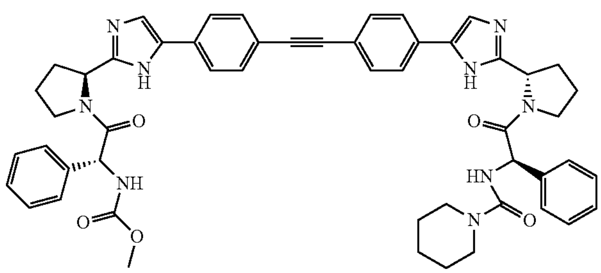 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCCCC5)c5ccccc5)[nH]4)cc3)cc2)[nH]1)c1ccccc1] | **** | 884.4 |
| 243 | 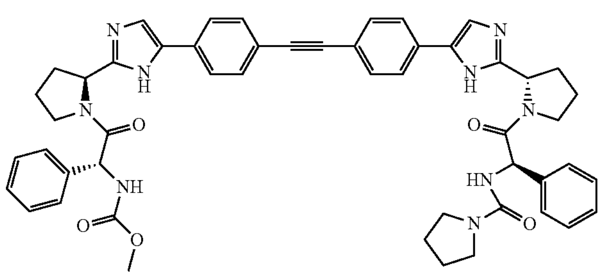 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCCC5)c5ccccc5)[nH]4)cc3)cc2)[nH]1)c1ccccc1] | **** | 870.4 |
| 244 | 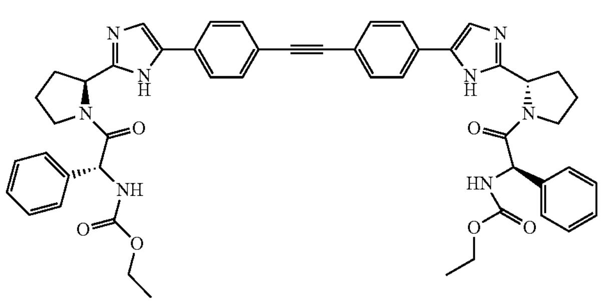 [SMILES: CCOC(=O)N[C@@H](C(=O)N1CCC[C@H]1c1ncc(-c2ccc(C#Cc3ccc(-c4cnc([C@@H]5CCCN5C(=O)[C@H](NC(=O)OCC)c5ccccc5)[nH]4)cc3)cc2)[nH]1)c1ccccc1] | **** | 859.4 |

TABLE 2-continued

| Compound # | Structure | Inhibition of HCV genotype 1b | MS (M + H⁺) |
|---|---|---|---|
| 245 | 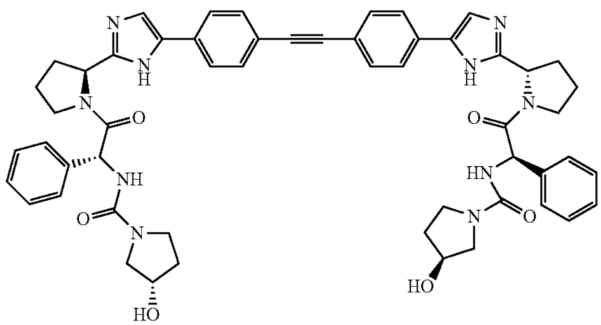 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)N5CC[C@H](O)C5)c5ccccc5)[nH]4)cc3)cc2)[nH]1)c1ccccc1)N1CC[C@H](O)C1] | **** | 941.4 |
| 246 | 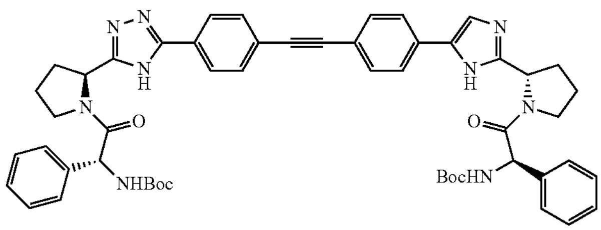 [SMILES: CC(C)(C)OC(=O)N[C@@H](C(=O)N1CCC[C@H]1c1ncc(-c2ccc(C#Cc3ccc(-c4nnc([C@@H]5CCCN5C(=O)[C@H](NC(=O)OC(C)(C)C)c5ccccc5)[nH]4)cc3)cc2)[nH]1)c1ccccc1] | **** | 916.4 |
| 247 | 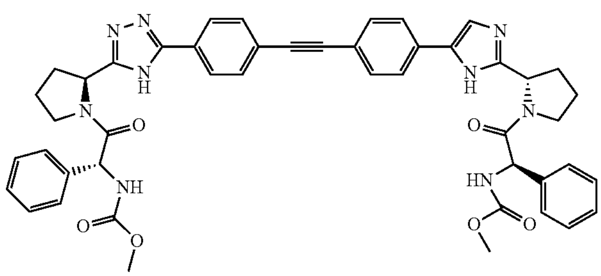 [SMILES: COC(=O)N[C@@H](C(=O)N1CCC[C@H]1c1ncc(-c2ccc(C#Cc3ccc(-c4nnc([C@@H]5CCCN5C(=O)[C@H](NC(=O)OC)c5ccccc5)[nH]4)cc3)cc2)[nH]1)c1ccccc1] | **** | 832.3 |
| 248 | 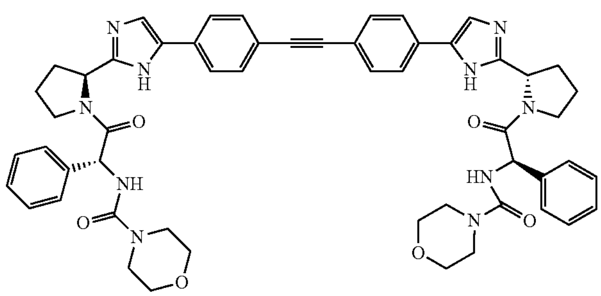 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)N5CCOCC5)c5ccccc5)[nH]4)cc3)cc2)[nH]1)c1ccccc1)N1CCOCC1] | **** | 941.4 |
| 249 | 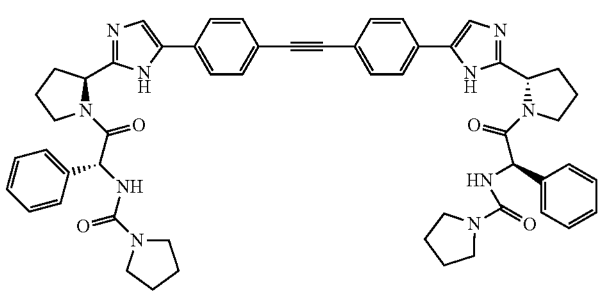 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)N5CCCC5)c5ccccc5)[nH]4)cc3)cc2)[nH]1)c1ccccc1)N1CCCC1] | **** | 909.4 |

TABLE 2-continued

| Compound # | Structure | Inhibition of HCV genotype 1b | MS (M + H+) |
|---|---|---|---|
| 250 | 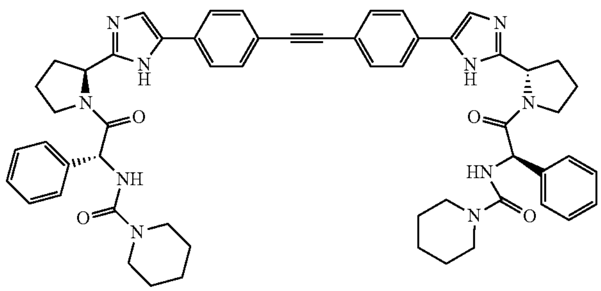 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)N5CCCCC5)c5ccccc5)[nH]4)cc3)cc2)[nH]1)c1ccccc1)N1CCCCC1] | **** | 937.5 |
| 251 | 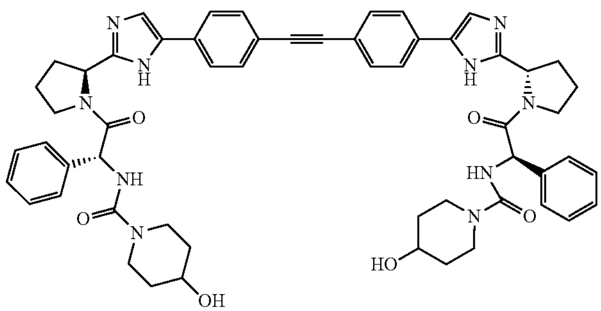 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)N5CCC(O)CC5)c5ccccc5)[nH]4)cc3)cc2)[nH]1)c1ccccc1)N1CCC(O)CC1] | **** | 969.5 |
| 252 | 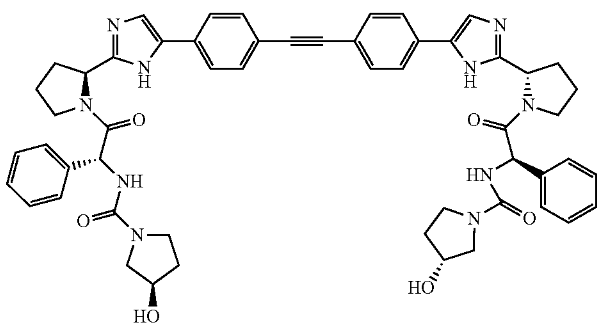 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)N5CC[C@@H](O)C5)c5ccccc5)[nH]4)cc3)cc2)[nH]1)c1ccccc1)N1CC[C@@H](O)C1] | **** | 941.4 |
| 253 | 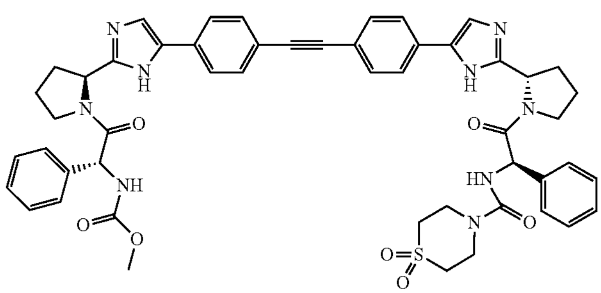 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCS(=O)(=O)CC5)c5ccccc5)[nH]4)cc3)cc2)[nH]1)c1ccccc1] | **** | 934.4 |
| 254 | 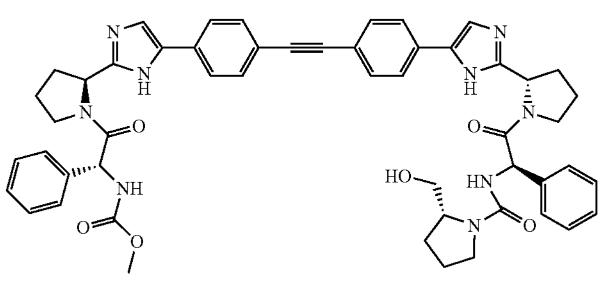 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC[C@@H]5CO)c5ccccc5)[nH]4)cc3)cc2)[nH]1)c1ccccc1] | **** | 900.4 |

TABLE 2-continued

| Compound # | Structure | Inhibition of HCV genotype 1b | MS (M + H⁺) |
|---|---|---|---|
| 255 | 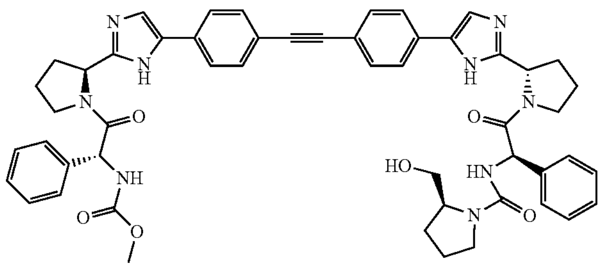 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC[C@H]5CO)c5ccccc5)[nH]4)cc3)cc2)[nH]1)c1ccccc1] | **** | 900.4 |
| 256 | 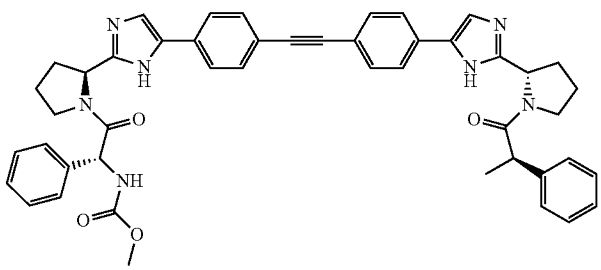 [SMILES: COC(=O)N[C@@H](C(=O)N1CCC[C@H]1c1ncc(-c2ccc(C#Cc3ccc(-c4cnc([C@@H]5CCCN5C(=O)[C@H](C)c5ccccc5)[nH]4)cc3)cc2)[nH]1)c1ccccc1] | **** | 772.4 |
| 257 | 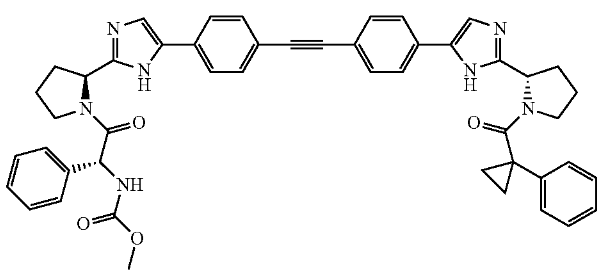 [SMILES: COC(=O)N[C@@H](C(=O)N1CCC[C@H]1c1ncc(-c2ccc(C#Cc3ccc(-c4cnc([C@@H]5CCCN5C(=O)C5(c6ccccc6)CC5)[nH]4)cc3)cc2)[nH]1)c1ccccc1] | **** | 784.4 |
| 258 | 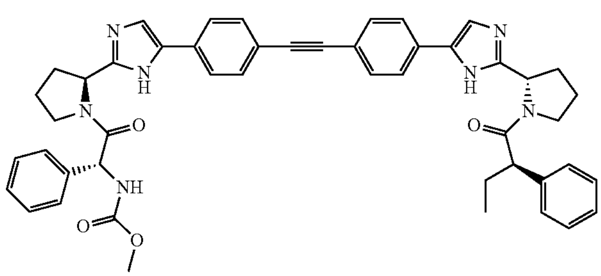 | **** | 786.4 |
| 259 | 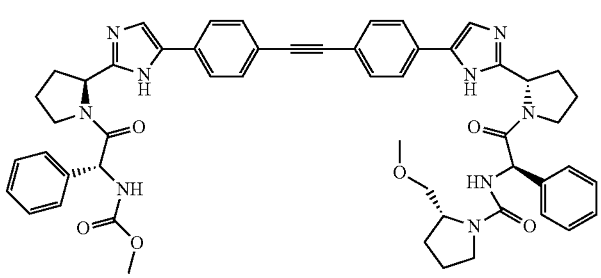 [SMILES: COC[C@H]1CCCN1C(=O)N[C@@H](C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cc3)cc2)[nH]1)c1ccccc1] | **** | 914.4 |

TABLE 2-continued

| Compound # | Structure | Inhibition of HCV genotype 1b | MS (M + H+) |
|---|---|---|---|
| 260 | 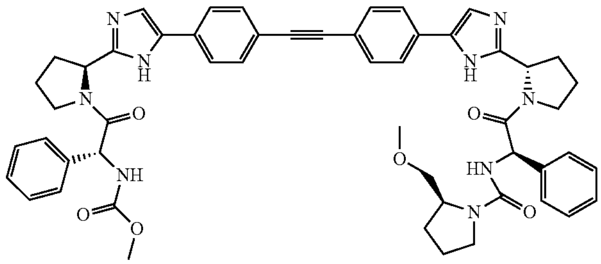 [SMILES: COC[C@@H]1CCCN1C(=O)N[C@@H](C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cc3)cc2)[nH]1)c1ccccc1] | **** | 914.4 |
| 261 | 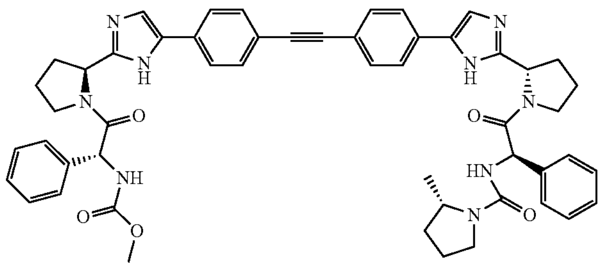 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC[C@@H]5C)c5ccccc5)[nH]4)cc3)cc2)[nH]1)c1ccccc1] | **** | 884.4 |
| 262 | 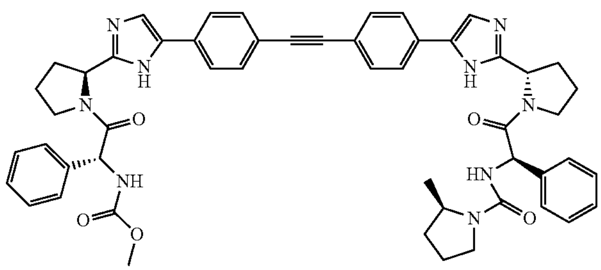 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC[C@H]5C)c5ccccc5)[nH]4)cc3)cc2)[nH]1)c1ccccc1] | **** | 884.4 |
| 263 | 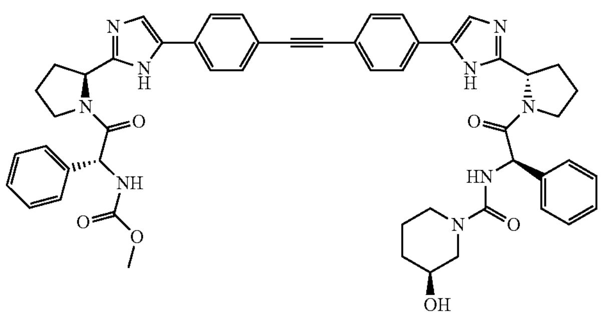 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC[C@H](O)C5)c5ccccc5)[nH]4)cc3)cc2)[nH]1)c1ccccc1] | **** | 900.4 |
| 264 | 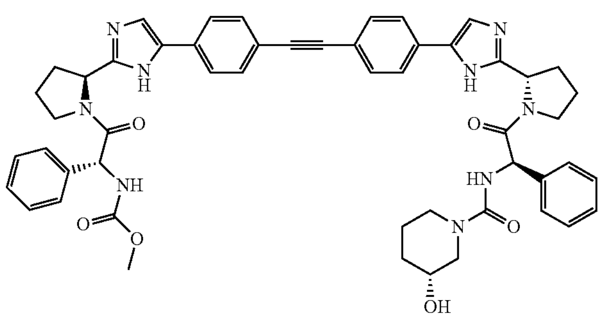 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC[C@@H](O)C5)c5ccccc5)[nH]4)cc3)cc2)[nH]1)c1ccccc1] | **** | 900.4 |

TABLE 2-continued

| Compound # | Structure | Inhibition of HCV genotype 1b | MS (M + H+) |
|---|---|---|---|
| 265 | 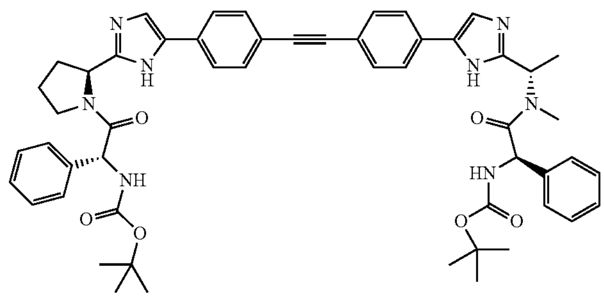 [SMILES: C[C@@H](c1ncc(-c2ccc(C#Cc3ccc(-c4cnc([C@@H]5CCCN5C(=O)[C@H](NC(=O)OC(C)(C)C)c5ccccc5)[nH]4)cc3)cc2)[nH]1)N(C)C(=O)[C@H](NC(=O)OC(C)(C)C)c1ccccc1] | **** | 903.4 |
| 266 | 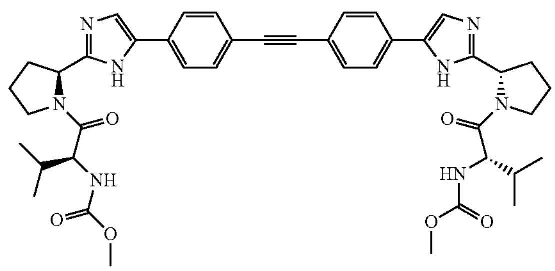 [SMILES: COC(=O)N[C@H](C(=O)N1CCC[C@H]1c1ncc(-c2ccc(C#Cc3ccc(-c4cnc([C@@H]5CCCN5C(=O)[C@@H](NC(=O)OC)C(C)C)[nH]4)cc3)cc2)[nH]1)C(C)C] | **** | 763.4 |
| 267 | 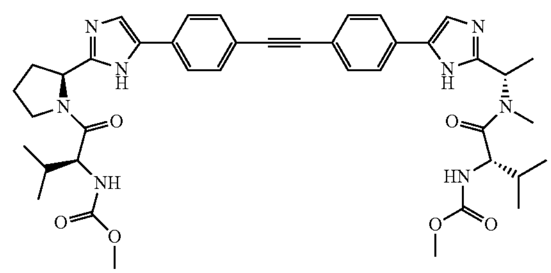 [SMILES: COC(=O)N[C@H](C(=O)N(C)[C@@H](C)c1ncc(-c2ccc(C#Cc3ccc(-c4cnc([C@@H]5CCCN5C(=O)[C@@H](NC(=O)OC)C(C)C)[nH]4)cc3)cc2)[nH]1)C(C)C] | **** | 751.4 |
| 268 | 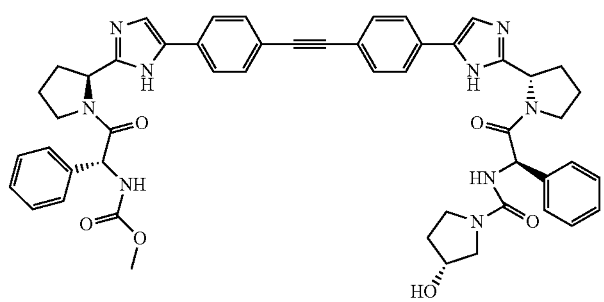 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CC[C@@H](O)C5)c5ccccc5)[nH]4)cc3)cc2)[nH]1)c1ccccc1] | **** | 886.4 |
| 269 | 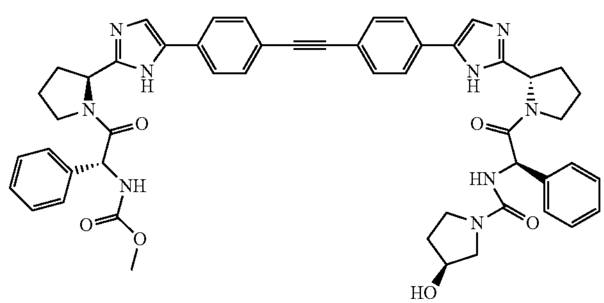 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CC[C@H](O)C5)c5ccccc5)[nH]4)cc3)cc2)[nH]1)c1ccccc1] | **** | 886.4 |

TABLE 2-continued

| Compound # | Structure | Inhibition of HCV genotype 1b | MS (M + H+) |
|---|---|---|---|
| 270 | 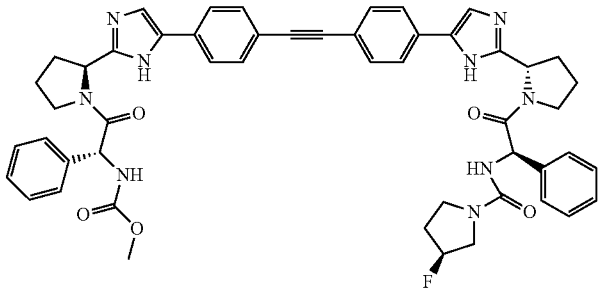 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CC[C@H](F)C5)c5ccccc5)[nH]4)cc3)cc2)[nH]1)c1ccccc1] | **** | 888.4 |
| 271 | 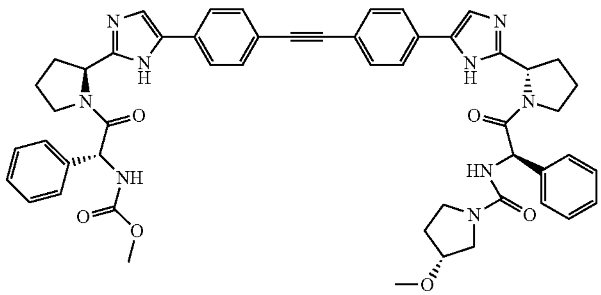 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CC[C@@H](OC)C5)c5ccccc5)[nH]4)cc3)cc2)[nH]1)c1ccccc1] | **** | 900.4 |
| 272 | 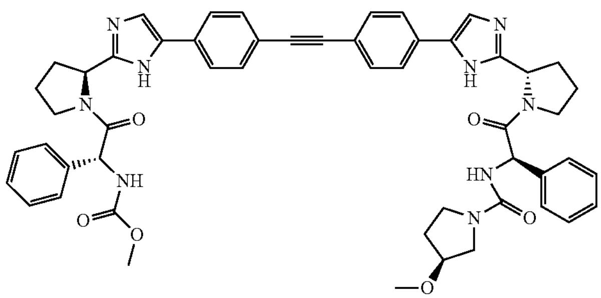 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CC[C@H](OC)C5)c5ccccc5)[nH]4)cc3)cc2)[nH]1)c1ccccc1] | **** | 900.4 |
| 273 | 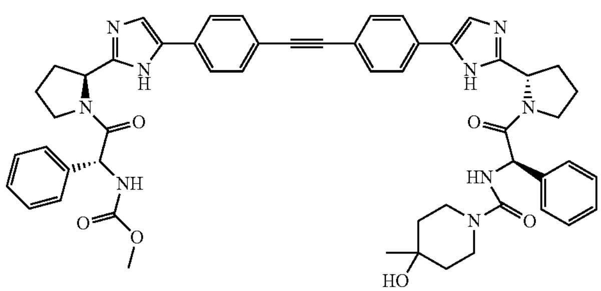 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)N5CCC(C)(O)CC5)c5ccccc5)[nH]4)cc3)cc2)[nH]1)c1ccccc1] | **** | 914.4 |
| 274 | 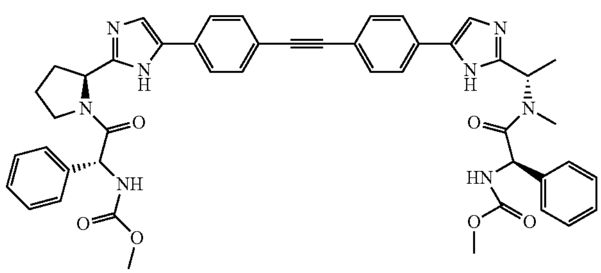 [SMILES: COC(=O)N[C@@H](C(=O)N(C)[C@@H](C)c1ncc(-c2ccc(C#Cc3ccc(-c4cnc([C@@H]5CCCN5C(=O)[C@H](NC(=O)OC)c5ccccc5)[nH]4)cc3)cc2)[nH]1)c1ccccc1] | **** | 819.4 |

TABLE 2-continued

| Compound # | Structure | Inhibition of HCV genotype 1b | MS (M + H⁺) |
|---|---|---|---|
| 275 | 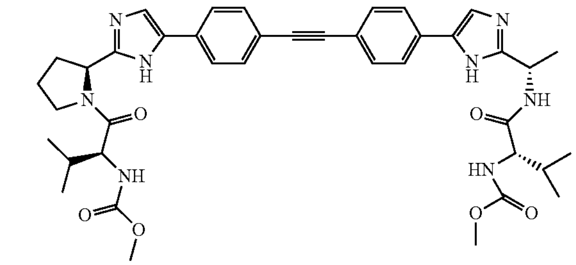 [SMILES: COC(=O)N[C@H](C(=O)N[C@@H](C)c1ncc(-c2ccc(C#Cc3ccc(-c4cnc([C@@H]5CCCN5C(=O)[C@@H](NC(=O)OC)C(C)C)[nH]4)cc3)cc2)[nH]1)C(C)C] | **** | 737.4 |
| 276 | 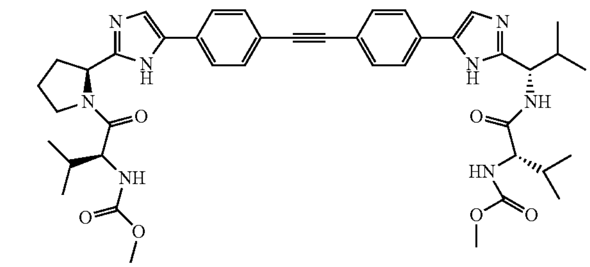 [SMILES: COC(=O)N[C@H](C(=O)N[C@H](c1ncc(-c2ccc(C#Cc3ccc(-c4cnc([C@@H]5CCCN5C(=O)[C@@H](NC(=O)OC)C(C)C)[nH]4)cc3)cc2)[nH]1)C(C)C)C(C)C] | *** | 765.4 |
| 277 | 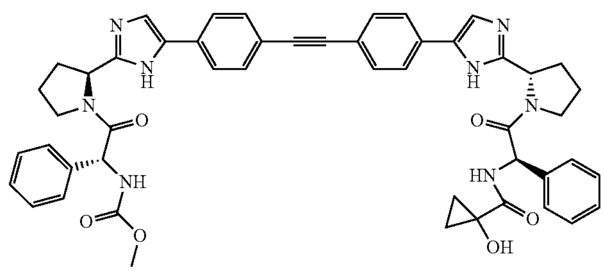 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)C5(O)CC5)c5ccccc5)[nH]4)cc3)cc2)[nH]1)c1ccccc1] | **** | 857.4 |
| 278 | 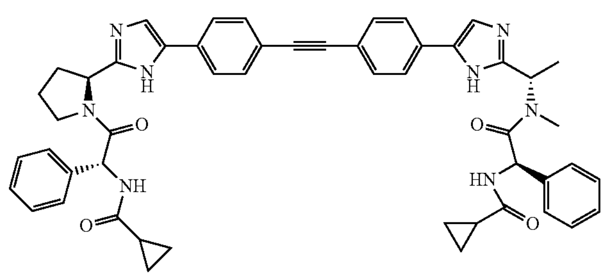 [SMILES: C[C@@H](c1ncc(-c2ccc(C#Cc3ccc(-c4cnc([C@@H]5CCCN5C(=O)[C@H](NC(=O)C5CC5)c5ccccc5)[nH]4)cc3)cc2)[nH]1)N(C)C(=O)[C@H](NC(=O)C1CC1)c1ccccc1] | **** | 839.4 |
| 279 | 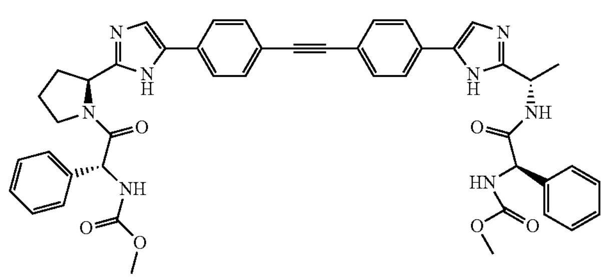 [SMILES: COC(=O)N[C@@H](C(=O)N[C@@H](C)c1ncc(-c2ccc(C#Cc3ccc(-c4cnc([C@@H]5CCCN5C(=O)[C@H](NC(=O)OC)c5ccccc5)[nH]4)cc3)cc2)[nH]1)c1ccccc1] | **** | 805.3 |

TABLE 2-continued

| Compound # | Structure | Inhibition of HCV genotype 1b | MS (M + H⁺) |
|---|---|---|---|
| 280 | 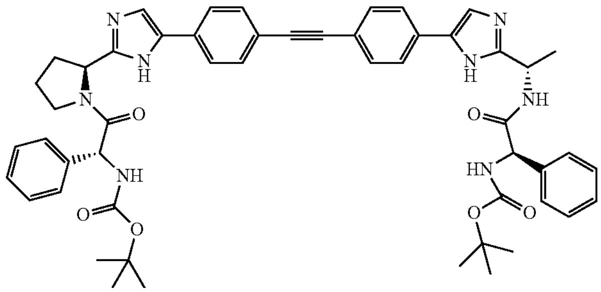 [SMILES: C[C@H](NC(=O)[C@H](NC(=O)OC(C)(C)C)c1ccccc1)c1ncc(-c2ccc(C#Cc3ccc(-c4cnc([C@@H]5CCCN5C(=O)[C@H](NC(=O)OC(C)(C)C)c5ccccc5)[nH]4)cc3)cc2)[nH]1] | **** | 889.4 |
| 281 | 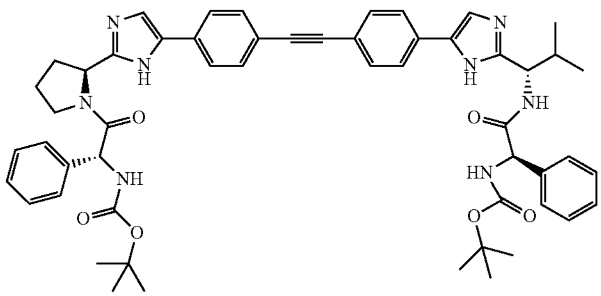 [SMILES: CC(C)[C@H](NC(=O)[C@H](NC(=O)OC(C)(C)C)c1ccccc1)c1ncc(-c2ccc(C#Cc3ccc(-c4cnc([C@@H]5CCCN5C(=O)[C@H](NC(=O)OC(C)(C)C)c5ccccc5)[nH]4)cc3)cc2)[nH]1] | *** | 917.5 |
| 282 | 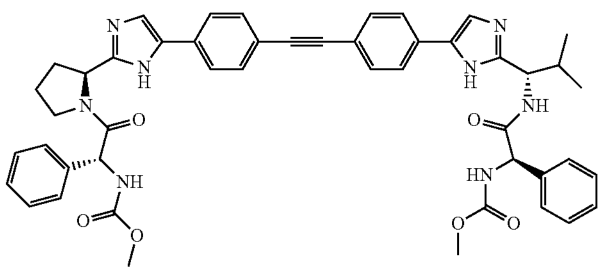 [SMILES: COC(=O)N[C@@H](C(=O)N[C@H](c1ncc(-c2ccc(C#Cc3ccc(-c4cnc([C@@H]5CCCN5C(=O)[C@H](NC(=O)OC)c5ccccc5)[nH]4)cc3)cc2)[nH]1)C(C)C)c1ccccc1] | **** | 833.4 |
| 283 | 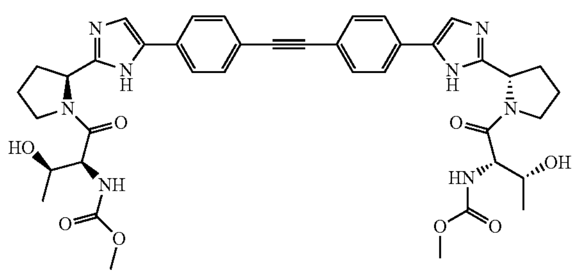 [SMILES: COC(=O)N[C@H](C(=O)N1CCC[C@H]1c1ncc(-c2ccc(C#Cc3ccc(-c4cnc([C@@H]5CCCN5C(=O)[C@@H](NC(=O)OC)[C@@H](C)O)[nH]4)cc3)cc2)[nH]1)[C@@H](C)O] | **** | 767.3 |
| 284 | 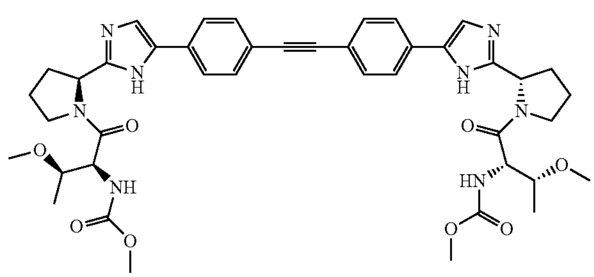 | **** | 795.4 |

TABLE 2-continued

| Compound # | Structure | Inhibition of HCV genotype 1b | MS (M + H⁺) |
|---|---|---|---|
| 285 | 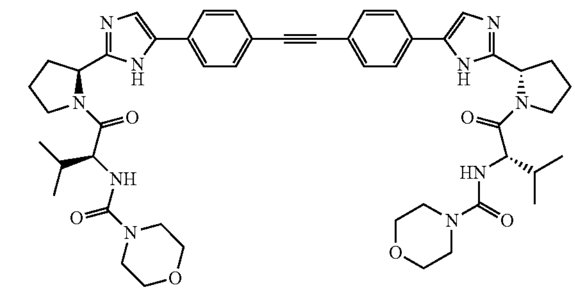 | * | 873.5 |
| 286 | 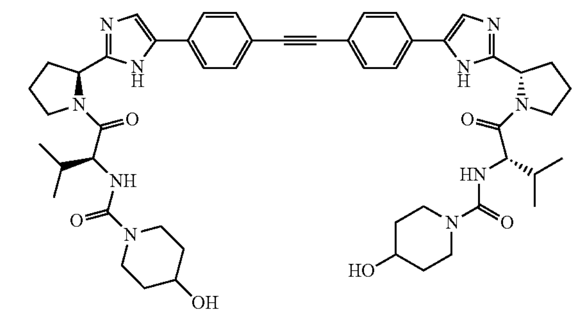 [SMILES: CC(C)[C@H](NC(=O)N1CCC(O)CC1)C(=O)N1CCC[C@H]1c1ncc(-c2ccc(C#Cc3ccc(-c4cnc([C@@H]5CCCN5C(=O)[C@@H](NC(=O)N5CCC(O)CC5)C(C)C)[nH]4)cc3)cc2)[nH]1] | * | 901.5 |
| 287 | 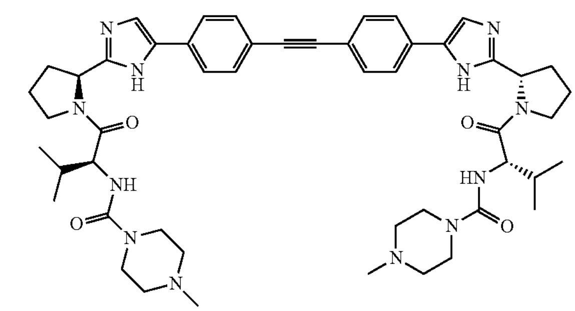 [SMILES: CC(C)[C@H](NC(=O)N1CCN(C)CC1)C(=O)N1CCC[C@H]1c1ncc(-c2ccc(C#Cc3ccc(-c4cnc([C@@H]5CCCN5C(=O)[C@@H](NC(=O)N5CCN(C)CC5)C(C)C)[nH]4)cc3)cc2)[nH]1] | * | 899.5 |
| 288 | 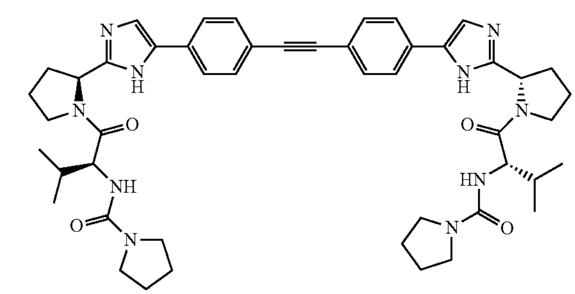 [SMILES: CC(C)[C@H](NC(=O)N1CCCC1)C(=O)N1CCC[C@H]1c1ncc(-c2ccc(C#Cc3ccc(-c4cnc([C@@H]5CCCN5C(=O)[C@@H](NC(=O)N5CCCC5)C(C)C)[nH]4)cc3)cc2)[nH]1] | * | 841.5 |
| 289 | 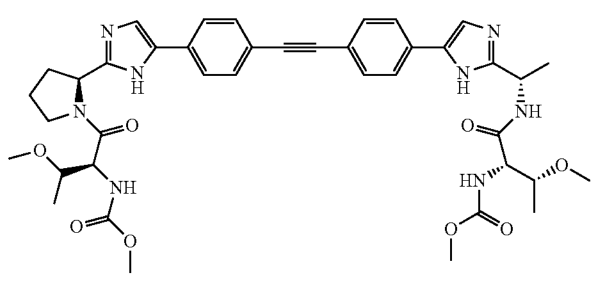 | **** | 769.4 |

TABLE 2-continued

| Compound # | Structure | Inhibition of HCV genotype 1b | MS (M + H⁺) |
|---|---|---|---|
| 290 | 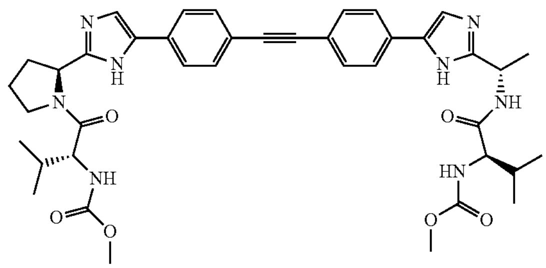 [SMILES: COC(=O)N[C@@H](C(=O)N[C@@H](C)c1ncc(-c2ccc(C#Cc3ccc(-c4cnc([C@@H]5CCCN5C(=O)[C@H](NC(=O)OC)C(C)C)[nH]4)cc3)cc2)[nH]1)C(C)C] | * | 737.4 |
| 291 | 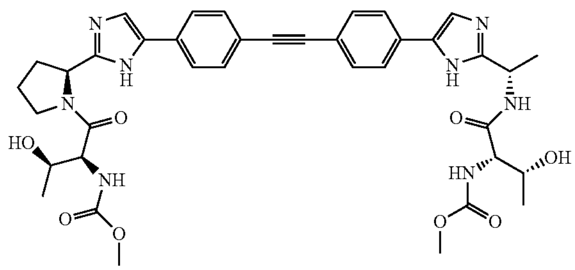 [SMILES: COC(=O)N[C@H](C(=O)N[C@@H](C)c1ncc(-c2ccc(C#Cc3ccc(-c4cnc([C@@H]5CCCN5C(=O)[C@@H](NC(=O)OC)[C@@H](C)O)[nH]4)cc3)cc2)[nH]1)[C@@H](C)O] | **** | 741.3 |
| 292 | 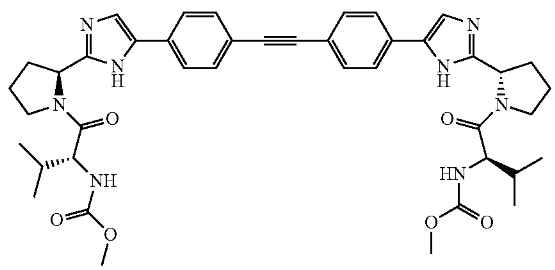 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)OC)C(C)C)[nH]4)cc3)cc2)[nH]1)C(C)C] | * | 763.4 |
| 293 | 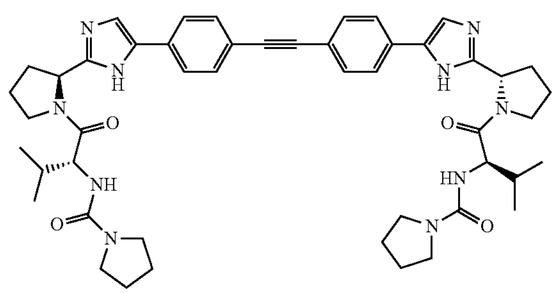 [SMILES: CC(C)[C@@H](NC(=O)N1CCCC1)C(=O)N1CCC[C@H]1c1ncc(-c2ccc(C#Cc3ccc(-c4cnc([C@@H]5CCCN5C(=O)[C@H](NC(=O)N5CCCC5)C(C)C)[nH]4)cc3)cc2)[nH]1] | * | 841.5 |
| 950 | 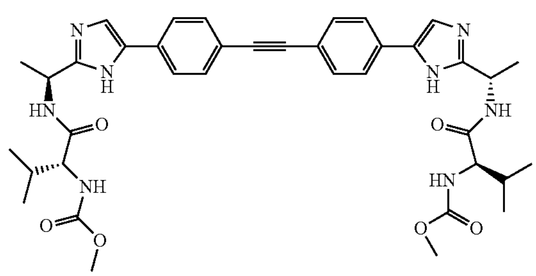 [SMILES: COC(=O)N[C@@H](C(=O)N[C@@H](C)c1ncc(-c2ccc(C#Cc3ccc(-c4cnc([C@H](C)NC(=O)[C@H](NC(=O)OC)C(C)C)[nH]4)cc3)cc2)[nH]1)C(C)C] | **** | 711.4 |

TABLE 2-continued
| Compound # | Structure | Inhibition of HCV genotype 1b | MS (M + H⁺) |
|---|---|---|---|
| 951 | 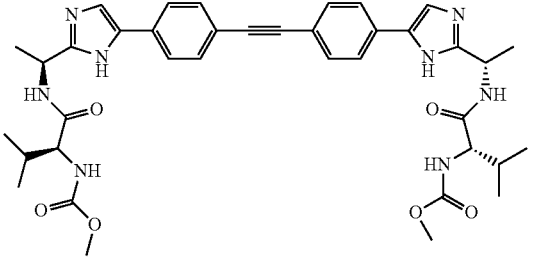 [SMILES: COC(=O)N[C@H](C(=O)N[C@@H](C)c1ncc(-c2ccc(C#Cc3ccc(-c4cnc([C@H](C)NC(=O)[C@@H](NC(=O)OC)C(C)C)[nH]4)cc3)cc2)[nH]1)C(C)C] | **** | 711.4 |
| 952 | 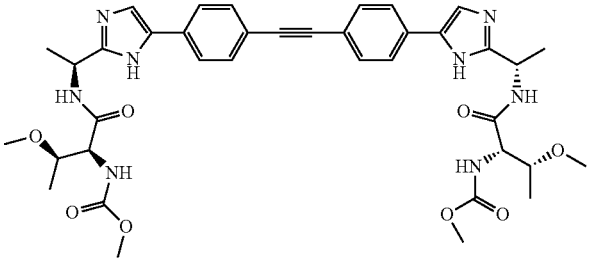 | *** | 743.3 |
| 953 | 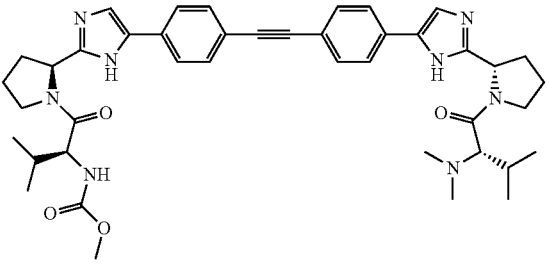 [SMILES: COC(=O)N[C@H](C(=O)N1CCC[C@H]1c1ncc(-c2ccc(C#Cc3ccc(-c4cnc([C@@H]5CCCN5C(=O)[C@H](C(C)C)N(C)C)[nH]4)cc3)cc2)[nH]1)C(C)C] | *** | 733.4 |
| 954 | 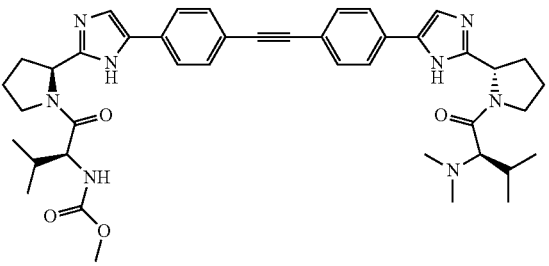 [SMILES: COC(=O)N[C@H](C(=O)N1CCC[C@H]1c1ncc(-c2ccc(C#Cc3ccc(-c4cnc([C@@H]5CCCN5C(=O)[C@@H](C(C)C)N(C)C)[nH]4)cc3)cc2)[nH]1)C(C)C] | *** | 733.4 |
| 955 | 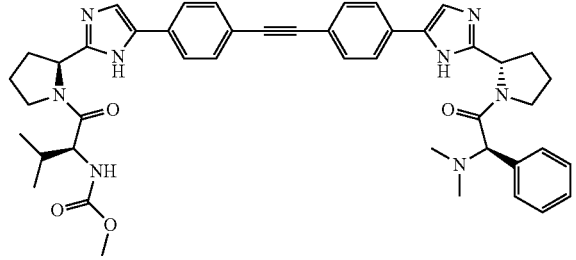 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N(C)C)[nH]4)cc3)cc2)[nH]1)C(C)C] | **** | 767.4 |

TABLE 2-continued
| Compound # | Structure | Inhibition of HCV genotype 1b | MS (M + H+) |
|---|---|---|---|
| 956 | 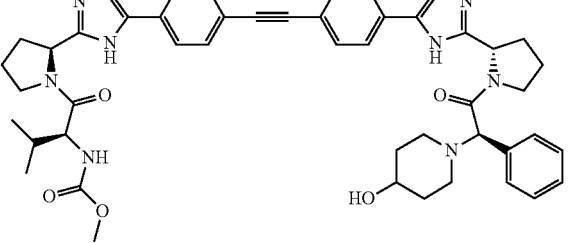 | **** | 823.4 |
| 957 | 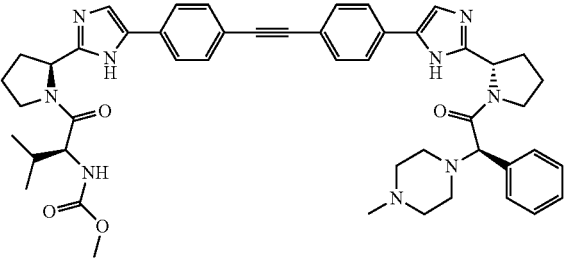 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N5CCN(C)CC5)[nH]4)cc3)cc2)[nH]1)C(C)C] | **** | 822.4 |
| 958 | 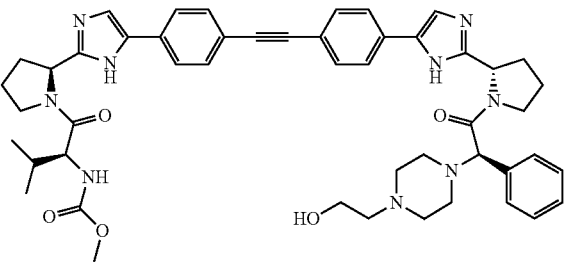 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N5CCN(CCO)CC5)[nH]4)cc3)cc2)[nH]1)C(C)C] | **** | 852.5 |
| 959 | 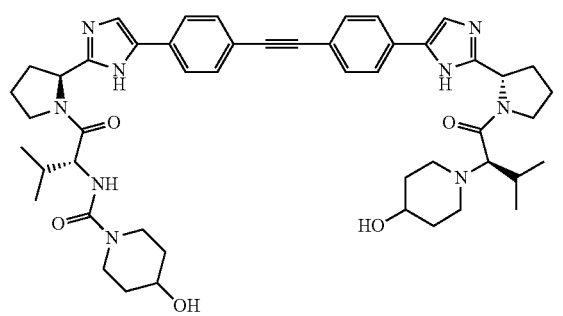 [SMILES: CC(C)[C@@H](NC(=O)N1CCC(O)CC1)C(=O)N1CCC[C@H]1c1ncc(-c2ccc(C#Cc3ccc(-c4cnc([C@@H]5CCCN5C(=O)[C@@H](C(C)C)N5CCC(O)CC5)[nH]4)cc3)cc2)[nH]1] | **** | 901.5 |
| 960 | 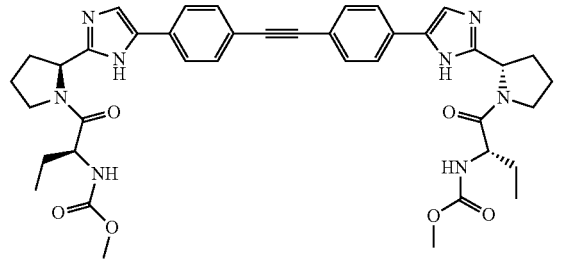 [SMILES: CC[C@H](NC(=O)OC)C(=O)N1CCC[C@H]1c1ncc(-c2ccc(C#Cc3ccc(-c4cnc([C@@H]5CCCN5C(=O)[C@H](CC)NC(=O)OC)[nH]4)cc3)cc2)[nH]1] | **** | 735.4 |

TABLE 2-continued

| Compound # | Structure | Inhibition of HCV genotype 1b | MS (M + H⁺) |
|---|---|---|---|
| 961 | 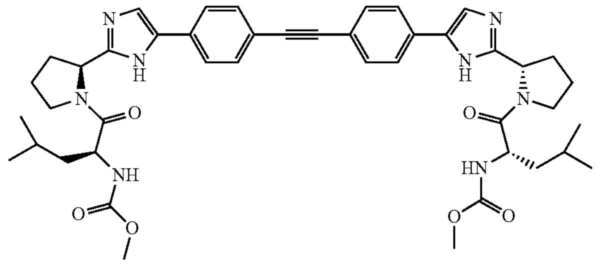 [SMILES: COC(=O)N[C@@H](CC(C)C)C(=O)N1CCC[C@H]1c1ncc(-c2ccc(C#Cc3ccc(-c4cnc([C@@H]5CCCN5C(=O)[C@H](CC(C)C)NC(=O)OC)[nH]4)cc3)cc2)[nH]1] | **** | 791.4 |
| 962 | 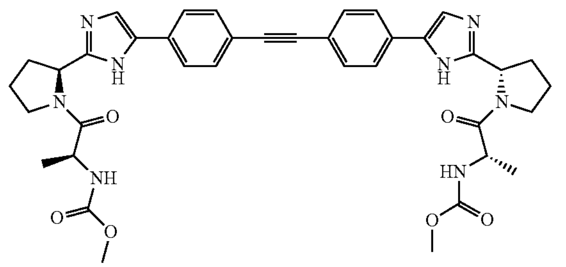 [SMILES: COC(=O)N[C@@H](C)C(=O)N1CCC[C@H]1c1ncc(-c2ccc(C#Cc3ccc(-c4cnc([C@@H]5CCCN5C(=O)[C@H](C)NC(=O)OC)[nH]4)cc3)cc2)[nH]1] | **** | 707.3 |
| 963 | 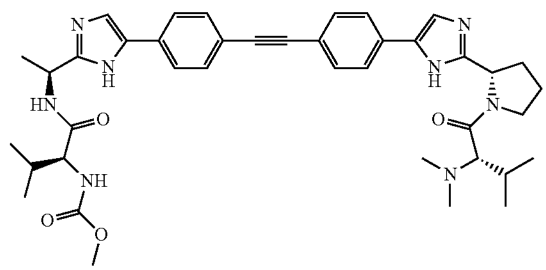 [SMILES: COC(=O)N[C@H](C(=O)N[C@@H](C)c1ncc(-c2ccc(C#Cc3ccc(-c4cnc([C@@H]5CCCN5C(=O)[C@H](C(C)C)N(C)C)[nH]4)cc3)cc2)[nH]1)C(C)C] | *** | 707.4 |
| 964 | 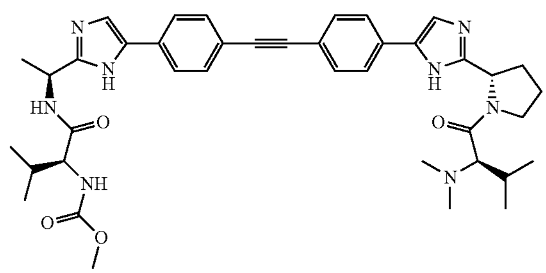 [SMILES: COC(=O)N[C@H](C(=O)N[C@@H](C)c1ncc(-c2ccc(C#Cc3ccc(-c4cnc([C@@H]5CCCN5C(=O)[C@@H](C(C)C)N(C)C)[nH]4)cc3)cc2)[nH]1)C(C)C] | *** | 707.4 |
| 965 | 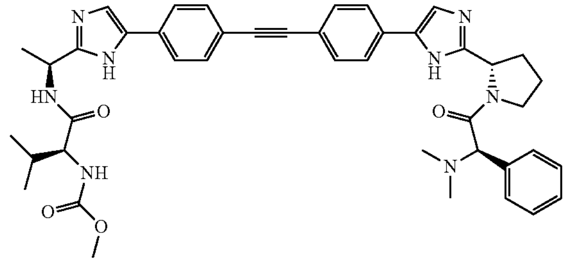 [SMILES: COC(=O)N[C@H](C(=O)N[C@@H](C)c1ncc(-c2ccc(C#Cc3ccc(-c4cnc([C@@H]5CCCN5C(=O)[C@@H](c5ccccc5)N(C)C)[nH]4)cc3)cc2)[nH]1)C(C)C] | **** | 741.4 |

TABLE 2-continued

| Compound # | Structure | Inhibition of HCV genotype 1b | MS (M + H+) |
|---|---|---|---|
| 966 | 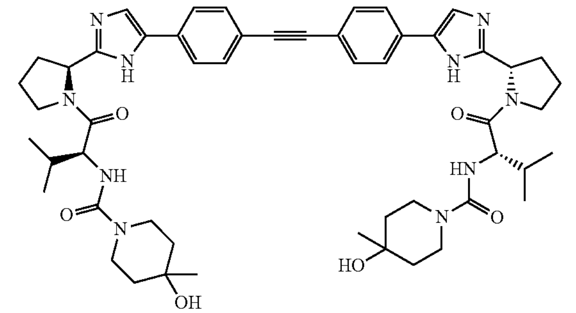 [SMILES: CC(C)[C@H](NC(=O)N1CCC(C)(O)CC1)C(=O)N1CCC[C@H]1c1ncc(-c2ccc(C#Cc3ccc(-c4cnc([C@@H]5CCCN5C(=O)[C@@H](NC(=O)N5CCC(C)(O)CC5)C(C)C)[nH]4)cc3)cc2)[nH]1] | ** | 929.5 |
| 967 | 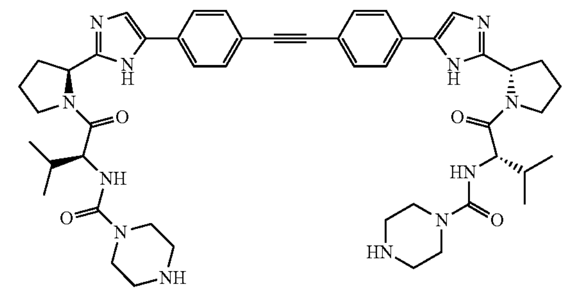 [SMILES: CC(C)[C@H](NC(=O)N1CCNCC1)C(=O)N1CCC[C@H]1c1ncc(-c2ccc(C#Cc3ccc(-c4cnc([C@@H]5CCCN5C(=O)[C@@H](NC(=O)N5CCNCC5)C(C)C)[nH]4)cc3)cc2)[nH]1] | ** | 871.5 |
| 968 | 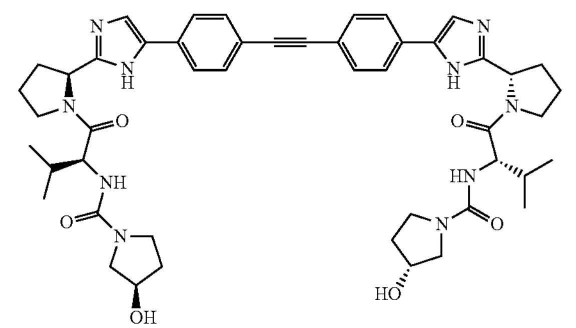 [SMILES: CC(C)[C@H](NC(=O)N1CC[C@@H](O)C1)C(=O)N1CCC[C@H]1c1ncc(-c2ccc(C#Cc3ccc(-c4cnc([C@@H]5CCCN5C(=O)[C@@H](NC(=O)N5CC[C@@H](O)C5)C(C)C)[nH]4)cc3)cc2)[nH]1] | ** | 873.5 |
| 969 | 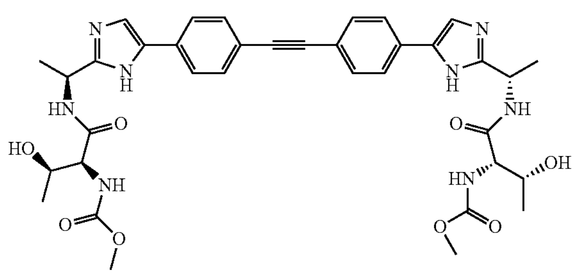 [SMILES: COC(=O)N[C@H](C(=O)N[C@@H](C)c1ncc(-c2ccc(C#Cc3ccc(-c4cnc([C@H](C)NC(=O)[C@@H](NC(=O)OC)[C@@H](C)O)[nH]4)cc3)cc2)[nH]1)[C@@H](C)O] | **** | 715.3 |
| 970 | 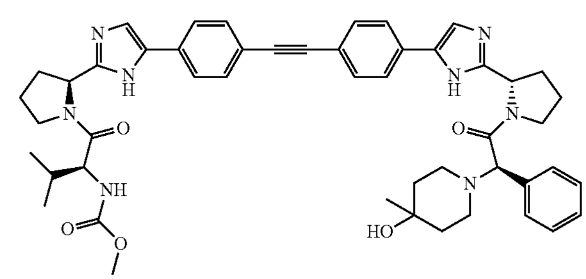 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N5CCC(C)(O)CC5)[nH]4)cc3)cc2)[nH]1)C(C)C] | **** | 837.4 |

TABLE 2-continued

| Compound # | Structure | Inhibition of HCV genotype 1b | MS (M + H+) |
|---|---|---|---|
| 971 | 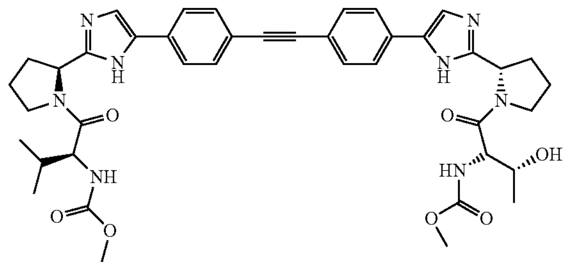 | **** | 765.4 |
| 972 | 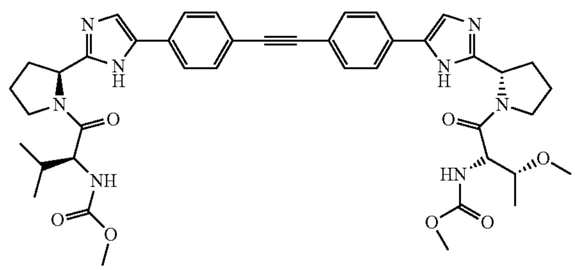 | **** | 779.4 |
| 973 | 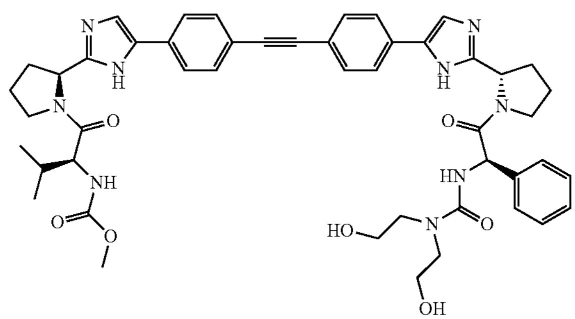 [SMILES: COC(=O)N[C@H](C(=O)N1CCC[C@H]1c1ncc(-c2ccc(C#Cc3ccc(-c4cnc([C@@H]5CCCN5C(=O)[C@H](NC(=O)N(CCO)CCO)c5ccccc5)[nH]4)cc3)cc2)[nH]1)C(C)C] | **** | 870.4 |
| 974 | 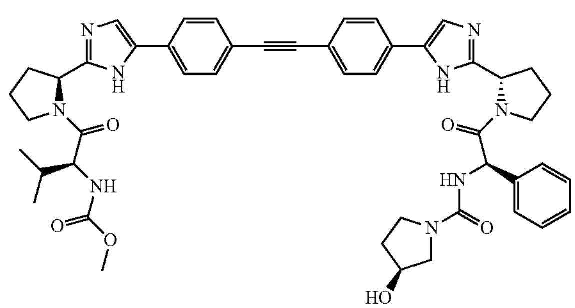 [SMILES: COC(=O)N[C@H](C(=O)N1CCC[C@H]1c1ncc(-c2ccc(C#Cc3ccc(-c4cnc([C@@H]5CCCN5C(=O)[C@H](NC(=O)N5CC[C@H](O)C5)c5ccccc5)[nH]4)cc3)cc2)[nH]1)C(C)C] | **** | 852.4 |
| 975 | 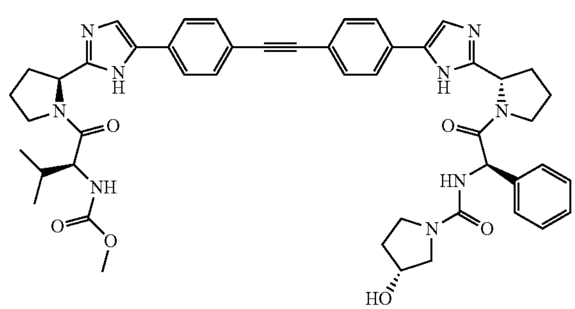 [SMILES: COC(=O)N[C@H](C(=O)N1CCC[C@H]1c1ncc(-c2ccc(C#Cc3ccc(-c4cnc([C@@H]5CCCN5C(=O)[C@H](NC(=O)N5CC[C@@H](O)C5)c5ccccc5)[nH]4)cc3)cc2)[nH]1)C(C)C] | **** | 852.4 |

TABLE 2-continued

| Compound # | Structure | Inhibition of HCV genotype 1b | MS (M + H+) |
|---|---|---|---|
| 976 | 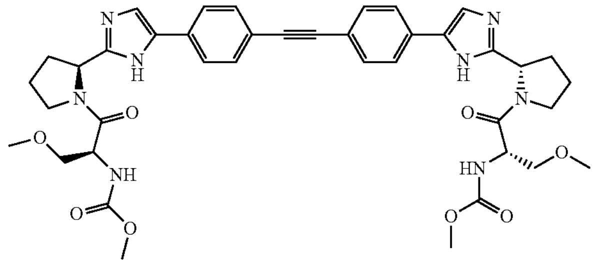 | **** | 767.3 |
| 977 | 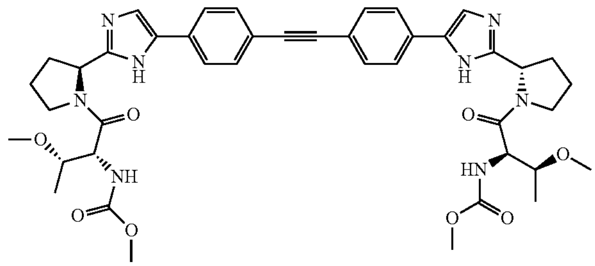 | ** | 795.4 |
| 978 | 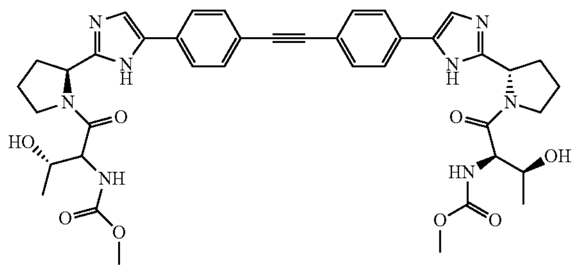 [SMILES: COC(=O)NC(C(=O)N1CCC[C@H]1c1ncc(-c2ccc(C#Cc3ccc(-c4cnc([C@@H]5CCCN5C(=O)[C@H](NC(=O)OC)[C@H](C)O)[nH]4)cc3)cc2)[nH]1)[C@H](C)O] | ** | 767.3 |
| 979 | 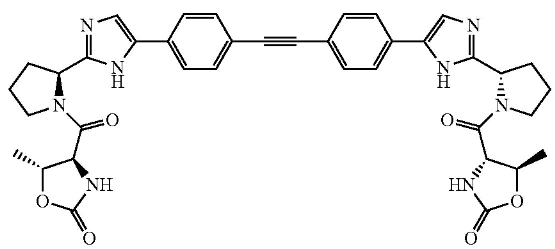 [SMILES: C[C@H]1OC(=O)N[C@@H]1C(=O)N1CCC[C@H]1c1ncc(-c2ccc(C#Cc3ccc(-c4cnc([C@@H]5CCCN5C(=O)[C@H]5NC(=O)O[C@@H]5C)[nH]4)cc3)cc2)[nH]1] | ** | 703.3 |
| 980 | 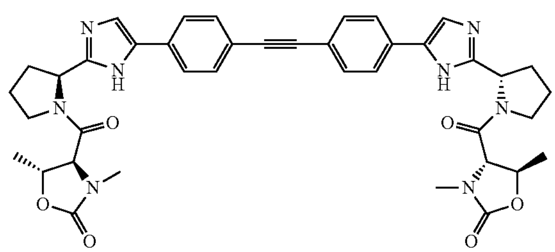 [SMILES: C[C@H]1OC(=O)N(C)[C@@H]1C(=O)N1CCC[C@H]1c1ncc(-c2ccc(C#Cc3ccc(-c4cnc([C@@H]5CCCN5C(=O)[C@@H]5[C@@H](C)OC(=O)N5C)[nH]4)cc3)cc2)[nH]1] | ** | 731.3 |
| 981 | 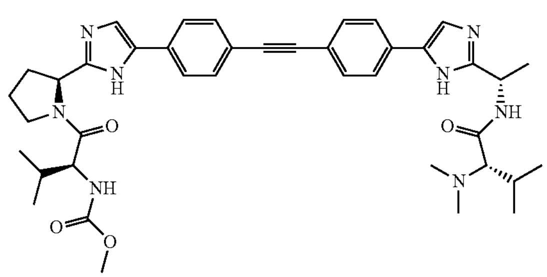 [SMILES: COC(=O)N[C@H](C(=O)N1CCC[C@H]1c1ncc(-c2ccc(C#Cc3ccc(-c4cnc([C@H](C)NC(=O)[C@H](C(C)C)N(C)C)[nH]4)cc3)cc2)[nH]1)C(C)C] | ** | 707.4 |

TABLE 2-continued

| Compound # | Structure | Inhibition of HCV genotype 1b | MS (M + H⁺) |
|---|---|---|---|
| 982 | 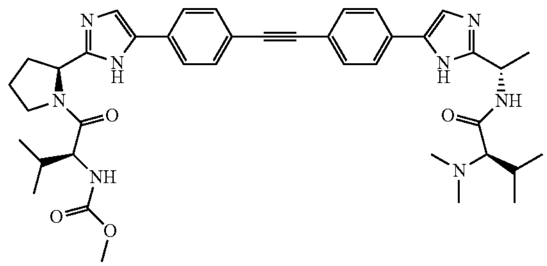 [SMILES: COC(=O)N[C@H](C(=O)N1CCC[C@H]1c1ncc(-c2ccc(C#Cc3ccc(-c4cnc([C@H](C)NC(=O)[C@@H](C(C)C)N(C)C)[nH]4)cc3)cc2)[nH]1)C(C)C] | ** | 707.4 |
| 983 | 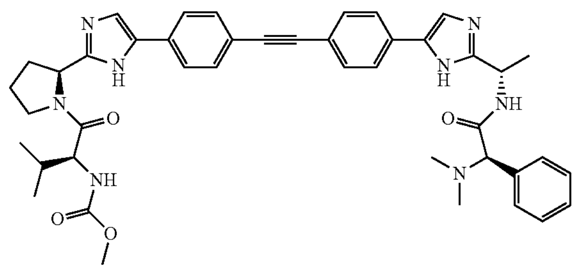 [SMILES: COC(=O)N[C@H](C(=O)N1CCC[C@H]1c1ncc(-c2ccc(C#Cc3ccc(-c4cnc([C@H](C)NC(=O)[C@@H](c5ccccc5)N(C)C)[nH]4)cc3)cc2)[nH]1)C(C)C] | **** | 741.4 |
| 984 | 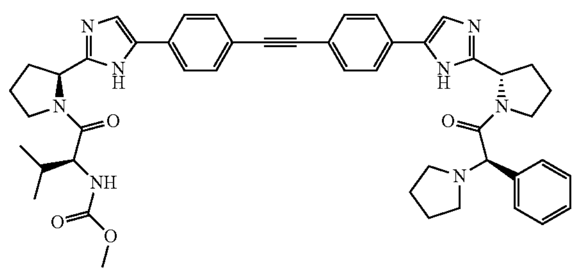 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N5CCCC5)[nH]4)cc3)cc2)[nH]1)C(C)C] | **** | 793.4 |
| 985 | 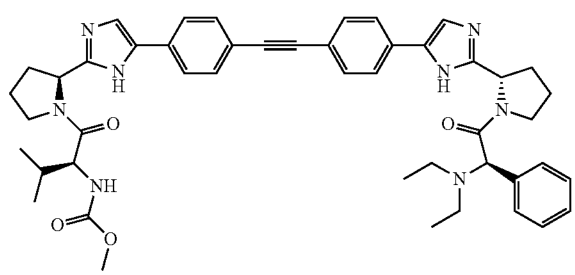 [SMILES: CCN(CC)[C@@H](C(=O)N1CCC[C@H]1c1ncc(-c2ccc(C#Cc3ccc(-c4cnc([C@@H]5CCCN5C(=O)[C@@H](NC(=O)OC)C(C)C)[nH]4)cc3)cc2)[nH]1)c1ccccc1] | **** | 795.4 |
| 986 | 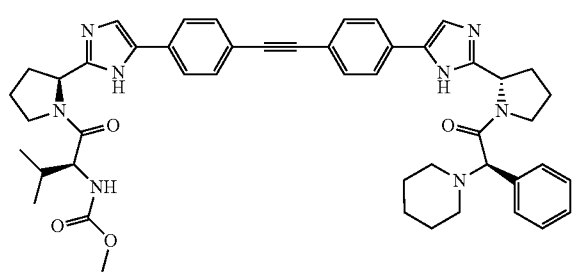 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N5CCCCC5)[nH]4)cc3)cc2)[nH]1)C(C)C] | **** | 807.4 |

TABLE 2-continued

| Compound # | Structure | Inhibition of HCV genotype 1b | MS (M + H+) |
|---|---|---|---|
| 987 | 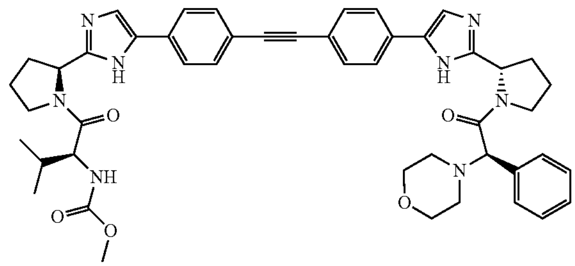 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N5CCOCC5)[nH]4)cc3)cc2)[nH]1)C(C)C] | **** | 809.4 |
| 988 | 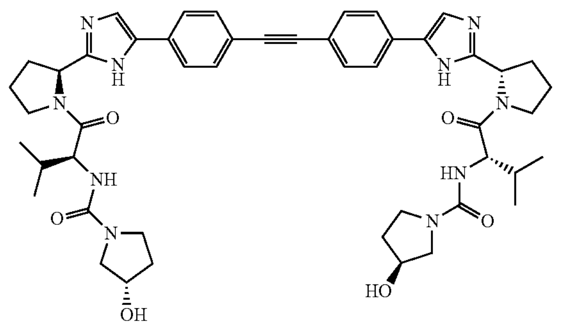 [SMILES: CC(C)[C@H](NC(=O)N1CC[C@H](O)C1)C(=O)N1CCC[C@H]1c1ncc(-c2ccc(C#Cc3ccc(-c4cnc([C@@H]5CCCN5C(=O)[C@@H](NC(=O)N5CC[C@H](O)C5)C(C)C)[nH]4)cc3)cc2)[nH]1] | ** | 873.5 |
| 989 | 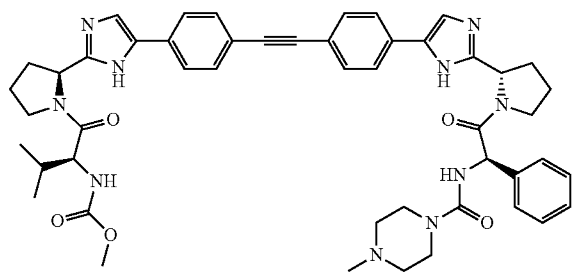 [SMILES: COC(=O)N[C@H](C(=O)N1CCC[C@H]1c1ncc(-c2ccc(C#Cc3ccc(-c4cnc([C@@H]5CCCN5C(=O)[C@H](NC(=O)N5CCN(C)CC5)c5ccccc5)[nH]4)cc3)cc2)[nH]1)C(C)C] | **** | 865.4 |
| 990 | 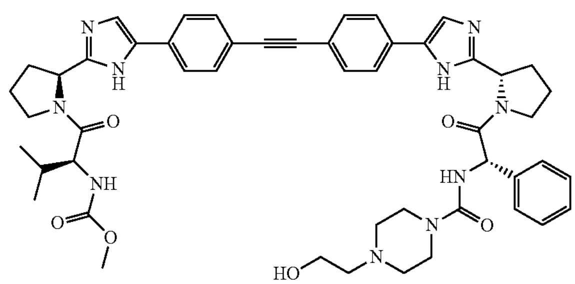 [SMILES: COC(=O)N[C@H](C(=O)N1CCC[C@H]1c1ncc(-c2ccc(C#Cc3ccc(-c4cnc([C@@H]5CCCN5C(=O)[C@@H](NC(=O)N5CCN(CCO)CC5)c5ccccc5)[nH]4)cc3)cc2)[nH]1)C(C)C] | *** | 895.5 |
| 991 | 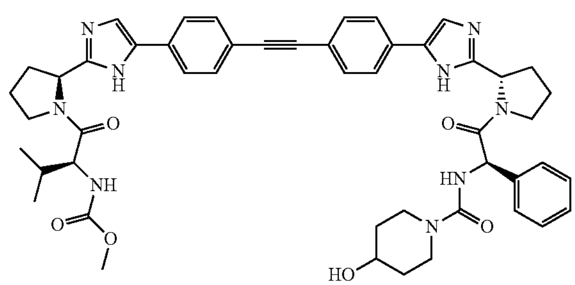 [SMILES: COC(=O)N[C@H](C(=O)N1CCC[C@H]1c1ncc(-c2ccc(C#Cc3ccc(-c4cnc([C@@H]5CCCN5C(=O)[C@H](NC(=O)N5CCC(O)CC5)c5ccccc5)[nH]4)cc3)cc2)[nH]1)C(C)C] | *** | 866.4 |

TABLE 2-continued

| Compound # | Structure | Inhibition of HCV genotype 1b | MS (M + H+) |
|---|---|---|---|
| 992 | 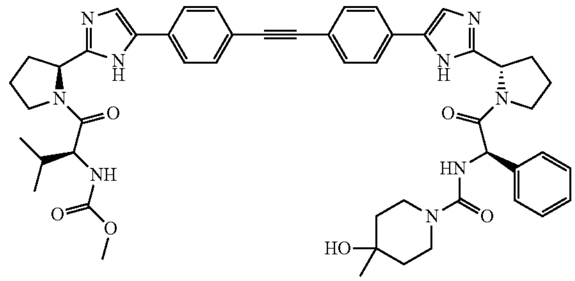 [SMILES: COC(=O)N[C@H](C(=O)N1CCC[C@H]1c1ncc(-c2ccc(C#Cc3ccc(-c4cnc([C@@H]5CCCN5C(=O)[C@H](NC(=O)N5CCC(C)(O)CC5)c5ccccc5)[nH]4)cc3)cc2)[nH]1)C(C)C] | **** | 880.4 |
| 993 | 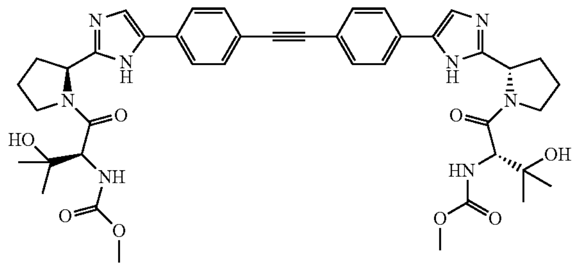 [SMILES: COC(=O)N[C@H](C(=O)N1CCC[C@H]1c1ncc(-c2ccc(C#Cc3ccc(-c4cnc([C@@H]5CCCN5C(=O)[C@@H](NC(=O)OC)C(C)(C)O)[nH]4)cc3)cc2)[nH]1)C(C)(C)O] | **** | 795.4 |
| 994 | 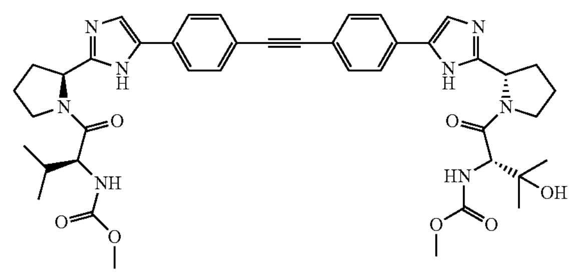 [SMILES: COC(=O)N[C@H](C(=O)N1CCC[C@H]1c1ncc(-c2ccc(C#Cc3ccc(-c4cnc([C@@H]5CCCN5C(=O)[C@@H](NC(=O)OC)C(C)(C)O)[nH]4)cc3)cc2)[nH]1)C(C)C] | **** | 779.4 |
| 995 | 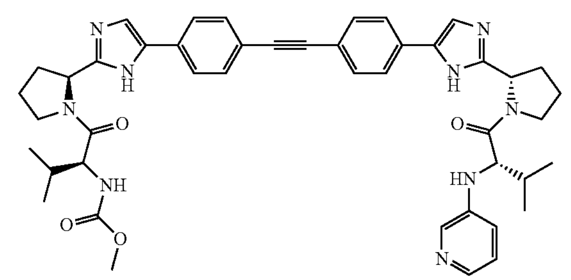 [SMILES: COC(=O)N[C@H](C(=O)N1CCC[C@H]1c1ncc(-c2ccc(C#Cc3ccc(-c4cnc([C@@H]5CCCN5C(=O)[C@@H](Nc5cccnc5)C(C)C)[nH]4)cc3)cc2)[nH]1)C(C)C] | **** | 782.4 |
| 996 | 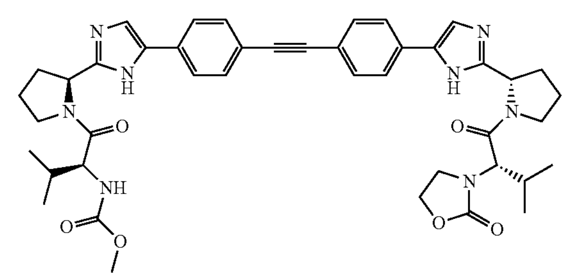 [SMILES: COC(=O)N[C@H](C(=O)N1CCC[C@H]1c1ncc(-c2ccc(C#Cc3ccc(-c4cnc([C@@H]5CCCN5C(=O)[C@H](C(C)C)N5CCOC5=O)[nH]4)cc3)cc2)[nH]1)C(C)C] | **** | 775.4 |

TABLE 2-continued

| Compound # | Structure | Inhibition of HCV genotype 1b | MS (M + H+) |
|---|---|---|---|
| 997 | 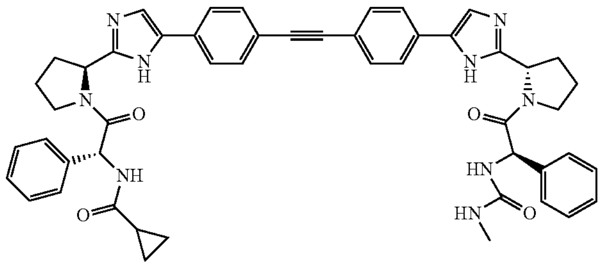 [SMILES: CNC(=O)N[C@@H](C(=O)N1CCC[C@H]1c1ncc(-c2ccc(C#Cc3ccc(-c4cnc([C@@H]5CCCN5C(=O)[C@H](NC(=O)C5CC5)c5ccccc5)[nH]4)cc3)cc2)[nH]1)c1ccccc1] | **** | 840.4 |
| 1000 | 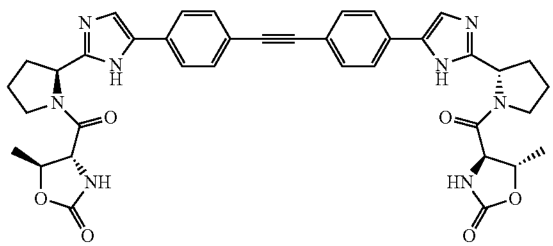 [SMILES: C[C@@H]1OC(=O)N[C@H]1C(=O)N1CCC[C@H]1c1ncc(-c2ccc(C#Cc3ccc(-c4cnc([C@@H]5CCCN5C(=O)[C@@H]5NC(=O)O[C@H]5C)[nH]4)cc3)cc2)[nH]1] | ** | 703.3 |
| 1001 | 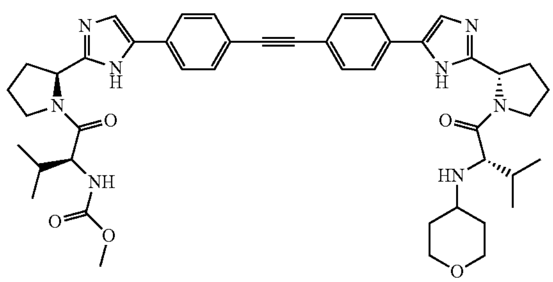 [SMILES: COC(=O)N[C@H](C(=O)N1CCC[C@H]1c1ncc(-c2ccc(C#Cc3ccc(-c4cnc([C@@H]5CCCN5C(=O)[C@@H](NC5CCOCC5)C(C)C)[nH]4)cc3)cc2)[nH]1)C(C)C] | *** | 789.4 |
| 1002 | 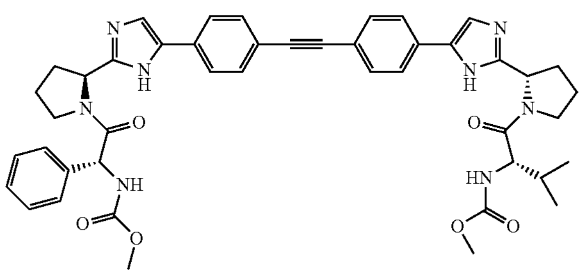 [SMILES: COC(=O)N[C@H](C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cc3)cc2)[nH]1)C(C)C] | **** | 797.4 |
| 1003 | 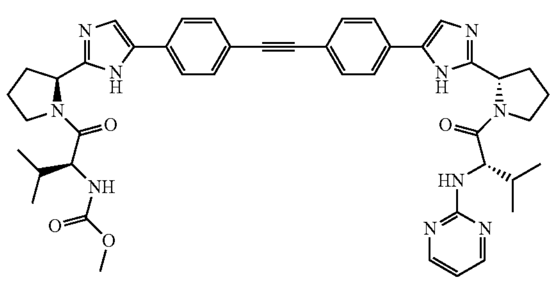 [SMILES: COC(=O)N[C@H](C(=O)N1CCC[C@H]1c1ncc(-c2ccc(C#Cc3ccc(-c4cnc([C@@H]5CCCN5C(=O)[C@@H](Nc5ncccn5)C(C)C)[nH]4)cc3)cc2)[nH]1)C(C)C] | **** | 783.4 |

TABLE 2-continued

| Compound # | Structure | Inhibition of HCV genotype 1b | MS (M + H⁺) |
|---|---|---|---|
| 1004 | 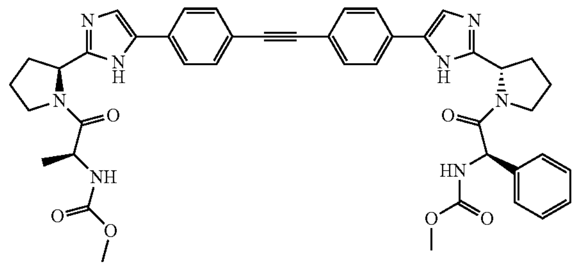 [SMILES: COC(=O)N[C@@H](C)C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cc3)cc2)[nH]1] | **** | 769.4 |
| 1005 | 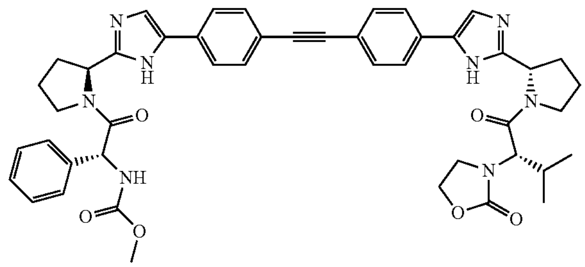 [SMILES: COC(=O)N[C@@H](C(=O)N1CCC[C@H]1c1ncc(-c2ccc(C#Cc3ccc(-c4cnc([C@@H]5CCCN5C(=O)[C@H](C(C)C)N5CCOC5=O)[nH]4)cc3)cc2)[nH]1)c1ccccc1] | **** | 809.4 |
| 1006 | 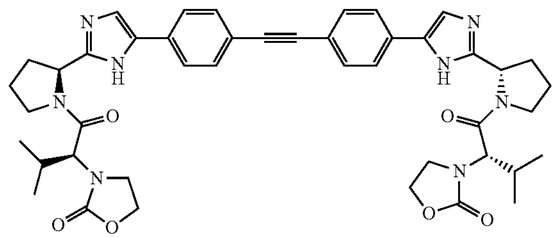 [SMILES: CC(C)[C@@H](C(=O)N1CCC[C@H]1c1ncc(-c2ccc(C#Cc3ccc(-c4cnc([C@@H]5CCCN5C(=O)[C@H](C(C)C)N5CCOC5=O)[nH]4)cc3)cc2)[nH]1)N1CCOC1=O] | ** | 787.4 |
| 1007 | 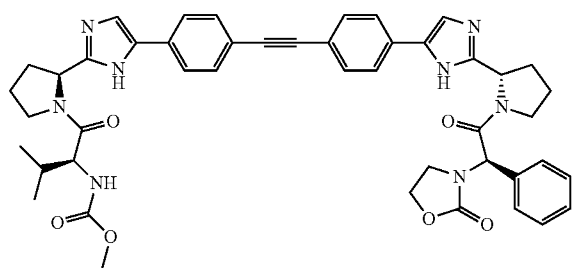 [SMILES: COC(=O)N[C@H](C(=O)N1CCC[C@H]1c1ncc(-c2ccc(C#Cc3ccc(-c4cnc([C@@H]5CCCN5C(=O)[C@@H](c5ccccc5)N5CCOC5=O)[nH]4)cc3)cc2)[nH]1)C(C)C] | **** | 809.4 |
| 1008 | 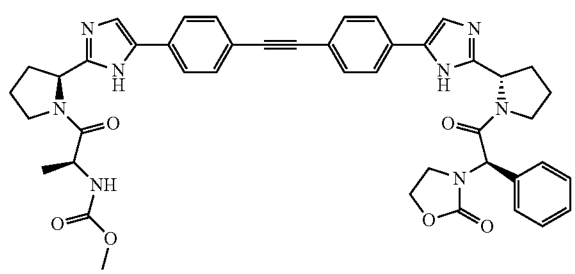 [SMILES: COC(=O)N[C@@H](C)C(=O)N1CCC[C@H]1c1ncc(-c2ccc(C#Cc3ccc(-c4cnc([C@@H]5CCCN5C(=O)[C@@H](c5ccccc5)N5CCOC5=O)[nH]4)cc3)cc2)[nH]1] | **** | 781.3 |
| 1009 | 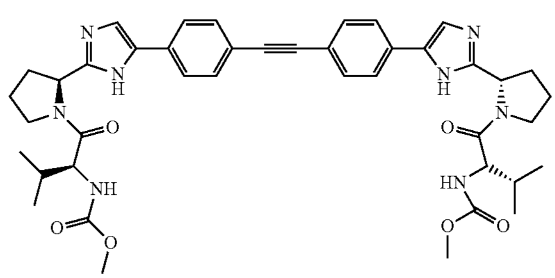 | **** | 764.4 |

TABLE 2-continued

| Compound # | Structure | Inhibition of HCV genotype 1b | MS (M + H+) |
|---|---|---|---|
| 1010 | 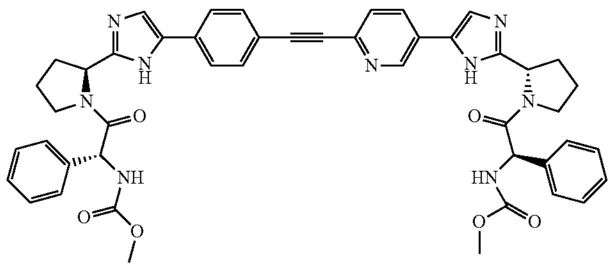 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)cn3)cc2)[nH]1)c1ccccc1] | **** | 832.3 |
| 1011 | 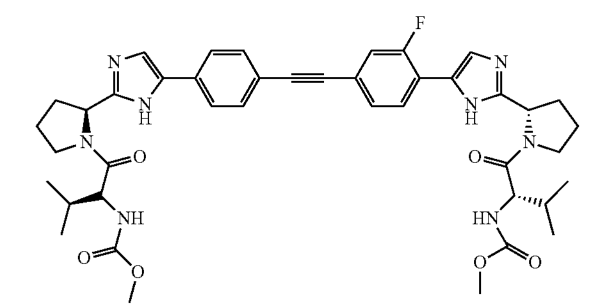 | **** | 781.4 |
| 1012 | 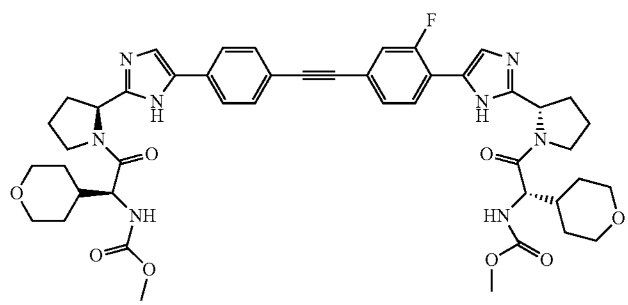 [SMILES: COC(=O)N[C@H](C(=O)N1CCC[C@H]1c1ncc(-c2ccc(C#Cc3ccc(-c4cnc([C@@H]5CCCN5C(=O)[C@@H](NC(=O)OC)C5CCOCC5)[nH]4)c(F)c3)cc2)[nH]1)C1CCOCC1] | **** | 865.4 |
| 1013 | 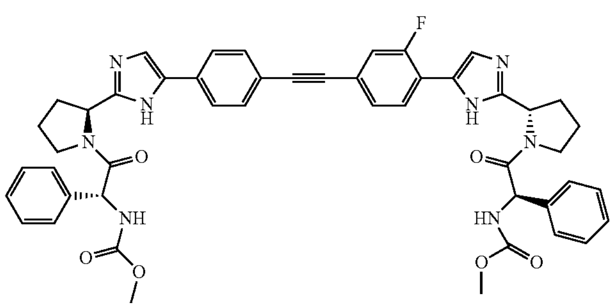 [SMILES: COC(=O)N[C@@H](C(=O)N1CCC[C@H]1c1ncc(-c2ccc(C#Cc3ccc(-c4cnc([C@@H]5CCCN5C(=O)[C@H](NC(=O)OC)c5ccccc5)[nH]4)c(F)c3)cc2)[nH]1)c1ccccc1] | **** | 849.3 |
| 1014 | 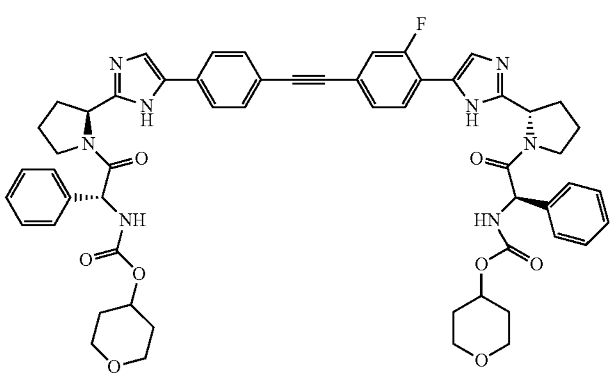 [SMILES: O=C(N[C@@H](C(=O)N1CCC[C@H]1c1ncc(-c2ccc(C#Cc3ccc(-c4cnc([C@@H]5CCCN5C(=O)[C@H](NC(=O)OC5CCOCC5)c5ccccc5)[nH]4)c(F)c3)cc2)[nH]1)c1ccccc1)OC1CCOCC1] | **** | 989.4 |

TABLE 2-continued

| Compound # | Structure | Inhibition of HCV genotype 1b | MS (M + H+) |
|---|---|---|---|
| 1015 | 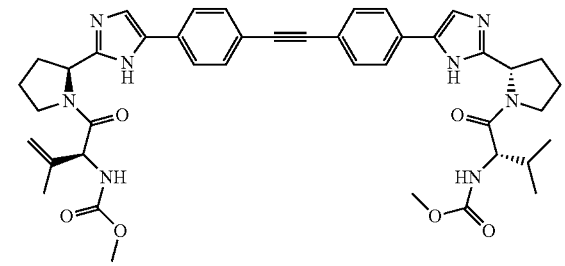 [SMILES: C=C(C)[C@H](NC(=O)OC)C(=O)N1CCC[C@H]1c1ncc(-c2ccc(C#Cc3ccc(-c4cnc([C@@H]5CCCN5C(=O)[C@@H](NC(=O)OC)C(C)C)[nH]4)cc3)cc2)[nH]1] | | |
| 1016 | 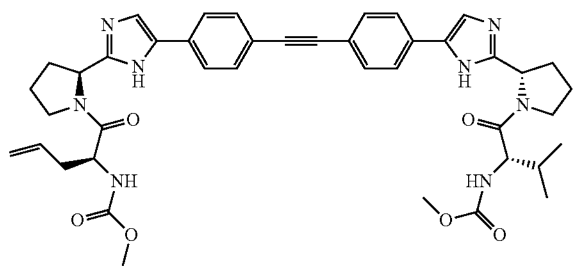 [SMILES: C=CC[C@H](NC(=O)OC)C(=O)N1CCC[C@H]1c1ncc(-c2ccc(C#Cc3ccc(-c4cnc([C@@H]5CCCN5C(=O)[C@@H](NC(=O)OC)C(C)C)[nH]4)cc3)cc2)[nH]1] | | |
| 1017 | 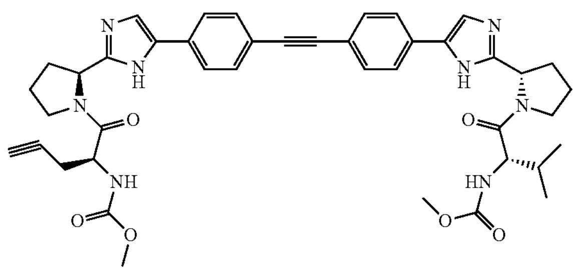 [SMILES: C#CC[C@H](NC(=O)OC)C(=O)N1CCC[C@H]1c1ncc(-c2ccc(C#Cc3ccc(-c4cnc([C@@H]5CCCN5C(=O)[C@@H](NC(=O)OC)C(C)C)[nH]4)cc3)cc2)[nH]1] | | |
| 1018 | 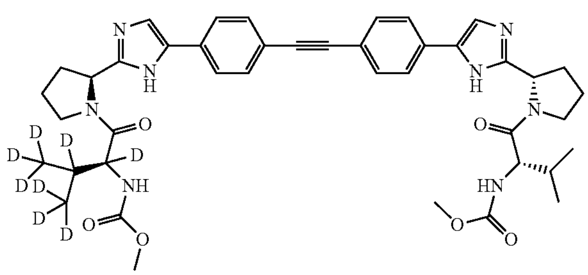 [SMILES: [2H]C([2H])([2H])C([2H])(C([2H])([2H])[2H])[C@@]([2H])(NC(=O)OC)C(=O)N1CCC[C@H]1c1ncc(-c2ccc(C#Cc3ccc(-c4cnc([C@@H]5CCCN5C(=O)[C@@H](NC(=O)OC)C(C)C)[nH]4)cc3)cc2)[nH]1] | | |
| 1019 | 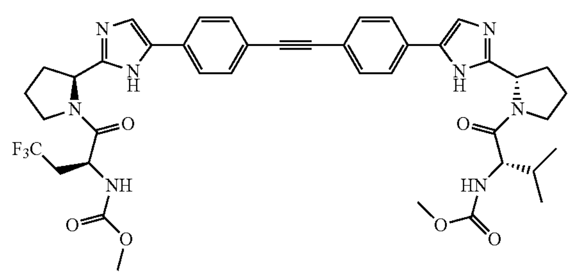 [SMILES: COC(=O)N[C@@H](CC(F)(F)F)C(=O)N1CCC[C@H]1c1ncc(-c2ccc(C#Cc3ccc(-c4cnc([C@@H]5CCCN5C(=O)[C@@H](NC(=O)OC)C(C)C)[nH]4)cc3)cc2)[nH]1] | | |

TABLE 3

| Compound # | Structure | Inhibition of HCV genotype 1b | MS (M + H⁺) |
|---|---|---|---|
| 300 | 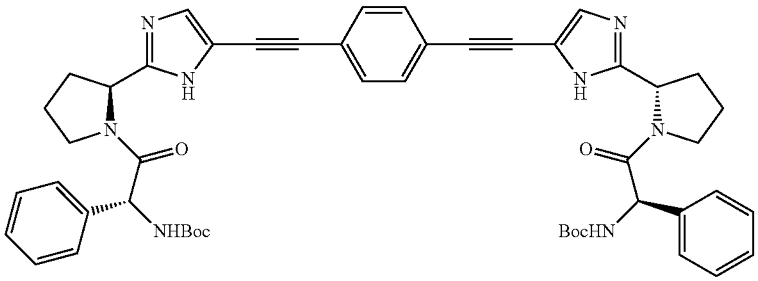 [SMILES: CC(C)(C)OC(=O)N[C@@H](C(=O)N1CCC[C@H]1c1ncc(C#Cc2ccc(C#Cc3cnc([C@@H]4CCCN4C(=O)[C@H](NC(=O)OC(C)(C)C)c4ccccc4)[nH]3)cc2)[nH]1)c1ccccc1] | **** | 863.4 |
| 301 | 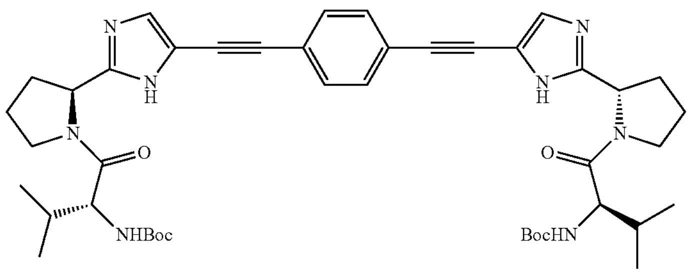 [SMILES: CC(C)[C@@H](NC(=O)OC(C)(C)C)C(=O)N1CCC[C@H]1c1ncc(C#Cc2ccc(C#Cc3cnc([C@@H]4CCCN4C(=O)[C@H](NC(=O)OC(C)(C)C)C(C)C)[nH]3)cc2)[nH]1] | * | 795.5 |
| 302 | 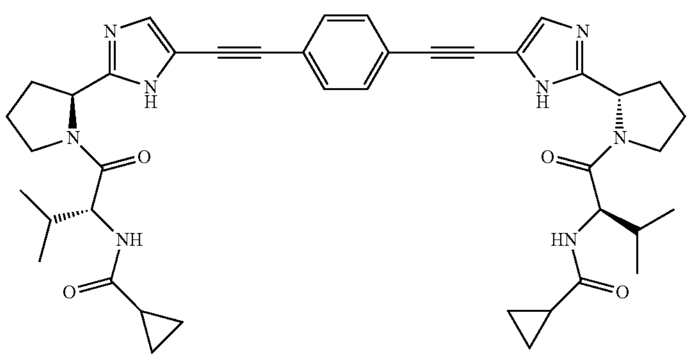 [SMILES: CC(C)[C@@H](NC(=O)C1CC1)C(=O)N1CCC[C@H]1c1ncc(C#Cc2ccc(C#Cc3cnc([C@@H]4CCCN4C(=O)[C@H](NC(=O)C4CC4)C(C)C)[nH]3)cc2)[nH]1] | * | 731.4 |
| 303 | 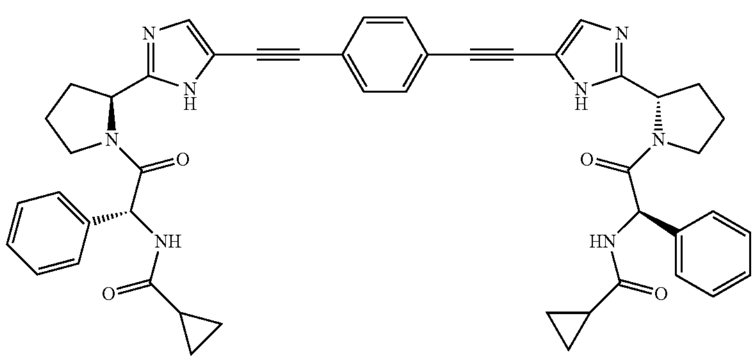 [SMILES: O=C(N[C@@H](C(=O)N1CCC[C@H]1c1ncc(C#Cc2ccc(C#Cc3cnc([C@@H]4CCCN4C(=O)[C@H](NC(=O)C4CC4)c4ccccc4)[nH]3)cc2)[nH]1)c1ccccc1)C1CC1] | **** | 799.4 |

TABLE 3-continued

| Compound # | Structure | Inhibition of HCV genotype 1b | MS (M + H⁺) |
|---|---|---|---|
| 304 | 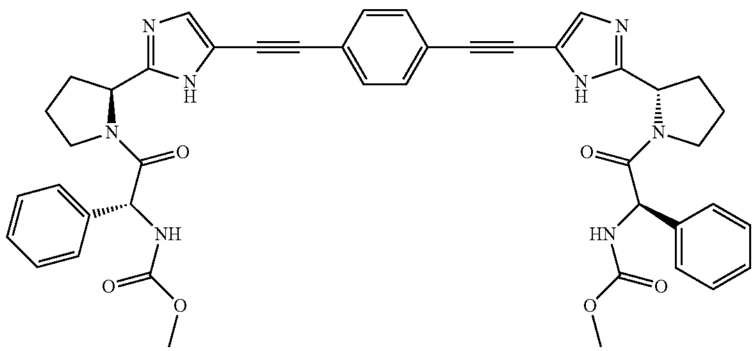 [SMILES: COC(=O)N[C@@H](C(=O)N1CCC[C@H]1c1ncc(C#Cc2ccc(C#Cc3cnc([C@@H]4CCCN4C(=O)[C@H](NC(=O)OC)c4ccccc4)[nH]3)cc2)[nH]1)c1ccccc1] | **** | 779.3 |
| 305 | 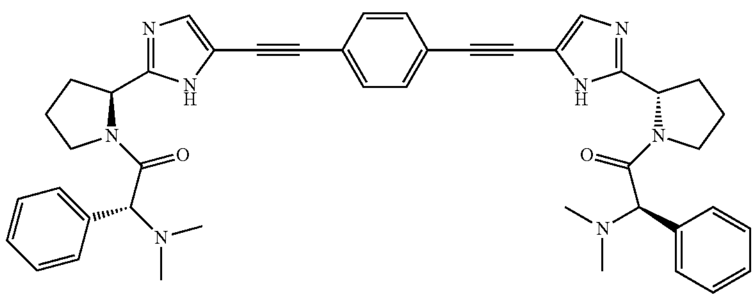 [SMILES: CN(C)[C@@H](C(=O)N1CCC[C@H]1c1ncc(C#Cc2ccc(C#Cc3cnc([C@@H]4CCCN4C(=O)[C@@H](c4ccccc4)N(C)C)[nH]3)cc2)[nH]1)c1ccccc1] | **** | 719.4 |
| 306 | 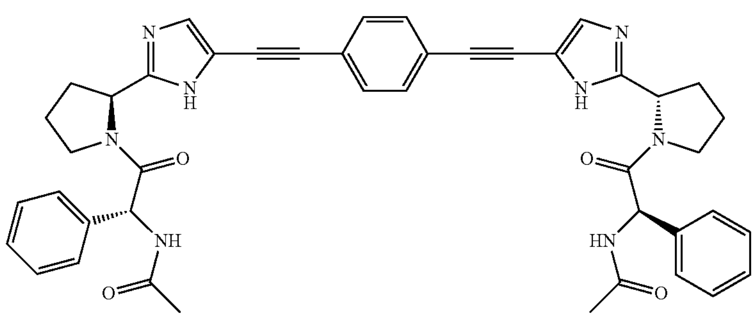 [SMILES: CC(=O)N[C@@H](C(=O)N1CCC[C@H]1c1ncc(C#Cc2ccc(C#Cc3cnc([C@@H]4CCCN4C(=O)[C@H](NC(C)=O)c4ccccc4)[nH]3)cc2)[nH]1)c1ccccc1] | **** | 747.3 |
| 307 | 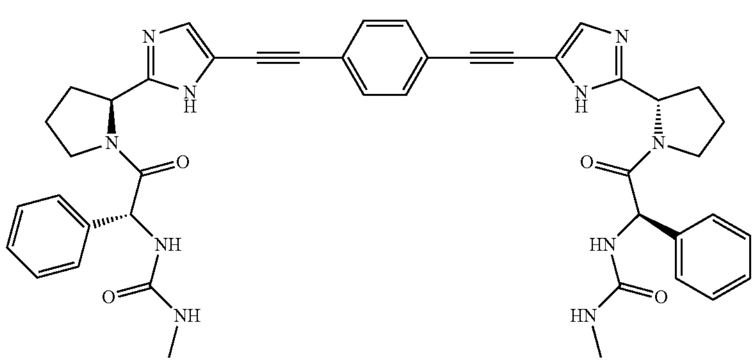 [SMILES: CNC(=O)N[C@@H](C(=O)N1CCC[C@H]1c1ncc(C#Cc2ccc(C#Cc3cnc([C@@H]4CCCN4C(=O)[C@H](NC(=O)NC)c4ccccc4)[nH]3)cc2)[nH]1)c1ccccc1] | **** | 777.4 |

TABLE 3-continued

| Compound # | Structure | Inhibition of HCV genotype 1b | MS (M + H⁺) |
|---|---|---|---|
| 308 | 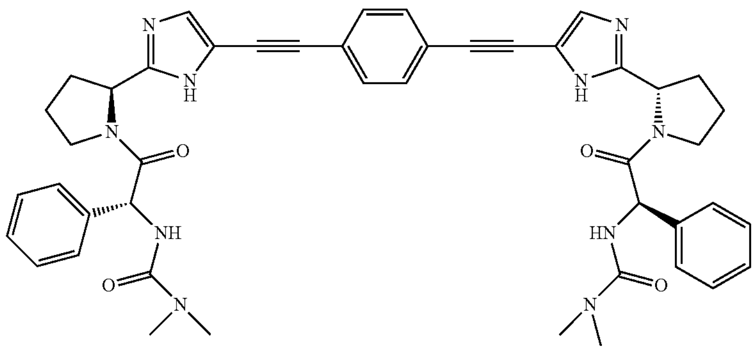 [SMILES: CN(C)C(=O)N[C@@H](C(=O)N1CCC[C@H]1c1ncc(C#Cc2ccc(C#Cc3cnc([C@@H]4CCCN4C(=O)[C@H](NC(=O)N(C)C)c4ccccc4)[nH]3)cc2)[nH]1)c1ccccc1] | **** | 805.4 |
| 309 | 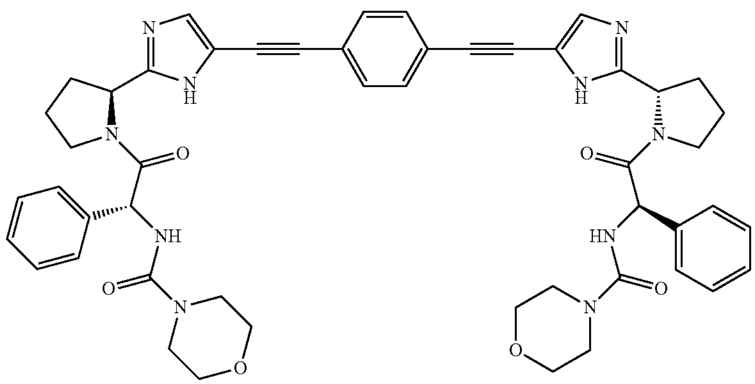 [SMILES: O=C(N[C@@H](C(=O)N1CCC[C@H]1c1ncc(C#Cc2ccc(C#Cc3cnc([C@@H]4CCCN4C(=O)[C@H](NC(=O)N4CCOCC4)c4ccccc4)[nH]3)cc2)[nH]1)c1ccccc1)N1CCOCC1] | **** | 889.4 |
| 310 | 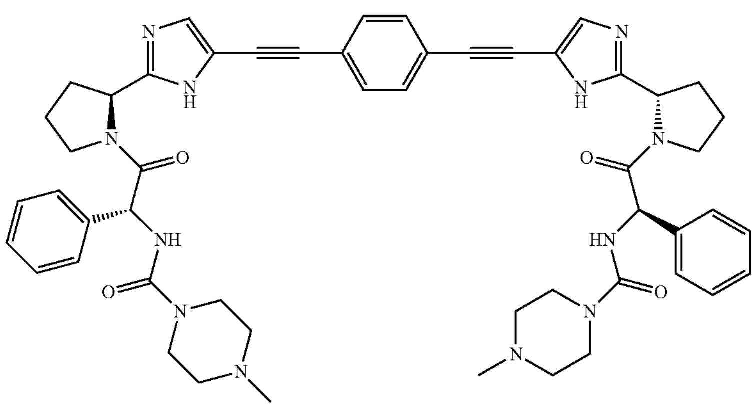 [SMILES: CN1CCN(C(=O)N[C@@H](C(=O)N2CCC[C@H]2c2ncc(C#Cc3ccc(C#Cc4cnc([C@@H]5CCCN5C(=O)[C@H](NC(=O)N5CCN(C)CC5)c5ccccc5)[nH]4)cc3)[nH]2)c2ccccc2)CC1] | *** | 915.5 |
| 311 | 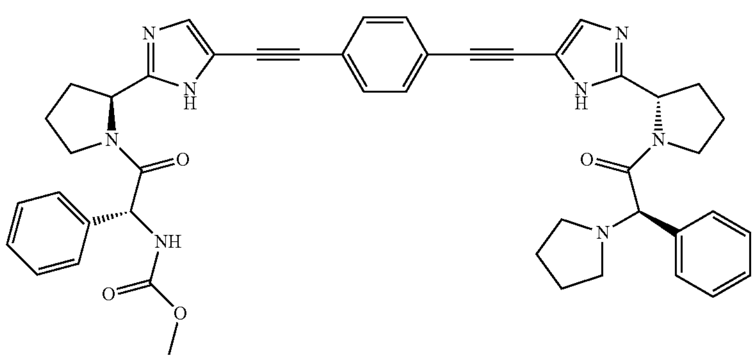 | **** | 775.4 |

TABLE 3-continued

| Compound # | Structure | Inhibition of HCV genotype 1b | MS (M + H+) |
|---|---|---|---|
| 312 | 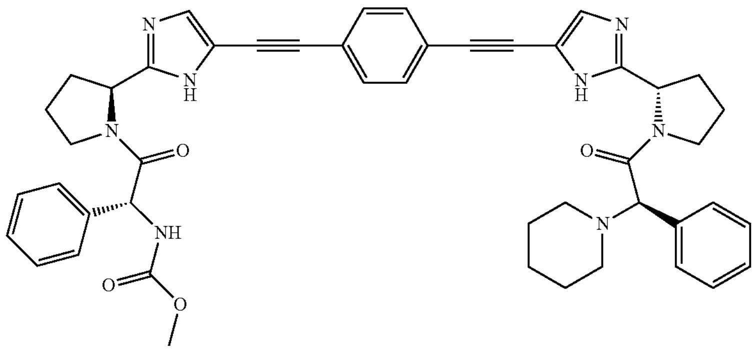 [SMILES: COC(=O)N[C@@H](C(=O)N1CCC[C@H]1c1ncc(C#Cc2ccc(C#Cc3cnc([C@@H]4CCCN4C(=O)[C@@H](c4ccccc4)N4CCCCC4)[nH]3)cc2)[nH]1)c1ccccc1] | **** | 789.4 |
| 313 | 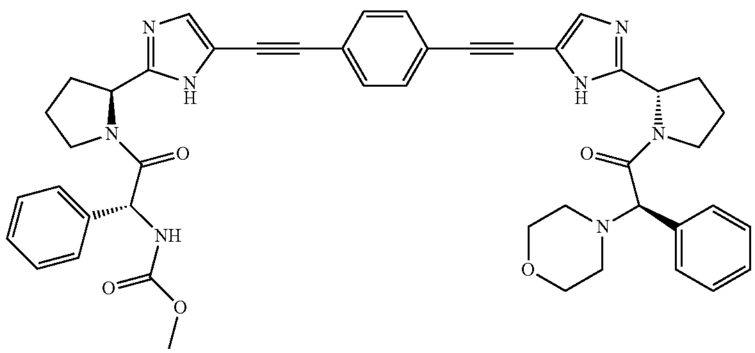 [SMILES: COC(=O)N[C@@H](C(=O)N1CCC[C@H]1c1ncc(C#Cc2ccc(C#Cc3cnc([C@@H]4CCCN4C(=O)[C@@H](c4ccccc4)N4CCOCC4)[nH]3)cc2)[nH]1)c1ccccc1] | **** | 791.4 |
| 314 | 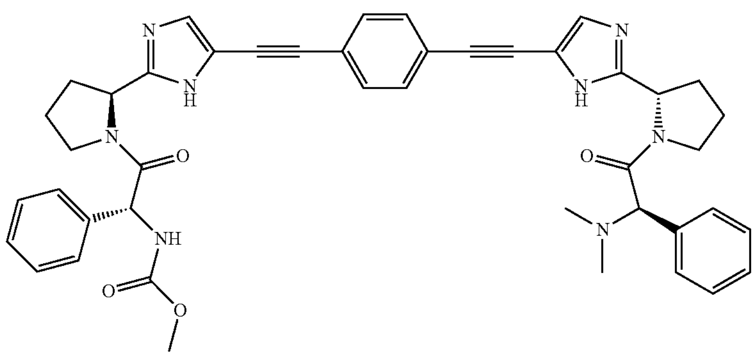 [SMILES: COC(=O)N[C@@H](C(=O)N1CCC[C@H]1c1ncc(C#Cc2ccc(C#Cc3cnc([C@@H]4CCCN4C(=O)[C@@H](c4ccccc4)N(C)C)[nH]3)cc2)[nH]1)c1ccccc1] | **** | 749.3 |
| 315 | 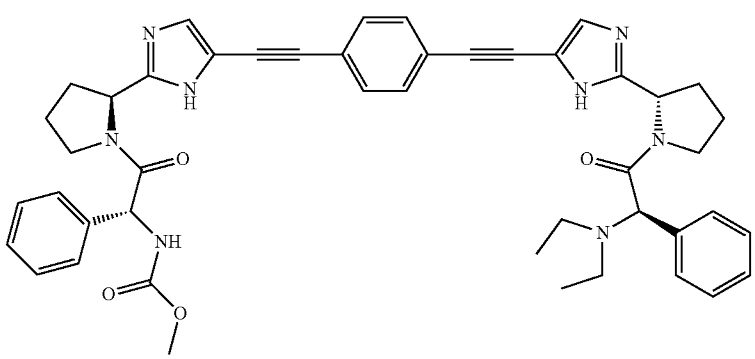 [SMILES: CCN(CC)[C@@H](C(=O)N1CCC[C@H]1c1ncc(C#Cc2ccc(C#Cc3cnc([C@@H]4CCCN4C(=O)[C@H](NC(=O)OC)c4ccccc4)[nH]3)cc2)[nH]1)c1ccccc1] | **** | 777.4 |

TABLE 4

| Compound # | Structure | Inhibition of HCV genotype 1b | MS (M + H+) |
|---|---|---|---|
| 800 | 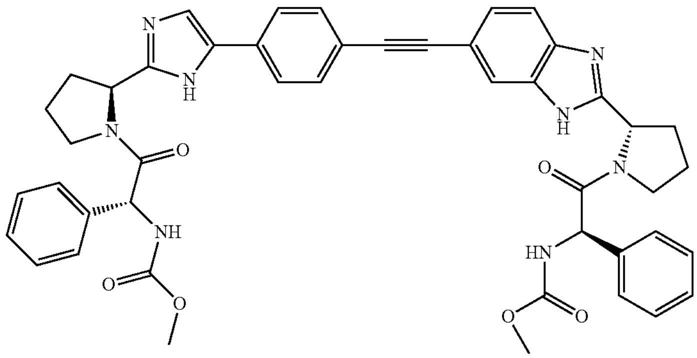 [SMILES: COC(=O)N[C@@H](C(=O)N1CCC[C@H]1c1ncc(-c2ccc(C#Cc3ccc4nc([C@@H]5CCCN5C(=O)[C@H](NC(=O)OC)c5ccccc5)[nH]c4c3)cc2)[nH]1)c1ccccc1] | **** | 805.3 |
| 801 | 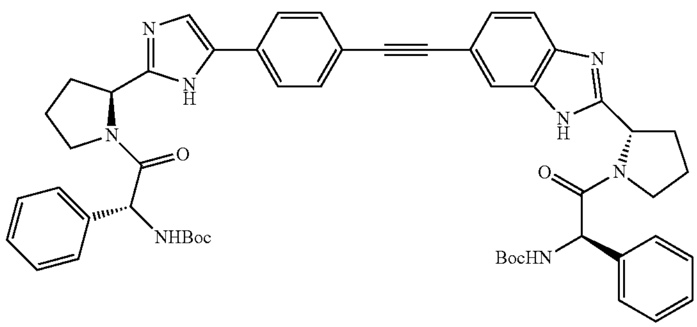 [SMILES: CC(C)(C)OC(=O)N[C@@H](C(=O)N1CCC[C@H]1c1ncc(-c2ccc(C#Cc3ccc4nc([C@@H]5CCCN5C(=O)[C@H](NC(=O)OC(C)(C)C)c5ccccc5)[nH]c4c3)cc2)[nH]1)c1ccccc1] | **** | 889.4 |
| 802 | 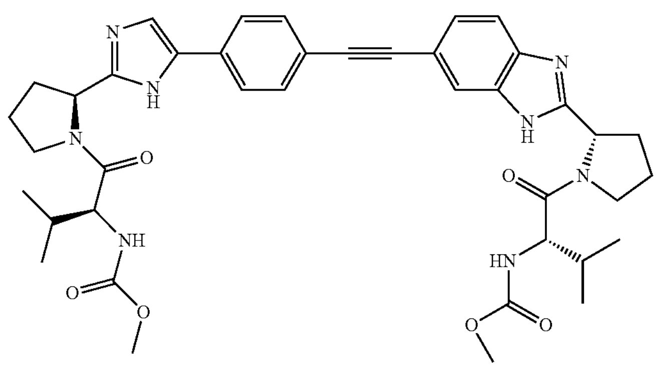 [SMILES: COC(=O)N[C@H](C(=O)N1CCC[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 737.4 |
| 860 | 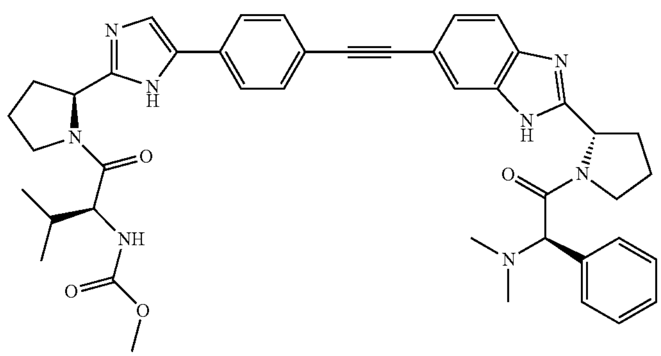 [SMILES: COC(=O)N[C@H](C(=O)N1CCC[C@H]1c1ncc(-c2ccc(C#Cc3ccc4nc([C@@H]5CCCN5C(=O)[C@@H](c5ccccc5)N(C)C)[nH]c4c3)cc2)[nH]1)C(C)C] | **** | 741.4 |

TABLE 4-continued

| Compound # | Structure | Inhibition of HCV genotype 1b | MS (M + H⁺) |
|---|---|---|---|
| 861 | 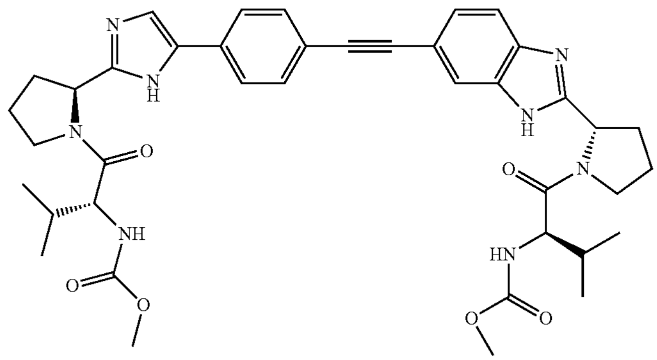 [SMILES: COC(=O)N[C@@H](C(=O)N1CCC[C@H]1c1ncc(-c2ccc(C#Cc3ccc4nc([C@@H]5CCCN5C(=O)[C@H](NC(=O)OC)C(C)C)[nH]c4c3)cc2)[nH]1)C(C)C] | ** | 737.4 |
| 862 | 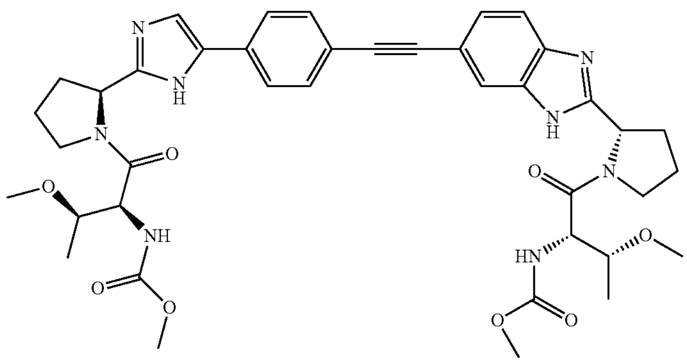 | **** | 769.4 |
| 863 | 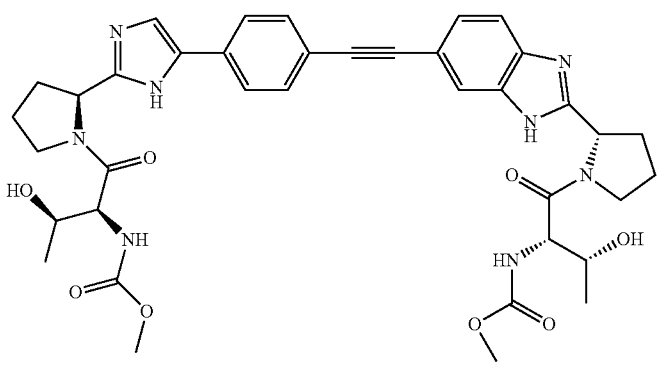 [SMILES: COC(=O)N[C@H](C(=O)N1CCC[C@H]1c1ncc(-c2ccc(C#Cc3ccc4nc([C@@H]5CCCN5C(=O)[C@@H](NC(=O)OC)[C@@H](C)O)[nH]c4c3)cc2)[nH]1)[C@@H](C)O] | **** | 741.3 |
| 864 | 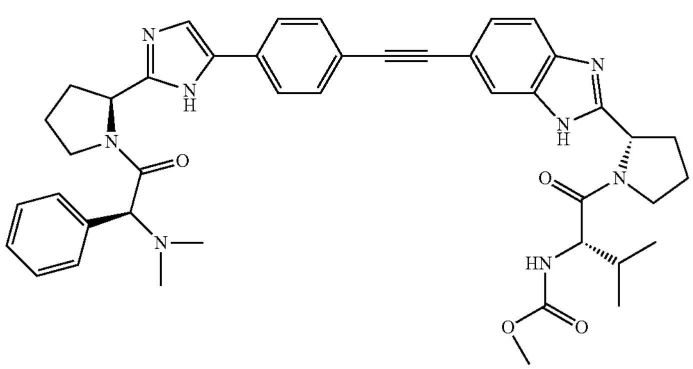 [SMILES: COC(=O)N[C@H](C(=O)N1CCC[C@H]1c1nc2ccc(C#Cc3ccc(-c4cnc([C@@H]5CCCN5C(=O)[C@H](c5ccccc5)N(C)C)[nH]4)cc3)cc2[nH]1)C(C)C] | **** | 741.3 |

TABLE 4-continued

| Compound # | Structure | Inhibition of HCV genotype 1b | MS (M + H+) |
|---|---|---|---|
| 865 | 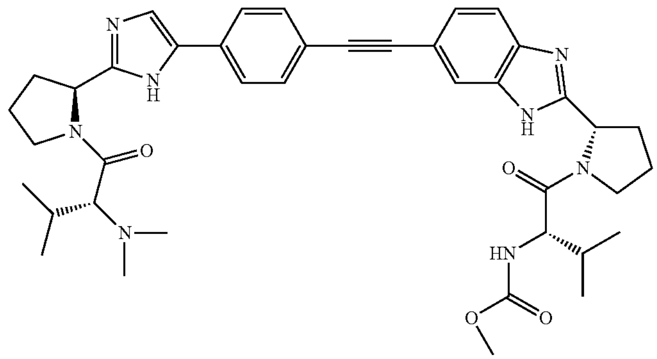 [SMILES: COC(=O)N[C@H](C(=O)N1CCC[C@H]1c1nc2ccc(C#Cc3ccc(-c4cnc([C@@H]5CCCN5C(=O)[C@@H](C(C)C)N(C)C)[nH]4)cc3)cc2[nH]1)C(C)C] | **** | 707.4 |
| 866 | 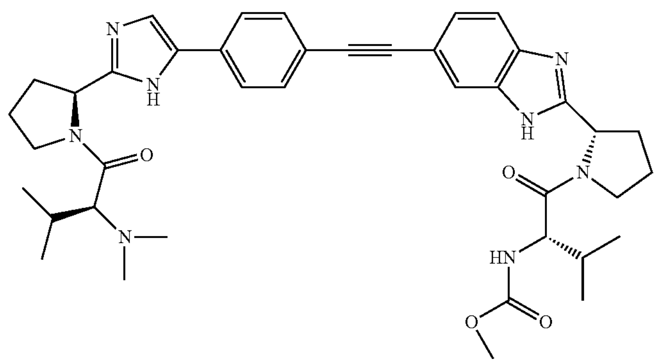 [SMILES: COC(=O)N[C@H](C(=O)N1CCC[C@H]1c1nc2ccc(C#Cc3ccc(-c4cnc([C@@H]5CCCN5C(=O)[C@H](C(C)C)N(C)C)[nH]4)cc3)cc2[nH]1)C(C)C] | **** | 707.4 |
| 867 | 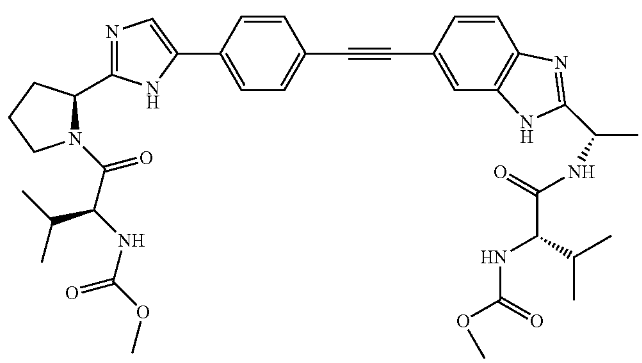 [SMILES: COC(=O)N[C@H](C(=O)N[C@@H](C)c1nc2ccc(C#Cc3ccc(-c4cnc([C@@H]5CCCN5C(=O)[C@@H](NC(=O)OC)C(C)C)[nH]4)cc3)cc2[nH]1)C(C)C] | **** | 711.4 |
| 868 | 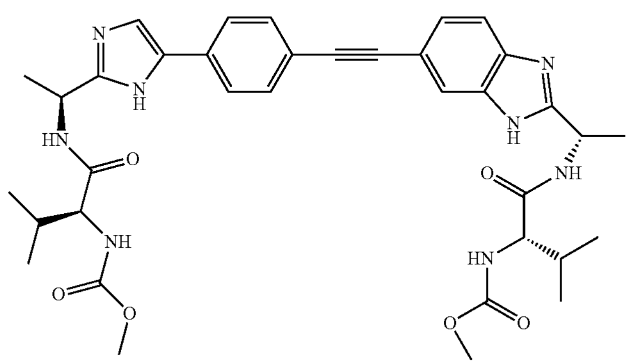 [SMILES: COC(=O)N[C@H](C(=O)N[C@@H](C)c1ncc(-c2ccc(C#Cc3ccc4nc([C@H](C)NC(=O)[C@@H](NC(=O)OC)C(C)C)[nH]c4c3)cc2)[nH]1)C(C)C] | **** | 685.3 |

TABLE 4-continued

| Compound # | Structure | Inhibition of HCV genotype 1b | MS (M + H+) |
|---|---|---|---|
| 869 | 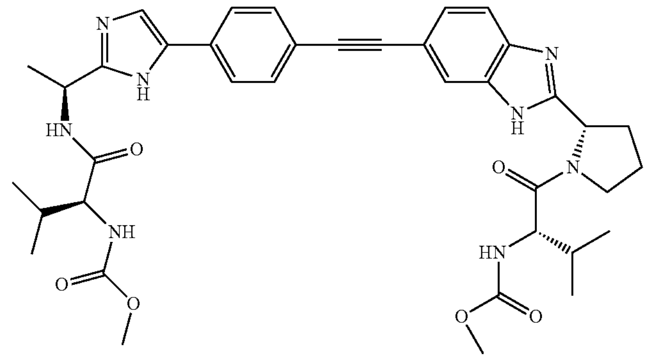 [SMILES: COC(=O)N[C@H](C(=O)N[C@@H](C)c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 711.4 |
| 1020 | 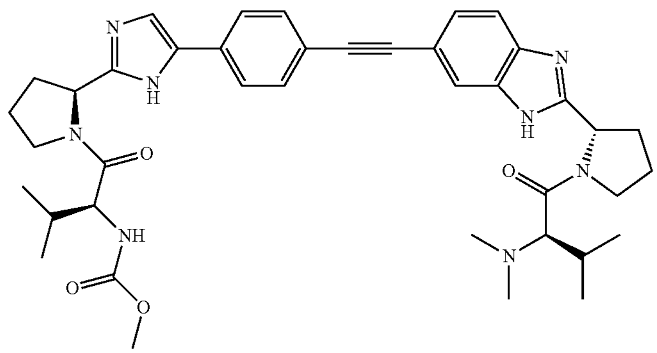 [SMILES: COC(=O)N[C@H](C(=O)N1CCC[C@H]1c1ncc(-c2ccc(C#Cc3ccc4nc([C@@H]5CCCN5C(=O)[C@@H](C(C)C)N(C)C)[nH]c4c3)cc2)[nH]1)C(C)C] | **** | 707.4 |
| 1021 | 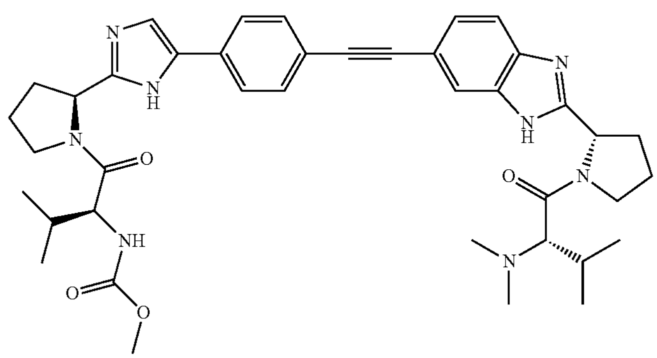 [SMILES: COC(=O)N[C@H](C(=O)N1CCC[C@H]1c1ncc(-c2ccc(C#Cc3ccc4nc([C@@H]5CCCN5C(=O)[C@H](C(C)C)N(C)C)[nH]c4c3)cc2)[nH]1)C(C)C] | **** | 707.4 |
| 1022 | 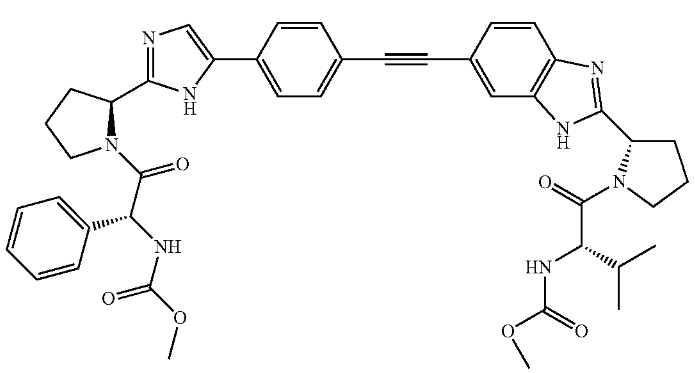 [SMILES: COC(=O)N[C@H](C(=O)N1CCC[C@H]1c1nc2ccc(C#Cc3ccc(-c4cnc([C@@H]5CCCN5C(=O)[C@H](NC(=O)OC)c5ccccc5)[nH]4)cc3)cc2[nH]1)C(C)C] | **** | 771.4 |

TABLE 4-continued

| Compound # | Structure | Inhibition of HCV genotype 1b | MS (M + H⁺) |
|---|---|---|---|
| 1023 | 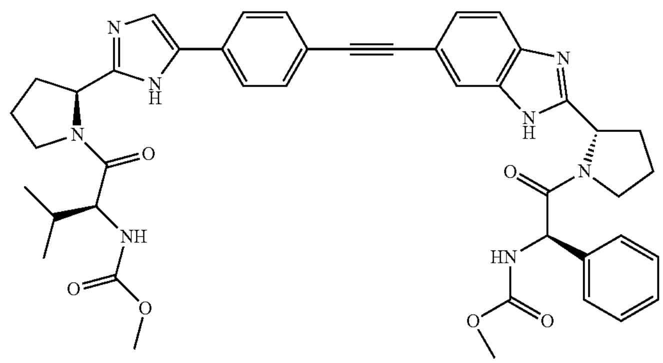 [SMILES: COC(=O)N[C@H](C(=O)N1CCC[C@H]1c1ncc(-c2ccc(C#Cc3ccc4nc([C@@H]5CCCN5C(=O)[C@H](NC(=O)OC)c5ccccc5)[nH]c4c3)cc2)[nH]1)C(C)C] | **** | 771.4 |
| 1024 | 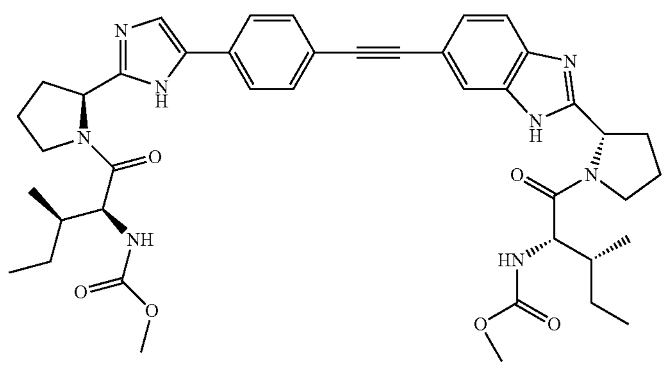 [SMILES: CC[C@@H](C)[C@H](NC(=O)OC)C(=O)N1CCC[C@H]1c1ncc(-c2ccc(C#Cc3ccc4nc([C@@H]5CCCN5C(=O)[C@@H](NC(=O)OC)[C@H](C)CC)[nH]c4c3)cc2)[nH]1] | **** | 765.4 |
| 1025 | 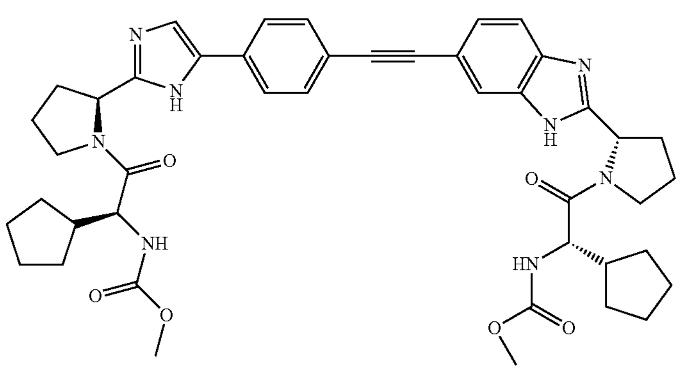 [SMILES: COC(=O)N[C@H](C(=O)N1CCC[C@H]1c1ncc(-c2ccc(C#Cc3ccc4nc([C@@H]5CCCN5C(=O)[C@@H](NC(=O)OC)C5CCCC5)[nH]c4c3)cc2)[nH]1)C1CCCC1] | **** | 789.4 |
| 1026 | 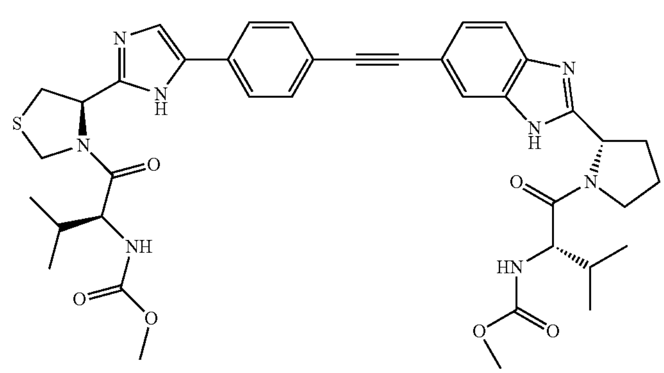 [SMILES: COC(=O)N[C@H](C(=O)N1CSC[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 755.3 |

TABLE 4-continued
| Compound # | Structure | Inhibition of HCV genotype 1b | MS (M + H+) |
|---|---|---|---|
| 1027 | 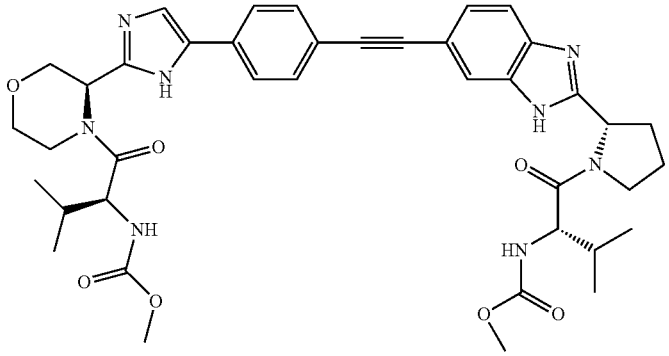 [SMILES: COC(=O)N[C@H](C(=O)N1CCOC[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 753.4 |
| 1028 | 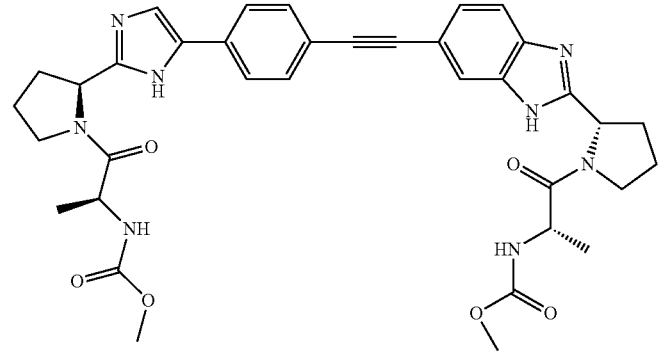 [SMILES: COC(=O)N[C@@H](C)C(=O)N1CCC[C@H]1c1ncc(-c2ccc(C#Cc3ccc4nc([C@@H]5CCCN5C(=O)[C@H](C)NC(=O)OC)[nH]c4c3)cc2)[nH]1] | **** | 681.3 |
| 1029 | 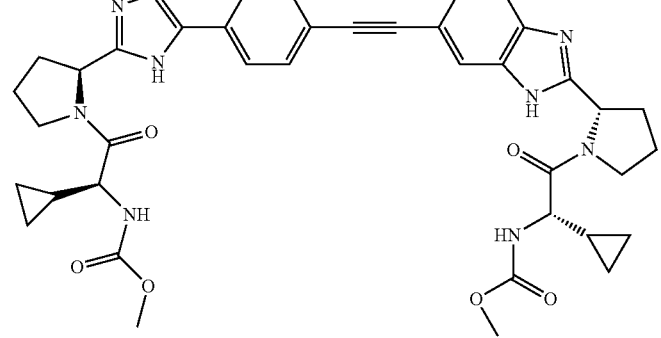 | **** | 733.3 |
| 1030 | 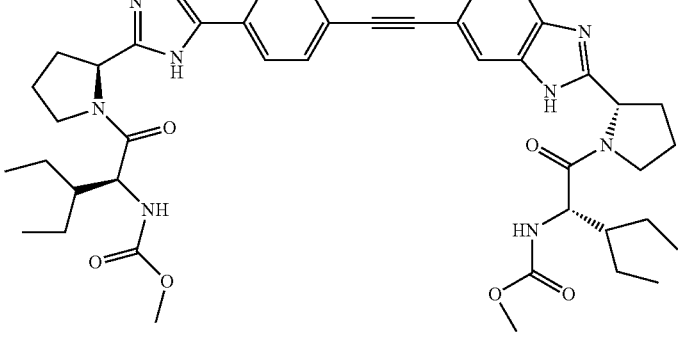 | **** | 793.4 |

TABLE 4-continued

| Compound # | Structure | Inhibition of HCV genotype 1b | MS (M + H+) |
|---|---|---|---|
| 1031 | 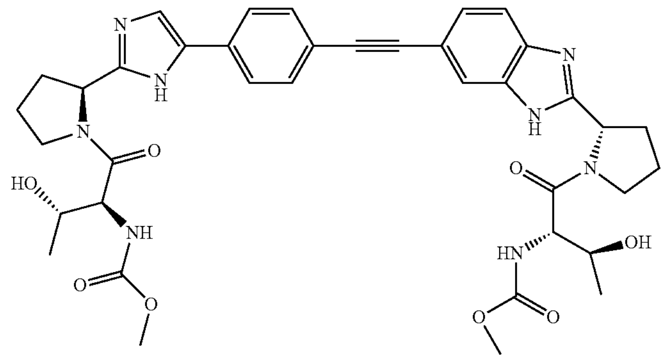 [SMILES: COC(=O)N[C@H](C(=O)N1CCC[C@H]1c1ncc(-c2ccc(C#Cc3ccc4nc([C@@H]5CCCN5C(=O)[C@@H](NC(=O)OC)[C@H](C)O)[nH]c4c3)cc2)[nH]1)[C@H](C)O] | **** | 741.3 |
| 1032 | 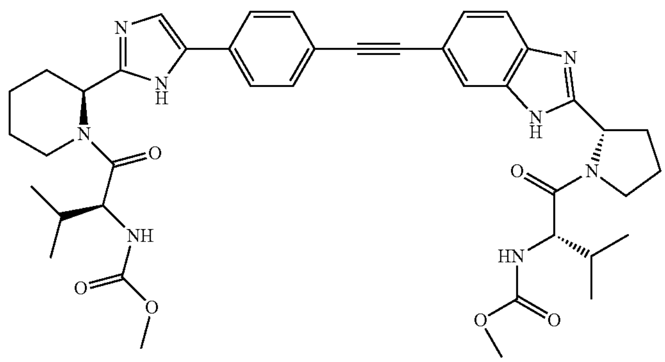 [SMILES: COC(=O)N[C@H](C(=O)N1CCCC[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 751.4 |
| 1033 | 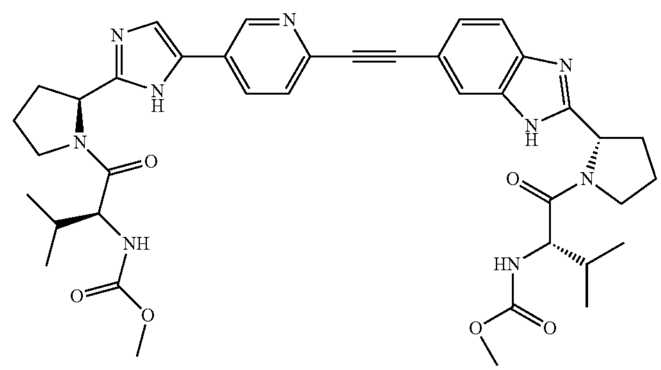 [SMILES: COC(=O)N[C@H](C(=O)N1CCC[C@H]1c1ncc(-c2ccc(C#Cc3ccc4nc([C@@H]5CCCN5C(=O)[C@@H](NC(=O)OC)C(C)C)[nH]c4c3)nc2)[nH]1)C(C)C] | **** | 738.4 |
| 1034 | 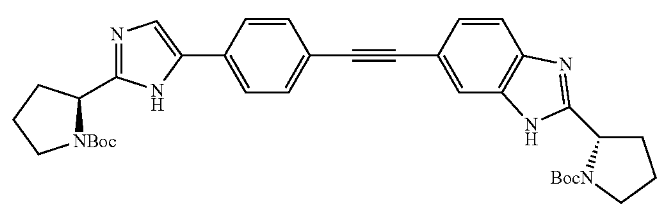 | *** | 623.3 |
| 1035 | 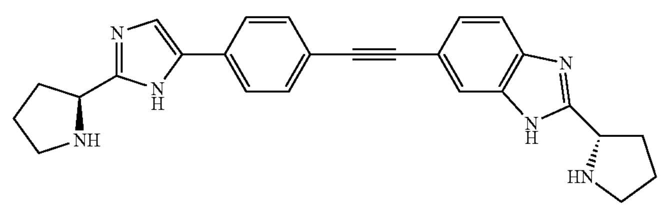 [SMILES: C(#Cc1ccc2nc([C@@H]3CCCN3)[nH]c2c1)c1ccc(-c2cnc([C@@H]3CCCN3)[nH]2)cc1] | ** | 423.3 |

TABLE 4-continued

| Compound # | Structure | Inhibition of HCV genotype 1b | MS (M + H+) |
|---|---|---|---|
| 1036 | 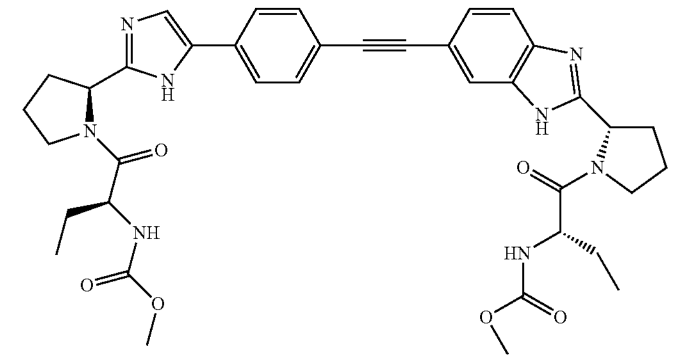 [SMILES: CC[C@H](NC(=O)OC)C(=O)N1CCC[C@H]1c1ncc(-c2ccc(C#Cc3ccc4nc([C@@H]5CCCN5C(=O)[C@H](CC)NC(=O)OC)[nH]c4c3)cc2)[nH]1] | **** | 709.3 |
| 1037 | 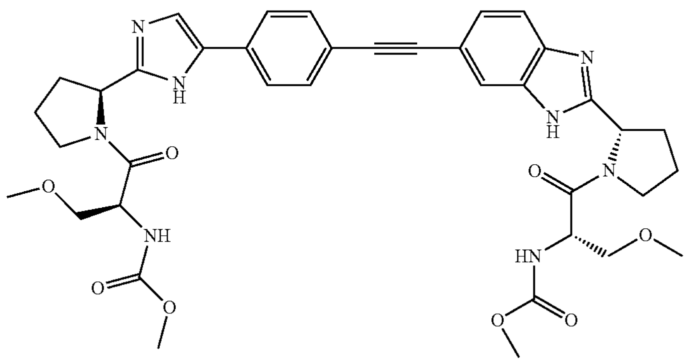 | **** | 741.3 |
| 1038 | 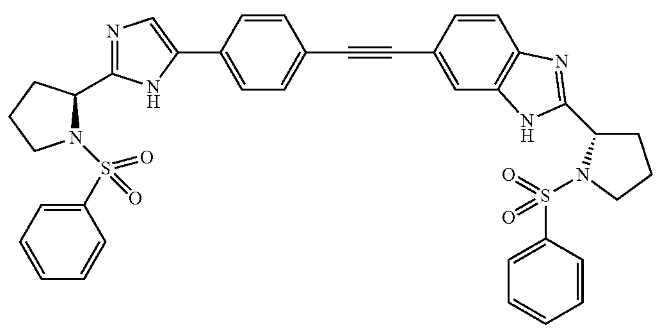 [SMILES: O=S(=O)(c1ccccc1)N1CCC[C@H]1c1ncc(-c2ccc(C#Cc3ccc4nc([C@@H]5CCCN5S(=O)(=O)c5ccccc5)[nH]c4c3)cc2)[nH]1] | * | 703.2 |
| 1039 | 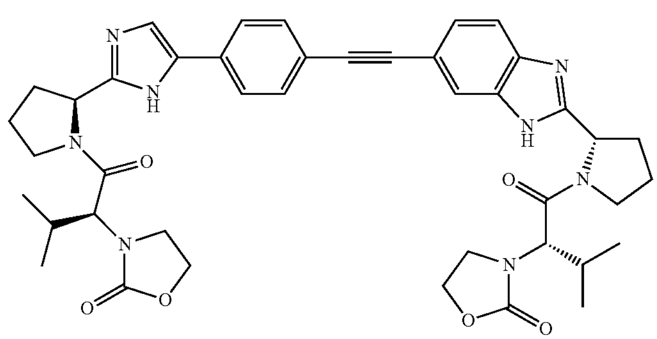 [SMILES: CC(C)[C@@H](C(=O)N1CCC[C@H]1c1ncc(-c2ccc(C#Cc3ccc4nc([C@@H]5CCCN5C(=O)[C@H](C(C)C)N5CCOC5=O)[nH]c4c3)cc2)[nH]1)N1CCOC1=O] | *** | 761.4 |

TABLE 4-continued

| Compound # | Structure | Inhibition of HCV genotype 1b | MS (M + H⁺) |
|---|---|---|---|
| 1040 | 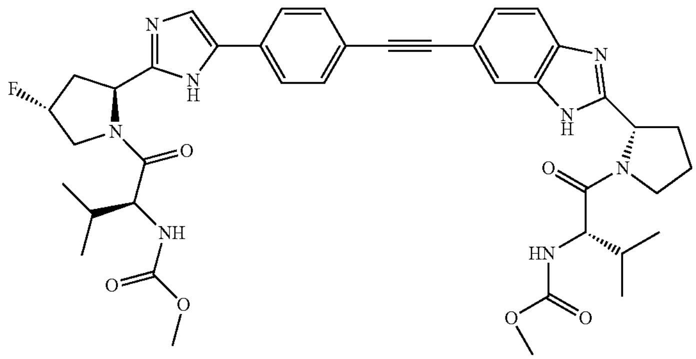 [SMILES: COC(=O)N[C@H](C(=O)N1C[C@H](F)C[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 755.4 |
| 1041 | 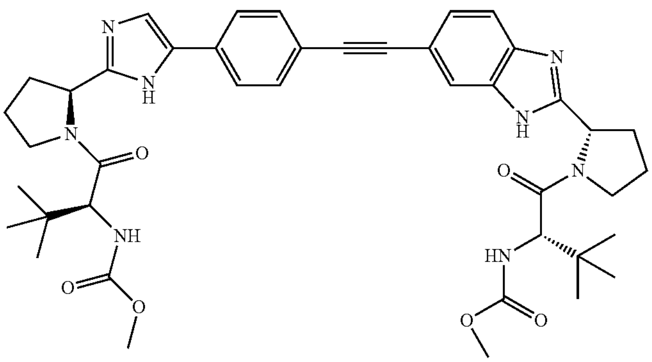 [SMILES: COC(=O)N[C@H](C(=O)N1CCC[C@H]1c1ncc(-c2ccc(C#Cc3ccc4nc([C@@H]5CCCN5C(=O)[C@@H](NC(=O)OC)C(C)(C)C)[nH]c4c3)cc2)[nH]1)C(C)(C)C] | **** | 765.4 |
| 1042 | 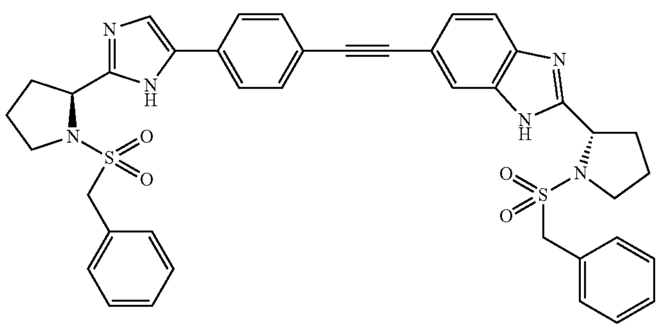 [SMILES: O=S(=O)(Cc1ccccc1)N1CCC[C@H]1c1ncc(-c2ccc(C#Cc3ccc4nc([C@@H]5CCCN5S(=O)(=O)Cc5ccccc5)[nH]c4c3)cc2)[nH]1] | * | 731.2 |
| 1043 | 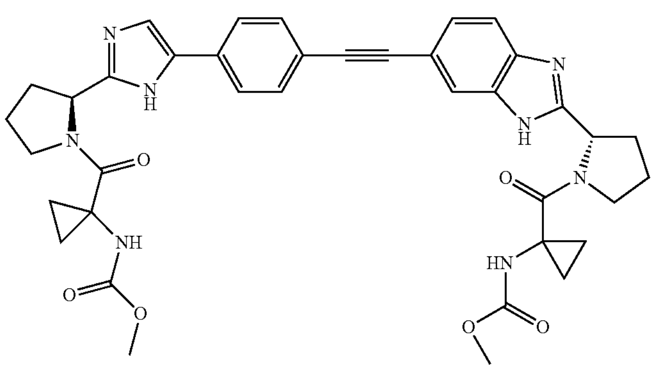 [SMILES: COC(=O)NC1(C(=O)N2CCC[C@H]2c2ncc(-c3ccc(C#Cc4ccc5nc([C@@H]6CCCN6C(=O)C6(NC(=O)OC)CC6)[nH]c5c4)cc3)[nH]2)CC1] | ** | 705.3 |

TABLE 4-continued

| Compound # | Structure | Inhibition of HCV genotype 1b | MS (M + H⁺) |
|---|---|---|---|
| 1044 | 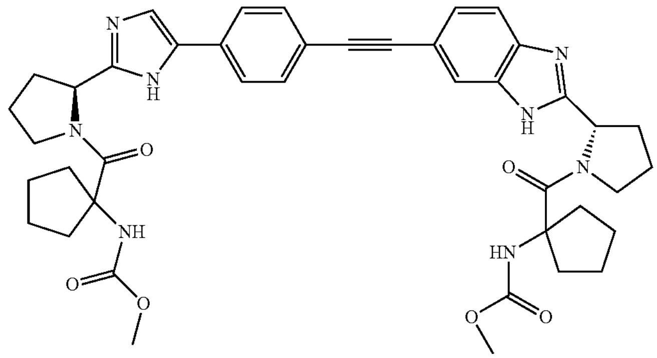 [SMILES: COC(=O)NC1(C(=O)N2CCC[C@H]2c2ncc(-c3ccc(C#Cc4ccc5nc([C@@H]6CCCN6C(=O)C6(NC(=O)OC)CCCC6)[nH]c5c4)cc3)[nH]2)CCCC1] | ** | 761.4 |
| 1045 | 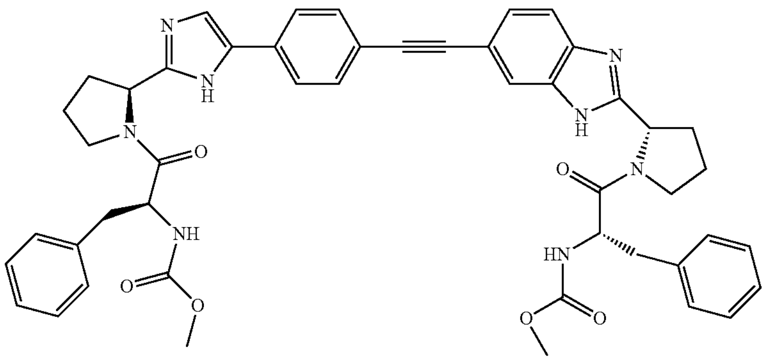 [SMILES: COC(=O)N[C@@H](Cc1ccccc1)C(=O)N1CCC[C@H]1c1ncc(-c2ccc(C#Cc3ccc4nc([C@@H]5CCCN5C(=O)[C@H](Cc5ccccc5)NC(=O)OC)[nH]c4c3)cc2)[nH]1] | **** | 833.4 |
| 1046 | 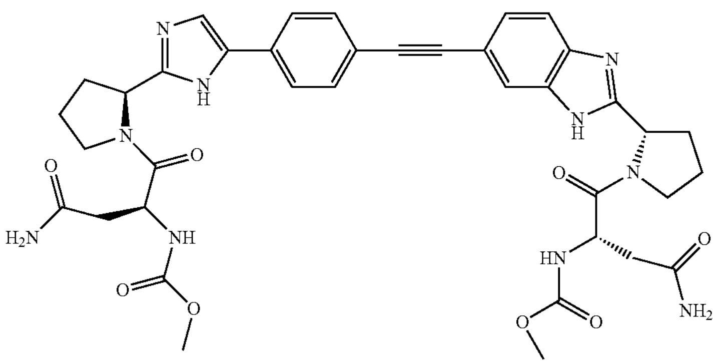 [SMILES: COC(=O)N[C@@H](CC(N)=O)C(=O)N1CCC[C@H]1c1ncc(-c2ccc(C#Cc3ccc4nc([C@@H]5CCCN5C(=O)[C@H](CC(N)=O)NC(=O)OC)[nH]c4c3)cc2)[nH]1] | *** | 767.3 |
| 1047 | 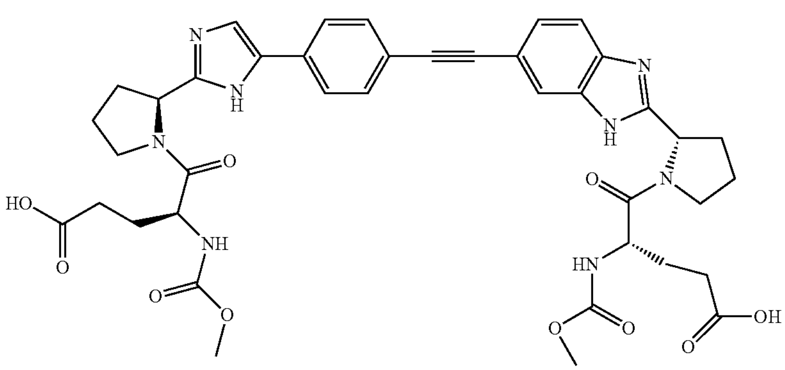 [SMILES: COC(=O)N[C@@H](CCC(=O)O)C(=O)N1CCC[C@H]1c1ncc(-c2ccc(C#Cc3ccc4nc([C@@H]5CCCN5C(=O)[C@H](CCC(=O)O)NC(=O)OC)[nH]c4c3)cc2)[nH]1] | ** | 797.3 |

TABLE 4-continued
| Compound # | Structure | Inhibition of HCV genotype 1b | MS (M + H+) |
|---|---|---|---|
| 1048 | 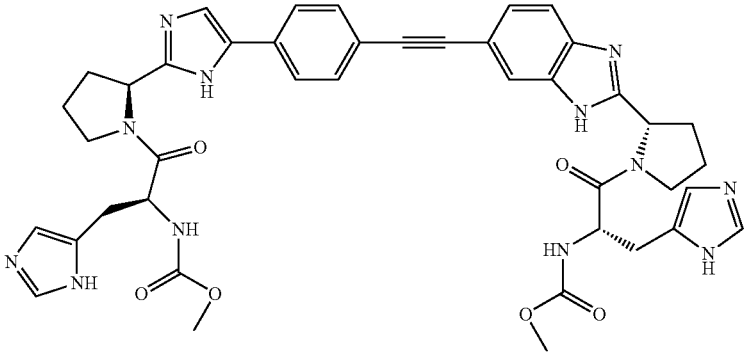 [SMILES: COC(=O)N[C@@H](Cc1cnc[nH]1)C(=O)N1CCC[C@H]1c1ncc(-c2ccc(C#Cc3ccc4nc([C@@H]5CCCN5C(=O)[C@H](Cc5cnc[nH]5)NC(=O)OC)[nH]c4c3)cc2)[nH]1] | *** | 813.4 |
| 1049 | 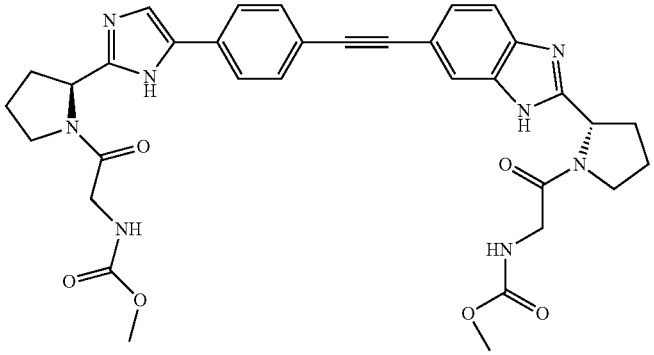 [SMILES: COC(=O)NCC(=O)N1CCC[C@H]1c1ncc(-c2ccc(C#Cc3ccc4nc([C@@H]5CCCN5C(=O)CNC(=O)OC)[nH]c4c3)cc2)[nH]1] | ** | 653.3 |
| 1050 | 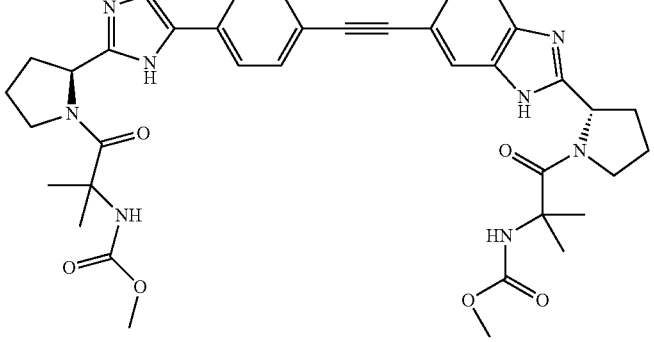 | ** | 709.3 |
| 1051 | 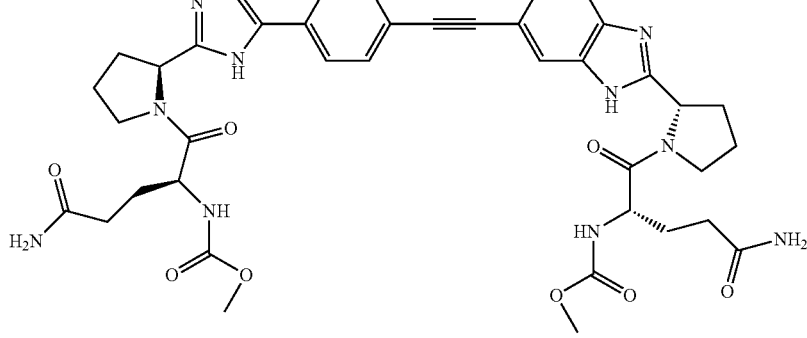 | *** | 795.3 |

TABLE 4-continued

| Compound # | Structure | Inhibition of HCV genotype 1b | MS (M + H⁺) |
|---|---|---|---|
| 1052 | 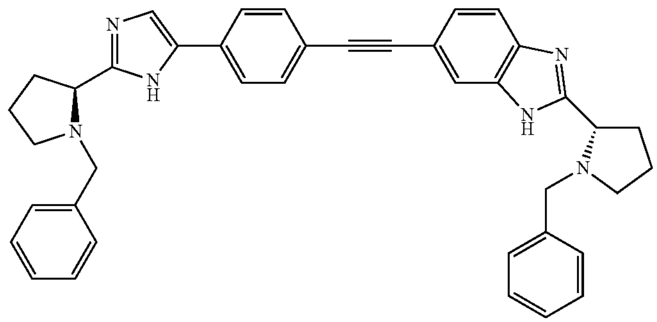 [SMILES: C(#Cc1ccc2nc([C@@H]3CCCN3Cc3ccccc3)[nH]c2c1)c1ccc(-c2cnc([C@@H]3CCCN3Cc3ccccc3)[nH]2)cc1] | * | 603.3 |
| 1053 | 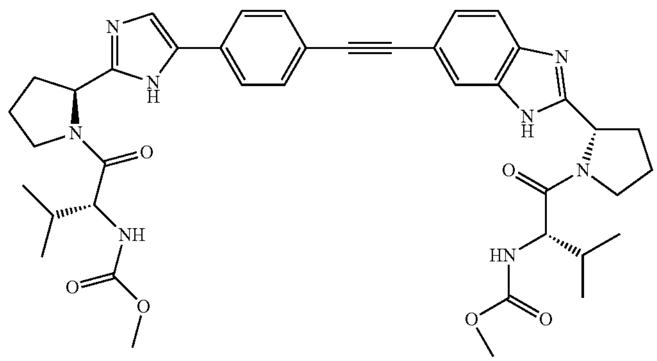 [SMILES: COC(=O)N[C@H](C(=O)N1CCC[C@H]1c1nc2ccc(C#Cc3ccc(-c4cnc([C@@H]5CCCN5C(=O)[C@H](NC(=O)OC)C(C)C)[nH]4)cc3)cc2[nH]1)C(C)C] | **** | 737.4 |
| 1054 | 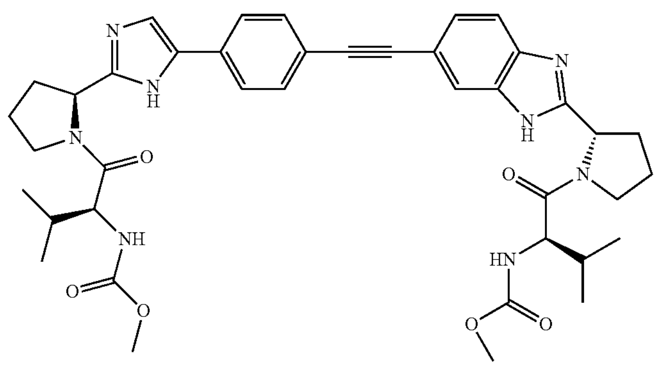 [SMILES: COC(=O)N[C@H](C(=O)N1CCC[C@H]1c1ncc(-c2ccc(C#Cc3ccc4nc([C@@H]5CCCN5C(=O)[C@H](NC(=O)OC)C(C)C)[nH]c4c3)cc2)[nH]1)C(C)C] | **** | 737.4 |
| 1055 | 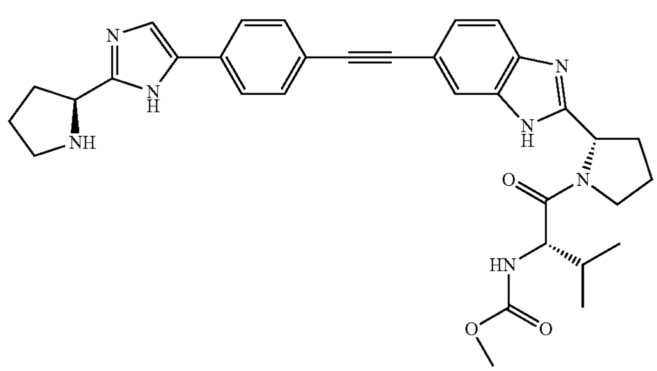 [SMILES: COC(=O)N[C@H](C(=O)N1CCC[C@H]1c1nc2ccc(C#Cc3ccc(-c4cnc([C@@H]5CCCN5)[nH]4)cc3)cc2[nH]1)C(C)C] | ** | 580.3 |

TABLE 4-continued

| Compound # | Structure | Inhibition of HCV genotype 1b | MS (M + H+) |
|---|---|---|---|
| 1056 | 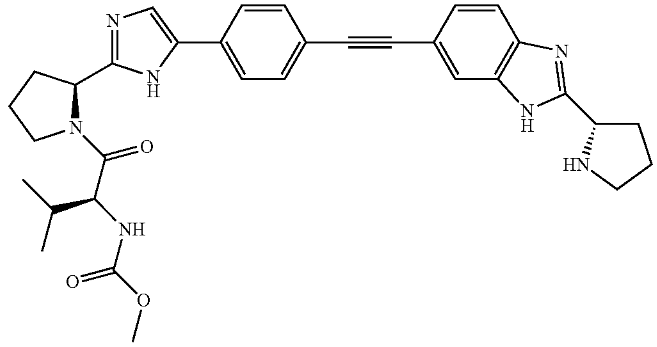 [SMILES: COC(=O)N[C@H](C(=O)N1CCC[C@H]1c1ncc(-c2ccc(C#Cc3ccc4nc([C@@H]5CCCN5)[nH]c4c3)cc2)[nH]1)C(C)C] | ** | 580.3 |
| 1057 | 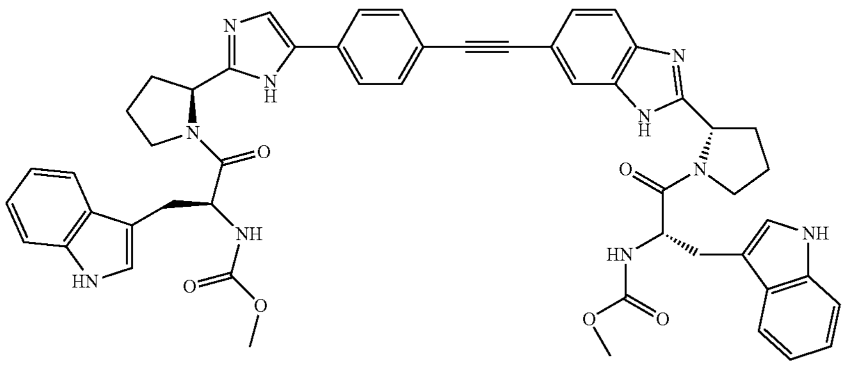 [SMILES: COC(=O)N[C@@H](Cc1c[nH]c2ccccc12)C(=O)N1CCC[C@H]1c1ncc(-c2ccc(C#Cc3ccc4nc([C@@H]5CCCN5C(=O)[C@H](Cc5c[nH]c6ccccc56)NC(=O)OC)[nH]c4c3)cc2)[nH]1] | **** | 911.4 |
| 1058 | 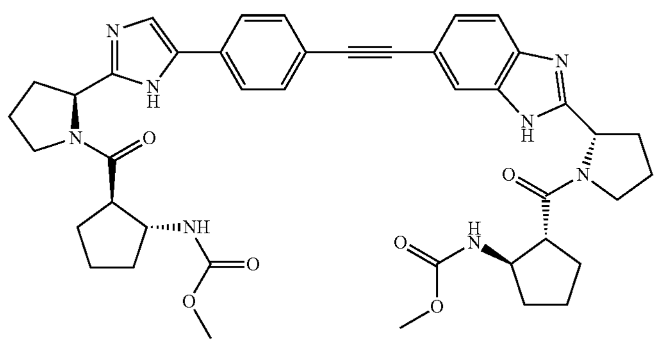 [SMILES: COC(=O)N[C@@H]1CCC[C@H]1C(=O)N1CCC[C@H]1c1ncc(-c2ccc(C#Cc3ccc4nc([C@@H]5CCCN5C(=O)[C@@H]5CCC[C@H]5NC(=O)OC)[nH]c4c3)cc2)[nH]1] | ** | 761.4 |
| 1059 | 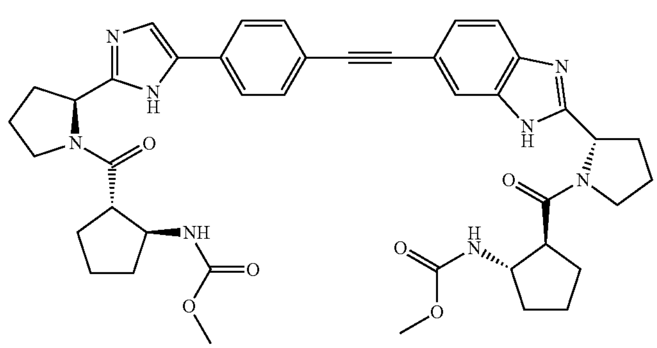 [SMILES: COC(=O)N[C@H]1CCC[C@@H]1C(=O)N1CCC[C@H]1c1ncc(-c2ccc(C#Cc3ccc4nc([C@@H]5CCCN5C(=O)[C@H]5CCC[C@@H]5NC(=O)OC)[nH]c4c3)cc2)[nH]1] | ** | 761.4 |

TABLE 4-continued

| Compound # | Structure | Inhibition of HCV genotype 1b | MS (M + H+) |
|---|---|---|---|
| 1060 | 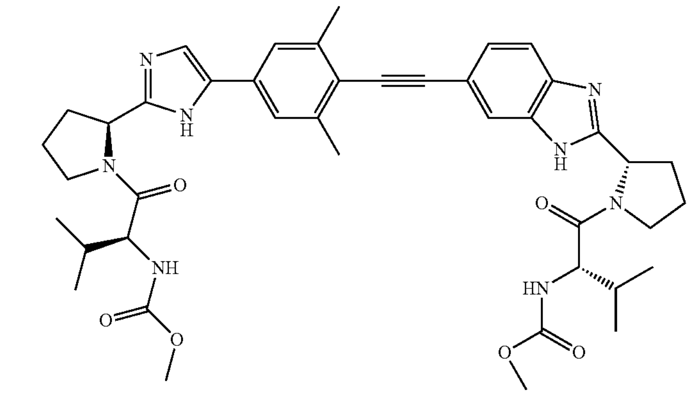 [SMILES: COC(=O)N[C@H](C(=O)N1CCC[C@H]1c1ncc(-c2cc(C)c(C#Cc3ccc4nc([C@@H]5CCCN5C(=O)[C@@H](NC(=O)OC)C(C)C)[nH]c4c3)c(C)c2)[nH]1)C(C)C] | **** | 765.4 |
| 1061 | 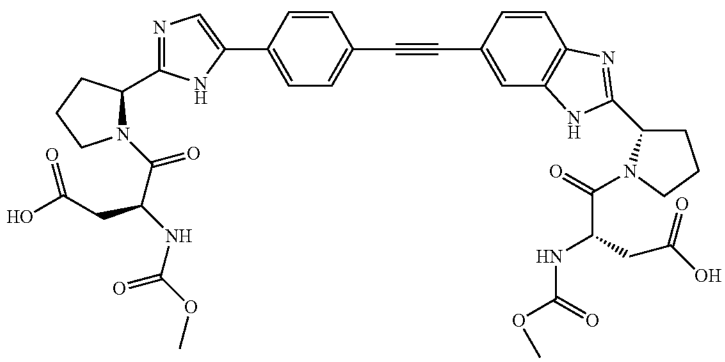 [SMILES: COC(=O)N[C@@H](CC(=O)O)C(=O)N1CCC[C@H]1c1ncc(-c2ccc(C#Cc3ccc4nc([C@@H]5CCCN5C(=O)[C@H](CC(=O)O)NC(=O)OC)[nH]c4c3)cc2)[nH]1] | ** | 769.3 |
| 1062 | 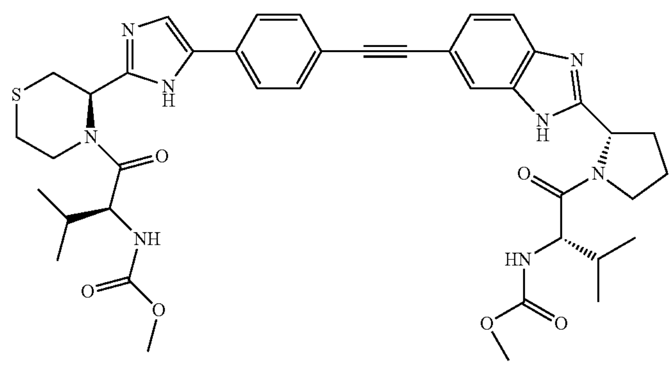 [SMILES: COC(=O)N[C@H](C(=O)N1CCSC[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 769.3 |
| 1063 | 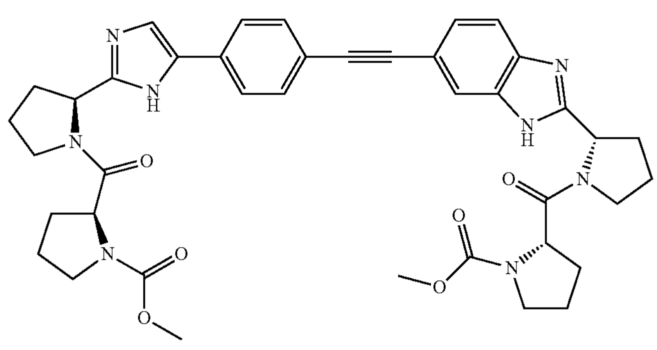 [SMILES: COC(=O)N1CCC[C@H]1C(=O)N1CCC[C@H]1c1ncc(-c2ccc(C#Cc3ccc4nc([C@@H]5CCCN5C(=O)[C@@H]5CCCN5C(=O)OC)[nH]c4c3)cc2)[nH]1] | ** | 733.3 |

TABLE 4-continued
| Compound # | Structure | Inhibition of HCV genotype 1b | MS (M + H+) |
|---|---|---|---|
| 1064 | 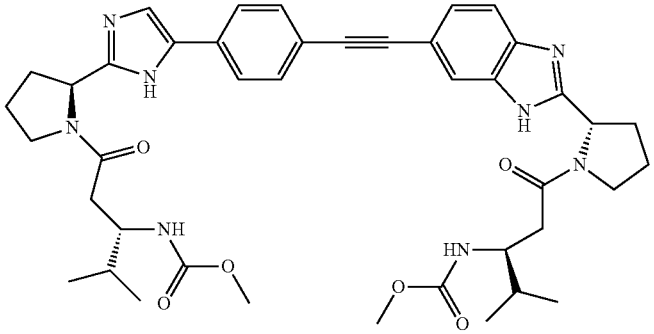 [SMILES: COC(=O)N[C@@H](CC(=O)N1CCC[C@H]1c1ncc(-c2ccc(C#Cc3ccc4nc([C@@H]5CCCN5C(=O)C[C@H](NC(=O)OC)C(C)C)[nH]c4c3)cc2)[nH]1)C(C)C] | ** | 765.4 |
| 1065 | 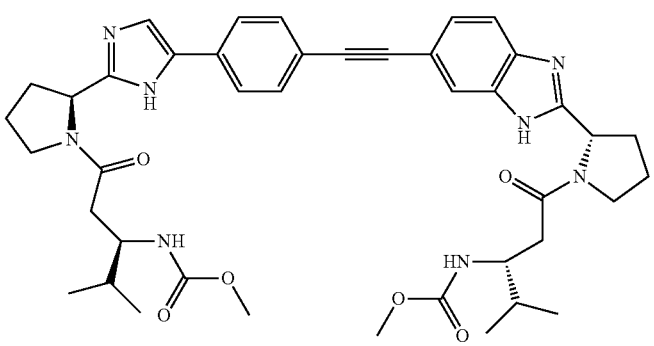 [SMILES: COC(=O)N[C@H](CC(=O)N1CCC[C@H]1c1ncc(-c2ccc(C#Cc3ccc4nc([C@@H]5CCCN5C(=O)C[C@@H](NC(=O)OC)C(C)C)[nH]c4c3)cc2)[nH]1)C(C)C] | ** | 765.4 |
| 1066 | 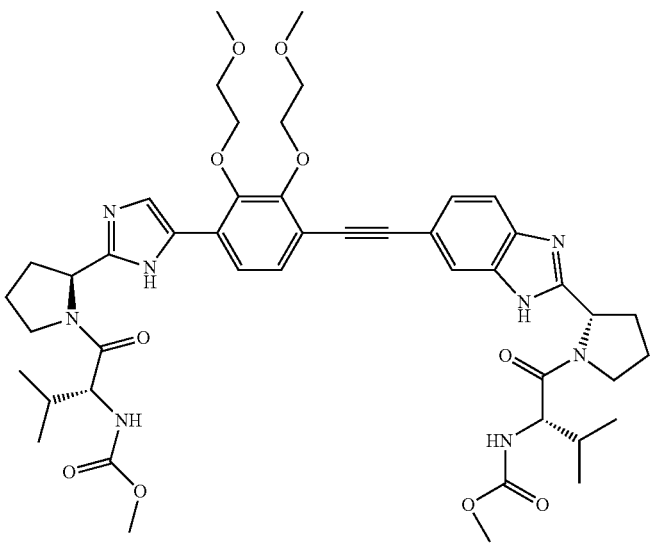 [SMILES: COCCOc1c(C#Cc2ccc3nc([C@@H]4CCCN4C(=O)[C@@H](NC(=O)OC)C(C)C)[nH]c3c2)ccc(-c2cnc([C@@H]3CCCN3C(=O)[C@H](NC(=O)OC)C(C)C)[nH]2)c1OCCOC] | **** | 885.4 |
| 1067 | 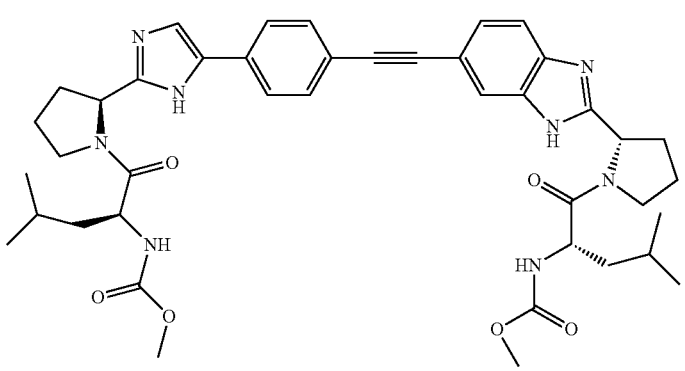 [SMILES: COC(=O)N[C@@H](CC(C)C)C(=O)N1CCC[C@H]1c1ncc(-c2ccc(C#Cc3ccc4nc([C@@H]5CCCN5C(=O)[C@H](CC(C)C)NC(=O)OC)[nH]c4c3)cc2)[nH]1] | **** | 765.4 |

TABLE 4-continued

| Compound # | Structure | Inhibition of HCV genotype 1b | MS (M + H+) |
|---|---|---|---|
| 1068 | 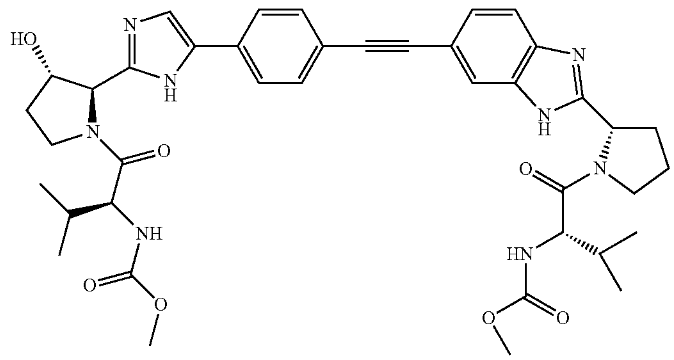 [SMILES: COC(=O)N[C@H](C(=O)N1CC[C@H](O)[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 753.4 |
| 1069 | 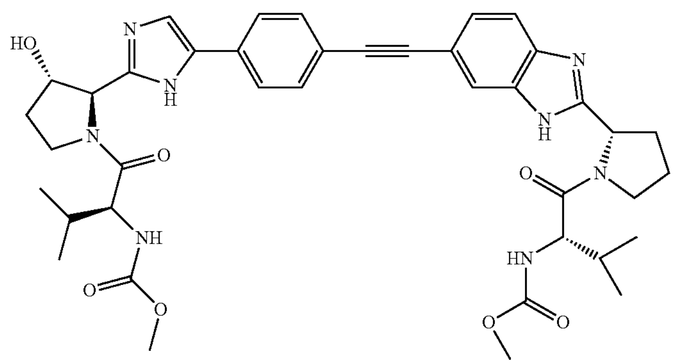 [SMILES: COC(=O)N[C@H](C(=O)N1CC[C@H](O)[C@H]1c1ncc(-c2ccc(C#Cc3ccc4nc([C@@H]5CCCN5C(=O)[C@@H](NC(=O)OC)C(C)C)[nH]c4c3)cc2)[nH]1)C(C)C] | **** | 755.4 |
| 1070 | 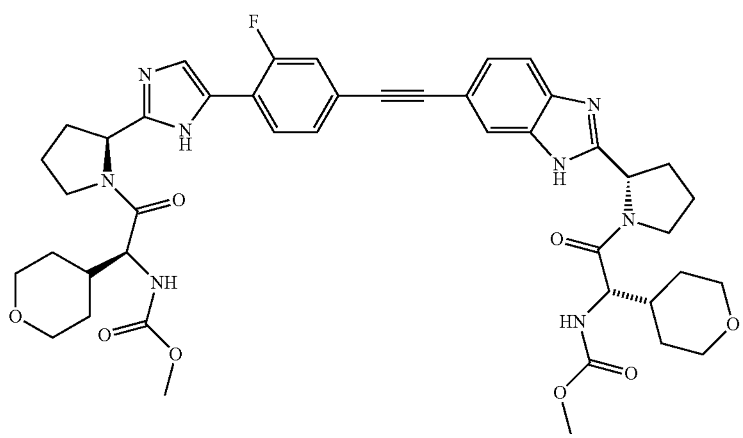 [SMILES: COC(=O)N[C@H](C(=O)N1CCC[C@H]1c1ncc(-c2ccc(C#Cc3ccc4nc([C@@H]5CCCN5C(=O)[C@@H](NC(=O)OC)C5CCOCC5)[nH]c4c3)cc2F)[nH]1)C1CCOCC1] | **** | 839.4 |
| 1071 | 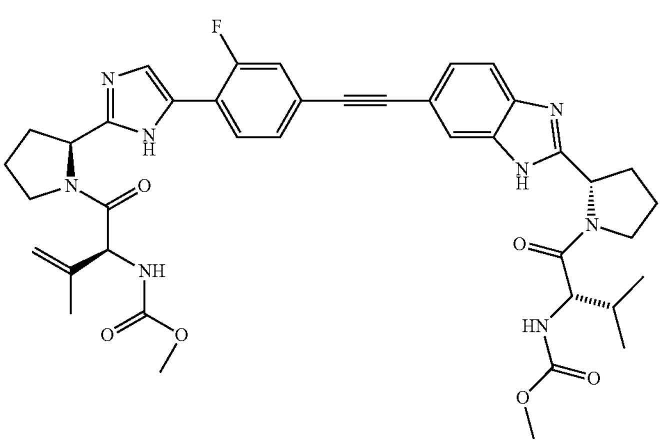 [SMILES: C=C(C)[C@H](NC(=O)OC)C(=O)N1CCC[C@H]1c1ncc(-c2ccc(C#Cc3ccc4nc([C@@H]5CCCN5C(=O)[C@@H](NC(=O)OC)C(C)C)[nH]c4c3)cc2F)[nH]1] | | |

| Compound # | Structure | Inhibition of HCV genotype 1b | MS (M + H+) |
|---|---|---|---|
| 1072 | 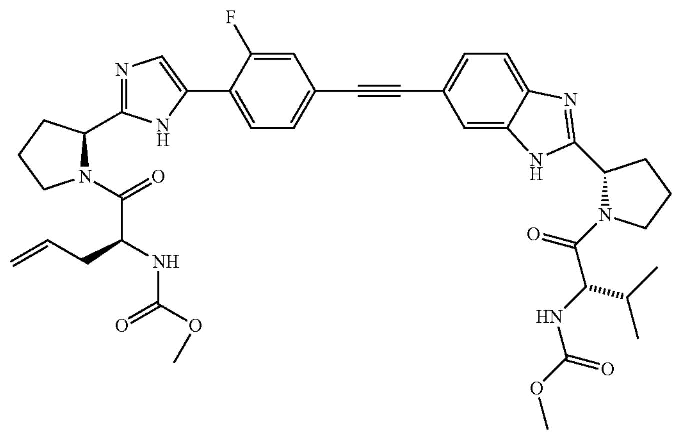 [SMILES: C=CC[C@H](NC(=O)OC)C(=O)N1CCC[C@H]1c1ncc(-c2ccc(C#Cc3ccc4nc([C@@H]5CCCN5C(=O)[C@@H](NC(=O)OC)C(C)C)[nH]c4c3)cc2F)[nH]1] | | |
| 1073 | 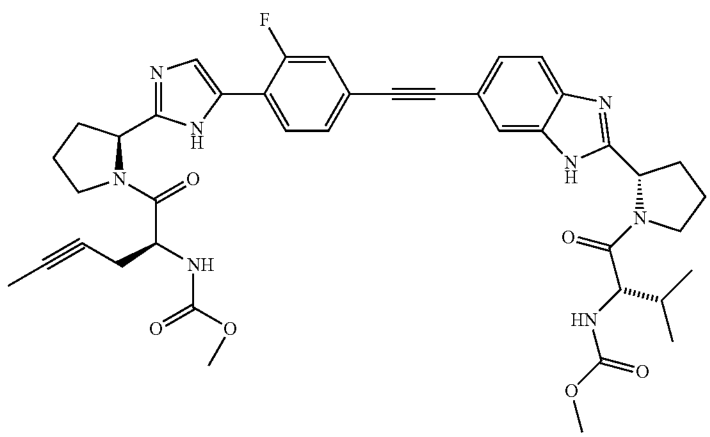 [SMILES: CC#CC[C@H](NC(=O)OC)C(=O)N1CCC[C@H]1c1ncc(-c2ccc(C#Cc3ccc4nc([C@@H]5CCCN5C(=O)[C@@H](NC(=O)OC)C(C)C)[nH]c4c3)cc2F)[nH]1] | | |
| 1074 | 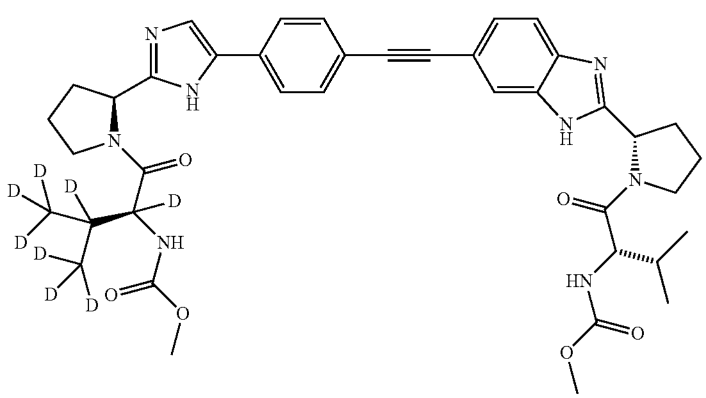 [SMILES: [2H]C([2H])([2H])C([2H])(C([2H])([2H])[2H])[C@@]([2H])(NC(=O)OC)C(=O)N1CCC[C@H]1c1ncc(-c2ccc(C#Cc3ccc4nc([C@@H]5CCCN5C(=O)[C@@H](NC(=O)OC)C(C)C)[nH]c4c3)cc2)[nH]1] | | |

TABLE 4-continued

| Compound # | Structure | Inhibition of HCV genotype 1b | MS (M + H+) |
|---|---|---|---|
| 1075 | 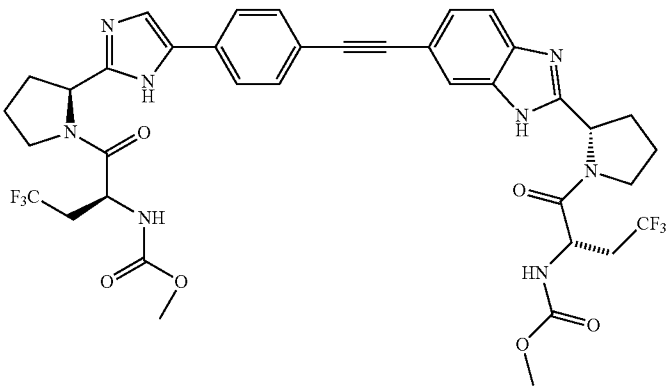 [SMILES: COC(=O)N[C@@H](CC(F)(F)F)C(=O)N1CCC[C@H]1c1ncc(-c2ccc(C#Cc3ccc4nc([C@@H]5CCCN5C(=O)[C@H](CC(F)(F)F)NC(=O)OC)[nH]c4c3)cc2)[nH]1] | | |

TABLE 5

| Compound # | Structure | Inhibition of HCV genotype 1b | MS (M + H+) |
|---|---|---|---|
| 803 | | **** | 737.4 |
| 803 | | **** | 889.4 |

TABLE 5-continued

| Compound # | Structure | Inhibition of HCV genotype 1b | MS (M + H⁺) |
|---|---|---|---|
| 804 | 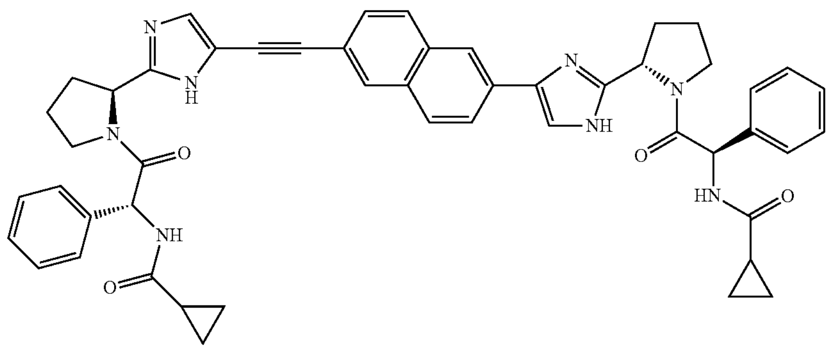 [SMILES: O=C(N[C@@H](C(=O)N1CCC[C@H]1c1nc(-c2ccc3cc(C#Cc4cnc([C@@H]5CCCN5C(=O)[C@H](NC(=O)C5CC5)c5ccccc5)[nH]4)ccc3c2)c[nH]1)c1ccccc1)C1CC1] | **** | 825.4 |
| 805 | 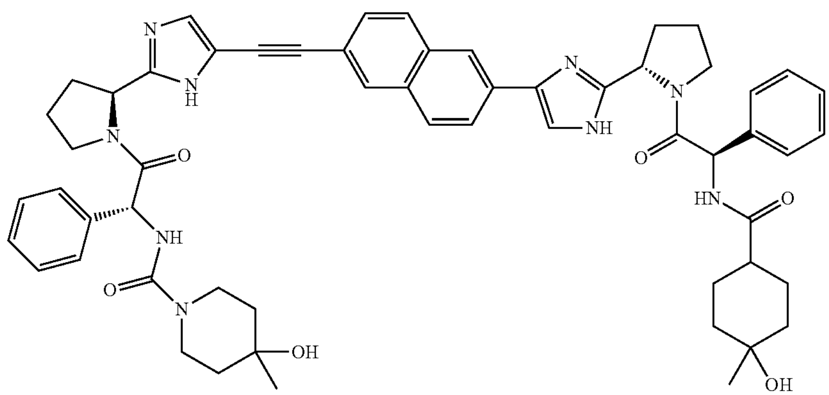 [SMILES: CC1(O)CCC(C(=O)N[C@@H](C(=O)N2CCC[C@H]2c2nc(-c3ccc4cc(C#Cc5cnc([C@@H]6CCCN6C(=O)[C@H](NC(=O)N6CCC(C)(O)CC6)c6ccccc6)[nH]5)ccc4c3)c[nH]2)c2ccccc2)CC1] | **** | 971.5 |
| 806 | 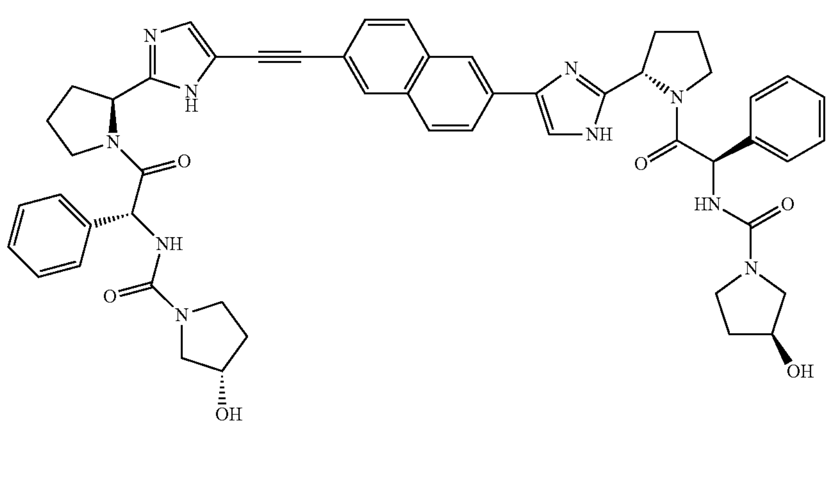 [SMILES: O=C(N[C@@H](C(=O)N1CCC[C@H]1c1nc(-c2ccc3cc(C#Cc4cnc([C@@H]5CCCN5C(=O)[C@H](NC(=O)N5CC[C@H](O)C5)c5ccccc5)[nH]4)ccc3c2)c[nH]1)c1ccccc1)N1CC[C@H](O)C1] | *** | 915.4 |

TABLE 5-continued

| Compound # | Structure | Inhibition of HCV genotype 1b | MS (M + H+) |
|---|---|---|---|
| 807 | 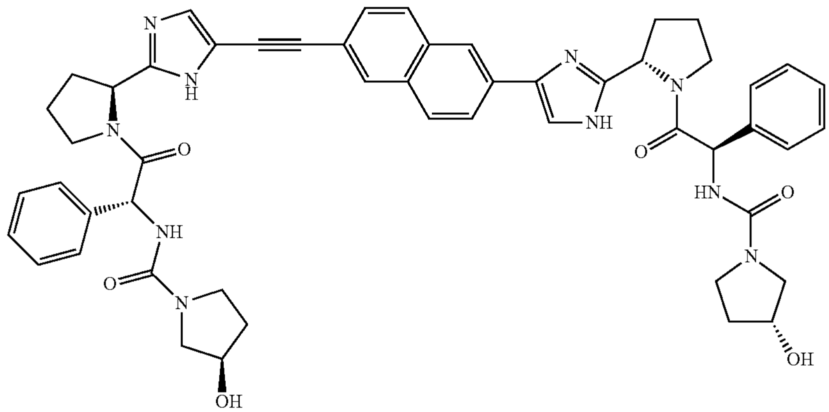 [SMILES: O=C(N[C@@H](C(=O)N1CCC[C@H]1c1nc(-c2ccc3cc(C#Cc4cnc([C@@H]5CCCN5C(=O)[C@H](NC(=O)N5CC[C@@H](O)C5)c5ccccc5)[nH]4)ccc3c2)c[nH]1)c1ccccc1)N1CC[C@@H](O)C1] | *** | 915.4 |
| 808 | 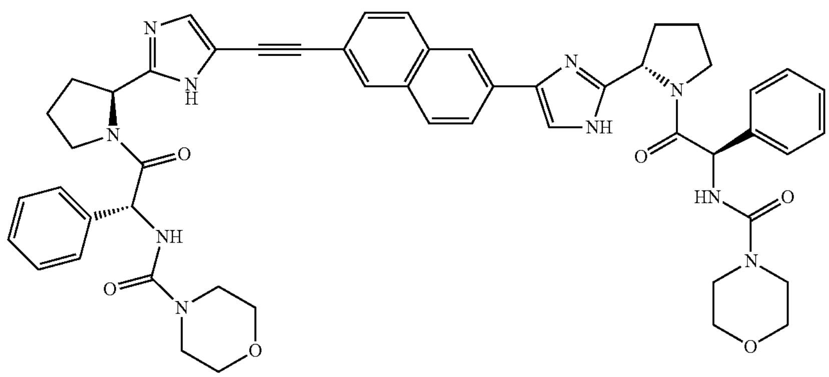 [SMILES: O=C(N[C@@H](C(=O)N1CCC[C@H]1c1nc(-c2ccc3cc(C#Cc4cnc([C@@H]5CCCN5C(=O)[C@H](NC(=O)N5CCOCC5)c5ccccc5)[nH]4)ccc3c2)c[nH]1)c1ccccc1)N1CCOCC1] | **** | 915.4 |
| 1076 | 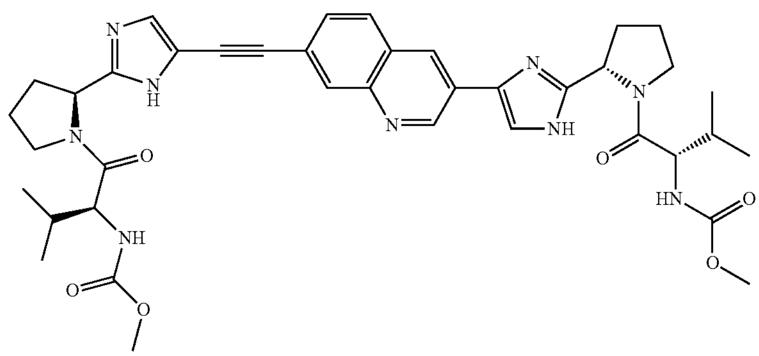 [SMILES: COC(=O)N[C@H](C(=O)N1CCC[C@H]1c1nc(-c2cnc3cc(C#Cc4cnc([C@@H]5CCCN5C(=O)[C@@H](NC(=O)OC)C(C)C)[nH]4)ccc3c2)c[nH]1)C(C)C] | **** | 738.4 |
| 1077 | 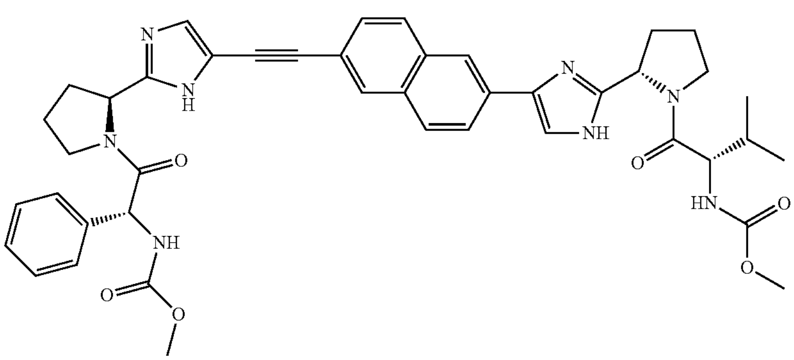 [SMILES: COC(=O)N[C@H](C(=O)N1CCC[C@H]1c1nc(-c2ccc3cc(C#Cc4cnc([C@@H]5CCCN5C(=O)[C@H](NC(=O)OC)c5ccccc5)[nH]4)ccc3c2)c[nH]1)C(C)C] | **** | 771.4 |

TABLE 5-continued

| Compound # | Structure | Inhibition of HCV genotype 1b | MS (M + H+) |
|---|---|---|---|
| 1078 | 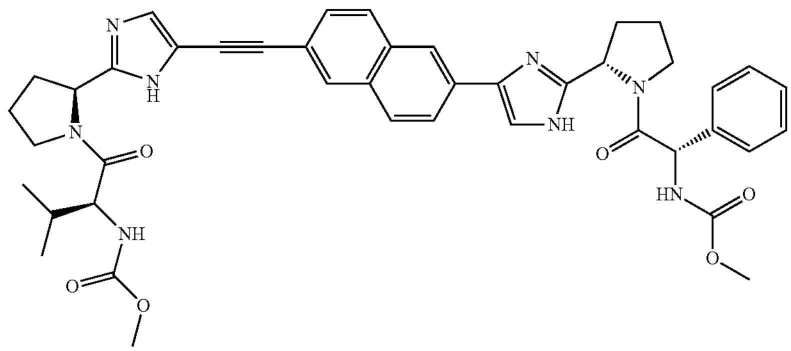 [SMILES: COC(=O)N[C@H](C(=O)N1CCC[C@H]1c1nc(-c2ccc3cc(C#Cc4cnc([C@@H]5CCCN5C(=O)[C@@H](NC(=O)OC)C(C)C)[nH]4)ccc3c2)c[nH]1)c1ccccc1] | **** | 771.4 |
| 1079 | 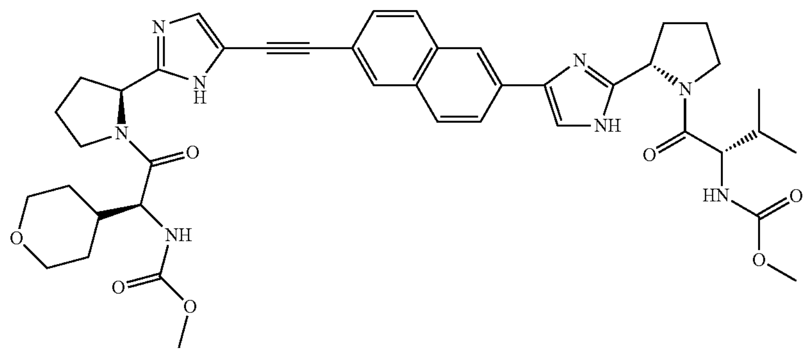 [SMILES: COC(=O)N[C@H](C(=O)N1CCC[C@H]1c1nc(-c2ccc3cc(C#Cc4cnc([C@@H]5CCCN5C(=O)[C@@H](NC(=O)OC)C5CCOCC5)[nH]4)ccc3c2)c[nH]1)C(C)C] | **** | 779.4 |
| 1080 | 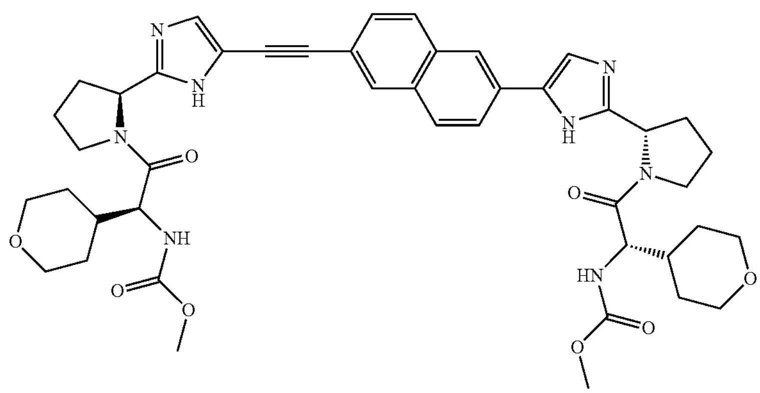 [SMILES: COC(=O)N[C@H](C(=O)N1CCC[C@H]1c1ncc(C#Cc2ccc3cc(-c4cnc([C@@H]5CCCN5C(=O)[C@@H](NC(=O)OC)C5CCOCC5)[nH]4)ccc3c2)[nH]1)C1CCOCC1] | | 821.4 |
| 1081 | 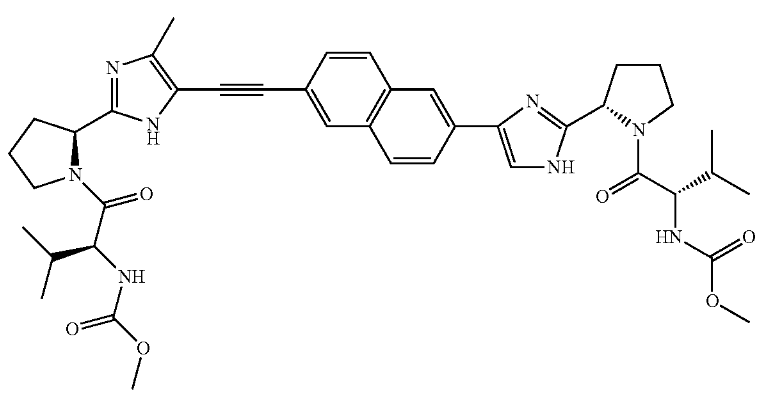 [SMILES: COC(=O)N[C@H](C(=O)N1CCC[C@H]1c1nc(-c2ccc3cc(C#Cc4[nH]c([C@@H]5CCCN5C(=O)[C@@H](NC(=O)OC)C(C)C)nc4C)ccc3c2)c[nH]1)C(C)C] | | |

TABLE 5-continued

| Compound # | Structure | Inhibition of HCV genotype 1b | MS (M + H+) |
|---|---|---|---|
| 1082 | 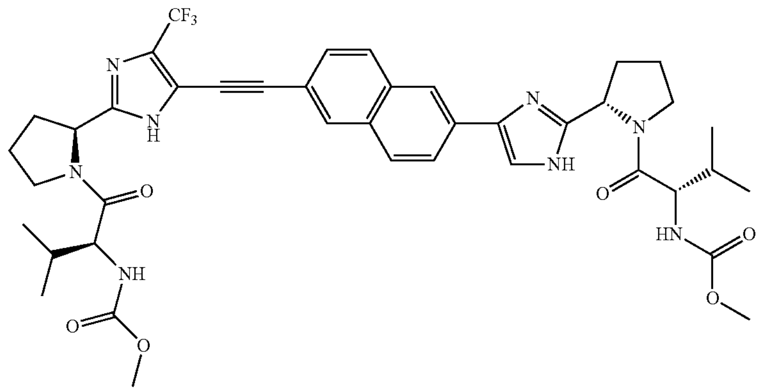 [SMILES: COC(=O)N[C@H](C(=O)N1CCC[C@H]1c1nc(-c2ccc3cc(C#Cc4[nH]c([C@@H]5CCCN5C(=O)[C@@H](NC(=O)OC)C(C)C)nc4C(F)(F)F)ccc3c2)c[nH]1)C(C)C] | | |

TABLE 6

| Compound # | Structure | Inhibition of HCV genotype 1b | MS (M + H+) |
|---|---|---|---|
| 851 | 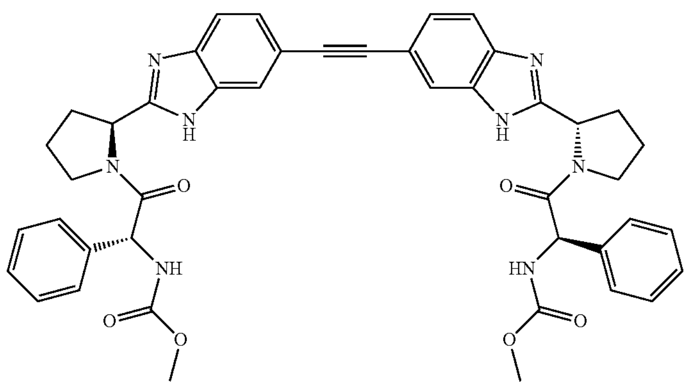 [SMILES: COC(=O)N[C@@H](C(=O)N1CCC[C@H]1c1nc2ccc(C#Cc3ccc4nc([C@@H]5CCCN5C(=O)[C@H](NC(=O)OC)c5ccccc5)[nH]c4c3)cc2[nH]1)c1ccccc1] | **** | 779.3 |
| 852 | 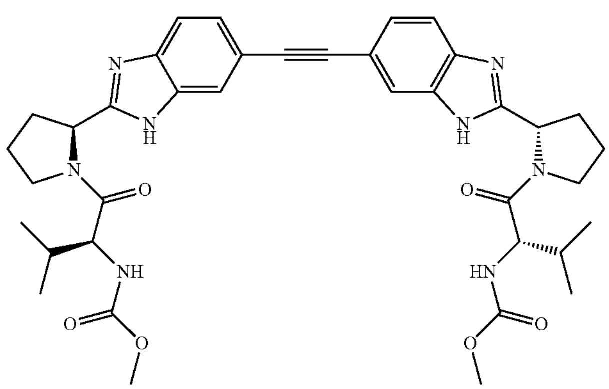 [SMILES: COC(=O)N[C@H](C(=O)N1CCC[C@H]1c1nc2ccc(C#Cc3ccc4nc([C@@H]5CCCN5C(=O)[C@@H](NC(=O)OC)C(C)C)[nH]c4c3)cc2[nH]1)C(C)C] | **** | 711.4 |

TABLE 6-continued

| Compound # | Structure | Inhibition of HCV genotype 1b | MS (M + H+) |
|---|---|---|---|
| 853 | 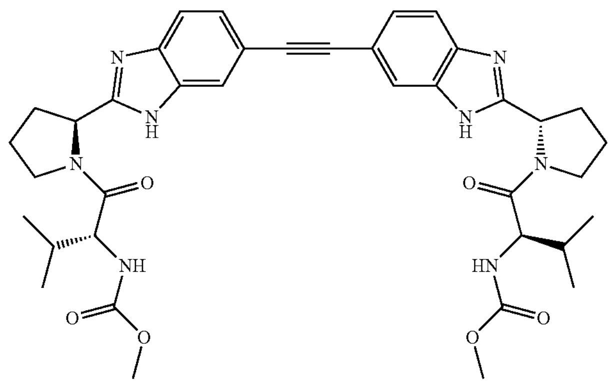 [SMILES: COC(=O)N[C@@H](C(=O)N1CCC[C@H]1c1nc2ccc(C#Cc3ccc4nc([C@@H]5CCCN5C(=O)[C@H](NC(=O)OC)C(C)C)[nH]c4c3)cc2[nH]1)C(C)C] | **** | 711.4 |

TABLE 7

| Compound # | Structure | Inhibition of HCV genotype 1b | MS (M + H+) |
|---|---|---|---|
| 1083 | 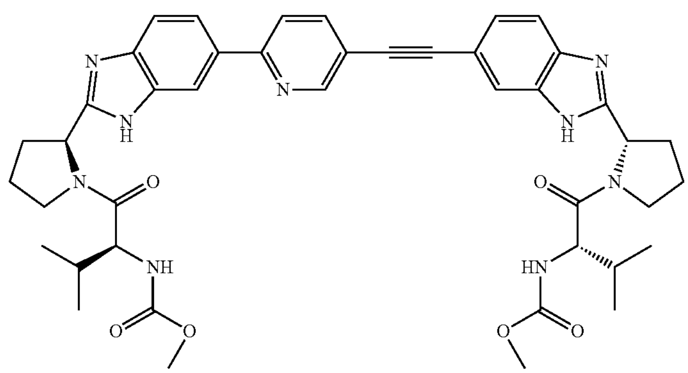 [SMILES: COC(=O)N[C@H](C(=O)N1CCC[C@H]1c1nc2ccc(C#Cc3ccc(-c4ccc5nc([C@@H]6CCCN6C(=O)[C@@H](NC(=O)OC)C(C)C)[nH]c5c4)nc3)cc2[nH]1)C(C)C] | **** | 788.4 |

TABLE 8

| Compound # | Structure | Inhibition of HCV genotype 1b | MS (M + H+) |
|---|---|---|---|
| 1084 | 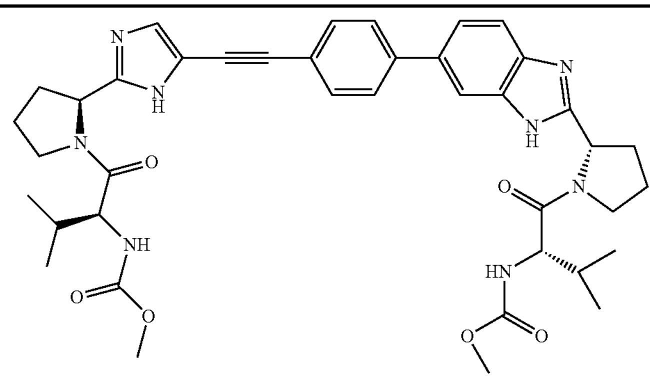 | **** | 737.4 |

TABLE 8-continued

| Compound # | Structure | Inhibition of HCV genotype 1b | MS (M + H⁺) |
|---|---|---|---|
| 1085 | 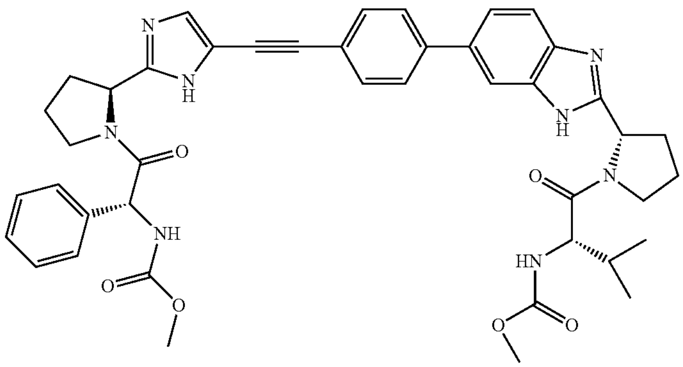 [SMILES: COC(=O)N[C@H](C(=O)N1CCC[C@H]1c1nc2ccc(-c3ccc(C#Cc4cnc([C@@H]5CCCN5C(=O)[C@H](NC(=O)OC)c5ccccc5)[nH]4)cc3)cc2[nH]1)C(C)C] | **** | 771.4 |
| 1086 | 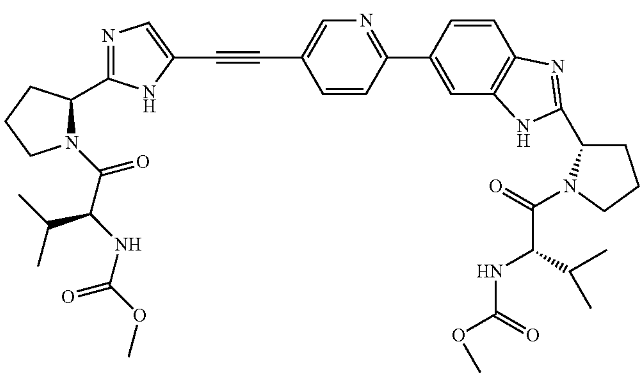 [SMILES: COC(=O)N[C@H](C(=O)N1CCC[C@H]1c1ncc(C#Cc2ccc(-c3ccc4nc([C@@H]5CCCN5C(=O)[C@@H](NC(=O)OC)C(C)C)[nH]c4c3)nc2)[nH]1)C(C)C] | **** | 738.4 |
| 1087 | 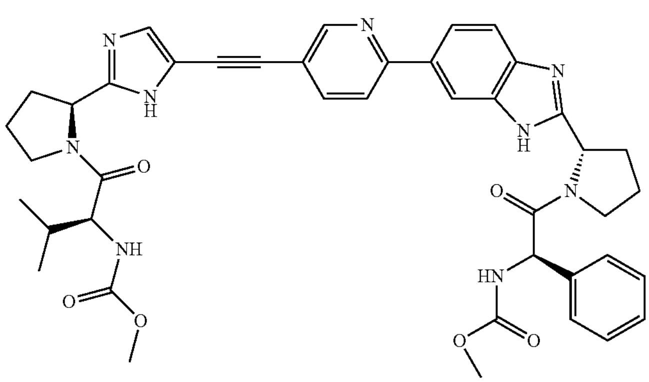 [SMILES: COC(=O)N[C@H](C(=O)N1CCC[C@H]1c1ncc(C#Cc2ccc(-c3ccc4nc([C@@H]5CCCN5C(=O)[C@H](NC(=O)OC)c5ccccc5)[nH]c4c3)nc2)[nH]1)C(C)C] | **** | 772.3 |

TABLE 9
| Compound # | Structure | Inhibition of HCV genotype 1b | MS (M + H+) |
|---|---|---|---|
| 700 | 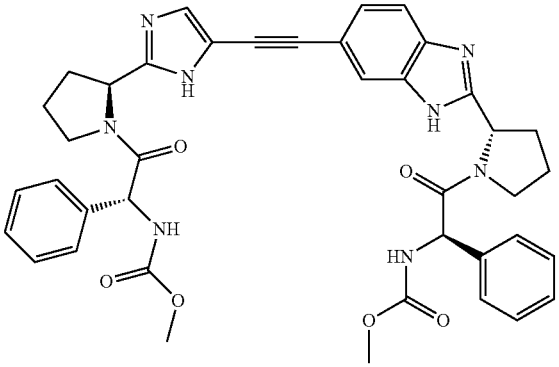 [SMILES: COC(=O)N[C@@H](C(=O)N1CCC[C@H]1c1ncc(C#Cc2ccc3nc([C@@H]4CCCN4C(=O)[C@H](NC(=O)OC)c4ccccc4)[nH]c3c2)[nH]1)c1ccccc1] | **** | 729.3 |
| 1088 | 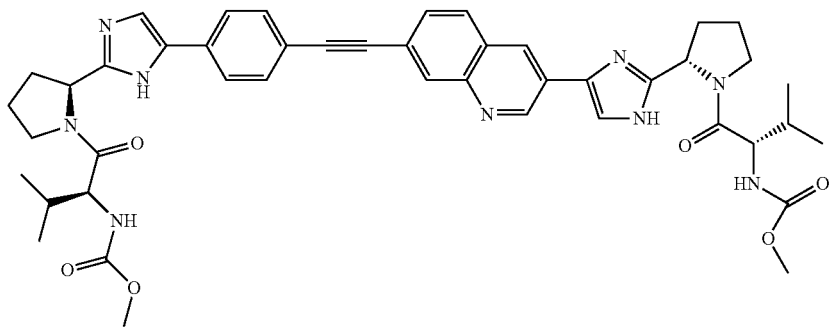 [SMILES: COC(=O)N[C@H](C(=O)N1CCC[C@H]1c1nc(-c2cnc3cc(C#Cc4ccc(-c5cnc([C@@H]6CCCN6C(=O)[C@@H](NC(=O)OC)C(C)C)[nH]5)cc4)ccc3c2)c[nH]1)C(C)C] | *** | 814.4 |
| 1089 | 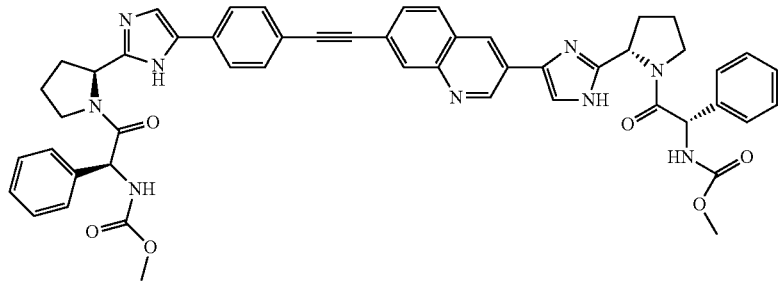 [SMILES: COC(=O)N[C@H](C(=O)N1CCC[C@H]1c1nc(-c2cnc3cc(C#Cc4ccc(-c5cnc([C@@H]6CCCN6C(=O)[C@@H](NC(=O)OC)c6ccccc6)[nH]5)cc4)ccc3c2)c[nH]1)c1ccccc1] | *** | 882.4 |
TABLE 10
| Compound # | Structure | Inhibition of HCV genotype 1b | MS (M + H+) |
|---|---|---|---|
| 750 | 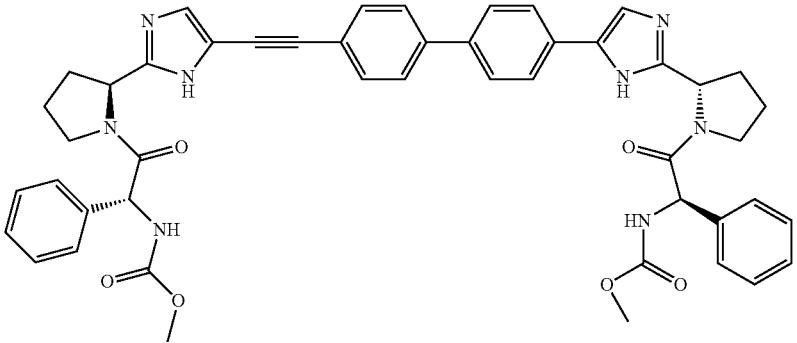 [SMILES: COC(=O)N[C@@H](C(=O)N1CCC[C@H]1c1ncc(C#Cc2ccc(-c3ccc(-c4cnc([C@@H]5CCCN5C(=O)[C@H](NC(=O)OC)c5ccccc5)[nH]4)cc3)cc2)[nH]1)c1ccccc1] | **** | 831.4 |

TABLE 10-continued

| Compound # | Structure | Inhibition of HCV genotype 1b | MS (M + H⁺) |
|---|---|---|---|
| 751 | 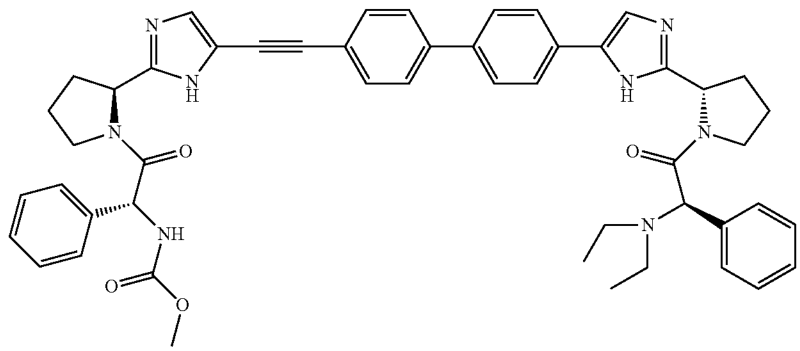 [SMILES: CCN(CC)[C@@H](C(=O)N1CCC[C@H]1c1ncc(-c2ccc(-c3ccc(C#Cc4cnc([C@@H]5CCCN5C(=O)[C@H](NC(=O)OC)c5ccccc5)[nH]4)cc3)cc2)[nH]1)c1ccccc1] | **** | 829.4 |
| 752 | 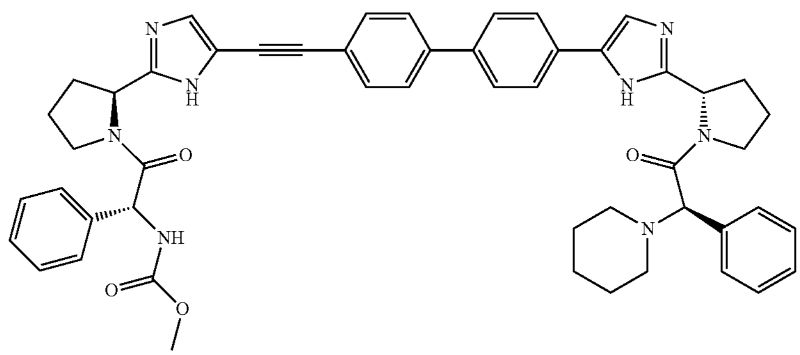 [SMILES: COC(=O)N[C@@H](C(=O)N1CCC[C@H]1c1ncc(C#Cc2ccc(-c3ccc(-c4cnc([C@@H]5CCCN5C(=O)[C@@H](c5ccccc5)N5CCCCC5)[nH]4)cc3)cc2)[nH]1)c1ccccc1] | **** | 841.4 |
| 753 | 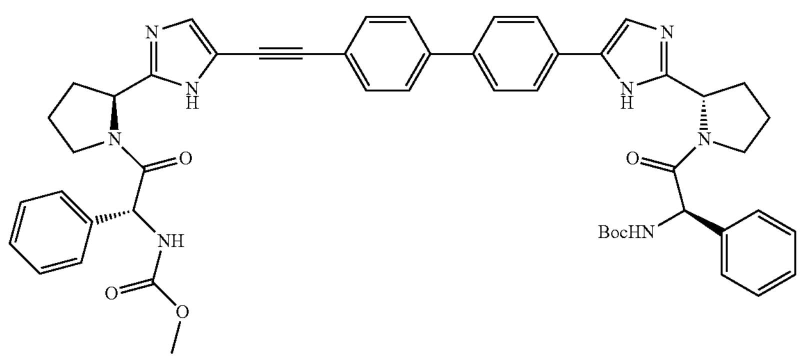 [SMILES: COC(=O)N[C@@H](C(=O)N1CCC[C@H]1c1ncc(C#Cc2ccc(-c3ccc(-c4cnc([C@@H]5CCCN5C(=O)[C@H](NC(=O)OC(C)(C)C)c5ccccc5)[nH]4)cc3)cc2)[nH]1)c1ccccc1] | **** | 873.4 |
| 754 | 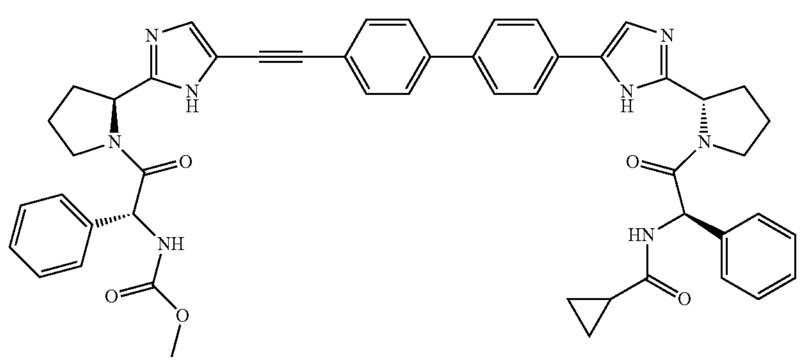 [SMILES: COC(=O)N[C@@H](C(=O)N1CCC[C@H]1c1ncc(C#Cc2ccc(-c3ccc(-c4cnc([C@@H]5CCCN5C(=O)[C@H](NC(=O)C5CC5)c5ccccc5)[nH]4)cc3)cc2)[nH]1)c1ccccc1] | **** | 841.4 |

TABLE 10-continued

| Compound # | Structure | Inhibition of HCV genotype 1b | MS (M + H+) |
|---|---|---|---|
| 755 | 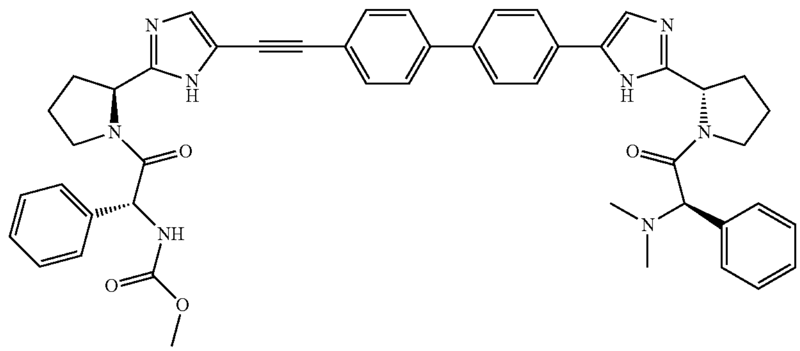 [SMILES: COC(=O)N[C@@H](C(=O)N1CCC[C@H]1c1ncc(C#Cc2ccc(-c3ccc(-c4cnc([C@@H]5CCCN5C(=O)[C@@H](c5ccccc5)N(C)C)[nH]4)cc3)cc2)[nH]1)c1ccccc1] | **** | 801.4 |
| 756 | 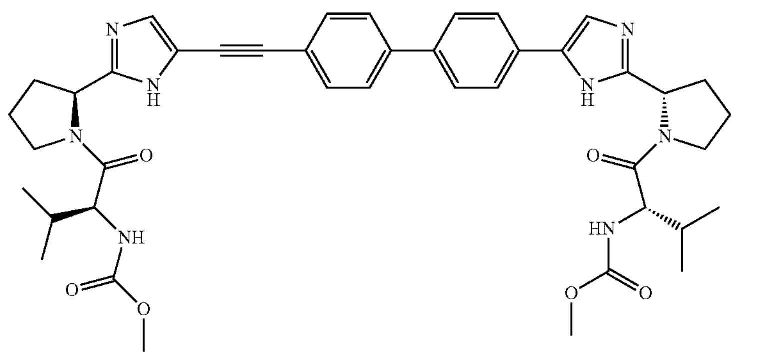 [SMILES: COC(=O)N[C@H](C(=O)N1CCC[C@H]1c1ncc(C#Cc2ccc(-c3ccc(-c4cnc([C@@H]5CCCN5C(=O)[C@@H](NC(=O)OC)C(C)C)[nH]4)cc3)cc2)[nH]1)C(C)C] | **** | 763.4 |
| 757 | 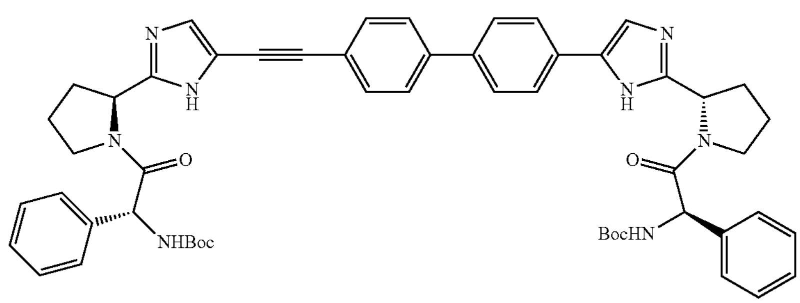 [SMILES: CC(C)(C)OC(=O)N[C@@H](C(=O)N1CCC[C@H]1c1ncc(C#Cc2ccc(-c3ccc(-c4cnc([C@@H]5CCCN5C(=O)[C@H](NC(=O)OC(C)(C)C)c5ccccc5)[nH]4)cc3)cc2)[nH]1)c1ccccc1] | **** | 915.4 |
| 758 | 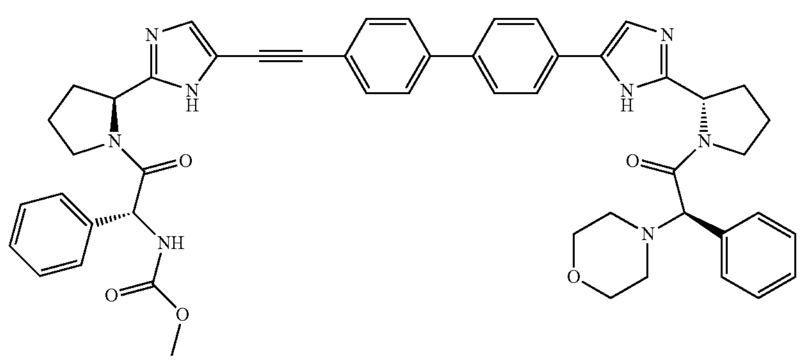 [SMILES: COC(=O)N[C@@H](C(=O)N1CCC[C@H]1c1ncc(C#Cc2ccc(-c3ccc(-c4cnc([C@@H]5CCCN5C(=O)[C@@H](c5ccccc5)N5CCOCC5)[nH]4)cc3)cc2)[nH]1)c1ccccc1] | **** | 843.4 |

TABLE 10-continued

| Compound # | Structure | Inhibition of HCV genotype 1b | MS (M + H+) |
|---|---|---|---|
| 759 | 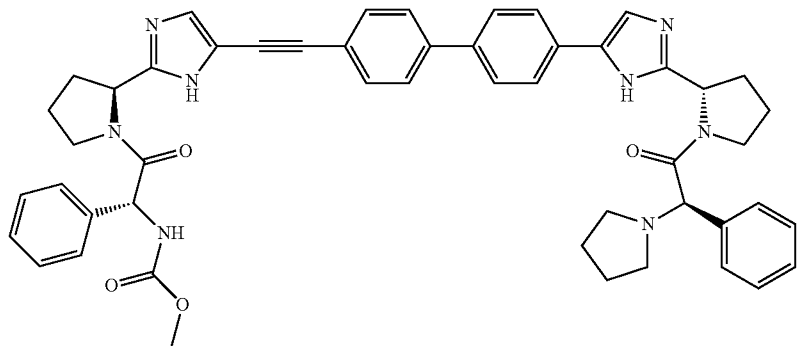 [SMILES: COC(=O)N[C@@H](C(=O)N1CCC[C@H]1c1ncc(C#Cc2ccc(-c3ccc(-c4cnc([C@@H]5CCCN5C(=O)[C@@H](c5ccccc5)N5CCCC5)[nH]4)cc3)cc2)[nH]1)c1ccccc1] | **** | 827.4 |
| 760 | 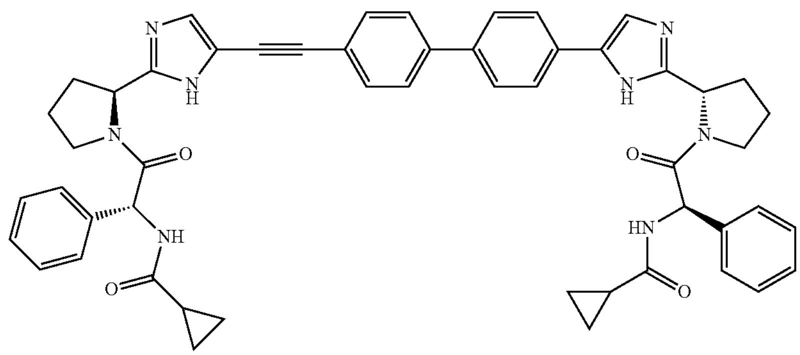 [SMILES: O=C(N[C@@H](C(=O)N1CCC[C@H]1c1ncc(C#Cc2ccc(-c3ccc(-c4cnc([C@@H]5CCCN5C(=O)[C@H](NC(=O)C5CC5)c5ccccc5)[nH]4)cc3)cc2)[nH]1)c1ccccc1)C1CC1] | **** | 851.4 |
| 761 | 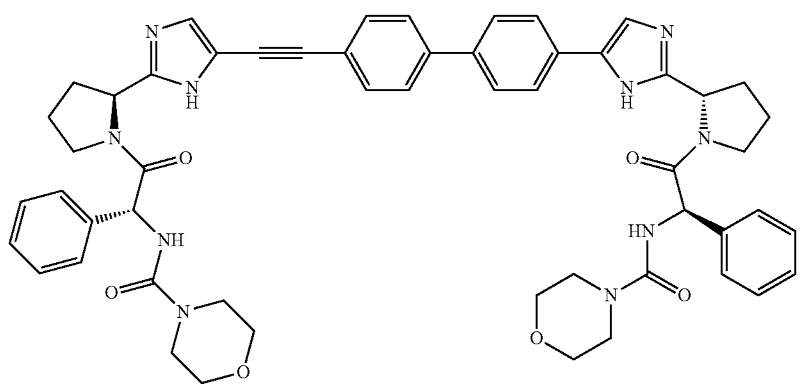 [SMILES: O=C(N[C@@H](C(=O)N1CCC[C@H]1c1ncc(C#Cc2ccc(-c3ccc(-c4cnc([C@@H]5CCCN5C(=O)[C@H](NC(=O)N5CCOCC5)c5ccccc5)[nH]4)cc3)cc2)[nH]1)c1ccccc1)N1CCOCC1] | **** | 941.4 |
| 762 | 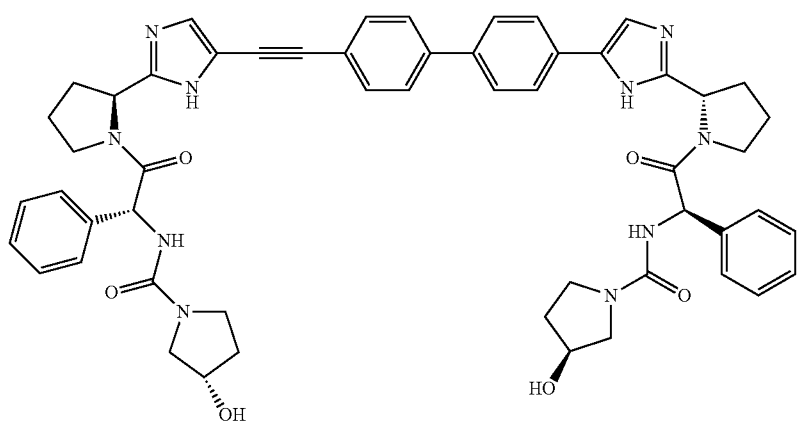 [SMILES: O=C(N[C@@H](C(=O)N1CCC[C@H]1c1ncc(C#Cc2ccc(-c3ccc(-c4cnc([C@@H]5CCCN5C(=O)[C@H](NC(=O)N5CC[C@H](O)C5)c5ccccc5)[nH]4)cc3)cc2)[nH]1)c1ccccc1)N1CC[C@H](O)C1] | **** | 941.4 |

TABLE 10-continued

| Compound # | Structure | Inhibition of HCV genotype 1b | MS (M + H+) |
|---|---|---|---|
| 763 | 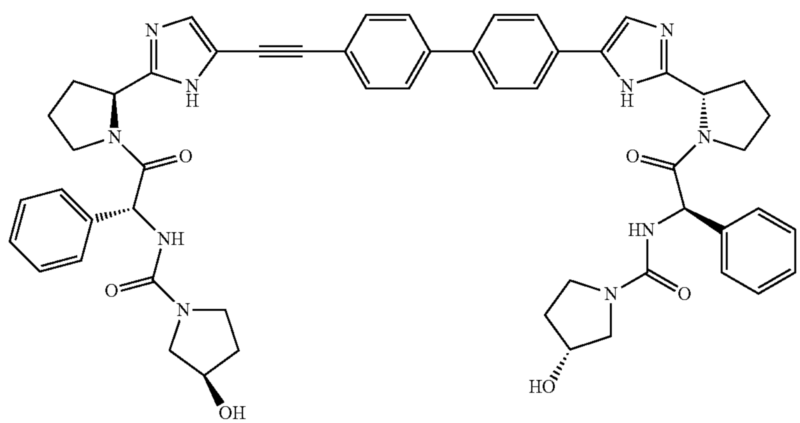 [SMILES: O=C(N[C@@H](C(=O)N1CCC[C@H]1c1ncc(C#Cc2ccc(-c3ccc(-c4cnc([C@@H]5CCCN5C(=O)[C@H](NC(=O)N5CC[C@@H](O)C5)c5ccccc5)[nH]4)cc3)cc2)[nH]1)c1ccccc1)N1CC[C@@H](O)C1] | **** | 941.4 |
| 870 | 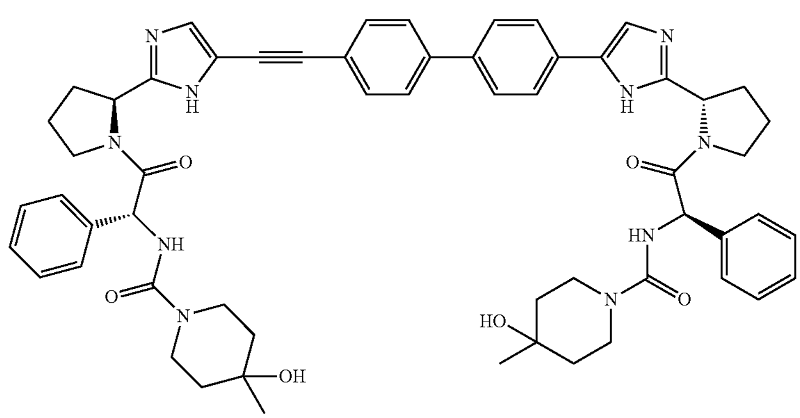 [SMILES: CC1(O)CCN(C(=O)N[C@@H](C(=O)N2CCC[C@H]2c2ncc(C#Cc3ccc(-c4ccc(-c5cnc([C@@H]6CCCN6C(=O)[C@H](NC(=O)N6CCC(C)(O)CC6)c6ccccc6)[nH]5)cc4)cc3)[nH]2)c2ccccc2)CC1] | **** | 997.6 |
| 1100 | 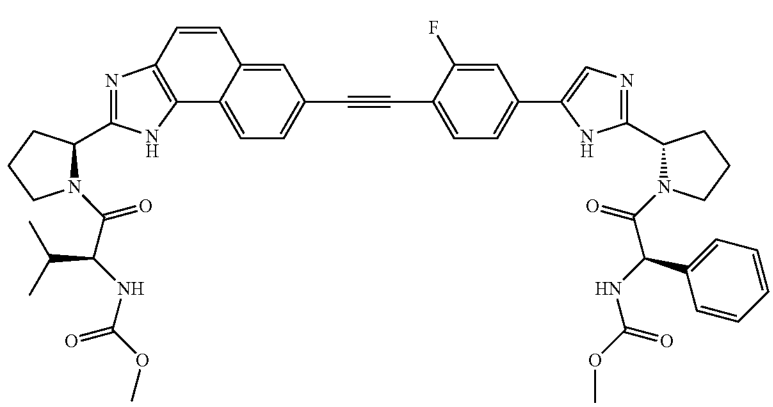 [SMILES: COC(=O)N[C@H](C(=O)N1CCC[C@H]1c1nc2ccc3cc(C#Cc4ccc(-c5cnc([C@@H]6CCCN6C(=O)[C@H](NC(=O)OC)c6ccccc6)[nH]5)cc4F)ccc3c2[nH]1)C(C)C] | **** | 839.4 |

TABLE 11

| Compound | Structure | Inhibition of HCV genotype 1b | MS (M + H)+ |
|---|---|---|---|
| 1101 | 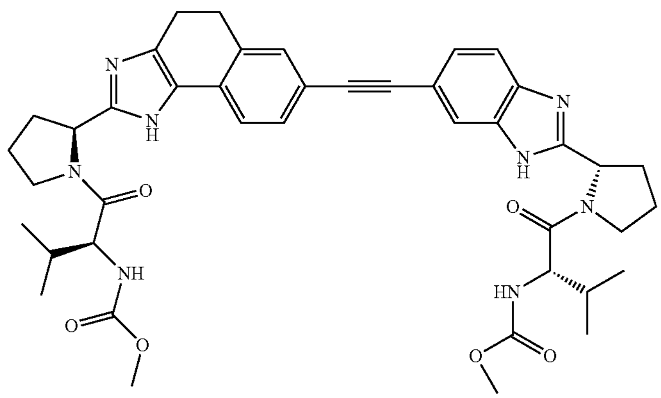 [SMILES: COC(=O)N[C@H](C(=O)N1CCC[C@H]1c1nc2c([nH]1)-c1ccc(C#Cc3ccc4nc([C@@H]5CCCN5C(=O)[C@@H](NC(=O)OC)C(C)C)[nH]c4c3)cc1CC2)C(C)C] | | 763.4 |
| 1102 | 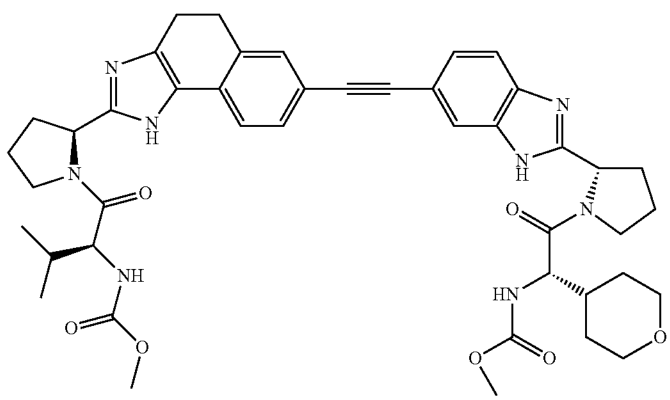 [SMILES: COC(=O)N[C@H](C(=O)N1CCC[C@H]1c1nc2c([nH]1)-c1ccc(C#Cc3ccc4nc([C@@H]5CCCN5C(=O)[C@@H](NC(=O)OC)C5CCOCC5)[nH]c4c3)cc1CC2)C(C)C] | | 805.4 |
| 1103 | 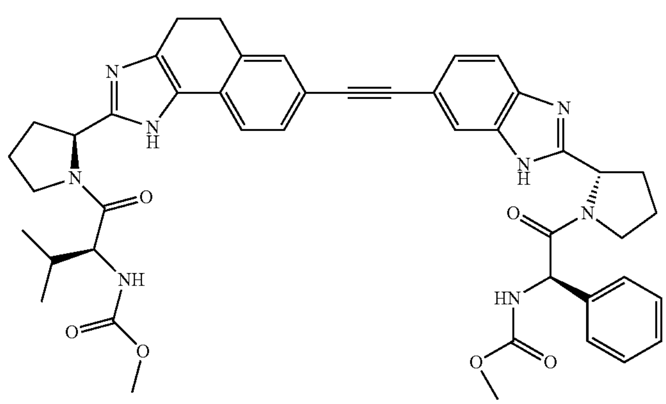 [SMILES: COC(=O)N[C@H](C(=O)N1CCC[C@H]1c1nc2c([nH]1)-c1ccc(C#Cc3ccc4nc([C@@H]5CCCN5C(=O)[C@H](NC(=O)OC)c5ccccc5)[nH]c4c3)cc1CC2)C(C)C] | | 797.4 |

TABLE 11-continued

| Compound | Structure | Inhibition of HCV genotype 1b | MS (M + H)+ |
|---|---|---|---|
| 1104 | 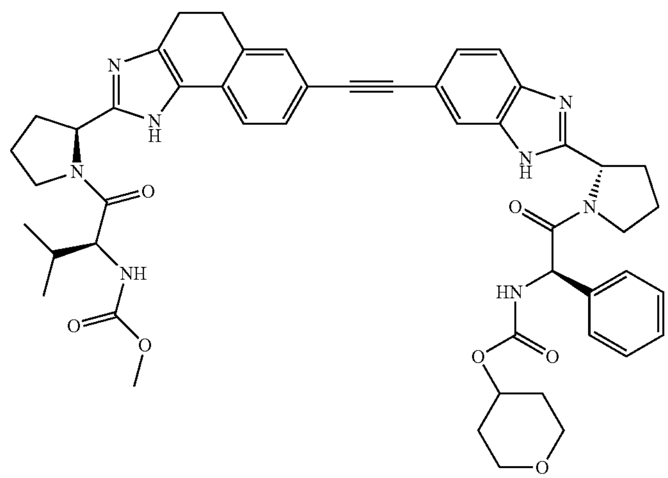 [SMILES: COC(=O)N[C@H](C(=O)N1CCC[C@H]1c1nc2c([nH]1)-c1ccc(C#Cc3ccc4nc([C@@H]5CCCN5C(=O)[C@H](NC(=O)OC5CCOCC5)c5ccccc5)[nH]c4c3)cc1CC2)C(C)C] | | 867.4 |
| 1105 | 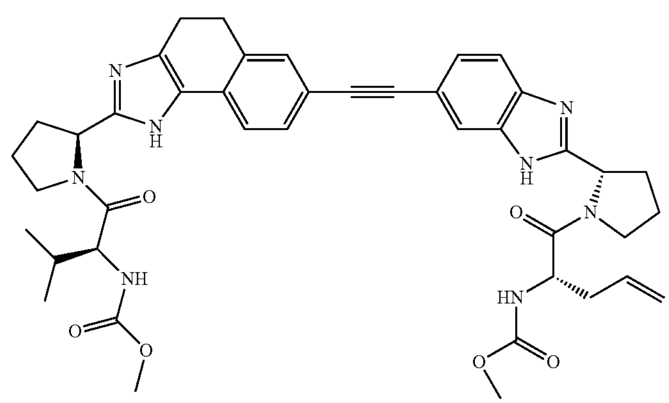 [SMILES: C=CC[C@H](NC(=O)OC)C(=O)N1CCC[C@H]1c1nc2ccc(C#Cc3ccc4c(c3)CCc3nc([C@@H]5CCCN5C(=O)[C@@H](NC(=O)OC)C(C)C)[nH]c3-4)cc2[nH]1] | | 761.4 |
| 1106 | 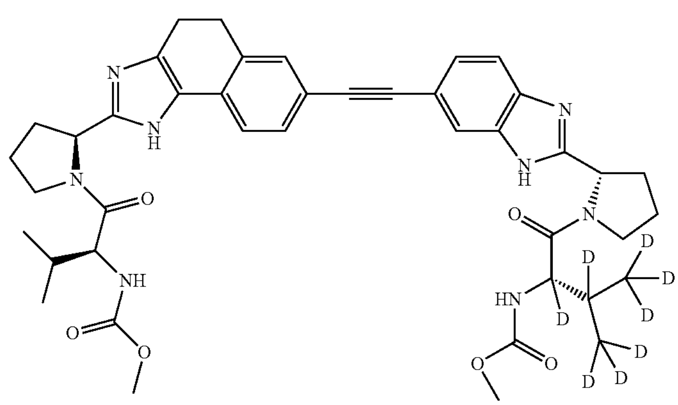 [SMILES: [2H]C([2H])([2H])C([2H])(C([2H])([2H])[2H])[C@]([2H])(NC(=O)OC)C(=O)N1CCC[C@H]1c1nc2ccc(C#Cc3ccc4c(c3)CCc3nc([C@@H]5CCCN5C(=O)[C@@H](NC(=O)OC)C(C)C)[nH]c3-4)cc2[nH]1] | | 771.4 |

TABLE 12

| Compound # | Structure | Inhibition of HCV genotype 1b | MS (M + H)+ |
|---|---|---|---|
| 1107 | 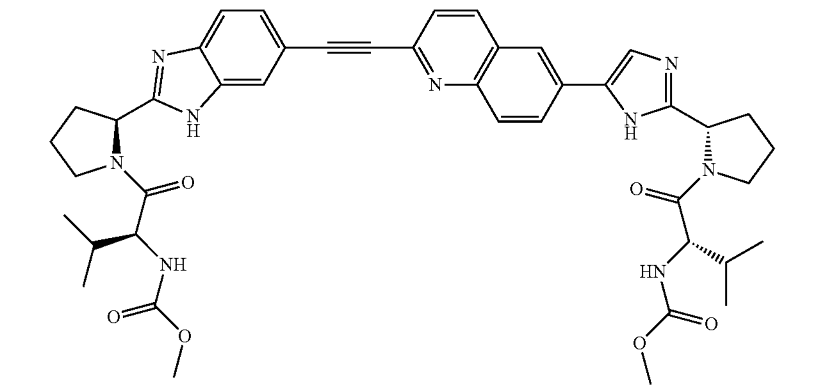 [SMILES: COC(=O)N[C@H](C(=O)N1CCC[C@H]1c1ncc(-c2ccc3nc(C#Cc4ccc5nc([C@@H]6CCCN6C(=O)[C@@H](NC(=O)OC)C(C)C)[nH]c5c4)ccc3c2)[nH]1)C(C)C] | | 788.4 |
| 1108 | 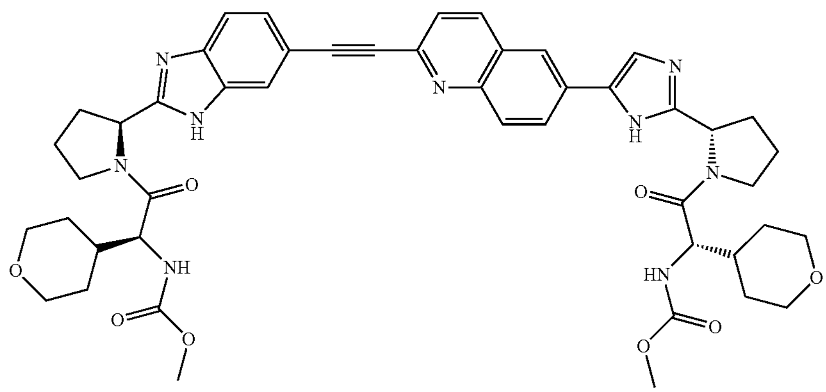 [SMILES: COC(=O)N[C@H](C(=O)N1CCC[C@H]1c1ncc(-c2ccc3nc(C#Cc4ccc5nc([C@@H]6CCCN6C(=O)[C@@H](NC(=O)OC)C6CCOCC6)[nH]c5c4)ccc3c2)[nH]1)C1CCOCC1] | | 872.4 |
| 1109 | 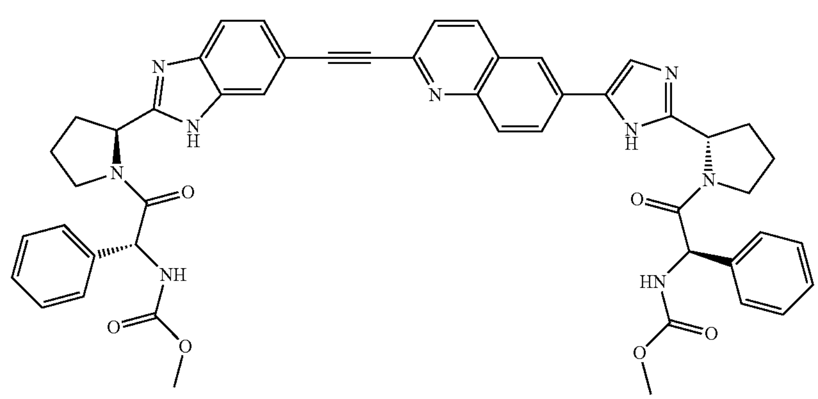 [SMILES: COC(=O)N[C@@H](C(=O)N1CCC[C@H]1c1ncc(-c2ccc3nc(C#Cc4ccc5nc([C@@H]6CCCN6C(=O)[C@H](NC(=O)OC)c6ccccc6)[nH]c5c4)ccc3c2)[nH]1)c1ccccc1] | | 856.3 |

TABLE 12-continued

| Compound # | Structure | Inhibition of HCV genotype 1b | MS (M + H)+ |
| --- | --- | --- | --- |
| 1110 | 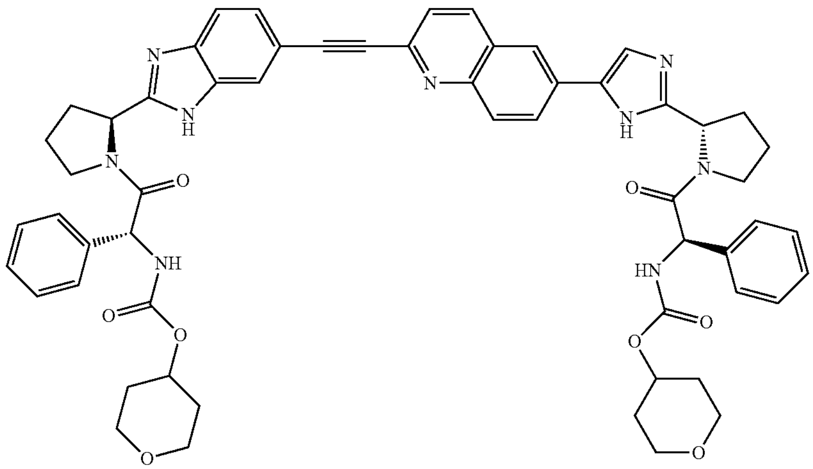 [SMILES: O=C(N[C@@H](C(=O)N1CCC[C@H]1c1ncc(-c2ccc3nc(C#Cc4ccc5nc([C@@H]6CCCN6C(=O)[C@H](NC(=O)OC6CCOCC6)c6ccccc6)[nH]c5c4)ccc3c2)[nH]1)c1ccccc1)OC1CCOCC1] | | 996.4 |
| 1111 | 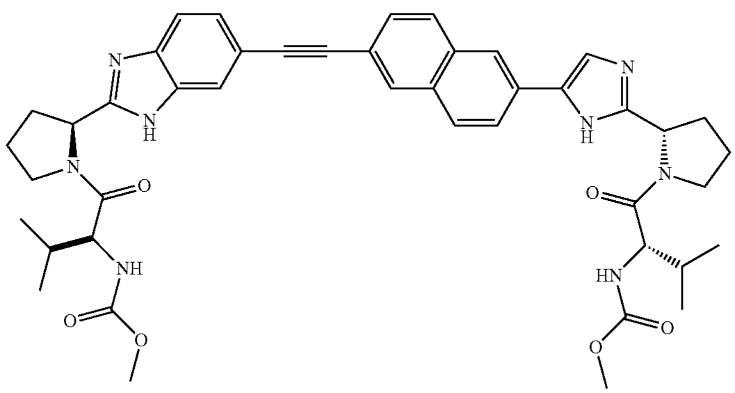 | | 787.4 |
| 1112 | 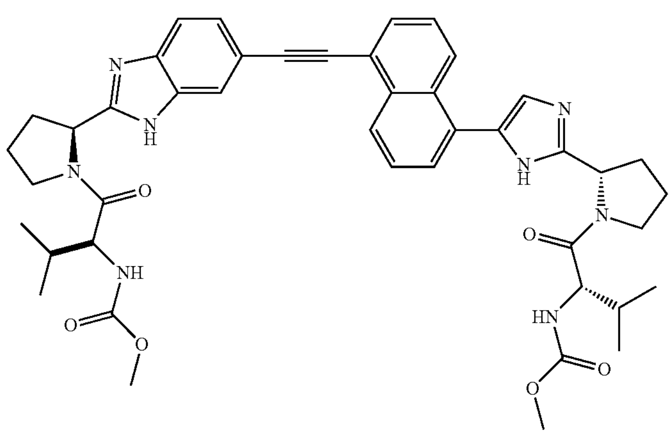 [SMILES: COC(=O)N[C@H](C(=O)N1CCC[C@H]1c1ncc(-c2cccc3c(C#Cc4ccc5nc([C@@H]6CCCN6C(=O)[C@@H](NC(=O)OC)C(C)C)[nH]c5c4)cccc23)[nH]1)C(C)C] | | 787.4 |

TABLE 13

| Compound # | Structure | Inhibition of HCV genotype 1b | MS (M + H)+ |
|---|---|---|---|
| 1113 | 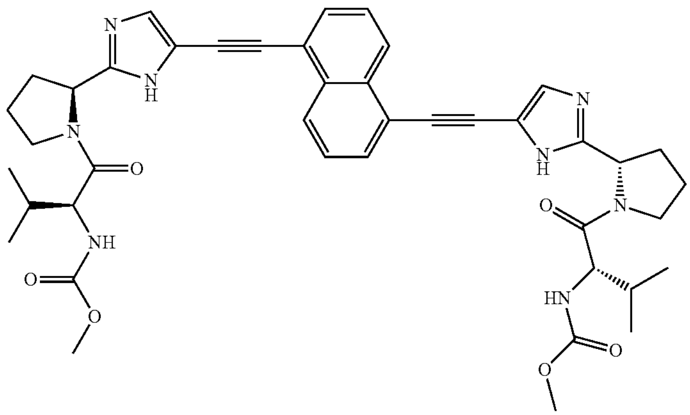 [SMILES: COC(=O)N[C@H](C(=O)N1CCC[C@H]1c1ncc(C#Cc2cccc3c(C#Cc4cnc([C@@H]5CCCN5C(=O)[C@@H](NC(=O)OC)C(C)C)[nH]4)cccc23)[nH]1)C(C)C] | | 761.4 |
| 1114 | 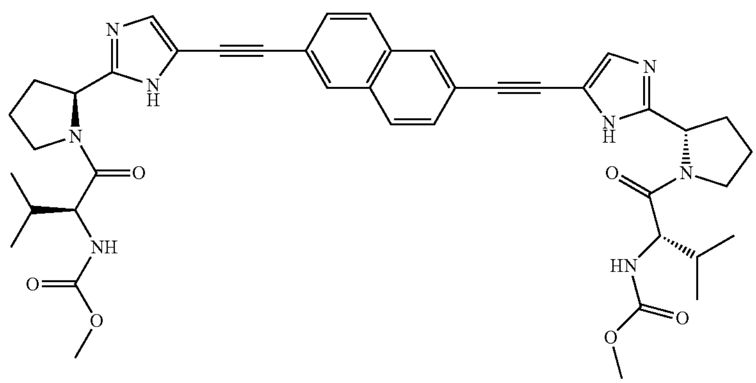 [SMILES: COC(=O)N[C@H](C(=O)N1CCC[C@H]1c1ncc(C#Cc2ccc3cc(C#Cc4cnc([C@@H]5CCCN5C(=O)[C@@H](NC(=O)OC)C(C)C)[nH]4)ccc3c2)[nH]1)C(C)C] | | |

TABLE 14

| Compound # | Structure | Inhibition of HCV genotype 1b | MS (M + H)+ |
|---|---|---|---|
| 1090 | 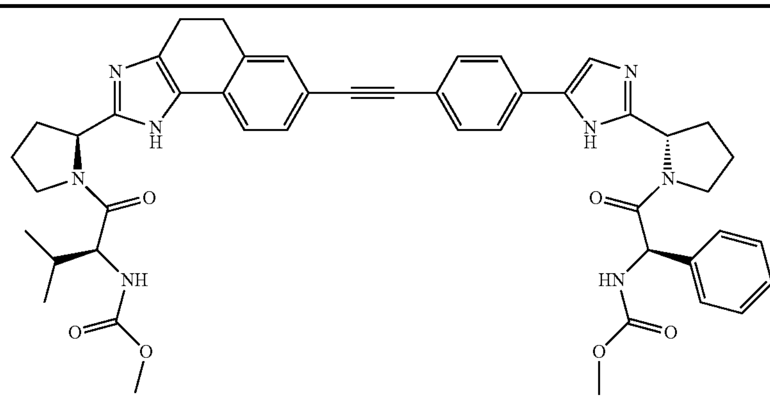 | **** | 832.4 |

TABLE 14-continued

| Compound # | Structure | Inhibition of HCV genotype 1b | MS (M + H)+ |
|---|---|---|---|
| 1091 | 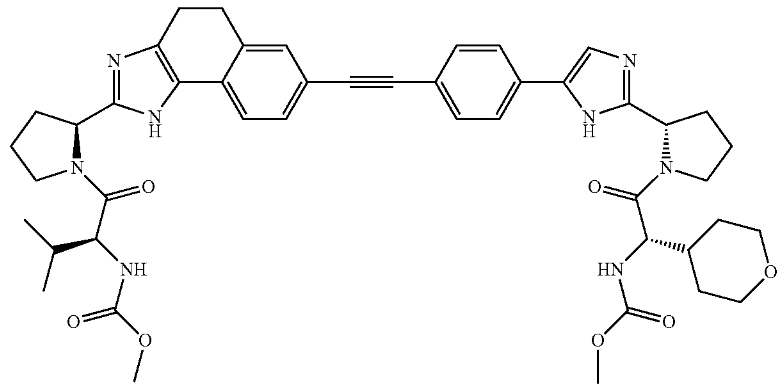 [SMILES: COC(=O)N[C@H](C(=O)N1CCC[C@H]1c1nc2c([nH]1)-c1ccc(C#Cc3ccc(-c4cnc([C@@H]5CCCN5C(=O)[C@@H](NC(=O)OC)C5CCOCC5)[nH]4)cc3)cc1CC2)C(C)C] | **** | 831.4 |
| 1092 | 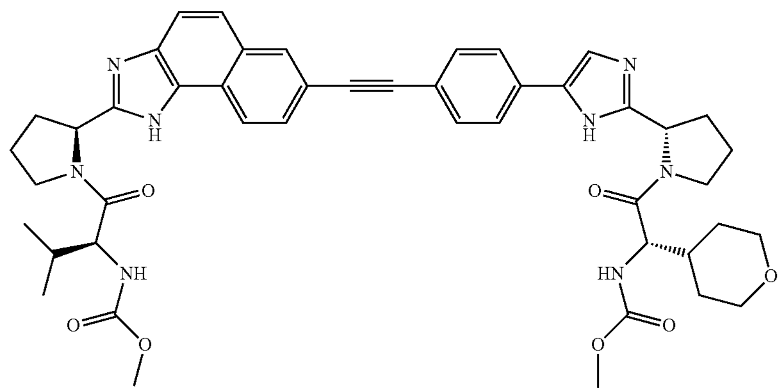 [SMILES: COC(=O)N[C@H](C(=O)N1CCC[C@H]1c1nc2ccc3cc(C#Cc4ccc(-c5cnc([C@@H]6CCCN6C(=O)[C@@H](NC(=O)OC)C6CCOCC6)[nH]5)cc4)ccc3c2[nH]1)C(C)C] | **** | 829.4 |
| 1093 | 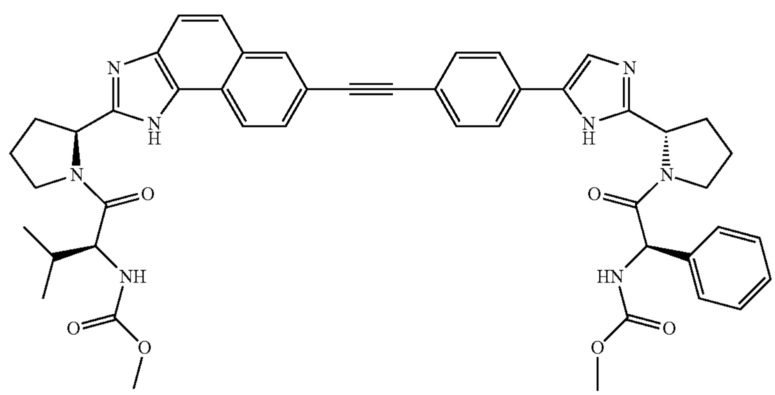 [SMILES: COC(=O)N[C@H](C(=O)N1CCC[C@H]1c1nc2ccc3cc(C#Cc4ccc(-c5cnc([C@@H]6CCCN6C(=O)[C@H](NC(=O)OC)c6ccccc6)[nH]5)cc4)ccc3c2[nH]1)C(C)C] | **** | 821.4 |
| 1094 | 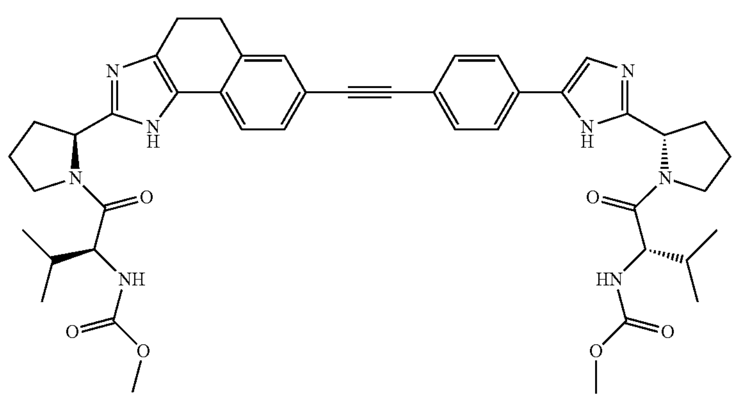 [SMILES: COC(=O)N[C@H](C(=O)N1CCC[C@H]1c1ncc(-c2ccc(C#Cc3ccc4c(c3)CCc3nc([C@@H]5CCCN5C(=O)[C@@H](NC(=O)OC)C(C)C)[nH]c3-4)cc2)[nH]1)C(C)C] | **** | 789.4 |

TABLE 14-continued
| Compound # | Structure | Inhibition of HCV genotype 1b | MS (M + H)+ |
|---|---|---|---|
| 1095 | 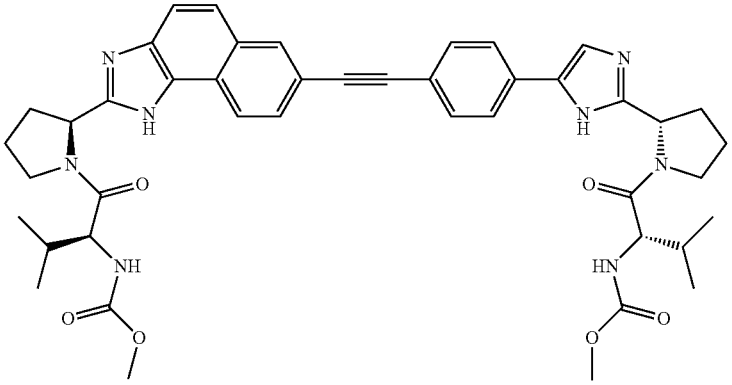 [SMILES: COC(=O)N[C@H](C(=O)N1CCC[C@H]1c1ncc(-c2ccc(C#Cc3ccc4c(ccc5nc([C@@H]6CCCN6C(=O)[C@@H](NC(=O)OC)C(C)C)[nH]c54)c3)cc2)[nH]1)C(C)C] | **** | 787.4 |
| 1096 | 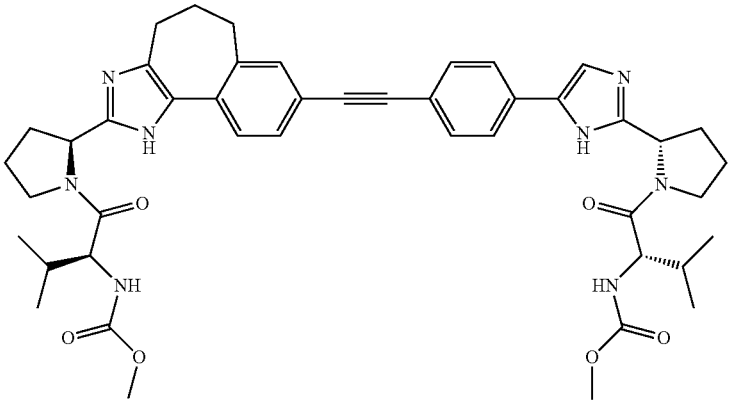 [SMILES: COC(=O)N[C@H](C(=O)N1CCC[C@H]1c1ncc(-c2ccc(C#Cc3ccc4c(c3)CCCc3nc([C@@H]5CCCN5C(=O)[C@@H](NC(=O)OC)C(C)C)[nH]c3-4)cc2)[nH]1)C(C)C] | **** | 803.4 |
| 1097 | 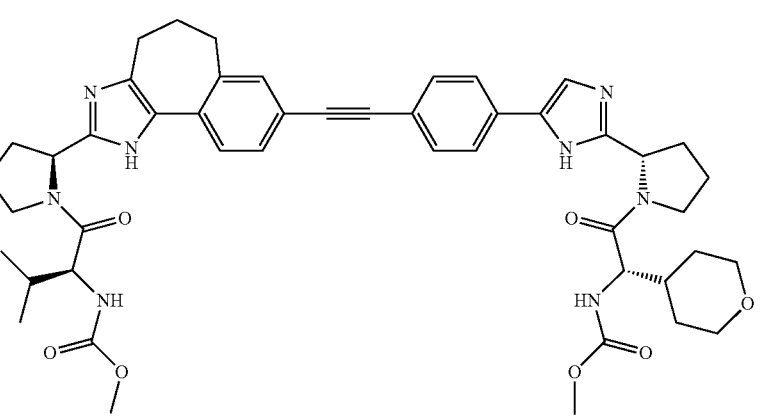 | **** | 845.4 |

TABLE 14-continued
| Compound # | Structure | Inhibition of HCV genotype 1b | MS (M + H)+ |
|---|---|---|---|
| 1098 | 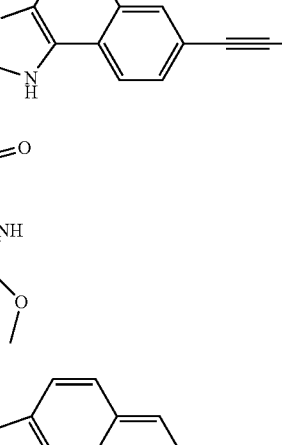 | **** | 841.4 |
| 1099 | 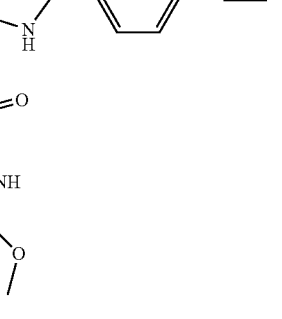 | **** | 847.4 |
| 1100 | 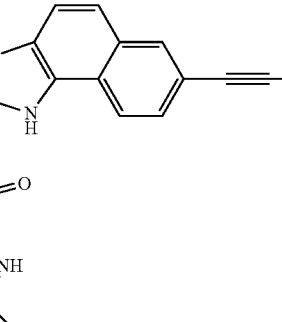 | **** | 839.4 |
We claim:
1. A compound having formula X:
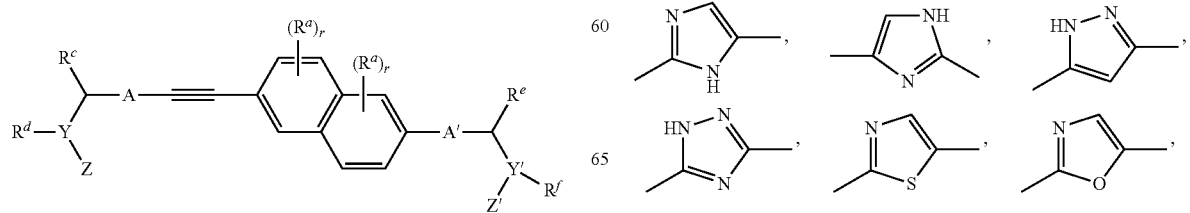
wherein
A and A' are independently selected from the group consisting of single bond,

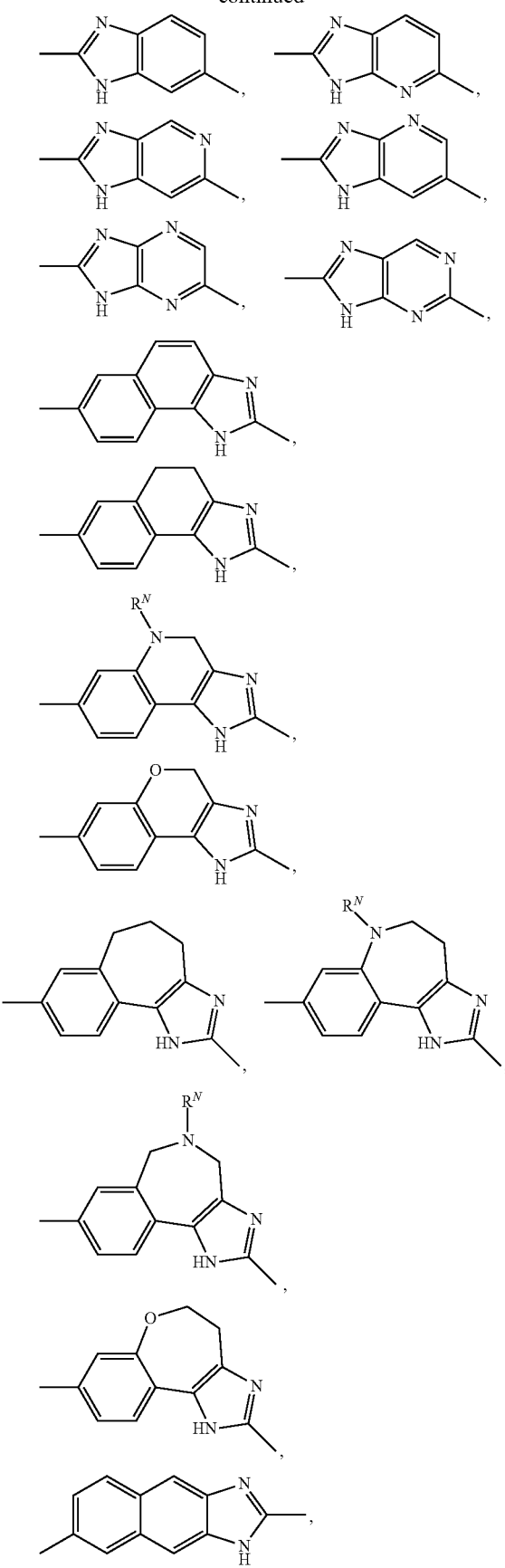

-continued

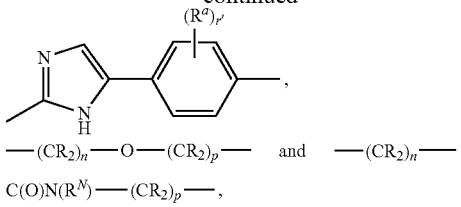

—(CR$_2$)$_n$—O—(CR$_2$)$_p$—    and    —(CR$_2$)$_n$—C(O)N(R$^N$)—(CR$_2$)$_p$—, wherein,
n and p are independently 0, 1, 2, or 3, and
each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

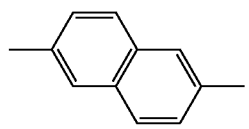

optionally includes 1, 2, 3 or 4 nitrogens as heteroatoms;
each R$^a$ is independently selected from the group consisting of —OH, —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino; and
each r is independently 0, 1, 2, or 3;
R$^c$, R$^d$, R$^e$ and R$^f$ are each independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein,
each hetero atom, if present, is independently N, O or S, each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S,
R$^c$ and R$^d$ are optionally joined to form a 4- to 8-membered heterocycle which is optionally fused to another 3- to 6-membered heterocycle or heteroaryl ring, and
R$^e$ and R$^f$ are optionally joined to form a 4- to 8-membered heterocycle which is optionally fused to another 3- to 6-membered heterocycle or heteroaryl ring;
Y and Y' are each independently carbon or nitrogen; and
Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein,
U is selected from the group consisting of —C(O)—, —C(S)— and —S(O)$_2$—,
each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl, R[8] is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R[81], —C(S)—R[81], —C(O)—O—R[81], —C(O)—N—R[81]$_2$, —S(O)$_2$—R[81] and —S(O)$_2$—N—R[81]$_2$, wherein each R[81] is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, R[7] and R[8] together form a 4-7 membered ring, each t is independently 0, 1, 2, 3, or 4, and u is 0, 1, or 2.

2. The compound of claim 1 having formula Xb:

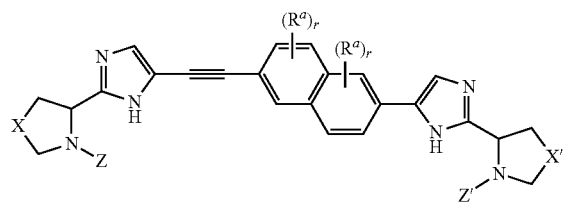

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R[1])—, wherein R[1] is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

3. The compound of claim 1 wherein:

A is selected from the group consisting of H

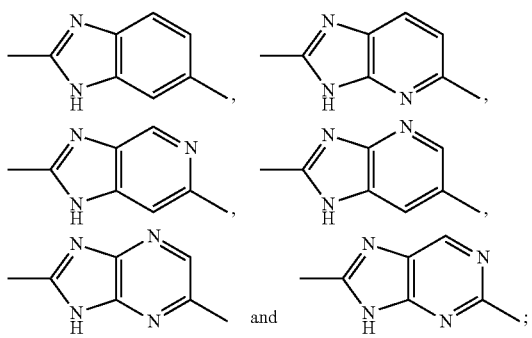

and
A' is

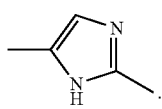

4. The compound of claim 1 having formula Xc:

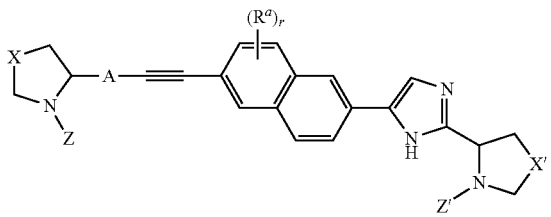

wherein:

A is selected from the group consisting of H

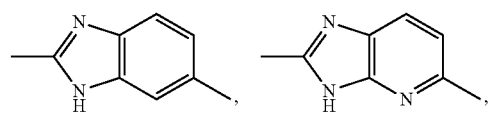

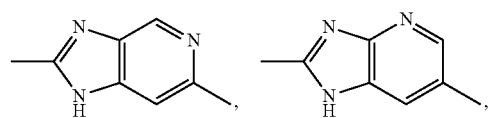

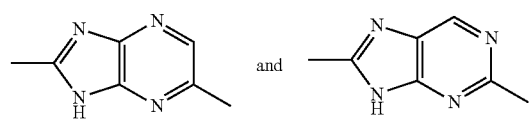

and

X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R[1])—, wherein R[1] is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

5. The compound of claim 1 having formula Xd:

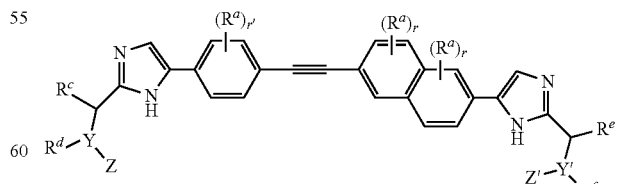

wherein:

r is 0, 1, 2, or 3; and r' is 0, 1, 2, 3, or 4.

6. The compound of claim 5 having formula Xe:

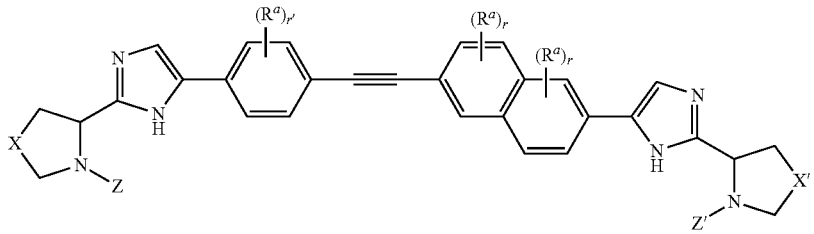

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein R$^1$ is chosen from the group consisting of hydrogen, C$_1$ to C$_8$ alkyl, C$_1$ to C$_8$ heteroalkyl, cycloalkyl, heterocycle, aryl, heteroaryl, aralkyl, alkanoyl, alkoxycarbonyl, carbamoyl and substituted sulfonyl.

7. The compound of claim 1, wherein Z and Z' are each 1-2 natural and unnatural amino acids.

8. The compound of claim 7, wherein the amino acids are in the D configuration.

9. The compound of claim 1, wherein Z and Z' are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$, —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$, —C(O)—(CR$^4_2$)$_t$—NR$^7$—(CR$^4_2$)$_t$—R$^8$, —C(O)—(CR$^4_2$)$_n$—NR$^7$—C(O)—R$^{81}$, and —C(O)—(CR$^4_2$)$_n$—NR$^7$—C(O)—O—R$^{81}$.

10. A compound having formula XIV:

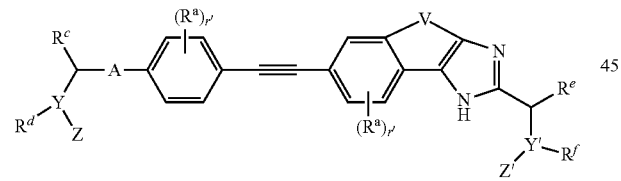

wherein:

A is selected from the group consisting of a single bond,

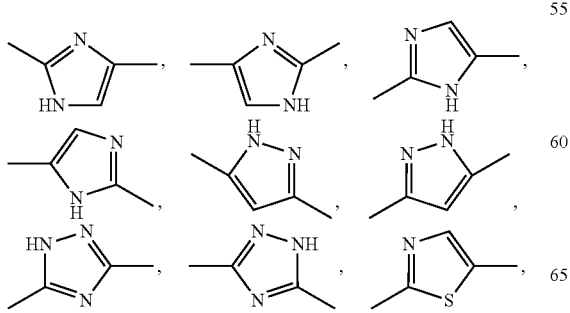

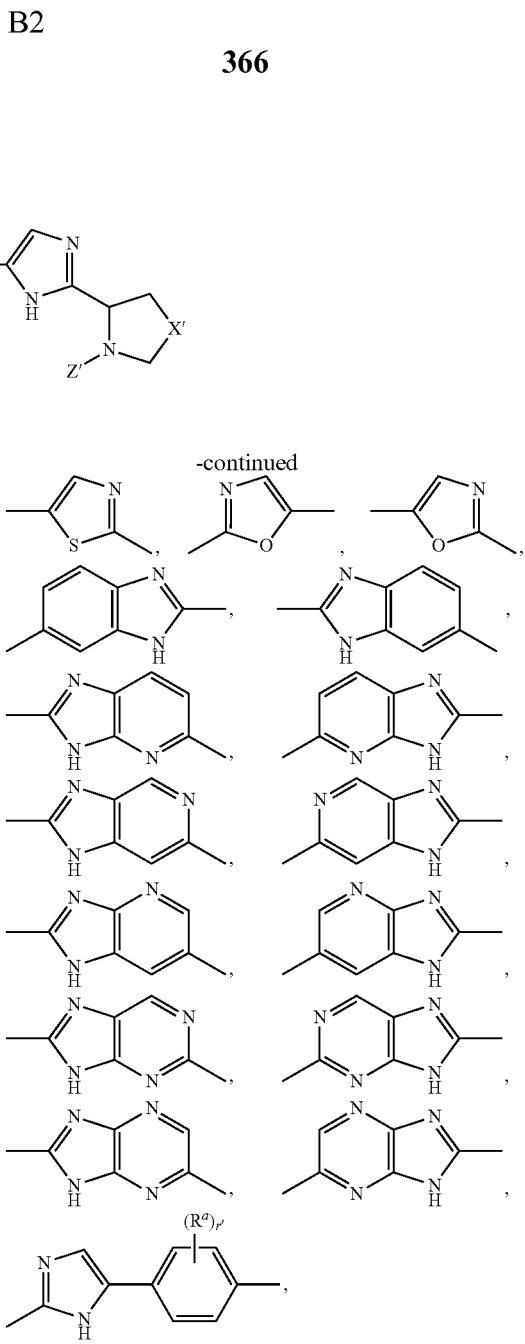

—(CR$_2$)$_n$—O—(CR$_2$)$_9$—, —(CR$_2$)$_n$—C(O)N(R$^N$)—(CR$_2$)$_p$— and —(CR$_2$)$_n$—N(R$^N$)C(O)—(CR$_2$)$_p$—;

wherein, n and p are independently 0, 1, 2, or 3, and each R$^N$ is independently selected from the group consisting of hydrogen, —OH, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide;

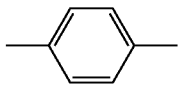

optionally includes 1 or 2 nitrogens as heteroatoms;

each $R^a$ is independently selected from the group consisting of —OH, —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

r is 0, 1, 2, or 3; and r' is 0, 1, 2, 3, or 4;

$R^c$, $R^d$, $R^e$ and $R^f$ are each independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 6-membered heterocycle or heteroaryl ring, and $R^e$ and $R^f$ are optionally joined to form a 4- to 8-membered heterocycle which is optionally fused to another 3- to 6-membered heterocycle or heteroaryl ring; and Y and Y' are each independently carbon or nitrogen; and Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}_2$, —S(O)$_2$—R$^{81}$ and —S(O)$_2$—N—R$^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2; and V is —CH$_2$—CH$_2$—, —CH=CH—, —N=CH—, (CH$_2$)$_a$—N(R$^N$)—(CH$_2$)$_b$— or —(CH$_2$)$_a$—O—(CH$_2$)$_b$—, wherein a and b are independently 0, 1, 2, or 3 with the proviso that a and b are not both 0.

11. The compound of claim 10 having formula XIVd:

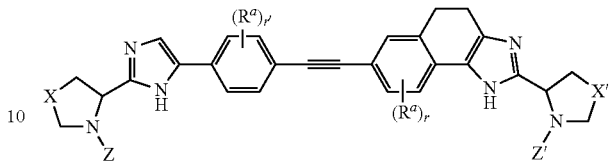

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

12. The compound of claim 10 having formula XIVf:

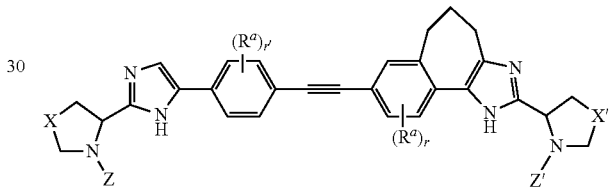

wherein X and X' are each independently selected from the group consisting of a bond, —CH$_2$—, —CH$_2$—CH$_2$—, —CH=CH—, —O—, —S—, —S(O)$_{1-2}$—, —CH$_2$O—, —CH$_2$S—, —CH$_2$S(O)$_{1-2}$— and —CH$_2$N(R$^1$)—, wherein $R^1$ is chosen from the group consisting of hydrogen, $C_1$ to $C_8$ alkyl, $C_1$ to $C_8$ heteroalkyl, cycloalkyl, heterocycle, aryl, heteroaryl, aralkyl, alkanoyl, alkoxycarbonyl, carbamoyl and substituted sulfonyl.

13. The compound of claim 10, wherein Z and Z' are each 1-3 amino acids.

14. The compound according to claim 13 wherein the amino acids are in the D configuration.

15. The compound of claim 10, wherein Z and Z' are each independently selected from the group consisting of —[U—(CR$^4_2$)$_t$—NR$^5$—(CR$^4_2$)$_t$]$_u$—U—(CR$^4_2$)$_t$—NR$^7$—(CR$^4_2$)$_t$—R$^8$, —U—(CR$^4_2$)$_t$—R$^8$ and —[U—(CR$^4_2$)$_t$—NR$^5$—(CR$^4_2$)$_t$]$_u$—U—(CR$^4_2$)$_t$—O—(CR$^4_2$)$_t$—R$^8$.

16. The compound of claim 10, wherein one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

17. The compound of claim 10, wherein one or both of Z and Z' are —C(O)—(CR$^4_2$)$_t$—NR$^7$—(CR$^4_2$)$_t$—R$^8$.

18. The compound of claim 10, wherein one or both of Z and Z' are —C(O)—(CR$^4_2$)$_n$—NR$^7$—C(O)—R$^{81}$.

19. The compound of claim 10, wherein one or both of Z and Z' are —C(O)—(CR$^4_2$)$_n$—NR$^7$—C(O)—O—R$^{81}$.

20. A compound selected from the group consisting of
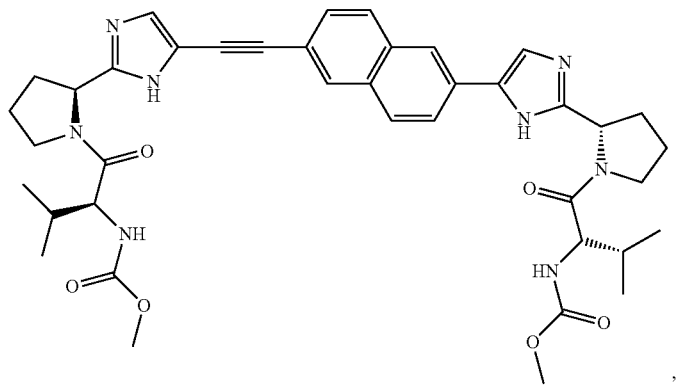
,
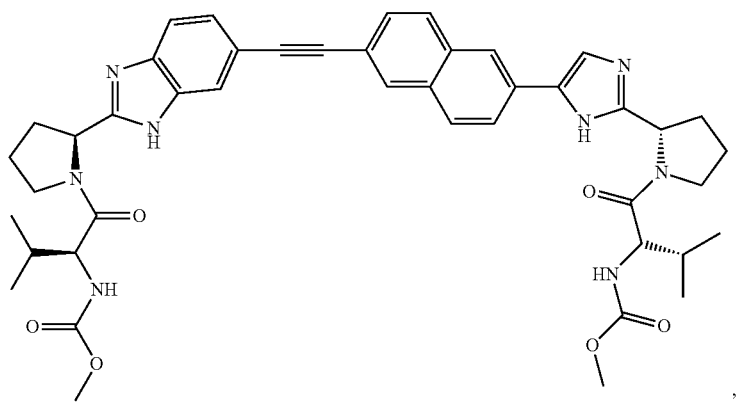
,
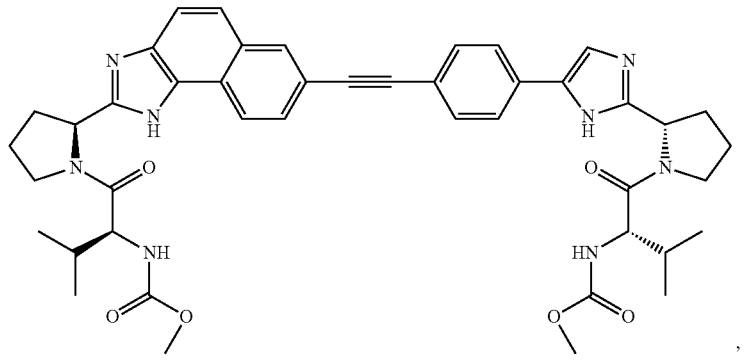
,
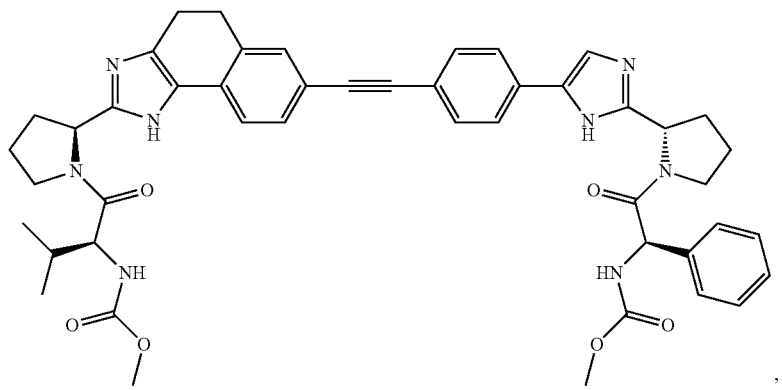
,

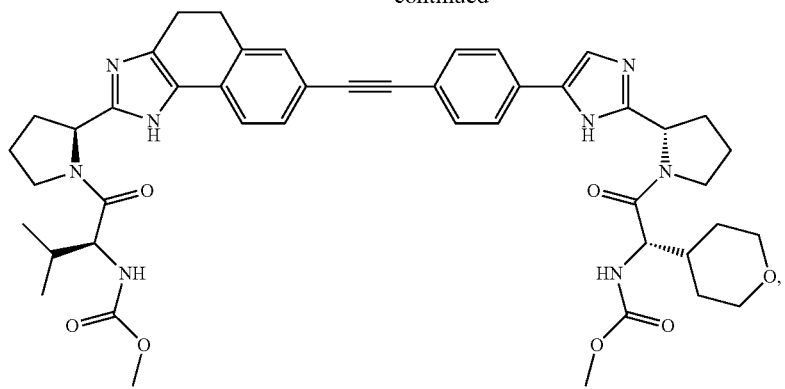
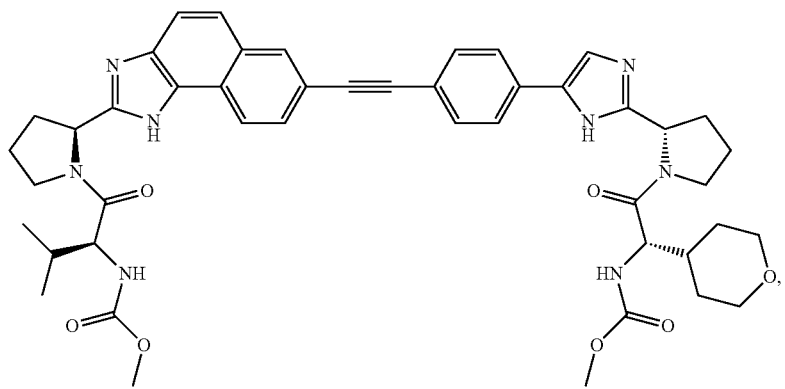
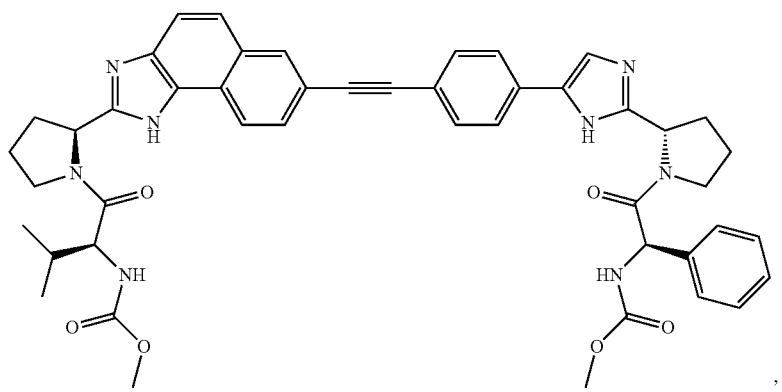
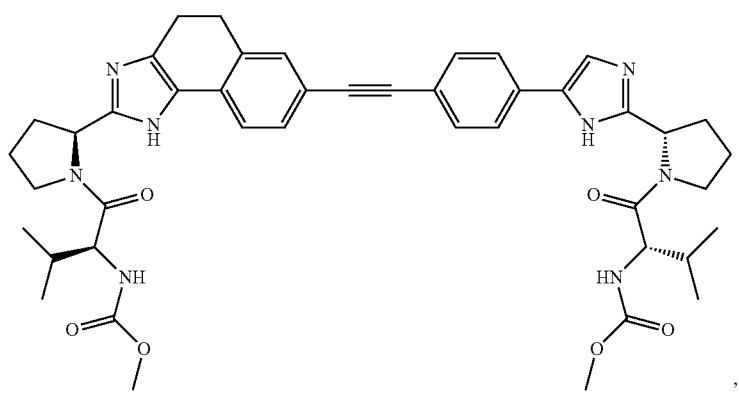

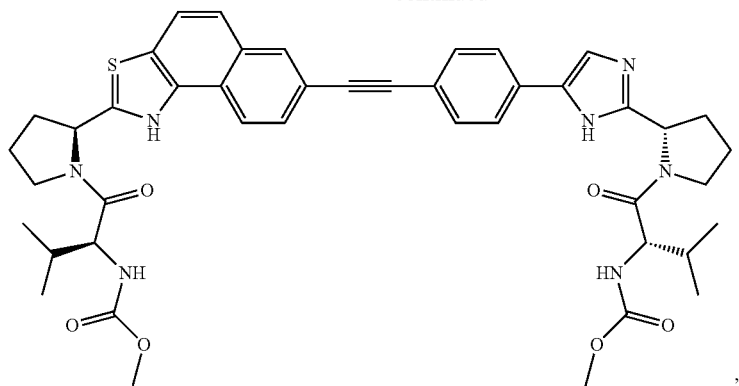
,
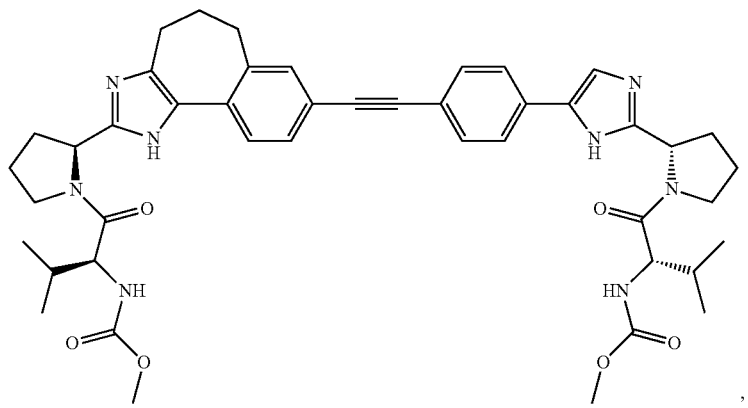
,
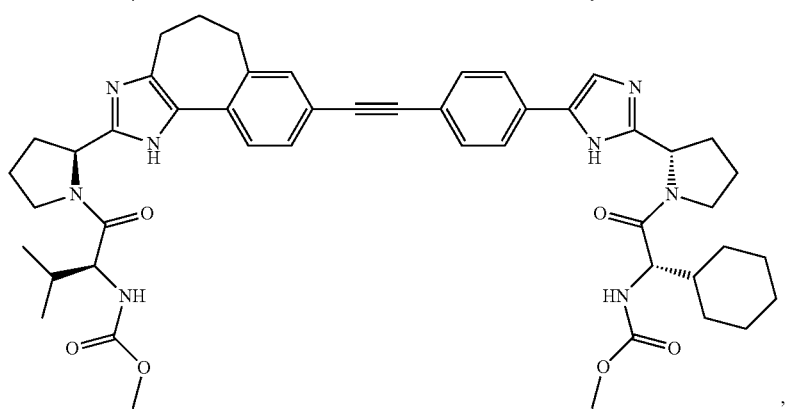
,
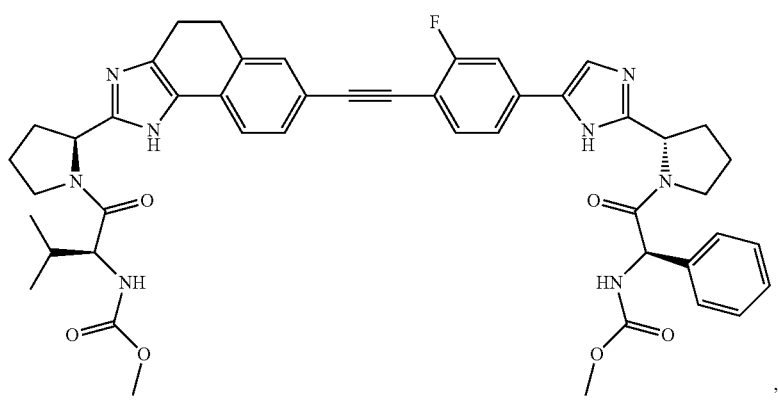
,

-continued

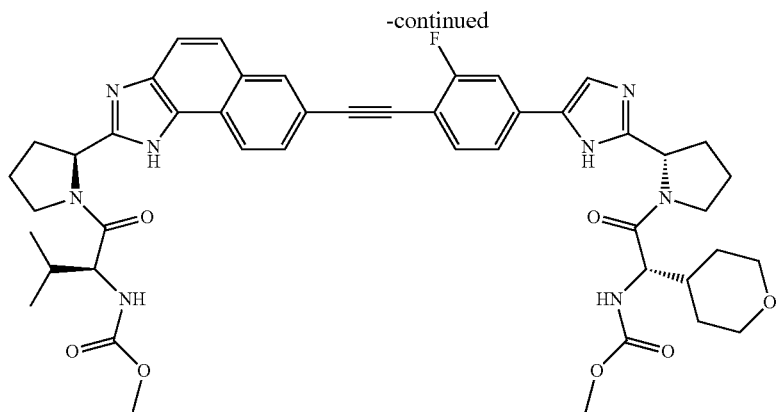

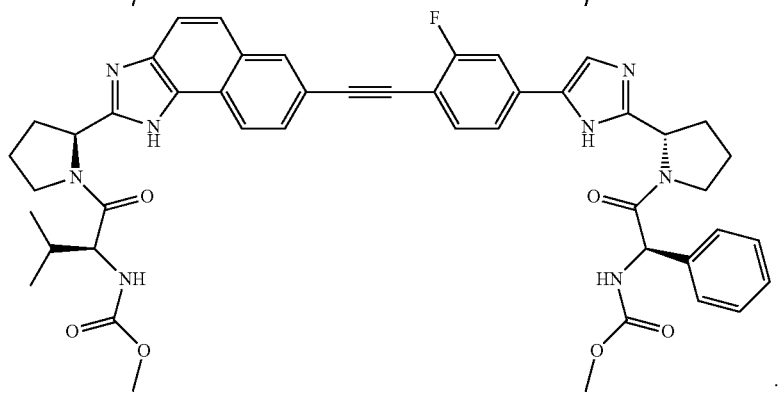

and

21. A pharmaceutical composition comprising a compound of claim 1.

22. A method of treating hepatitis C comprising administering to a subject in need thereof, a therapeutically effective amount of a compound of claim 1.

23. A pharmaceutical composition comprising a compound of claim 10.

24. A method of treating hepatitis C comprising administering to a subject in need thereof, a therapeutically effective amount of a compound of claim 10.

* * * * *